US012558107B2

(12) United States Patent
Bozung et al.

(10) Patent No.: US 12,558,107 B2
(45) Date of Patent: Feb. 24, 2026

(54) ROBOTIC HAND-HELD SURGICAL SYSTEM

(71) Applicant: MAKO Surgical Corp., Weston, FL (US)

(72) Inventors: Timothy J. Bozung, Belding, MI (US); Adam D. Downey, Kalamazoo, MI (US); Megan James, Portage, MI (US); James G. Walen, Portage, MI (US)

(73) Assignee: MAKO Surgical Corp., Weston, FL (US)

( * ) Notice: Subject to any disclaimer, the term of this patent is extended or adjusted under 35 U.S.C. 154(b) by 35 days.

(21) Appl. No.: 18/729,849

(22) PCT Filed: Jan. 20, 2023

(86) PCT No.: PCT/US2023/011232
§ 371 (c)(1),
(2) Date: Jul. 17, 2024

(87) PCT Pub. No.: WO2023/141265
PCT Pub. Date: Jul. 27, 2023

(65) Prior Publication Data
US 2025/0099113 A1     Mar. 27, 2025

Related U.S. Application Data

(60) Provisional application No. 63/320,299, filed on Mar. 16, 2022, provisional application No. 63/301,389, filed on Jan. 20, 2022.

(51) Int. Cl.
*A61B 17/16*     (2006.01)
*A61B 34/35*     (2016.01)
*A61B 34/30*     (2016.01)

(52) U.S. Cl.
CPC ...... *A61B 17/1622* (2013.01); *A61B 17/1626* (2013.01); *A61B 34/30* (2016.02); *A61B 34/35* (2016.02)

(58) Field of Classification Search
CPC ..... A61B 17/14; A61B 17/142; A61B 17/144; A61B 17/16; A61B 17/1613;
(Continued)

(56) References Cited

U.S. PATENT DOCUMENTS 7,035,716 B2     4/2006   Harris et al.
7,206,626 B2     4/2007   Quaid, III
(Continued)

FOREIGN PATENT DOCUMENTS

CN          114375183 A   *   4/2022   ............. A61B 34/20
CN          118871055 A   *   10/2024
(Continued)

OTHER PUBLICATIONS

International Search Report for Application No. PCT/US2023/011232 dated Aug. 9, 2023, 2 pages.
(Continued)

*Primary Examiner* — Eric S Gibson
(74) *Attorney, Agent, or Firm* — Howard & Howard Attorneys PLLC

(57) ABSTRACT

The present teachings provide for a hand-held robotic instrument for use with a surgical tool. In one configuration, the instrument comprises a housing configured to be held by a user, the housing defining a remote axis of motion. Control systems for controlling the hand-held robotic instrument are also contemplated, which are capable of switching control modes based on fixation, boundaries, and/or frames.

20 Claims, 80 Drawing Sheets

(58) Field of Classification Search
CPC ............ A61B 17/1615; A61B 17/1617; A61B
17/162; A61B 17/1622; A61B 17/1624;
A61B 17/1626; A61B 17/1628; A61B
17/1633; A61B 34/20; A61B 34/30; A61B
34/35; A61B 2034/2051; A61B
2034/2055; A61B 2034/2057; A61B
2034/2059
See application file for complete search history.

(56) References Cited

U.S. PATENT DOCUMENTS

| | | | |
|---|---|---|---|
| 7,206,627 | B2 | 4/2007 | Abovitz et al. |
| 7,422,582 | B2 | 9/2008 | Malackowski et al. |
| 7,559,935 | B2 | 7/2009 | Solar et al. |
| 7,741,802 | B2 | 6/2010 | Prisco et al. |
| 7,747,311 | B2 | 6/2010 | Quaid, III |
| 7,831,292 | B2 | 11/2010 | Quaid et al. |
| 7,984,663 | B2 | 7/2011 | Dent |
| 7,998,157 | B2 | 8/2011 | Culp et al. |
| 8,010,180 | B2 | 8/2011 | Quaid et al. |
| 8,062,288 | B2 | 11/2011 | Cooper et al. |
| 8,095,200 | B2 | 1/2012 | Quaid, III |
| 8,303,575 | B2 | 11/2012 | Rodriguez Y Baena |
| 8,391,954 | B2 | 3/2013 | Quaid, III |
| 8,498,744 | B2 | 7/2013 | Odermatt et al. |
| 8,571,628 | B2 | 10/2013 | Kang et al. |
| 8,617,174 | B2 | 12/2013 | Axelson, Jr. et al. |
| 8,644,988 | B2 | 2/2014 | Prisco et al. |
| 8,749,190 | B2 | 6/2014 | Nowlin et al. |
| 8,753,346 | B2 | 6/2014 | Suarez et al. |
| 8,898,043 | B2 | 11/2014 | Ashby et al. |
| 8,911,499 | B2 | 12/2014 | Quaid et al. |
| 8,961,536 | B2 | 2/2015 | Nikou et al. |
| 8,992,542 | B2 | 3/2015 | Hagag et al. |
| 8,996,169 | B2 | 3/2015 | Lightcap et al. |
| 9,002,426 | B2 | 4/2015 | Quaid et al. |
| 9,008,757 | B2 | 4/2015 | Wu |
| 9,060,794 | B2 | 6/2015 | Kang et al. |
| 9,119,638 | B2 | 9/2015 | Schwarz et al. |
| 9,119,655 | B2 | 9/2015 | Bowling et al. |
| 9,161,760 | B2 | 10/2015 | Suarez et al. |
| 9,192,394 | B2 | 11/2015 | Belagali |
| 9,354,552 | B2 | 5/2016 | Takeuchi |
| 9,399,298 | B2 | 7/2016 | Kang |
| 9,561,082 | B2 | 2/2017 | Yen et al. |
| 9,597,157 | B2 | 3/2017 | Hagag et al. |
| 9,622,823 | B2 | 4/2017 | Bozung et al. |
| 9,707,043 | B2 | 7/2017 | Bozung |
| 9,724,167 | B2 | 8/2017 | Ziaei et al. |
| 9,770,306 | B2 | 9/2017 | Hagag et al. |
| 9,775,681 | B2 | 10/2017 | Quaid et al. |
| 9,801,686 | B2 | 10/2017 | Lightcap et al. |
| 9,812,035 | B2 | 11/2017 | Stuart et al. |
| 9,820,818 | B2 | 11/2017 | Malackowski et al. |
| 9,937,014 | B2 | 4/2018 | Bowling et al. |
| 10,052,166 | B2 | 8/2018 | Ziaei et al. |
| 10,098,704 | B2 | 10/2018 | Bowling et al. |
| 10,117,713 | B2 | 11/2018 | Moctezuma de la Barrera et al. |
| 10,206,750 | B2 | 2/2019 | Hagag et al. |
| 10,231,790 | B2 | 3/2019 | Quaid et al. |
| 10,231,792 | B2 | 3/2019 | Shiels et al. |
| 10,327,849 | B2 | 6/2019 | Post |
| 10,368,878 | B2 | 8/2019 | Lavallee et al. |
| 10,369,708 | B2 | 8/2019 | Kang |
| 10,410,746 | B2 | 9/2019 | Moctezuma de la Barrera et al. |
| 10,483,881 | B2 | 11/2019 | Liao et al. |
| 10,492,870 | B2 * | 12/2019 | Shalayev ............... A61B 90/36 |
| 10,492,875 | B2 | 12/2019 | Janik et al. |
| 10,550,918 | B2 | 2/2020 | Cooper et al. |
| 10,568,640 | B2 * | 2/2020 | Bozung ............. A61B 17/1622 |
| 10,603,119 | B2 | 3/2020 | Ross et al. |
| 10,660,711 | B2 | 5/2020 | Moctezuma de la Barrera et al. |
| 10,660,715 | B2 | 5/2020 | Dozeman |
| 10,751,051 | B2 | 8/2020 | Weir et al. |

| | | | |
|---|---|---|---|
| 10,813,697 | B2 | 10/2020 | Bozung et al. |
| 10,828,786 | B2 | 11/2020 | Shoham |
| 10,864,011 | B2 | 12/2020 | Downey et al. |
| 10,864,047 | B2 | 12/2020 | Hagag et al. |
| 10,874,474 | B2 | 12/2020 | Wu et al. |
| 10,888,385 | B2 | 1/2021 | Ho et al. |
| 10,967,525 | B2 | 4/2021 | Kang |
| 11,045,264 | B2 | 6/2021 | Yen et al. |
| 11,076,918 | B2 | 8/2021 | Quaid, III |
| 11,123,881 | B2 | 9/2021 | Kang |
| 11,135,014 | B2 | 10/2021 | Bozung |
| 11,253,329 | B2 | 2/2022 | Bowling |
| 11,278,363 | B2 | 3/2022 | Ross et al. |
| 11,369,438 | B2 | 6/2022 | Malackowski et al. |
| 11,627,979 | B2 | 4/2023 | Keppler et al. |
| 11,633,248 | B2 | 4/2023 | Gilhooley et al. |
| 11,666,318 | B2 | 6/2023 | Otto et al. |
| 11,672,610 | B2 | 6/2023 | Hagag et al. |
| 11,684,374 | B2 | 6/2023 | Kang et al. |
| 11,896,314 | B2 | 2/2024 | Bozung |
| 11,944,396 | B2 | 4/2024 | Dozeman et al. |
| 12,232,744 | B2 * | 2/2025 | Bozung .................. A61B 34/20 |
| 12,329,461 | B2 * | 6/2025 | Kuznik ................. A61B 34/32 |
| 2011/0315413 | A1 | 12/2011 | Fisher et al. |
| 2013/0060278 | A1 * | 3/2013 | Bozung ................. A61F 2/4455 |
| | | | 606/205 |
| 2017/0258532 | A1 * | 9/2017 | Shalayev ........... A61B 17/1624 |
| 2018/0333207 | A1 | 11/2018 | Moctezuma De La Barrera |
| 2019/0328468 | A1 | 10/2019 | Schena et al. |
| 2019/0365391 | A1 | 12/2019 | Nikou et al. |
| 2019/0388099 | A1 * | 12/2019 | Zuhars ................... A61B 34/10 |
| 2020/0008884 | A1 | 1/2020 | Lavallee et al. |
| 2020/0008889 | A1 * | 1/2020 | Ho ........................ A61B 17/34 |
| 2020/0038108 | A1 * | 2/2020 | Chou .................... A61B 34/10 |
| 2020/0046438 | A1 | 2/2020 | Shalayev et al. |
| 2020/0069373 | A1 | 3/2020 | Yu et al. |
| 2020/0093500 | A1 | 3/2020 | Lavallee et al. |
| 2020/0146763 | A1 | 5/2020 | Schena et al. |
| 2020/0155175 | A1 | 5/2020 | Nikou et al. |
| 2020/0188034 | A1 | 6/2020 | Lequette et al. |
| 2020/0406480 | A1 | 12/2020 | Shoham |
| 2021/0068845 | A1 | 3/2021 | Schers et al. |
| 2021/0093400 | A1 | 4/2021 | Quaid et al. |
| 2021/0186632 | A1 | 6/2021 | Quaid et al. |
| 2021/0212767 | A1 | 7/2021 | Wapler |
| 2022/0233251 | A1 | 7/2022 | Bowling et al. |
| 2022/0273396 | A1 * | 9/2022 | Bozung ................. A61B 17/142 |
| 2022/0338935 | A1 * | 10/2022 | Bell ........................ G16H 20/40 |
| 2023/0105049 | A1 | 4/2023 | Becker et al. |
| 2023/0131101 | A1 * | 4/2023 | Bozung ............ A61B 17/32002 |
| | | | 606/1 |
| 2023/0255701 | A1 * | 8/2023 | Post ........................ A61B 34/30 |
| | | | 606/82 |
| 2024/0008910 | A1 * | 1/2024 | Michaelson ....... A61B 17/1778 |
| 2024/0108358 | A1 * | 4/2024 | VanDyken ........... B23D 59/003 |
| 2024/0252179 | A1 * | 8/2024 | Bell ........................ A61B 34/20 |
| 2025/0099113 | A1 * | 3/2025 | Bozung ................. A61B 34/30 |
| 2025/0221782 | A1 * | 7/2025 | Dozeman .............. A61B 17/14 |

FOREIGN PATENT DOCUMENTS

| | | | | | |
|---|---|---|---|---|---|
| CN | 118922146 | A | * | 11/2024 | |
| JP | 2024506242 | A | * | 2/2024 | ............. A61B 34/20 |
| JP | 2025503705 | A | * | 2/2025 | ........... A61B 17/142 |
| WO | 2019191420 | A1 | | 10/2019 | |
| WO | 2019212583 | A2 | | 11/2019 | |
| WO | 2019219348 | A1 | | 11/2019 | |
| WO | 2020257444 | A1 | | 12/2020 | |
| WO | WO-2021011646 | A2 | * | 1/2021 | ............. A61B 34/30 |
| WO | 2021062373 | A2 | | 4/2021 | |
| WO | WO-2021158367 | A1 | * | 8/2021 | ........... A61B 17/142 |
| WO | 2022055980 | A1 | | 3/2022 | |
| WO | WO-2022099002 | A1 | * | 5/2022 | ............. A61B 17/17 |
| WO | 2022159568 | A1 | | 7/2022 | |
| WO | 2022159574 | A1 | | 7/2022 | |
| WO | WO-2023136930 | A2 | * | 7/2023 | ........... A61B 17/142 |
| WO | WO-2023141265 | A2 | * | 7/2023 | ............. A61B 34/35 |
| WO | WO-2024020088 | A1 | * | 1/2024 | ............. A61B 34/30 |

(56) References Cited

FOREIGN PATENT DOCUMENTS

OTHER PUBLICATIONS

Partial International Search Report for Application No. PCT/US2023/011232 dated Jun. 19, 2023, 2 pages.

Vossel, Manuel et al., "MINARO HD: Control and Evaluation of a Handheld, Highly Dynnamic Surgical Robot", International Journal of Computer Assisted Radiology and Surgery, Dec. 29, 2020, 8 pages.

* cited by examiner

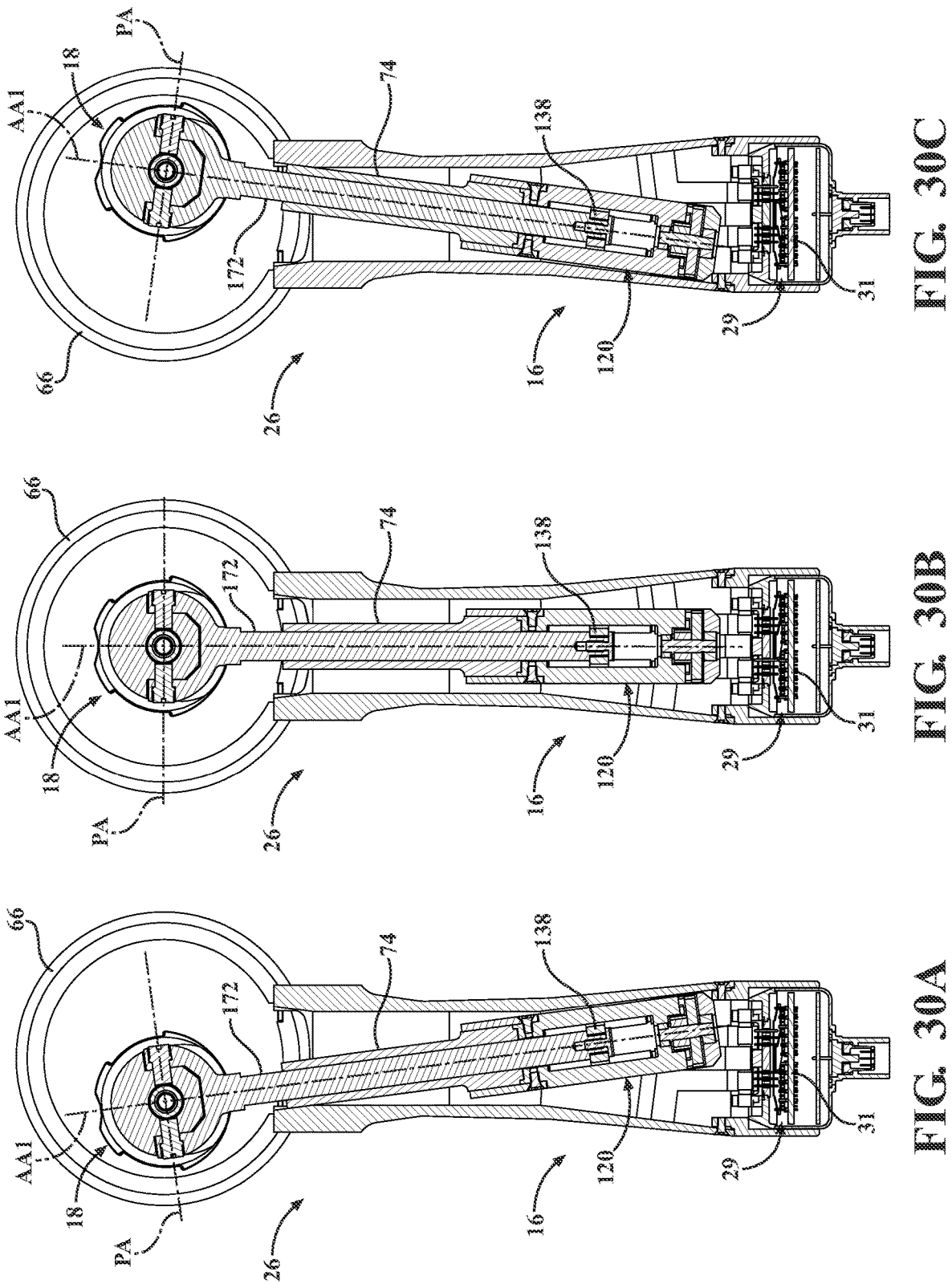

ROBOTIC HAND-HELD SURGICAL SYSTEM

CROSS-REFERENCE TO RELATED APPLICATIONS

The present application is a National Stage of PCT International Patent Application No. PCT/US2023/011232, filed on Jan. 20, 2023, which claims priority to and all the benefits of U.S. Provisional Patent Application No. 63/301, 389, filed on Jan. 20, 2022, and U.S. Provisional Patent Application No. 63/320,299, filed on Mar. 16, 2022, the entire contents of which are hereby expressly incorporated herein by reference.

BACKGROUND

Navigation systems (also referred to as tracking systems) can be used to properly align and secure jigs and/or trajectory guides, as well as track a position and/or orientation of a surgical tool used to resect tissue from a patient. Tracking systems typically employ one or more trackers associated with the tool and the tissue being resected. A display can then be viewed by a user to determine a current position of the tool relative to a desired drilling or driving location of tissue to be removed. The display may be arranged in a manner that requires the user to look away from the tissue and surgical site to visualize the tool's progress. This can distract the user from focusing on the surgical site. Also, it may be difficult for the user to place the tool in a desired manner.

Robotically assisted surgery typically relies on large robots with robotic arms that can move in six degrees of freedom (DOF). These large robots may be cumbersome to operate and maneuver in the operating room.

There is a need for systems and methods to address one or more of these challenges.

SUMMARY

The present teachings provide for a hand-held robotic instrument for use with a tool. The instrument comprises a housing configured to be held by a user, the housing defining a remote axis of motion. The robotic instrument includes a tool support being movably coupled to the housing and an anchor post pivotally coupled to the tool support, a first set of actuators connected to the anchor post and the housing, and a second set of actuators connected between the tool support and the housing. The first set of actuators includes a first actuator that extends the anchor post relative to the remote axis of motion, and a second actuator configured to pivot the anchor post about the remote axis of motion. The first set of actuators and the second set of actuators work in concert to change the pose of the tool support in a plurality of degrees of freedom.

One general aspect includes a hand-held robotic instrument for use with a tool to perform surgery. The hand-held robotic instrument also includes a housing configured to be held by a user. The instrument also includes a tool support to support the tool and being movably coupled to the housing, the tool support defining a tool axis. The instrument also includes an anchor post pivotably coupled to the tool support. The instrument also includes a first set of actuators operably coupled to the anchor post and the housing, the first set of actuators being configured to translate the anchor post relative to the housing and configured to pivot the anchor post about a remote axis of motion. The instrument also includes a second set of actuators coupled to the tool support. The instrument also includes a controller in communication with the first set of actuators and the second set of actuators to change a pose of the tool support relative to the housing to place the tool axis on a target trajectory while the user manipulates the housing. Other implementations of this aspect include corresponding computer systems, apparatus, and computer programs recorded on one or more computer storage devices, each configured to perform the actions of the methods.

One general aspect includes a hand-held robotic instrument for use with a tool to perform surgery. The hand-held robotic instrument includes a housing configured to be held by a user, and defining a mount location. The instrument also includes a tool support to support the tool. The instrument also includes a first linkage extending from the mount location on the housing to the tool support. The instrument also includes a first actuator coupled to the first linkage and configured to cause the first linkage to extend from a first length to a second length. The instrument also includes a second actuator coupled to the first linkage and configured to cause the first linkage to pivot about the mount location on the housing. Other implementations of this aspect include corresponding computer systems, apparatus, and computer programs recorded on one or more computer storage devices, each configured to perform the actions of the methods.

One general aspect includes a hand-held robotic instrument for use with a tool to perform surgery. The hand-held robotic instrument also includes a housing configured to be held by a user. The instrument also includes a tool support to support the tool and being movably coupled to the housing, including a positioning post. The instrument also includes a first actuator and a second actuator movably coupled to the positioning post of the tool support and the housing for moving the tool support relative to the housing in a plurality of degrees of freedom, each of the first and second actuators including. The instrument also includes a base. The instrument also includes a rod connected to the base and moveable from a first length to a second length relative to the base, with the rod including a yoke. The instrument also includes a post slide pivotably coupled to the yoke. The instrument also includes where the post slides of the first and second actuators are disposed about the positioning post and move along the positioning post. The instrument also includes a linkage including a third actuator connected between the tool support and the housing. Other implementations of this aspect include corresponding computer systems, apparatus, and computer programs recorded on one or more computer storage devices, each configured to perform the actions of the methods.

One general aspect includes a hand-held robotic instrument for use with a tool to perform surgery. The hand-held robotic instrument also includes a housing configured to be held by a user. The instrument also includes a tool support to support the tool and being movably coupled to the housing. The instrument also includes a first actuator. The instrument also includes a second actuator. The instrument also includes the first actuator coupling the second actuator and the housing. The instrument also includes the second actuator coupling the first actuator and the tool support. The instrument also includes where the first actuator includes a first motor, a first base coupled to the first motor, a first gear set coupled to the first motor, and a first rod coupled to the first gear set and the tool support, the first motor of the first actuator operable to extend and retract the first rod relative to the housing. The instrument also includes where the second actuator operably coupled to the first rod and configured to articulate the first rod of the first actuator about an axis. The instrument also includes a linkage. The instrument also includes a third actuator connected between the tool support and the housing, with the third actuator configured to move the tool support relative to the housing with the linkage. Other implementations of this aspect include corresponding computer systems, apparatus, and computer programs recorded on one or more computer storage devices, each configured to perform the actions of the methods.

One general aspect includes a hand-held robotic instrument for use with a tool to perform surgery. The hand-held robotic instrument also includes a housing configured to be held by a user. The instrument also includes a tool support to support the tool and being movably coupled to the housing, including a positioning post. The instrument also includes a first actuator and a second actuator movably coupled to the positioning post of the tool support and the housing for moving the tool support relative to the housing in a plurality of degrees of freedom. The instrument also includes the first actuator including a first motor and a first positioning link defining a first slot, the first motor configured to articulate the first positioning link about a first axis, with the first slot disposed about the positioning post. The instrument also includes the second actuator including a second motor and a second positioning link defining a second slot, the second motor configured to articulate the second positioning link about a second axis, with the second slot disposed about the positioning post. The instrument also includes a linkage. The instrument also includes a third actuator connected between the tool support and the housing with the third actuator configured to move the tool support relative to the housing with the linkage. Other implementations of this aspect include corresponding computer systems, apparatus, and computer programs recorded on one or more computer storage devices, each configured to perform the actions of the methods.

One general aspect includes a hand-held robotic instrument for use with a tool to perform surgery. The hand-held robotic instrument also includes a housing configured to be held by a user. The instrument also includes a tool support to support the tool and being movably coupled to the housing, the tool support defining a tool axis. The instrument also includes an anchor post pivotably coupled to the tool support. The instrument also includes a first set of actuators coupled between the anchor post and the housing, a first actuator of the first set of actuators is configured to change the position of the anchor post, and a second actuator of the first set configured to pivot the anchor post about a remote axis of motion. The instrument also includes a second set of actuators connected between the tool support and the housing, the second set of actuators including a first rotary actuator of the second set of actuators and a second linear actuator of the second set of actuators, the first rotary actuator being coupled to the second linear actuator to cause the second linear actuator to rotate about an axis and the second linear actuator of the second set of actuators configured to change length with the second linear actuator extending from the first rotary actuator of the second set of actuators to the tool support. The instrument also includes where the first set of actuators and the second set of actuators work in concert to change a pose of the tool support. Other implementations of this aspect include corresponding computer systems, apparatus, and computer programs recorded on one or more computer storage devices, each configured to perform the actions of the methods.

One general aspect includes a hand-held robotic instrument for use with a tool to perform surgery. The hand-held robotic instrument includes a housing configured to be held by a user. The instrument also includes a tool support to support the tool and being movably coupled to the housing, the tool support defining a tool axis. The instrument also includes a first alignment guide extending from a first portion of the housing and surrounding at least a first portion of the tool support. The instrument also includes a second alignment guide extending from a second portion of the housing and surrounding at least a second portion of the tool support, the second alignment guide spaced axially from the first alignment guide. The instrument also includes a plurality of actuators between the housing and the tool support configured to move the tool support in a plurality of degrees of freedom relative to the housing. The instrument also includes a controller operatively connected to the plurality of actuators to change a pose of a tool axis relative to the housing in a plurality of degrees of freedom, the controller configured to automatically control each of the actuators to actively move the tool axis towards a target trajectory axis relative to the housing. The instrument also includes where aligning the tool axis axially with the first alignment guide and second alignment guide, the tool support has an optimal range of motion relative to the housing. Other implementations of this aspect include corresponding computer systems, apparatus, and computer programs recorded on one or more computer storage devices, each configured to perform the actions of the methods.

One general aspect includes a hand-held robotic instrument for use with a tool to perform surgery. The hand-held robotic instrument includes a hand-held portion to be held by a user. The instrument also includes a tool support movably coupled to the hand-held portion to support the tool. The instrument also includes a plurality of actuators operatively interconnecting the tool support and the hand-held portion to move the tool support in at least four degrees of freedom relative to the hand-held portion. The instrument also includes. The instrument also includes a linkage operatively interconnecting the tool support and the hand-held portion, the linkage being coupled to the tool support and the hand-held portion in a manner configured to constrain movement of the tool support relative to the hand-held portion in at least two degrees of freedom, where the linkage operatively interconnects the tool support and the hand-held portion independently of the plurality of actuators. Other implementations of this aspect include corresponding computer systems, apparatus, and computer programs recorded on one or more computer storage devices, each configured to perform the actions of the methods.

One general aspect includes a hand-held robotic instrument for use with a tool to perform surgery. The hand-held robotic instrument includes a housing configured to be held by a user. The instrument also includes a tool support to support the tool and being movably coupled to the housing, the tool support defining a tool axis, the tool support including a drive motor with a position sensor, the drive motor configured to rotate the tool, and the position sensor configured to determine a rotational position of the drive motor. The instrument also includes a control system operatively connected to the plurality of actuators to change a pose of a tool axis relative to the housing in a plurality of degrees of freedom, the control system configured to control each of the actuators to actively move the tool towards a target trajectory axis, where the control system is further configured to determine a pose of tool support, determine a target trajectory axis, and determine a commanded pose of the tool support based on the target trajectory axis and the pose of the tool support. Control system also is configured to control the drive motor based on an input signal from the position sensor and based on the commanded pose of the tool support to minimize additional torque on the tool caused by moving of the tool support relative to the housing and/or relative to the anatomy. Other implementations of this aspect include corresponding computer systems, apparatus, and computer programs recorded on one or more computer storage devices, each configured to perform the actions of the methods.

One general aspect includes a hand-held robotic instrument for use with a tool to perform surgery. The hand-held robotic instrument also includes a housing configured to be held by a user. The instrument also includes a tool support to support the tool and being movably coupled to the housing, the tool support defining a tool axis, the tool support including a drive motor with a position sensor, the drive motor configured to rotate the tool, and the position sensor configured to determine a rotational position of the drive motor. The instrument also includes a plurality of actuators between the housing and the tool support configured to move the tool support in a plurality of degrees of freedom relative to the housing. The instrument also includes a control system operatively connected to the plurality of actuators to change a pose of a tool axis relative to the housing in a plurality of degrees of freedom, the control system configured to control each of the actuators to actively move the tool towards a target trajectory axis. The control system is also configured to determine a pose of the tool, tool support, or the housing; determine a target trajectory axis; and determine a commanded pose of the tool, the tool support, or the housing based on the target trajectory axis and the pose of one of the tool, tool support or housing. The control system is also configured to control the drive motor based on an input signal from the position sensor and based on the commanded pose of the tool, tool support, or housing to minimize additional torque on the tool caused by the movement of the tool support relative to the housing. Other implementations of this aspect include corresponding computer systems, apparatus, and computer programs recorded on one or more computer storage devices, each configured to perform the actions of the methods.

One general aspect includes a hand-held robotic system for use with a surgical tool. The system includes a control system coupled to the plurality of actuators, the localizer, and the tool drive motor, the control system configured to: determine a target pose of the surgical tool in a known coordinate system; determine a state of one of the surgical tool, hand-held portion, and the tool support in the known coordinate system; determine a commanded joint position or angle for each of the plurality of actuators based on the target pose of the surgical tool and the state of one of the surgical tool, hand-held portion, and the tool support; control the plurality of actuators based on the respective commanded joint positions or angles; monitor fixation between the surgical tool and a workpiece; and select a control mode of the plurality of actuators based on the fixation. Other implementations of this aspect include corresponding computer systems, apparatus, and computer programs recorded on one or more computer storage devices, each configured to perform the actions of the methods.

One general aspect includes a hand-held robotic system for use with a surgical tool. The system includes a control system coupled to the plurality of actuators, the localizer, and the tool drive motor, the control system configured to determine a target pose of the surgical tool in a known coordinate system; determine a state of one of the surgical tool, hand-held portion, and the tool support in the known coordinate system; determine a commanded joint position or angle for each of the plurality of actuators based on the target pose and based on the state of one of the surgical tool, hand-held portion, and the tool support; control the plurality of actuators based on the respective commanded joint positions or angles. The system also includes select a control mode from a first control mode and a second control mode based on the pose of the tool, the tool support, or the hand-held portion where in the first control mode, the plurality of actuators are controlled to move the tool in at least four degrees of freedom and in the second control mode the plurality of actuators are controlled to move the tool in two or fewer degrees of freedom. Other implementations of this aspect include corresponding computer systems, apparatus, and computer programs recorded on one or more computer storage devices, each configured to perform the actions of the methods.

One general aspect includes a hand-held robotic system for use with a surgical tool. The system includes a control system coupled to the plurality of actuators, the localizer, and the tool drive motor, the control system configured to determine a target pose of the surgical tool in a known coordinate system; determine a state of one of the surgical tool, hand-held portion, and the tool support in the known coordinate system; determine a commanded joint position or angle for each of the plurality of actuators based on the target pose and based on the state of one of the surgical tool, hand-held portion, and the tool support; control the plurality of actuators based on the respective commanded joint positions or angles; and select a control mode from a first control mode and a second control mode based on the pose of the tool, the tool support, or the hand-held portion where in the first control mode, the plurality of actuators are controlled to move the tool in at a first set of two degrees of freedom and in the second control mode the plurality of actuators are controlled to move the tool in a second set of two degrees of freedom, the first set of two degrees of freedom differing from the second set of two degrees of freedom.

One general aspect includes a hand-held robotic system for use with a surgical tool. The system includes a control system coupled to the plurality of actuators, the localizer, and the tool drive motor, the control system configured to determine a target pose of the surgical tool in a known coordinate system; determine a state of one of the surgical tool, hand-held portion, and the tool support in the known coordinate system; determine a commanded joint position or angle for each of the plurality of actuators based on the target pose and based on the state of one of the surgical tool, hand-held portion, and the tool support; control the plurality of actuators based on the respective commanded joint positions or angles; and where the control system is configured to select one of a pointing sub-mode and a trajectory sub-mode based on a target trajectory, a workspace limit, and the pose of one of the surgical tool, the tool support, and the hand-held portion, where the target trajectory includes a target axis extending between a bone entry point or tissue and a second point, where the control system is configured to control the plurality of actuators such that an axis of the tool is aligned with both the bone or tissue entry point and the second point when in the trajectory sub-mode and the control system is configured to control the plurality of actuators such that the axis of the tool is aligned with the bone or tissue entry point and a portion of the axis engages the workspace limit when in the pointing sub-mode. Other implementations of this aspect include corresponding computer systems, apparatus, and computer programs recorded on one or more computer storage devices, each configured to perform the actions of the methods.

One general aspect includes a hand-held robotic system for use with a surgical tool. The system includes a control system coupled to the plurality of actuators, the localizer, and the tool drive motor, the control system configured to: determine a target pose of the surgical tool in a known coordinate system; determine a state of one of the surgical tool, hand-held portion, and the tool support in the known coordinate system; determine a commanded joint position or angle for each of the plurality of actuators based on the target pose and based on the state of one of the surgical tool, hand-held portion, and the tool support; control the plurality of actuators based on the respective commanded joint positions or angles; and where the control system is configured to select one of a pointing sub-mode and a trajectory sub-mode based on a target trajectory, a joint limit, and a state of at least one actuator of the plurality of actuators, where the target trajectory includes a target axis extending between a bone or tissue entry point and a second point, where the control system is configured to control the plurality of actuators such that an axis of the tool is aligned with both the bone or tissue entry point and the second point when in the trajectory sub-mode and the control system is configured to control the plurality of actuators such that the axis of the tool is aligned with the bone or tissue entry point and the state of at least one actuators of the plurality of actuators is at the joint limit for that actuator. Other implementations of this aspect include corresponding computer systems, apparatus, and computer programs recorded on one or more computer storage devices, each configured to perform the actions of the methods.

One general aspect includes a hand-held robotic system for use with a surgical tool. The system includes a control system coupled to the plurality of actuators, the localizer, and the tool drive motor, the control system configured to: receive a first target trajectory of the surgical tool in a known coordinate system, where the first target trajectory includes a first target axis extending between a planned first bone or tissue entry point and a second point; determine a state of one of the surgical tool, hand-held portion, and the tool support in the known coordinate system; determine a first commanded joint position or angle for each of the plurality of actuators based on the first target trajectory and based on the state of one of the surgical tool, hand-held portion, and the tool support; control the plurality of actuators based on the respective first commanded joint positions or angles; select a second target trajectory, where the second target trajectory includes a second target axis extending through a second bone or tissue entry point, the second bone or tissue entry point being different from the planned first bone or tissue entry point; and determine a second commanded joint position or angle for each of the plurality of actuators based on the second target trajectory and based on the state of one of the surgical tool, hand-held portion, and the tool support. Other implementations of this aspect include corresponding computer systems, apparatus, and computer programs recorded on one or more computer storage devices, each configured to perform the actions of the methods.

BRIEF DESCRIPTION OF THE DRAWINGS

Advantages of the present disclosure will be readily appreciated as the same becomes better understood by reference to the following detailed description when considered in connection with the accompanying drawings.

FIGS. 30A, 30B, and 30C illustrate cross-sectional views of the first configuration of the robotic instrument with the angular movement assembly and tool support in three different poses.

DETAILED DESCRIPTION

Overview

Figure 1:
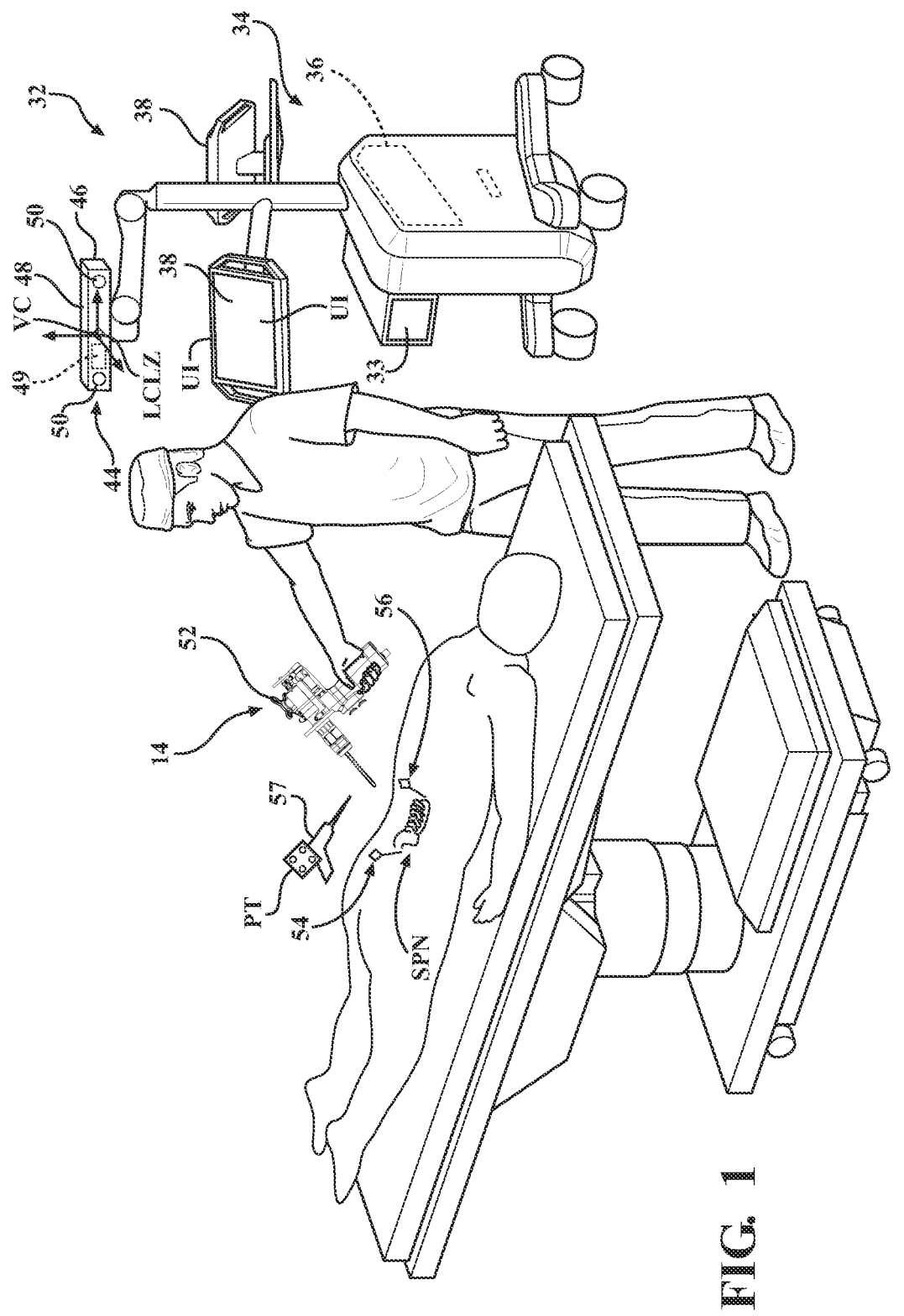
FIG. 1 is a perspective view of a robotic system.

Referring to FIG. 1, a robotic system 10 is illustrated. The robotic system 10 is shown performing a spinal fusion on a patient 12 to drill one or more holes in a spine SPN of the patient 12 so that the patient 12 can receive one or more spinal implants. The robotic system 10 may be used to perform other types of surgical procedures, including procedures that involve hard/soft tissue removal, or other forms of treatment. For example, treatment may include cutting tissue, pre-drilling holes, drive implants, tapping holes, guiding and/or placing wires, coagulating tissue, inserting implants, ablating tissue, stapling tissue, suturing tissue, or the like. In some examples, the surgical procedure involves knee surgery, hip surgery, shoulder surgery, spine surgery, and/or ankle surgery, and may involve removing tissue to be replaced by surgical implants, such as screws or pins. The robotic system 10 and techniques disclosed herein may be used to perform other procedures, surgical or non-surgical, and may be used in industrial applications or other applications where robotic systems are utilized.

Figure 2:
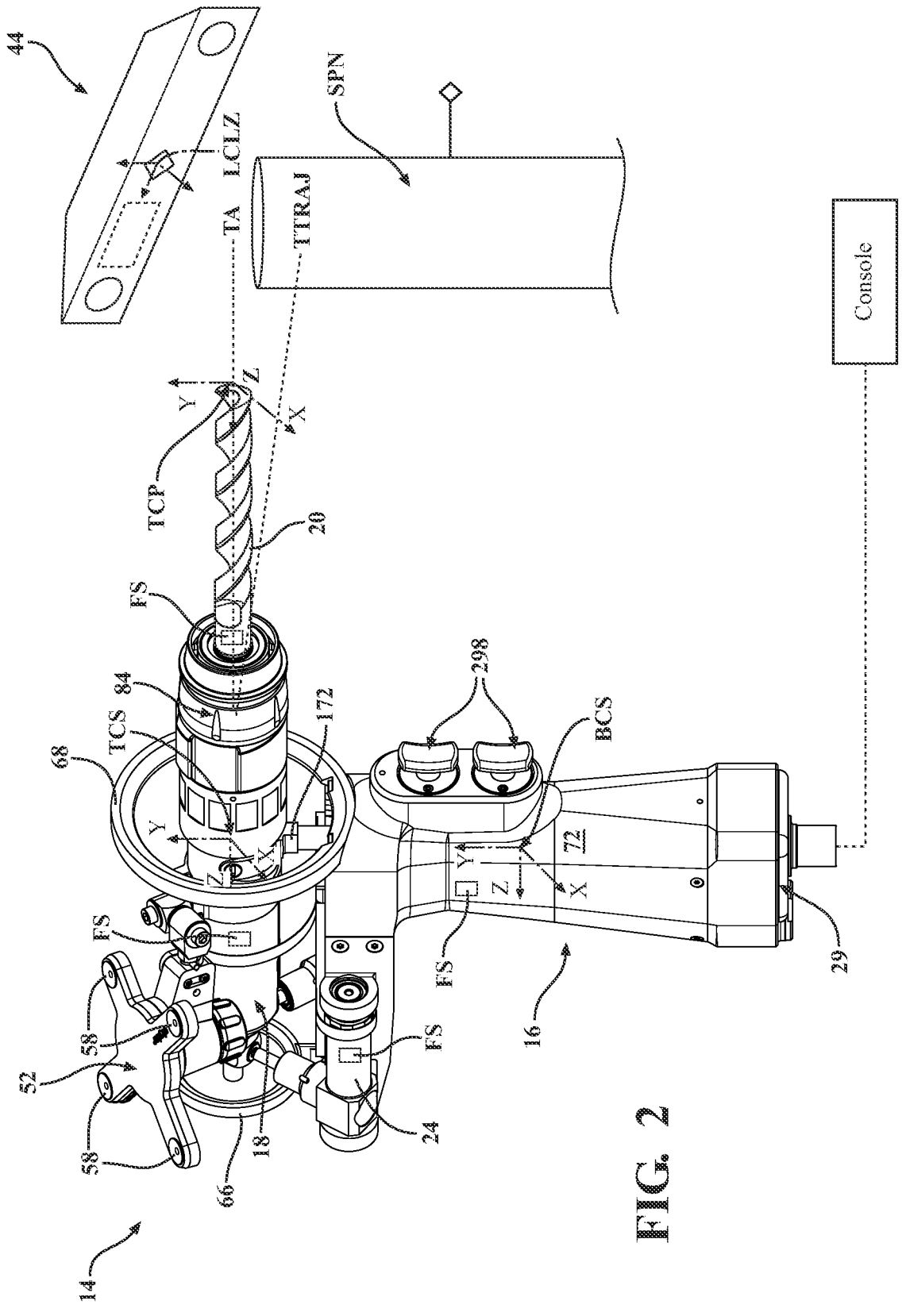
FIG. 2 are perspective views of a first configuration of a robotic instrument.

Referring to FIGS. 1 and 2, the robotic system 10 includes an instrument 14. In some examples, a user manually holds and supports the instrument 14 (as shown in FIG. 1). In some other examples, the user may manually hold the instrument 14 while the instrument is being at least partially, or fully, supported by an assistive device, such as a passive arm (e.g., linkage arm with locking joints, weight-balancing arm), an active arm, and/or the like. As best shown in FIGS. 1 and 2, the instrument 14 comprises a hand-held portion 16 for being supported by the user. The hand-held portion 16 defines a housing. The instrument 14 may be freely moved and supported by a user without the aid of a guide arm/assistive device, e.g., configured to be held by a human user while effecting physical removal of material or cutting of material such that the weight of the tool is supported solely by a hand or hands of the user during the procedure. Put another way, the instrument 14 may be configured to be held such that the user's hand is supporting the instrument 14 against the force of gravity. The instrument 14 may weigh 8 lbs. or less, 6 lbs. or less, 5 lbs. or less, or even 3 lbs. or less. The instrument 14 may have a weight corresponding to ANSI/AAMI HTE75:2009. In implementations where the weight of the instrument configured to be supported by the user without the aid of a guide arm or assistive device, the hand-held portion has no rigid reference to earth and moves relative to the earth while under control of the actuator assembly. This can be contrasted with robotic arms that feature bases that are coupled to tables, carts, imagers, or other components that remain static during a procedure. Because the hand-held portion of the instrument may move relative to earth, the pose of the hand-held portion is dynamic and may need to be accounted for during control of the hand-held robotic instrument to achieve optimal performance, including to achieve optimal range of motion, optimal balance and center of gravity relative to the user's hands, and optimal feel to a user to avoid providing sensations that may distract the user from positioning the hand-held portion in an ideal manner to complete the procedure. This is due to the fact that the control system of the instrument cannot assume that the housing (also known as the hand-held portion) is in a fixed location when calculating the navigation transforms between the various moving/conformable components of the system, including but not limited the tool, the tool support, the plurality of actuators, and/or the hand-held portion. Another complexity introduced for hand-held medical robotic instruments that are configured to have their weight supported by a user without use of a guide arm or assistive device is that reaction forces transmitted through the kinematic chain of the instrument are ultimately transmitted solely to the user's hand(s), as opposed to be being transmitted, at least in part, to the guide arm/assistive device. Because the user must bear the reaction forces in a hand-held robotic system, the control system for a hand-held robotic instrument needs to carefully control the plurality of actuators so as to ensure that these reactive forces do not compromise the useability of the system. If the control system results in significant reactive forces being applied to the user's hands at undesirable times and/or in undesirable directions, these reactive forces can influence the user's behavior and cause them to move their hand(s), and hence the robotic instrument, to undesirable positions, orientations, and/or poses. For example, if there is a discrepancy between the virtual world and the real world with respect to the bone, the tool, the tool support, and/or the hand-held portion, the discrepancy may lead to the control system controlling the plurality of actuators in a way that applies reactive forces to the user's hands.

The instrument 14 also comprises a tool support 18 for receiving a tool 20. In some examples, such as shown in FIG. 2, the tool 20 may be a drill bit. In other examples, the tool 20 may be a driver for screws, pins, wires, or other surgical devices. In still other examples, the tool may be a tap. The method for operating the instrument 14 may include a user supporting the weight of the instrument 14 without any assistance from a passive arm or robotic arm. Alternately, the weight of the instrument 14 may be supported through use of a counter-balanced passive arm, assistive device, or active robotic arm, such that the user does not have to support the entire weight of the instrument. In such cases, the user may still grasp the hand-held portion 16 in order to interact with and/or guide the instrument 14. The passive arm and the contents of U.S. Pat. No. 9,060,794 to Kang et al. are incorporated herein by reference. Furthermore, the robotic system 10, in some examples, may be free from a robot arm having more than one joint in series. The tool 20 couples to the tool support 18 to interact with the anatomy in certain operations of the robotic system 10 described further below. The tool 20 may also be referred to as an end effector. The tool 20 may be removable from the tool support 18 such that new/different tools 20 can be attached when needed. The tool 20 may also be permanently fixed to the tool support 18. The tool 20 may comprise an energy applicator designed to contact the tissue of the patient 12. In some examples, the tool 20 may be a drill bit, as shown in FIGS. 1 and 2, or other type of cutting, drilling, and/or driving accessory. However, other tools may be contemplated, such as the contents of U.S. Pat. No. 9,707, 043 to Bozung, which is hereby incorporated herein by reference. In some examples, the tool 20 may be, an ultrasonic vibrating tip, an awl, a bur, a stapler, a rotary cutting tool such as twist drill or tap, a screw driver bit, or the like. In instances where the tool is an ultrasonic vibrating tip, the tool drive motor would be implemented as an ultrasonic transducer, such as the ultrasonic transducer described in U.S. Pat. No. 10,864,011, which is hereby incorporated by reference.

Furthermore, the system and methods described in PCT/ US2020/042128, entitled "Robotic Handheld Surgical Instrument Systems and Methods", filed on Jul. 15, 2020, are also hereby incorporated by reference.

The instrument 14 includes a plurality of actuators 21, 22, 23, 24. The plurality of actuators may be configured in actuator assemblies to move the tool support 18 in a plurality of degrees of freedom to move the tool in accordance with a virtual object, such as to maintain a target trajectory TTRAJ (also known as a target axis). Each actuator 21, 22, 23, 24 includes a motor having a coil and a rotor, with the rotor connected with an output, such as a gear set. The control system 60 is connected with the actuators 21, 22, 23, 24 to change a pose of the tool support 18 and tool axis TA relative to the hand-held portion 16, automatically controlling each of the actuators 21, 22, 23, 24 to actively move the tool axis TA towards a target tool trajectory TTRAJ.

The virtual object 4 may be one-dimensional, two-dimensional, three-dimensional, and may comprise a point, line, axis, trajectory, plane, or other shapes, including complex geometric shapes. The virtual boundary could also be a plane or line defined perpendicular to a planned trajectory. In some embodiments, the virtual boundary is a surface defined by a triangle mesh. The virtual boundaries may also be referred to as virtual objects. The virtual object may be defined with respect to an anatomical model, such as a 3-D bone model, in an implant coordinate system. The anatomical model is associated with the real patient anatomy by virtue of the anatomical model being mapped to the patient's anatomy via registration or other process. The virtual object may be objects created pre-operatively or intraoperatively. In instances where the virtual object is a target trajectory, the target trajectory may be derived from a planned implant, where the target trajectory is aligned with the longitudinal axis of a pedicle screw based on its planned placement in the anatomy. Of course, the target trajectory may be derived from other types of surgical plan.

Figure 12:
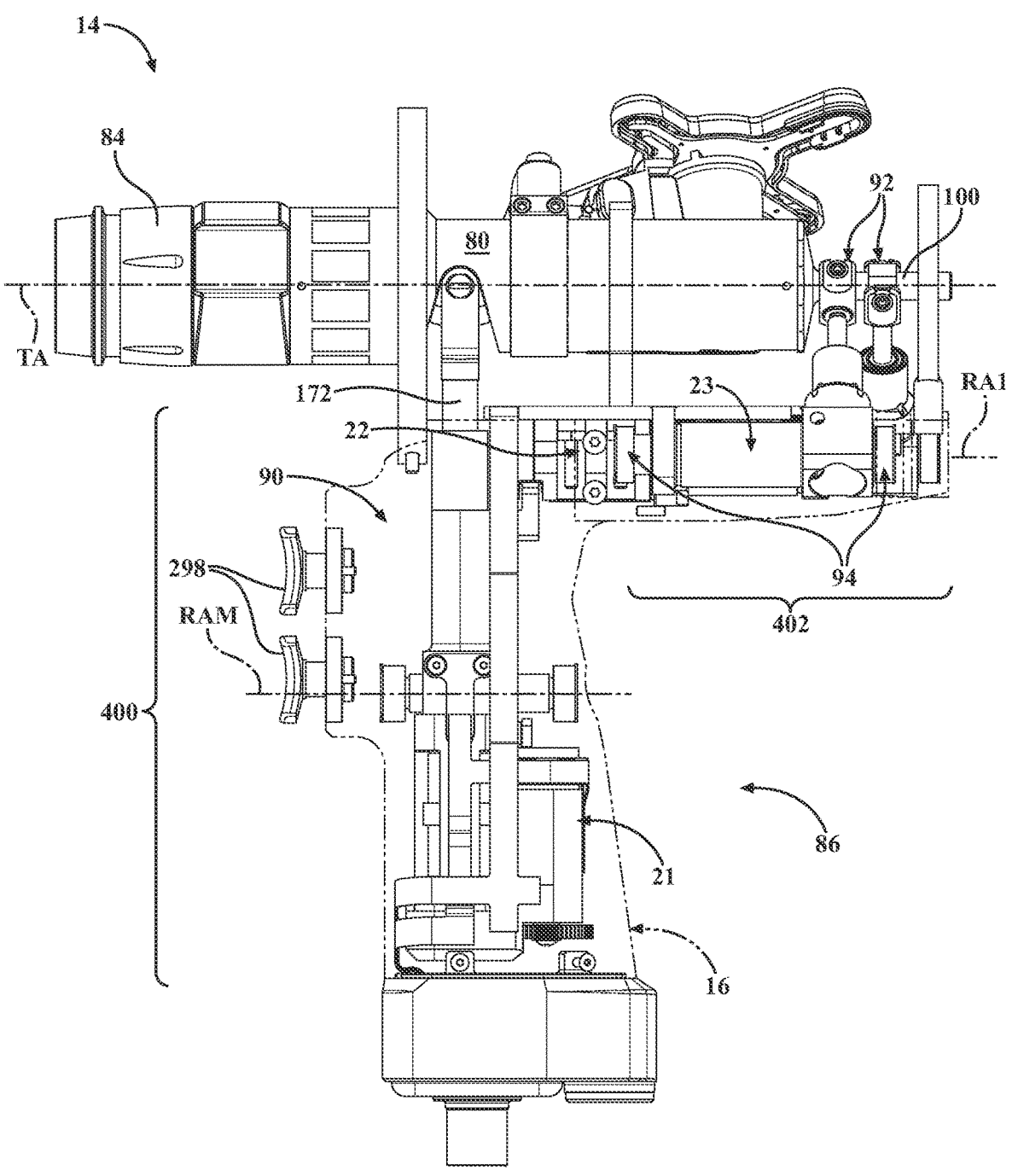
FIG. 12 is a side view of the first configuration of robotic instrument, with the housing hidden.

The actuator assemblies 400, 402, as shown in FIG. 12, comprising one or more actuators 21, 22, 23, 24 each move the tool support 18 in at least two degrees of freedom relative to the hand-held portion 16 to provide robotic motion that assists in placing the tool 20 at a desired position and/or orientation, such as a target trajectory TTRAJ (e.g., at a desired pose relative to the spine SPN during a surgical procedure), while the user holds the housing of hand-held portion 16. The control system 60 is configured to move the actuator assemblies 400, 402 to change the pose of the tool support 18 to place the tool axis TA on the target trajectory while a user manipulates the hand-held portion 16, adjusting the actuators 21, 22, 23, 24 to maintain the tool axis TA on the target trajectory TTRAJ, compensating for movements away from the target trajectory TTRAJ. The actuator assemblies 400, 402 may comprise actuators 21, 22, 23, 24 that are arranged in parallel, in series, or a combination thereof. In some examples, the actuators 21, 22, 23, 24 move the tool support 18 in at least three or more degrees of freedom relative to the hand-held portion 16. In some examples, actuators 21, 22, 23, 24 may move the tool support 18 in four or more degrees of freedom relative to the hand-held portion 16. In some examples, the actuator assemblies 400, 402 may be configured to move the tool support 18 relative to the hand-held portion 16 in at least two degrees of freedom, such as pitch and elevation translation. In addition, in certain configurations, the instrument could be constructed to provide for five degrees of freedom. In addition to the described actuators, an additional actuator could be provided to control depth of the tool. In other words, this additional actuator could provide for translation relative to the tool support along the longitudinal axis of the tool.

Figures 3A, 3B:
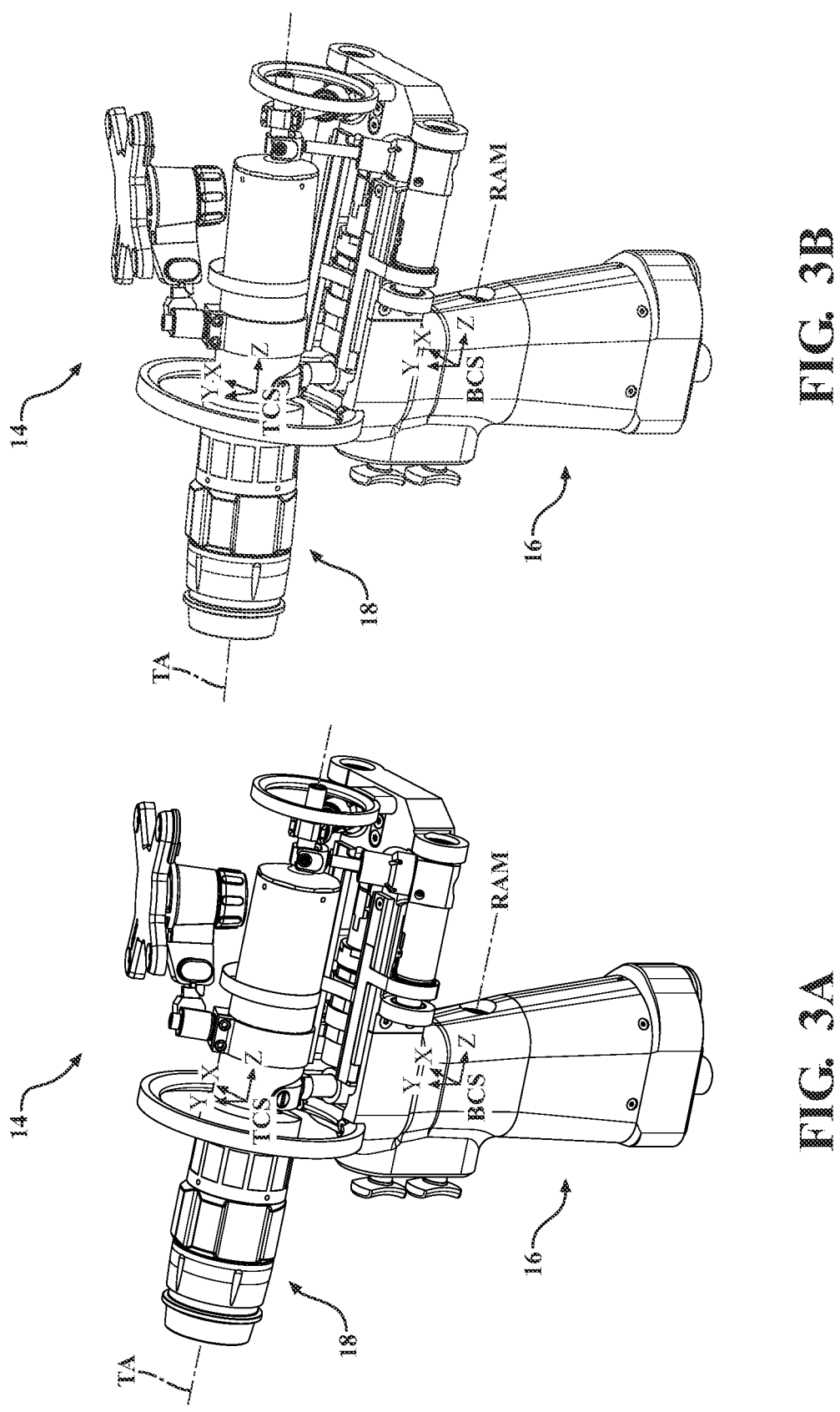
FIGS. 3A and 3B illustrate perspective views of the first configuration of the robotic instrument in two different poses.
Figures 8A, 8B, 8C:
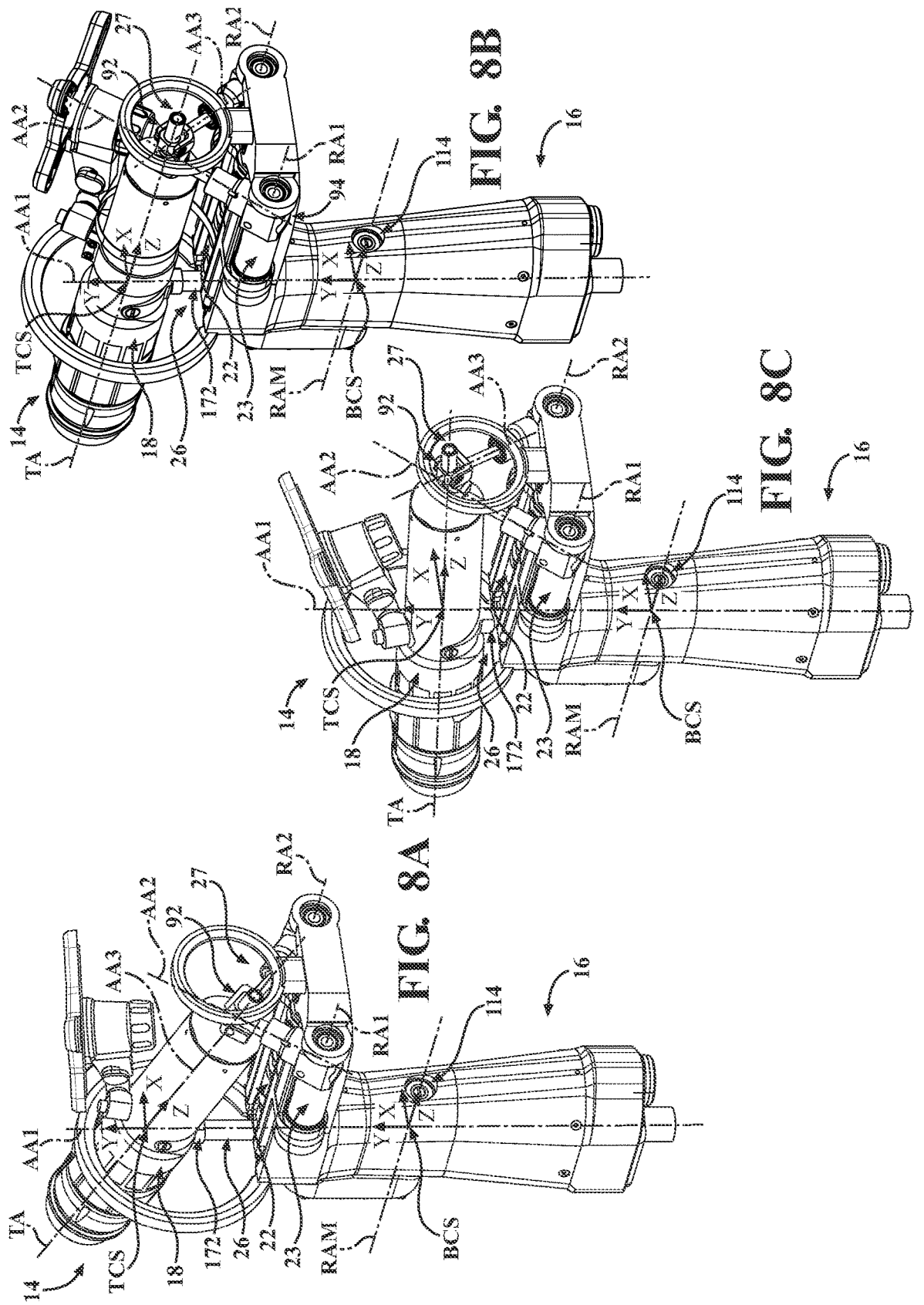
FIGS. 8A-8C are illustrations of various composite movements of the first configuration of the robotic instrument.

In some examples, such as shown herein, the actuators 21, 22, 23, 24 move the tool support 18 and its associated tool support coordinate system TCS in only four degrees of freedom relative to the hand-held portion 16 and its associated base coordinate system BCS. For example, such as shown in FIGS. 3A and 3B, the tool support 18 and its tool support coordinate system TCS may: rotate about its X-axis to provide pitch motion; rotate about its y-axis to provide yaw motion; translate along an axis Y coincident with a y-axis of the base coordinate system BCS to provide elevation translation motion; and translate along axis X coincident with an x-axis of the base coordinate system BCS to provide a side-to-side translation motion of the tool support 18. The allowed motions in pitch, elevation translation, yaw, and side-to-side movement are shown in the schematic illustrations of FIGS. 4A-4C, 5A-5C, 6A-6C and 7A-7C respectively. FIGS. 8A-8C illustrate compound movement of the tool support 18 relative to the hand-held portion 16, combining elements of the allowable movements shown in FIGS. 4A-7C. FIGS. 8A-8C provides several examples poses of the tool support 18 and a pose of the hand-held portion 16 within the range of motion of the instrument 14. Although not shown in FIGS. 4A-8C, the coordinate system associated with the tool center point TCP is not shown, however the TCP is related to the tool support coordinate system TCS.

In some examples, at least one actuator assembly 400, 402, may be arranged as a parallel manipulator configuration. For example, the second actuator assembly 402 may include actuators 23, 24 which are connected to different locations of the hand-held portion 16 and different locations on the tool support 18, arranged as a parallel manipulator, working in concert to adjust the tool support 18. In some examples, such as shown throughout the present application, there is no geometric parallelism required to be a parallel manipulator. The first actuator assembly 400 may include actuators 21, 22, operatively coupled with a distal linkage 26 capable of compound movement, operating in series with one another. In other examples, second actuator assembly 402 may include actuators 23, 24, operatively coupled with a proximal linkage 27 capable of compound movement. Other actuator assembly arrangements are contemplated, such as described in U.S. Pat. No. 9,707,043, entitled "Surgical instrument including housing, a cutting accessory that extends from the housing and actuators that establish the position of the cutting accessory relative to the housing" which is incorporated by reference.

Figure 9:
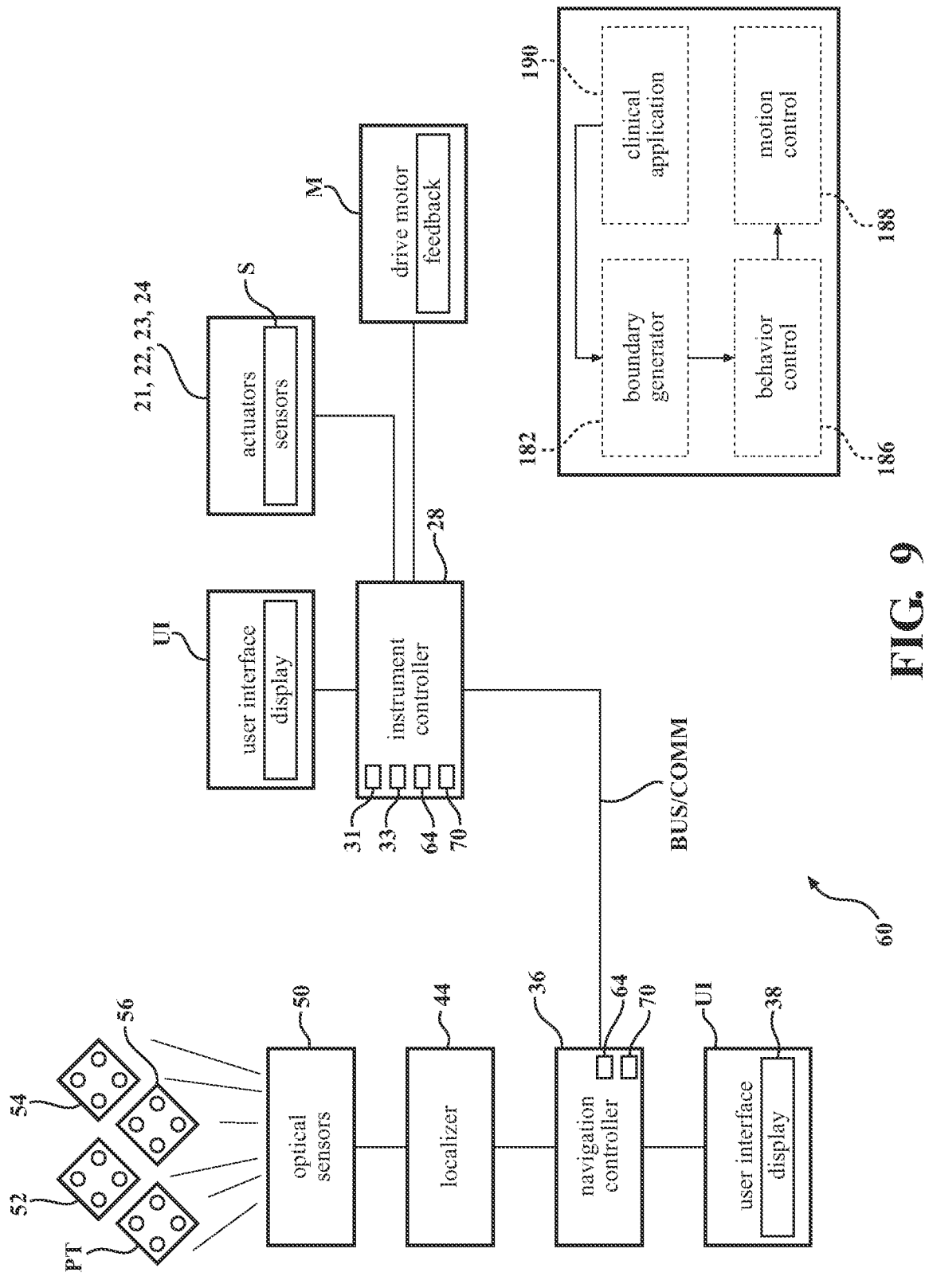
FIG. 9 is a block diagram of a control system of the robotic system, and also illustrates various software modules.
Figures 10, 11:
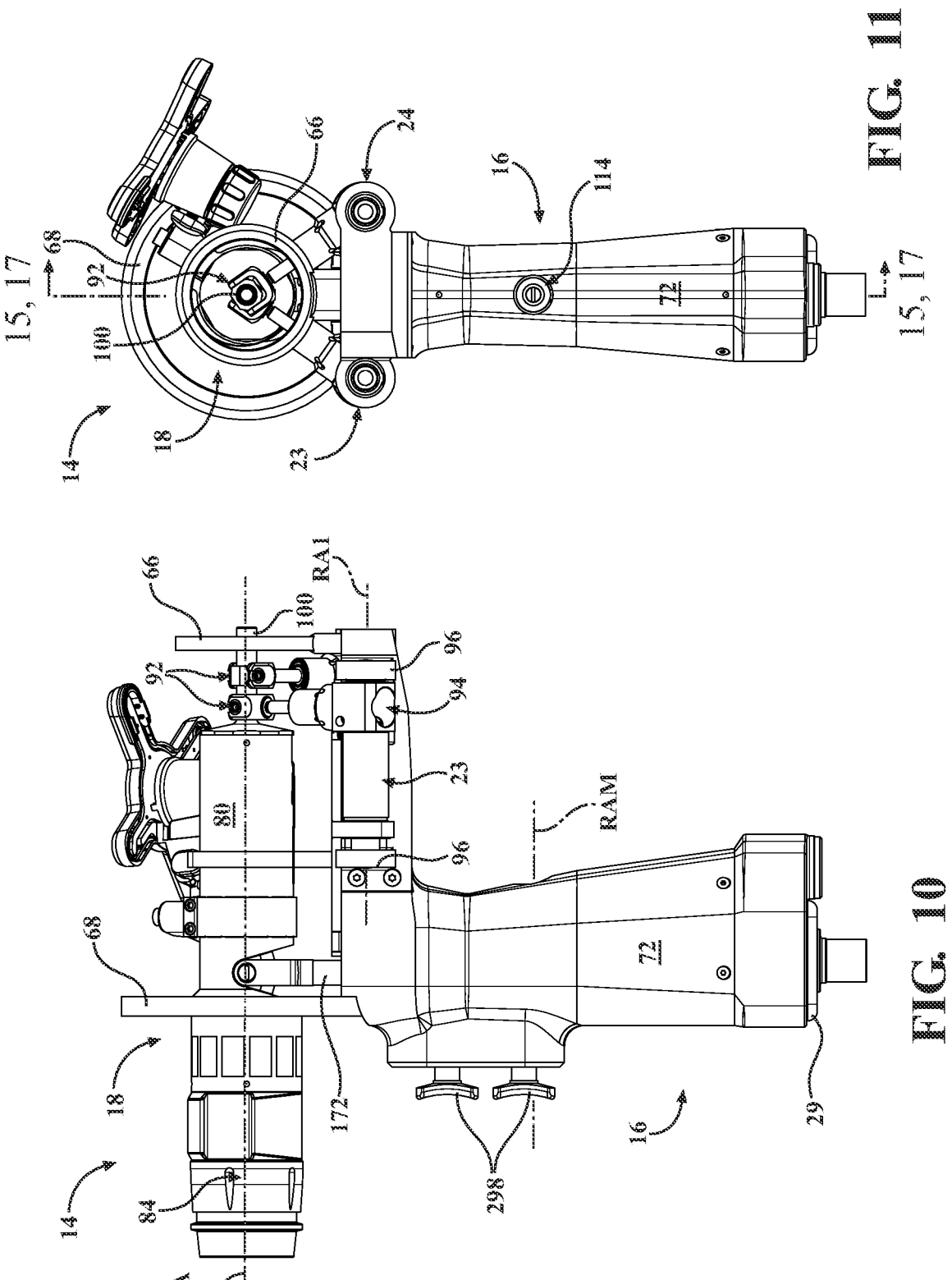
FIG. 10 is a side view of the first configuration of the robotic instrument.
FIG. 11 is a rear view of the first configuration of the robotic instrument.

The actuators 21, 22, 23, 24 may be configured to move the tool support from a home position to a plurality of positions and orientations. The tool support 18 has a home position which corresponds to a position in which all of the actuators 21, 22, 23, 24 have a maximum range of movement without colliding with the hand-held portion 16 or binding. In some examples, a home position is a midpoint between a minimum position and a maximum position of the plurality of actuators 21, 22, 23, 24, resulting in the tool support 18 having an optimal range of motion. For example, FIGS. 4B, 5B, 6B, 7B and 8B all illustrate the tool support 18 at a home position relative to the hand-held portion 16. Referring to FIG. 9, an instrument controller 28, or other type of control unit, is provided to control the instrument 14. The instrument controller 28 may comprise one or more computers, or any other suitable form of controller that directs operation of the instrument 14 and motion of the tool support 18 (and tool 20) relative to the hand-held portion 16. The instrument controller 28 may have a central processing unit (CPU) and/or other processors, memory, and storage (not shown). The instrument controller 28 is loaded with software as described below. The processors could include one or more processors to control operation of the instrument 14. The processors can be any type of microprocessor, multi-processor, and/or multi-core processing system. The instrument controller 28 may additionally, or alternatively, comprise one or more microcontrollers, field programmable gate arrays, systems on a chip, discrete circuitry, and/or other suitable hardware, software, or firmware that is capable of carrying out the functions described herein. The term processor is not intended to limit any embodiment to a single processor. The instrument 14 may also comprise a user interface UI with one or more displays and/or input devices (e.g., triggers, push buttons, foot switches, keyboard, mouse, microphone (voice-activation), gesture control devices, touchscreens, etc.).

The control system 60 further includes one or more software programs and software modules. The software modules may be part of the program or programs that operate on the navigation controller 36, instrument controller 28, or both, to process data to assist with control of the robotic system 10. The software programs and/or modules include computer readable instructions stored in non-transitory memory 64 on the navigation controller 36, instrument controller 28, or both, to be executed by one or more processors 70 of the controllers 28, 36. The memory 64 may be any suitable configuration of memory, such as random access memory, non-volatile memory, etc., and may be implemented locally or from a remote database. Additionally, software modules for prompting and/or communicating with the user may form part of the program or programs and may include instructions stored in memory 64 on the navigation controller 36, instrument controller 28, or both. The user may interact with any of the input devices of the navigation user interface UI or other user interface UI to communicate with the software modules. The user interface software may run on a separate device from the navigation controller 36, and/or instrument controller 28.

The instrument controller 28 controls operation of the tool 20, such as by controlling power to the tool 20 (e.g., to the drive motor M of the tool 20 that controls tool motion) and controlling movement of the tool support 18 relative to the hand-held portion 16 (e.g., by controlling the actuators 21, 22, 23, 24). The instrument controller 28 controls a state (e.g., position and/or orientation) of the tool support 18 and the tool 20 with respect to the hand-held portion 16. The instrument controller 28 can control velocity (linear or angular), acceleration, or other derivatives of motion of the tool 20 relative to the hand-held portion 16 and/or relative to the anatomy that is caused by the actuators 21, 22, 23, 24.

As shown in FIG. 2, the instrument controller 28 may comprise a control housing 29 mounted to the tool support 18, and/or the hand-held portion 16 or a combination thereof with one or more control boards 31 (e.g., one or more printed circuit boards and associated electronic components) located inside the control housing 29. The control boards 31 may comprise microcontrollers, field programmable gate arrays (FPGA), drivers, memory, sensors, or other electronic components for controlling the actuators 21, 22, 23, 24 and the drive motor M (e.g., via motor controllers). The instrument controller 28 may also comprise an off-board control console 33 in data and power communication with the control boards 31. The sensors S, actuators 21, 22, 23, 24, and/or drive motor M described herein may feed signals to the control boards 31, which transmit data signals out to the console 33 for processing, and the console 33 may feed control commands (e.g. current commands, torque commands, velocity commands, angle commands, position commands, or a combination thereof, as well as various control and configuration parameters) back to the control boards 31 in order to power and control the actuators 21, 22, 23, 24 and/or the drive motor M. It is contemplated that the processing may also be performed on the control board(s) of the control housing or using any other aspect of the control system. In some examples, the processing of the control algorithms may be distributed between the console and the control housing. In one example, the position control and velocity control calculations may be in the console and current control may be in the field programmable gate arrays located in the control house. Of course, it is contemplated that no separate control housing is necessary, and/or the processing can be performed in any number of different locations.

Figure 13:
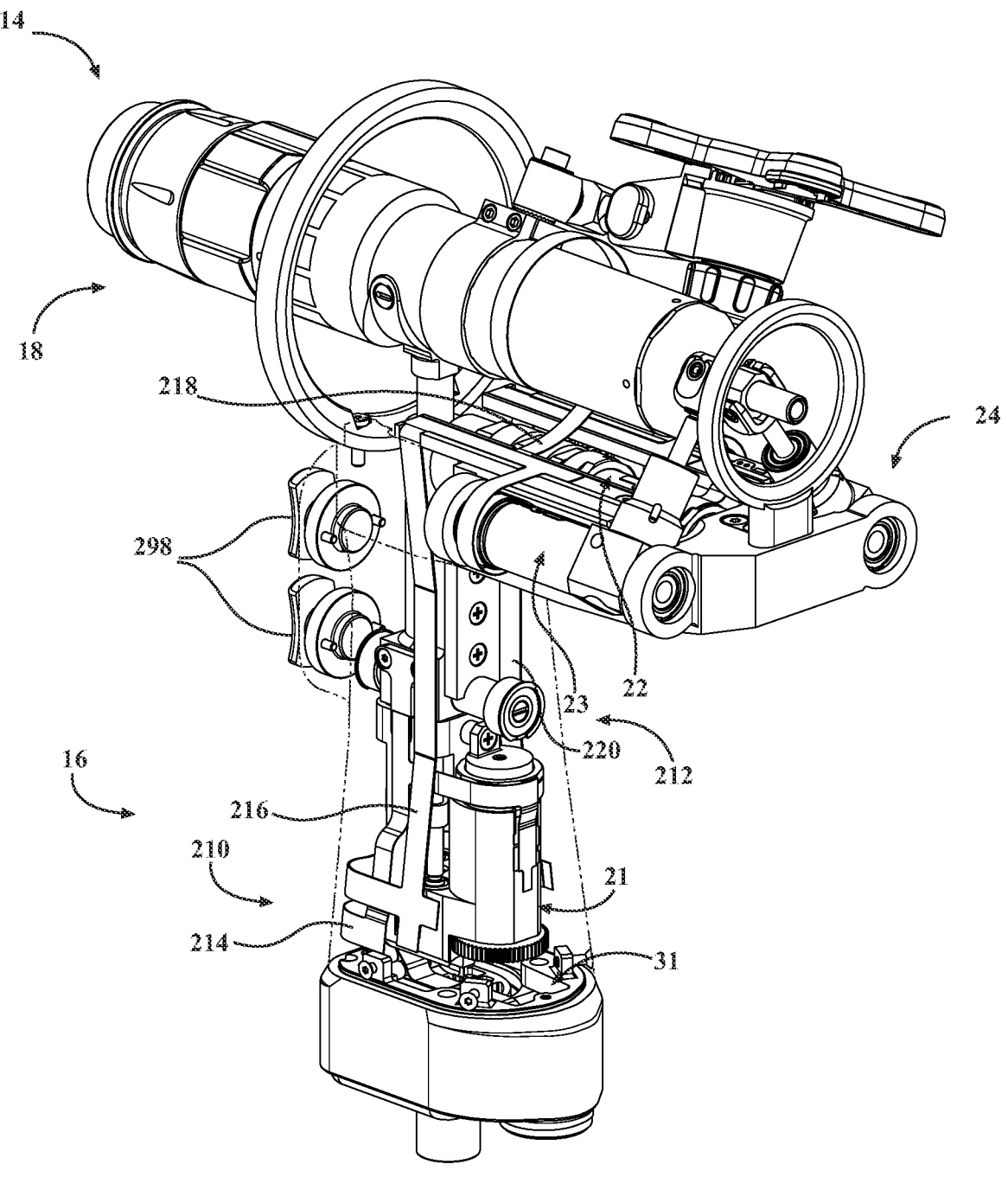
FIG. 13 illustrates a rear perspective view of the flexible circuits on the first configuration of robotic instrument.
Figure 14:
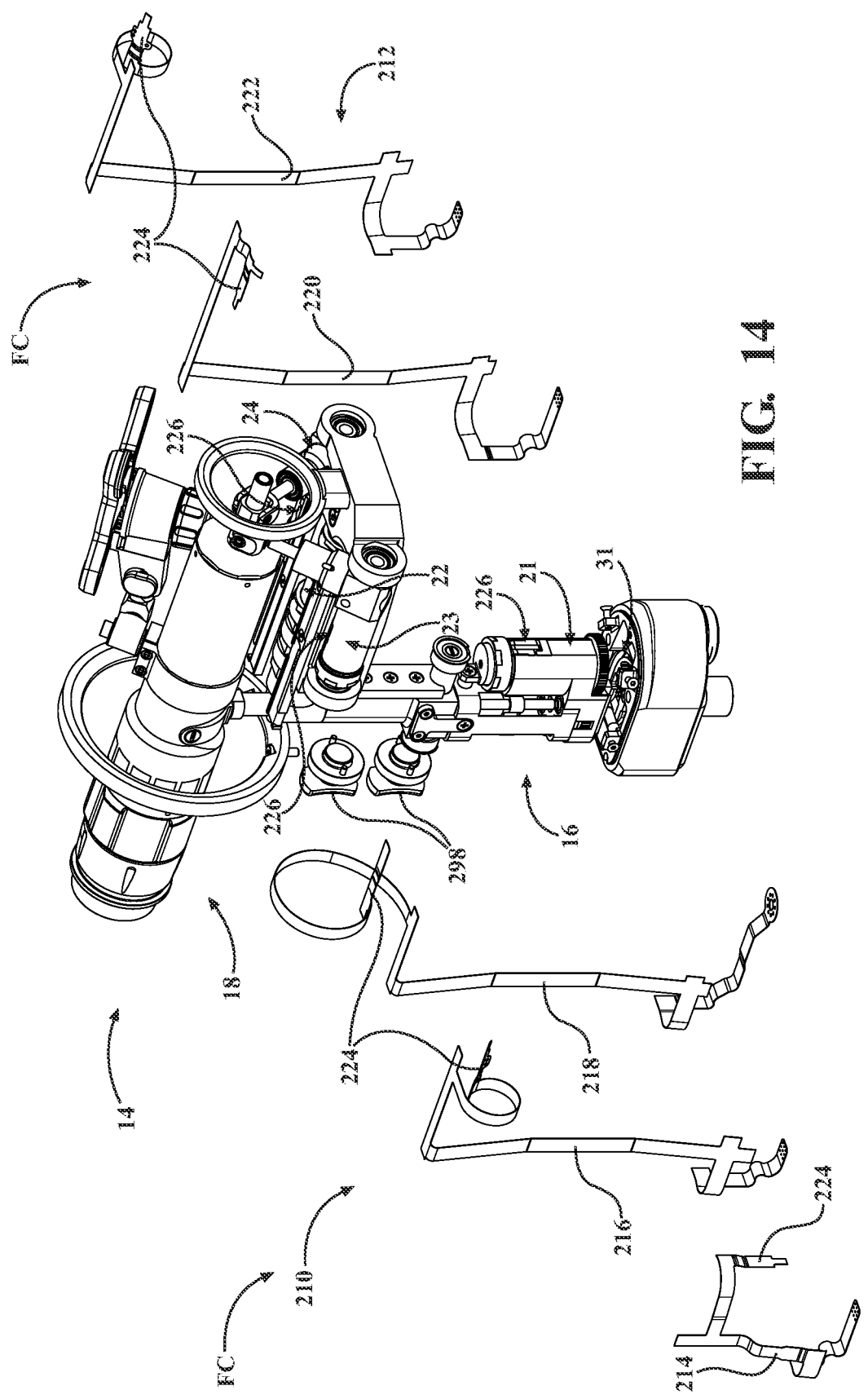
FIG. 14 is a partial exploded view of the first configuration of the robotic instrument with the flexible circuits exploded from the tool support and the hand-held portion.

In some versions, the console 33 may comprise a single console for powering and controlling the actuators 21, 22, 23, 24, and the drive motor M. In some versions, the console 33 may comprise one console for powering and controlling the actuators 21, 22, 23, 24 and a separate console for powering and controlling the drive motor M. One such console for powering and controlling the drive motor M may be like that described in U.S. Pat. No. 7,422,582, filed on Sep. 30, 2004, entitled, "Control Console to which Powered Surgical Handpieces are Connected, the Console Configured to Simultaneously Energize more than one and less than all of the Handpieces," hereby incorporated herein by reference. Flexible circuits FC, also known as flex circuits, may interconnect the actuators 21, 22, 23, 24 and/or other components with the instrument controller 28. For example, flexible circuits FC may be provided between the actuators 21, 22, 23, 24, and the control boards 31 (FIGS. 13 and 14). The control boards 31 may also be referred to as circuit boards 31 and/or control circuit boards 31. Other forms of connections, wired or wireless, may additionally, or alternatively, be present between components.

Referring briefly back to FIG. 1, the robotic system 10 further includes a navigation system 32. One example of the navigation system 32 is described in U.S. Pat. No. 9,008, 757, filed on Sep. 24, 2013, entitled, "Navigation System Including Optical and Non-Optical Sensors," hereby incorporated herein by reference. The navigation system 32 tracks movement of various objects. Such objects include, for example, the instrument 14, the tool 20 and the anatomy, e.g., the spine SPN or other bone structures, such as one or more vertebra, the pelvis, femur, scapula, or humerus or combinations thereof. Although it is contemplated that the instrument and system can be used with any suitable workpiece, and it should be appreciated that any instance of bone, tissue or workpiece can be replaced with one another throughout this disclosure. Thus, the instrument can be used to drill target trajectories on workpieces, such as inanimate wood, metal, or composite structures. The navigation system 32 tracks these objects to gather state information of each object with respect to a (navigation) localizer coordinate system LCLZ. As used herein, the state of an object includes, but is not limited to, data that defines the position and/or orientation of the tracked object (e.g., coordinate systems thereof) or equivalents/derivatives of the position and/or orientation. For example, the state may be a pose of the object, and/or may include linear velocity data, angular velocity data, and the like.

The navigation system 32 may include a cart assembly 34 that houses a navigation controller 36, and/or other types of control units. A navigation user interface UI is in operative communication with the navigation controller 36. The navigation user interface UI includes one or more displays 38. The navigation system 32 is capable of displaying graphical representations of the relative states of the tracked objects to the user using the one or more displays 38. The navigation user interface UI further comprises one or more input devices to input information into the navigation controller 36 or otherwise to select/control certain aspects of the navigation controller 36. Such input devices include interactive touchscreen displays. However, the input devices may include any one or more of push buttons, pointer, foot switches, a keyboard, a mouse, a microphone (voice-activation), gesture control devices, and the like. In some examples, the user may use buttons located on the pointer to navigate through icons and menus of the user interfaces UI to make selections, configuring the robotic surgical system 10 and/or advancing through the workflow.

The navigation system 32 also includes a localizer 44 coupled to the navigation controller 36. In one example, the localizer 44 is an optical localizer and includes a camera unit 46. The camera unit 46 has an outer casing 48 that houses one or more optical sensors 50. The localizer 44 may comprise its own localizer controller 49 and may further comprise a video camera VC. In certain configurations, the localizer may be coupled to the hand-held robotic instrument.

The navigation system 32 includes one or more trackers. In some examples, the trackers may include a pointer tracker PT, a tool tracker 52, a first patient tracker 54, and a second patient tracker 56. In the illustrated example of FIG. 1, the tool tracker 52 is firmly attached to the instrument 14, the first patient tracker 54 is firmly affixed to a first vertebra of the patient 12, and the second patient tracker 56 is firmly affixed to a second vertebra of the patient 12. In this example, the patient trackers 54, 56 are firmly affixed to sections of bone. The trackers 52, 54, 56 and pointer tracker are registered to their respective objects (e.g. bone, tool) and the navigation system 32 manually, automatically, or a combination thereof. In some examples, the pointer tracker PT is firmly affixed to a pointer 57 and used for registering the anatomy to one or more coordinate systems, including the localizer coordinate system LCLZ and/or used for other calibration and/or registration functions. In one example, the pointer 57 may be used to register the patient trackers 54, 56 to the bone which the tracker 54, 56 is attached, respectively, and the tool tracker 52 to the tool support 18, the tool 20, the hand-held portion 16, or a combination thereof. In some examples, the pointer tracker PT may be used to register the TCP of the instrument 14 to the tracker 52 relative to a tracker coordinate system. This way, if the localizer 44 is moved from position to position, the registration of the instrument 14 is located relative to the tool tracker 52. However, other means of registration of the trackers 52, 54, 56 are contemplated and may be implemented together or separately with the pointer tracker PT. Other tracker locations are also contemplated.

Throughout this description, various transforms are described, such as 'bone to tracker' or 'instrument TCP to tracker', i.e., relative to the 'tracker coordinate system' rather than to the LCTZ coordinate system. The localizer coordinate system may be used as an intermediate coordinate system during registration and bone prep, since all tracked objects are measured with respect to LCTZ. During registration, ultimately the various localizer-referred poses are combined mathematically and registration results are stored 'with respect to a tracker', such that if the camera (i.e., LCTZ) moves, the registration is still valid.

The tool tracker 52 may be affixed to any suitable component of the instrument 14, and in some versions may be attached to the hand-held portion 16, the tool support 18, directly to the tool 20, or a combination thereof. The trackers 52, 54, 56, PT may be fixed to their respective components in any suitable manner, such as by fasteners, clamps, or the like. For example, the trackers 52, 54, 56, PT may be rigidly fixed, flexibly connected (optical fiber), or not physically connected at all (ultrasound), as long as there is a suitable (supplemental) way to determine the relationship (measurement) of that respective tracker to the associated object. Any one or more of the trackers 52, 54, 56, PT may include active markers 58. The active markers 58 may include light emitting diodes (LEDs). Alternatively, the trackers 52, 54, 56, PT may have passive markers, such as reflectors, which reflect light emitted from the camera unit 46. Printed markers, or other suitable markers not specifically described herein, may also be utilized.

Various coordinate systems may be employed for purposes of tracking the objects. For instance, the coordinate systems may comprise the localizer coordinate system LCLZ, the tool support coordinate system TCS, the base coordinate system BCS, coordinate systems associated with each of the trackers 52, 54, 56, PT, one or more coordinate systems associated with the anatomy, one or more coordinate systems associated with pre-operative and/or intraoperative images (e.g., CT images, MRI images, etc.) and/or models (e.g., 2D or 3D models) of the anatomy—such as the implant coordinate system, and a TCP (tool center point) coordinate system. In some examples, the robotic system 10 does not rely on pre-operative and/or intraoperative imaging to create the 2D or 3D models of the target bone. Rather, the robotic system may be used in an imageless system using the pointer tracker PT to register the target anatomy, capturing various anatomical landmarks, which is then processed by the control system 60 to morph a nominal bone model to match the captured data. In other examples, pre-operative and intraoperative imaging is used to image the target area of the patient and then transform the 2D and/or 3D images into a 3D model of the target bone. It is also contemplated that the robotic surgical system 10 may use a combination of imaged and imageless procedures in creating a 3D model of the target surgical area. One exemplary system is described in U.S. Pat. No. 8,617,174, which is hereby incorporated by reference. Coordinates in the various coordinate systems may be transformed to other coordinate systems using transformations upon establishing relationships between the coordinate systems, e.g., via registration, calibration, geometric relationships, measuring, etc.

As shown in FIG. 2, in some examples, the TCP is a predetermined reference point or origin of the TCP coordinate system defined at the distal end of the tool 20. The geometry of the tool 20 may be defined relative to the TCP coordinate system and/or relative to the tool support coordinate system TCS. The tool 20 may comprise one or more geometric features, e.g., perimeter, circumference, radius, diameter, width, length, height, volume, area, surface/plane, range of motion envelope (along any one or more axes), etc. defined relative to the TCP coordinate system and/or relative to the tool support coordinate system TCS and stored in the non-volatile memory of the control boards 31 in the control housing 29 of the instrument 14, the navigation system 32, the instrument controller 28, or a combination thereof. For example, the tool 20 may define a longitudinal axis extending the length of the tool. The tool center point (TCP), in another example, is a predetermined reference point and corresponding coordinate system defined at the tool 20. The TCP has a known, or able to be calculated (i.e., not necessarily static), pose relative to other coordinate systems. The TCP coordinate system includes an origin point and a set of axes (e.g., x axis, y axis, z axis) which define the pose of the TCP. By tracking the TCP (or knowing the pose of the TCP), the control system 60 may calculate the position and orientation of the instrument 14 based on the pose of the TCP and the known positional relationship between the TCP and the features of the instrument 14. In some examples, the tool 20 has a tool trajectory (e.g., for drills and/or drivers) that will be described for convenience and ease of illustration but is not intended to limit the tool 20 to any particular form. For example, the tool support 18 may include a tool coupling assembly 84 defining the tool axis TA when a surgical tool is coupled thereto. Points, other primitives, meshes, other 3D models, etc., can be used to virtually represent the tool 20. The origin point of the TCP coordinate system may be located at the spherical center of the bur of the tool 20 or at the distal end of the tool 20 such that the TCP coordinate system is tracked relative to the origin point on the distal tip of the tool 20. Alternatively, the TCP may be tracked using a plurality of tracked points. The TCP may be defined in various ways depending on the configuration of the tool 20. The instrument may employ the joint/motor encoders, or any other non-encoder position sensing method, so the control system 60 may determine a pose and/or position of the TCP relative to the hand-held portion 16 and BCS. The tool support 18 may use joint measurements and/or motor measurements (e.g. encoder measurements of the rotor position) to determine TCP pose and/or could employ techniques to measure TCP pose directly. The control of the tool 20 is not limited to a center point. For example, any suitable primitives, meshes, etc., can be used to represent the tool 20. It should be appreciated that the TCP may alternatively be defined as a point, as opposed to a coordinate system. The TCP coordinate system allows calculate any required reference points or geometry aspects of the tool once you have determined the pose of the drill bit or other tool.

The TCP coordinate system, the tool support coordinate system TCS, and the coordinate system of the tool tracker 52 may be defined in various ways depending on the configuration of the tool 20. For example, the pointer 57 may be used with calibration divots CD in the tool support 18 and/or in the tool 20 for: registering (calibrating) a static pose of the tool support coordinate system TCS relative to the coordinate system of the tool tracker 52; determining a pose of the TCP coordinate system relative to the coordinate system of the tool tracker 52; and/or determining a pose of the TCP coordinate system relative to the tool support coordinate system TCS. Other techniques could be used to measure the pose of the TCP coordinate system directly, such as by attaching and fixing one or more additional trackers/markers directly to the tool 20. In some versions, trackers/markers may also be attached and fixed to the hand-held portion 16, the tool support 18, or both. In instances where the hand-held portion includes a tracker, the pose of the hand-held portion relative to the localizer coordinate system LCTZ may be measured directly. In still other alternatives, the TCP may be defined relative to the tool tracker, using the intermediate tool support coordinate system TCS.

Since the tool support 18 is movable in multiple degrees of freedom relative to the hand-held portion 16 via the actuators 21, 22, 23, 24, the instrument 14 may employ encoders, hall-effect sensors (with analog or digital output), and/or any other position sensing method, to measure a pose of the TCP coordinate system and/or tool support coordinate system TCS relative to the base coordinate system BCS. In one example, the instrument 14 may use measurements from sensors that measure actuation of the actuators 21, 22, 23, 24 to determine a pose of the TCP coordinate system and/or tool support coordinate system TCS relative to the base coordinate system BCS, as described further below. Various poses of the BCS relative to the TCS are shown in FIGS. 3A-3B, 4A, and 8A. Of course, innumerable other poses of the BCS relative to the TCS are also contemplated, but not explicitly shown.

The localizer 44 monitors the trackers 52, 54, 56, PT (e.g., coordinate systems thereof) to determine a state of each of the trackers 52, 54, 56, PT, which correspond respectively to the state of the object respectively attached thereto. The localizer 44 may perform known techniques to determine the states of the trackers 52, 54, 56, PT, and associated objects (such as the tool, the patient, the tool support, and the hand-held portion). The localizer 44 provides the states of the trackers 52, 54, 56, PT to the navigation controller 36. In some examples, the navigation controller 36 determines and communicates the states of the trackers 52, 54, 56, PT to the instrument controller 28.

The navigation controller 36 may comprise one or more computers, or any other suitable form of controller. Navigation controller 36 has a central processing unit (CPU) and/or other processors, memory, and storage (not shown). The processors can be any type of processor, microprocessor, or multi-processor system. The navigation controller 36 is loaded with software. The software, for example, converts the signals received from the localizer 44 into data representative of the position and/or orientation of the objects being tracked. The navigation controller 36 may additionally, or alternatively, comprise one or more microcontrollers, field programmable gate arrays, systems on a chip, discrete circuitry, and/or other suitable hardware, software, or firmware that is capable of carrying out the functions described herein. The term processor is not intended to limit any embodiment to a single processor.

Although one example of the navigation system 32 is shown to determine object states, the navigation system 32 may have any other suitable configuration for tracking the instrument 14, tool 20, and/or the patient 12. In another example, the navigation system 32 and/or localizer 44 are ultrasound-based. For example, the navigation system 32 may comprise an ultrasound imaging device coupled to the navigation controller 36. The ultrasound imaging device images any of the aforementioned objects, e.g., the instrument 14, the tool 20, and/or the patient 12, and generates state signals to the navigation controller 36 based on the ultrasound images. The ultrasound images may be 2D, 3D, or a combination of both. The navigation controller 36 may process the images in near real-time to determine states of the objects. The ultrasound imaging device may have any suitable configuration and may be different than the camera unit 46 as shown in FIG. 1.

In another example, the navigation system 32 and/or localizer 44 are radio frequency (RF)-based. For example, the navigation system 32 may comprise an RF transceiver coupled to the navigation controller 36. The instrument 14, the tool 20, and/or the patient 12 may comprise RF emitters or transponders attached thereto. The RF emitters or transponders may be passive or actively energized. In yet another example, the navigation system 32 and/or localizer 44 are electromagnetically based. For example, the navigation system 32 may comprise an EM transceiver coupled to the navigation controller 36. The instrument 14, the tool 20, and/or the patient 12 may comprise EM components attached thereto, such as any suitable magnetic tracker, electro-magnetic tracker, inductive tracker, or the like The navigation system 32 may have any other suitable components or structure not specifically recited herein. Furthermore, any of the techniques, methods, and/or components described above with respect to the navigation system 32 shown may be implemented or provided for any of the other examples of the navigation system 32 described herein. For example, the navigation system 32 may utilize solely inertial tracking or any combination of tracking techniques, and may additionally or alternatively comprise, fiber optic-based tracking, machine-vision tracking, and the like.

Referring to FIG. 9, the robotic system 10 includes a control system 60 that comprises, among other components, the instrument controller 28 and the navigation controller 36. The control system 60 further includes one or more software programs and software modules. The software modules may be part of the program or programs that operate on the instrument controller 28, navigation controller 36, or a combination thereof, to process data to assist with control of the robotic system 10. The software programs and/or modules include computer readable instructions stored in memory 64 on the instrument controller 28, navigation controller 36, or a combination thereof, to be executed by one or more processors 70 of the controllers 28, 36, 60. The memory 64 may be any suitable configuration of memory, such as non-transitory memory, random access memory, non-volatile memory, etc., and may be implemented locally or from a remote database. Additionally, software modules for prompting and/or communicating with the user may form part of the program or programs and may include instructions stored in memory 64 on the instrument controller 28, navigation controller 36, or a combination thereof. The user may interact with any of the input devices of the navigation user interface UI or other user interface UI to communicate with the software modules. The user interface software may run on a separate device from the instrument controller 28 and/or navigation controller 36. The instrument 14 may communicate with the instrument controller 28 via a power/data connection. The power/data connection may provide a path for the input and output used to control the instrument 14 based on the position and orientation data generated by the navigation system 32 and transmitted to the instrument controller 28, as shown as the BUS/COMM connection in FIG. 9.

The control system 60 may comprise any suitable configuration of input, output, and processing devices suitable for carrying out the functions and methods described herein. The control system 60 may comprise the instrument controller 28, the navigation controller 36, or a combination thereof, and/or may comprise only one of these controllers, or additional controllers. The controllers may communicate via a wired bus or communication network as shown in one example as the BUS/COMM connection in FIG. 9, via wireless communication, or otherwise. The control system 60 may also be referred to as a controller. The control system 60 may comprise one or more microcontrollers, field programmable gate arrays, systems on a chip, discrete circuitry, sensors, displays, user interfaces, indicators, and/or other suitable hardware, software, or firmware that is capable of carrying out the functions described herein.

Instrument

In one exemplary configuration, the instrument 14 is best shown in FIGS. 10 to 15. The instrument 14 includes the hand-held portion 16 defining the hand-held housing to be held by the user, the tool support 18 movably coupled to the hand-held portion 16 to support the tool 20, the actuator assemblies 400, 402 with the plurality of actuators 21, 22, 23, 24, operatively interconnecting the tool support 18 and the hand-held portion 16 to move the tool support 18 in at least four degrees of freedom relative to the hand-held portion 16.

The hand-held portion 16 comprises a grip 72 for being grasped by the user so that the user is able to manipulate, guide, and/or grasp the instrument 14. The hand-held portion 16 may be configured with ergonomic features such as a grip for a hand of a user to hold, a textured or mixed material coating for preventing a user's hand from slipping when wet and/or covered in blood. The hand-held portion 16 may include a taper to accommodate users with different hand sizes and contoured to mate with the contours of a user's hand and/or fingers. The grip 72 is attached to the hand-held portion 16 by one or more fasteners, adhesive, welding, or the like. In some examples, the grip 72 may be integral with the hand-held portion 16. The hand-held portion 16 defines a housing with an interior volume. The hand-held portion 16 defines the housing which may function to surround a portion of the distal linkage 26 The hand-held portion 16 may house a portion of the actuator assembly 400, the control housing 29 including control boards 31, or both. The housing may support one or more input devices 298, shown as a trigger in this particular example, however, other input devices are contemplated.

The tool support 18 comprises a tool support body 80 to which the tool tracker 52 can be fixed to or removably mounted via one or more tracker mounts fixed to the tool support 18 at one or more mounting locations. In one example, the tool tracker 52 is integrated with the tool support 18. In another example, the tool tracker 52 is removably mounted at the one or more mounting locations. The tool 20 is removably coupled to the tool support 18 in the version shown. In other configurations, a tracker may be coupled directly to the surgical tool, such as described in U.S. Publication No. 2020/0188034, which is hereby incorporated by reference. In particular, the tool support 18 comprises a tool coupler assembly 84 to which the tool 20 is mounted. In the present example, tool coupler may be configured as a chuck to receive a drill bit, an attachment to receive a screwdriver, a wire driver, or similar. In some examples, other tool attachments, such as described in U.S. Pat. No. 9,192,394, incorporated herein by reference, may be employed. The tool support body 80 defines a housing. The drive motor M that drives operation of the tool 20 is disposed in the tool support body 80 (e.g., to drive drill bit/driver in some versions).

Figures 17, 19:
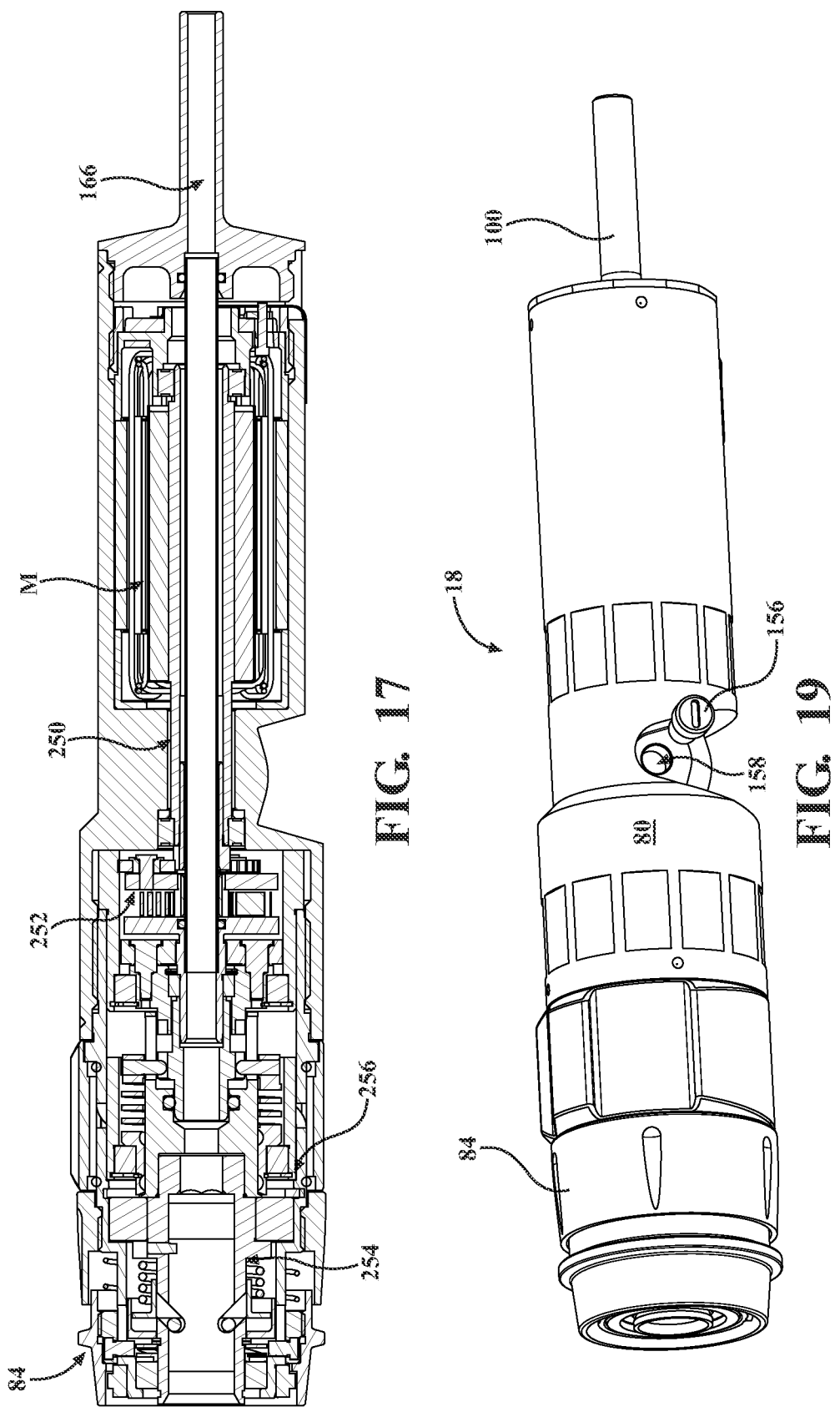
FIG. 17 is a longitudinal cross section view of the tool support of the first configuration of the robotic instrument.
FIG. 19 is a partial exploded view of the tool support of the first configuration of the robotic instrument.

Referring to FIG. 17, the drive motor M is disposed within the tool support 18. The motor shaft 250 may be integral with the drive motor M. A gear train 252 is connected to the exposed distally located front end of the motor shaft 250. Gear train 252 includes gears that reduce the speed and increase the torque of the rotational moment output by motor shaft 250. A clutch 254 selectively connects one aspect of the gear train 252 to spindle 256 so that the spindle 256 and the aspect of the gear train 252 rotate in unison. A tool coupler assembly 84 releasably holds a surgical tool 20 to the spindle 256. In some versions, the positioning post 100 and motor shaft 250 may define a lumen/include cannulation 166, to allow a wire to be inserted therethrough, and used in conjunction with a wire driver attachment. Thus, the drive motor may be cannulated.

The tool support 18 is connected to the hand-held portion 16 by a distal linkage 26 and a proximal linkage 27. The distal linkage 26 and the proximal linkage 27 are assemblies for connecting to and moving the tool support 18 relative to the hand-held portion 16. Each of the linkages 26, 27 are configured to interconnect the hand-held portion 16 and the tool support 18 and constrain movement of the tool support 18 relative to the hand-held portion 16 in at least two degrees of freedom. In the examples shown throughout the present application, each of the distal linkage 26 and the proximal linkage 27 each may be in communication with at least two actuators 21, 22, 23, 24, working in concert with each other to align a tool axis TA with a target trajectory axis TTRAJ or other virtual object. Each linkage 26, 27 is operatively connected with the hand-held portion 16 and the tool support 18, which is described further below.

In some examples, one or more of the actuators 21, 22, 23, 24 in communication with both the distal linkage 26 and the proximal linkage 27 comprise electric actuators, with the distal linkage 26 and proximal linkage 27 extending between the hand-held portion 16 and the tool support 18. When actuated, the actuators 21, 22, 23, 24 changes to vary a position and/or orientation of the tool support 18 relative to the hand-held portion 16 along a corresponding axis or angularly about an axis. The axis may correspond to a portion of the actuator 21, 22, 23, 24, a portion of the linkages 26, 27, a portion of the tool support 18, a portion of the hand-held portion 16, or a combination thereof. 21, 22, 23, 24. For example, as described further below, actuator 21 is connected with gears 130, 133 for rotating the lift assembly 86 which travels along AA1 defined by the anchor post 172. Each actuator 21, 22, 23, 24 may be configured with a motor 200 including a coil 154 and a rotor 152. Accordingly, the control system 60 commands the actuators 21, 22, 23, 24 to work in a coordinated fashion, responding to individual inputs given to each actuator 21, 22, 23, 24, respectively, by the control system 60 to change their position and/or orientation and move the tool support 18 in at least four degrees of freedom or only four degrees of freedom relative to the hand-held portion 16 to the target trajectory or relative to a virtual object. In the version shown, four actuators 21, 22, 23, 24 are provided, and may be referred to as first, second, third, and fourth actuators 21, 22, 23, 24 or distal actuators 21, 22, and proximal actuators 23, 24. Similarly, the actuators 21, 22, 23, 24 may comprise actuator assemblies 400, 402 in communication with the distal linkage 26 and the proximal linkage 27. The first actuator 21 may be a part of a lift assembly 86 which adjusts a linear position of the anchor post 172 along a first active axis AA1. The second actuator 22 may be operatively coupled with the first actuator 21, angularly displacing the entire distal linkage 26 between positions about remote axis of motion RAM, moving the tool support 18 (FIGS. 27-29 and 30A-30C). The third and fourth actuators 23, 24 adjust the effective length of threaded rod 107 along a second active axis AA2 and a third active axis AA3, respectively. Each of the actuators 21, 22, 23, 24 are configured to adjust the tool support 18 relative to the hand-held portion 16 in one or more of a pitch, yaw, elevation translation, and side-to-side translation as previously described. More actuators may be provided in some examples. The actuators 21, 22, 23, 24 may be in communication with linkages 26, 27 having one or more links of any suitable size or shape. The actuators 21, 22, 23, 24 may have any configuration suitable to enable movement of the tool support 18 relative to the hand-held portion 16 in at least four degrees of freedom. For example, in some versions, actuators 23, 24 may be located distal to actuators 21, 22. Other configurations of actuator arrangements are contemplated, with several examples explained below.

FIGS. 13 and 14 illustrate one example of how the flexible circuits FC are routed from the control housing 29 on the instrument 14 to the plurality of actuators 21, 22, 23, 24. The flex circuit assembly 210, 212 may comprise multiple, flexible elongated portions (or legs) formed in one-piece or the portions may be formed separately and attached together. The flexible elongated portions may comprise one or more flexible plastic substrates, such as polyimide, transparent conductive polyester film, or the like As best seen in FIG. 14, the flex circuit assembly 210, 212 comprises electronic circuits mounted and/or embedded in the flexible plastic substrates. The electronic circuits may include one or more circuits 214, 216, 218, 220, 222 for transmitting data and/or power between the actuators 21, 22, 23, 24 and one or more of the circuit boards 31 in the control housing 29. Each actuator 21, 22, 23, 24 and drive motor M includes a connector 226 for connecting with a connection portion 224 of the flex circuits 214, 216, 218, 220, 222. The electronic circuits may also comprise one or more circuits for transmitting data and/or power between the various sensors throughout instrument 14, the actuators 21, 22, 23, 24, one or more input devices 298 and one or more of the circuit boards 31. The flex circuits 214, 216, 218, 220, 222 may have features that allow the flex circuits to maintain connection from the circuit boards 31 to the actuators 21, 22, 23, 24, the input device 298, various sensors, or a combination thereof through the range of motion of the instrument 14 as the tool support 18 is moved relative to the hand-held portion 16 in a plurality of degrees of freedom.

Figure 15:
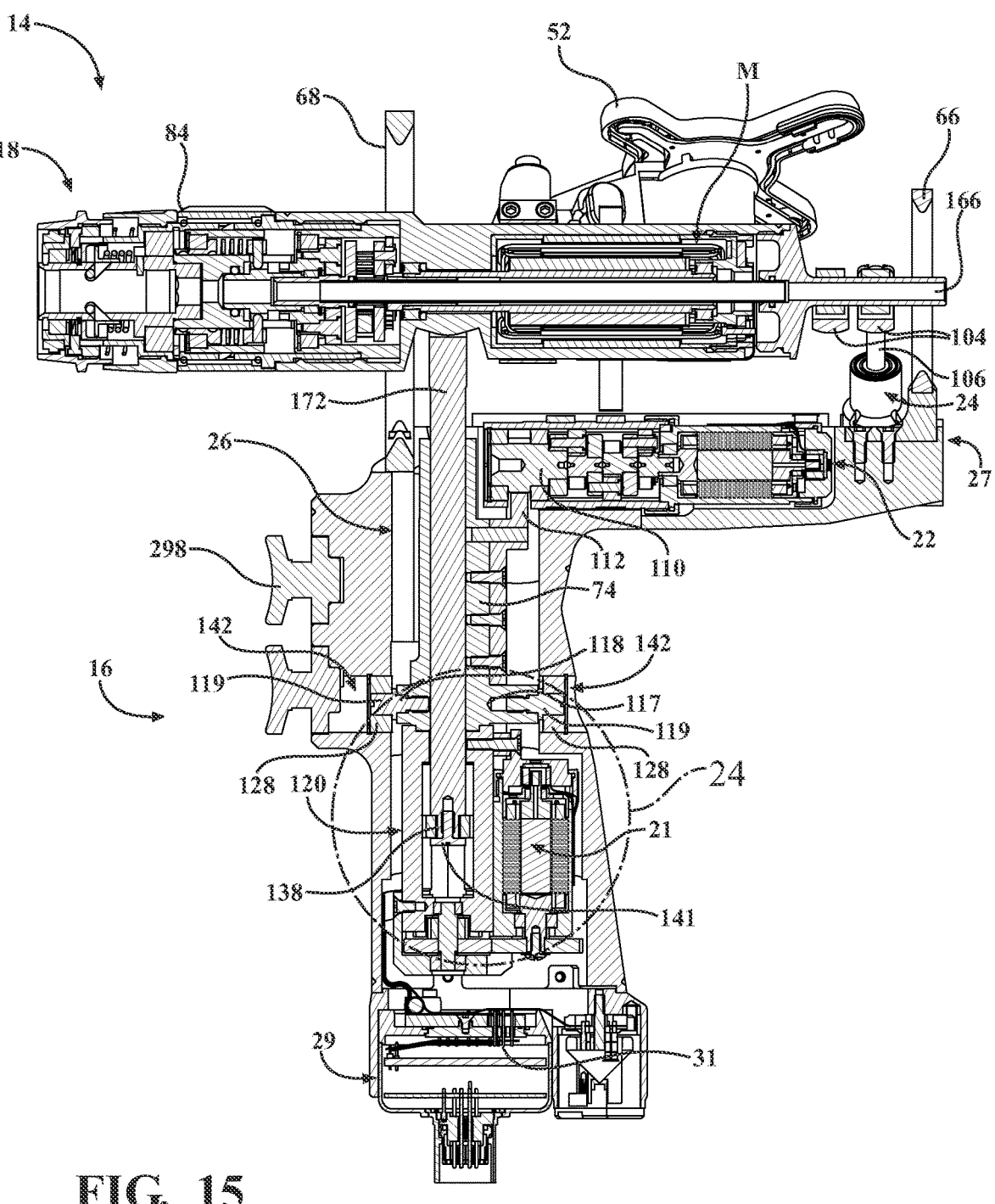
FIG. 15 is a cross sectional view of the first configuration of the robotic instrument taken along cutting plane A illustrated in FIG. 11.
Figures 16, 18:
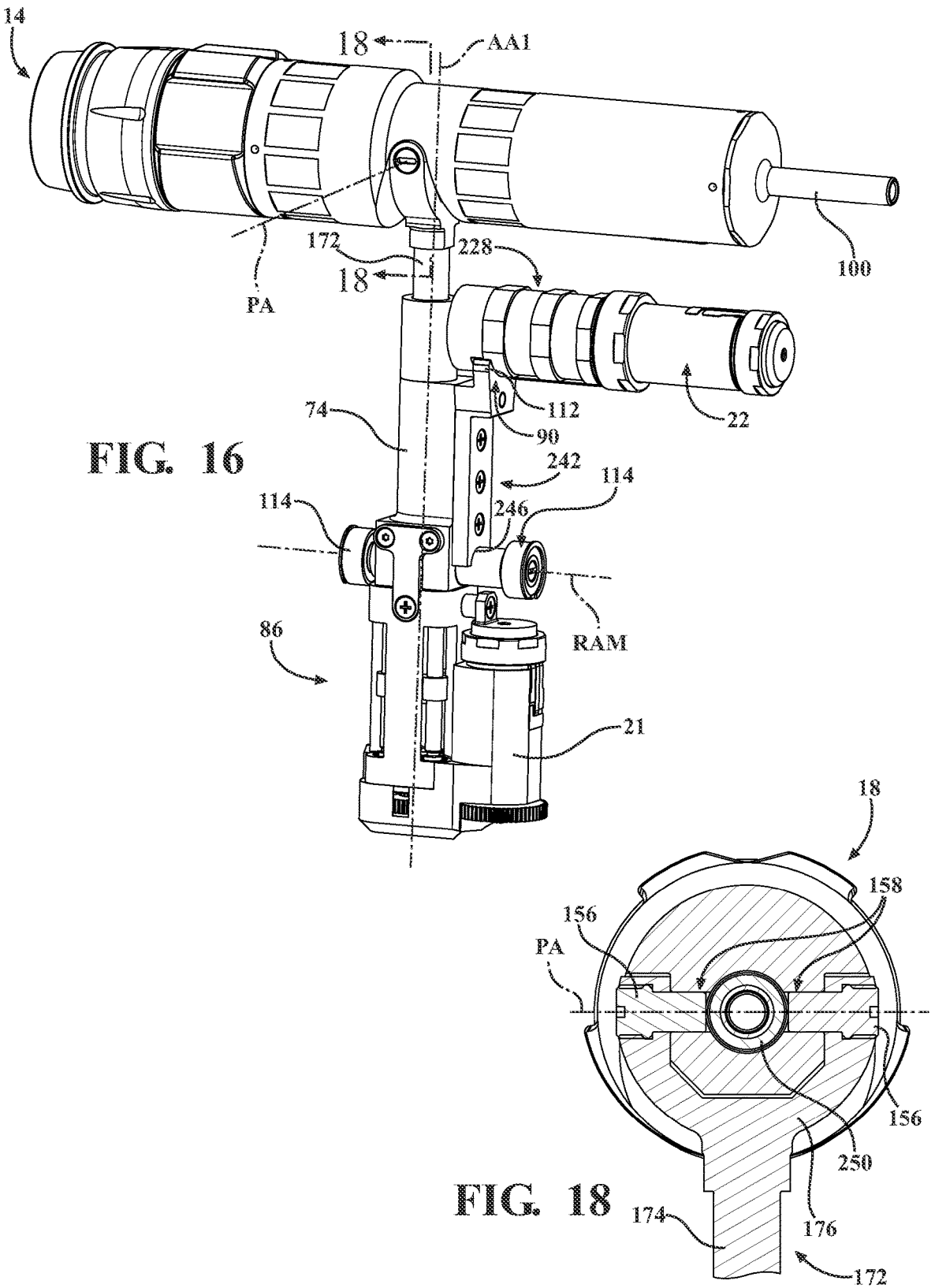
FIG. 16 illustrates a partial perspective view of a first distal linkage connected with the tool support of the first configuration of the robotic instrument.
FIG. 18 is a transverse cross section view of the tool support of the first configuration of the robotic instrument.
Figures 20, 21:
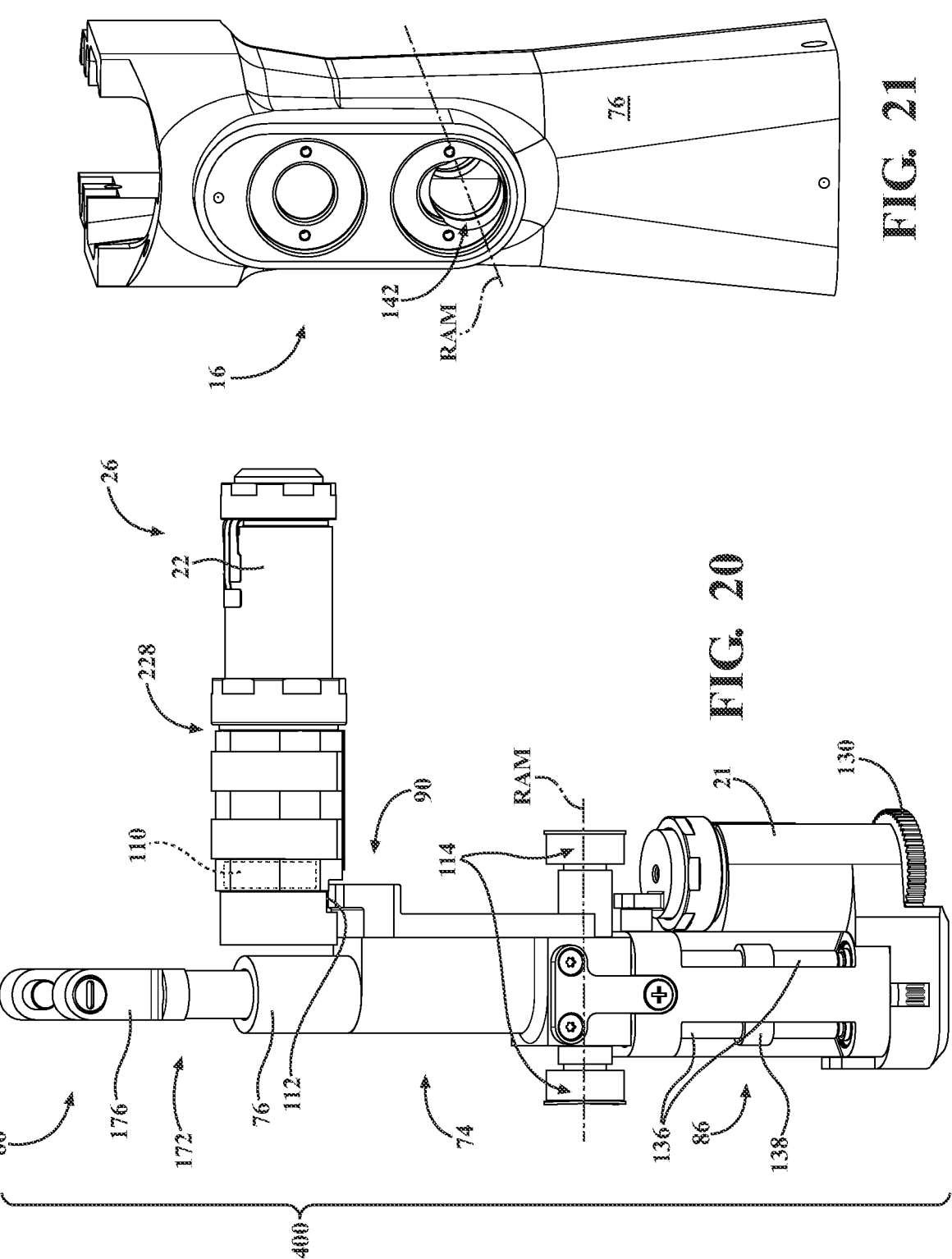
FIG. 20 illustrates a side view of distal linkage with the first actuator assembly of the first configuration of the robotic instrument.
FIG. 21 is a front perspective view of the hand-held portion of the first configuration of the robotic instrument with the distal linkage removed.
Figures 22, 23:
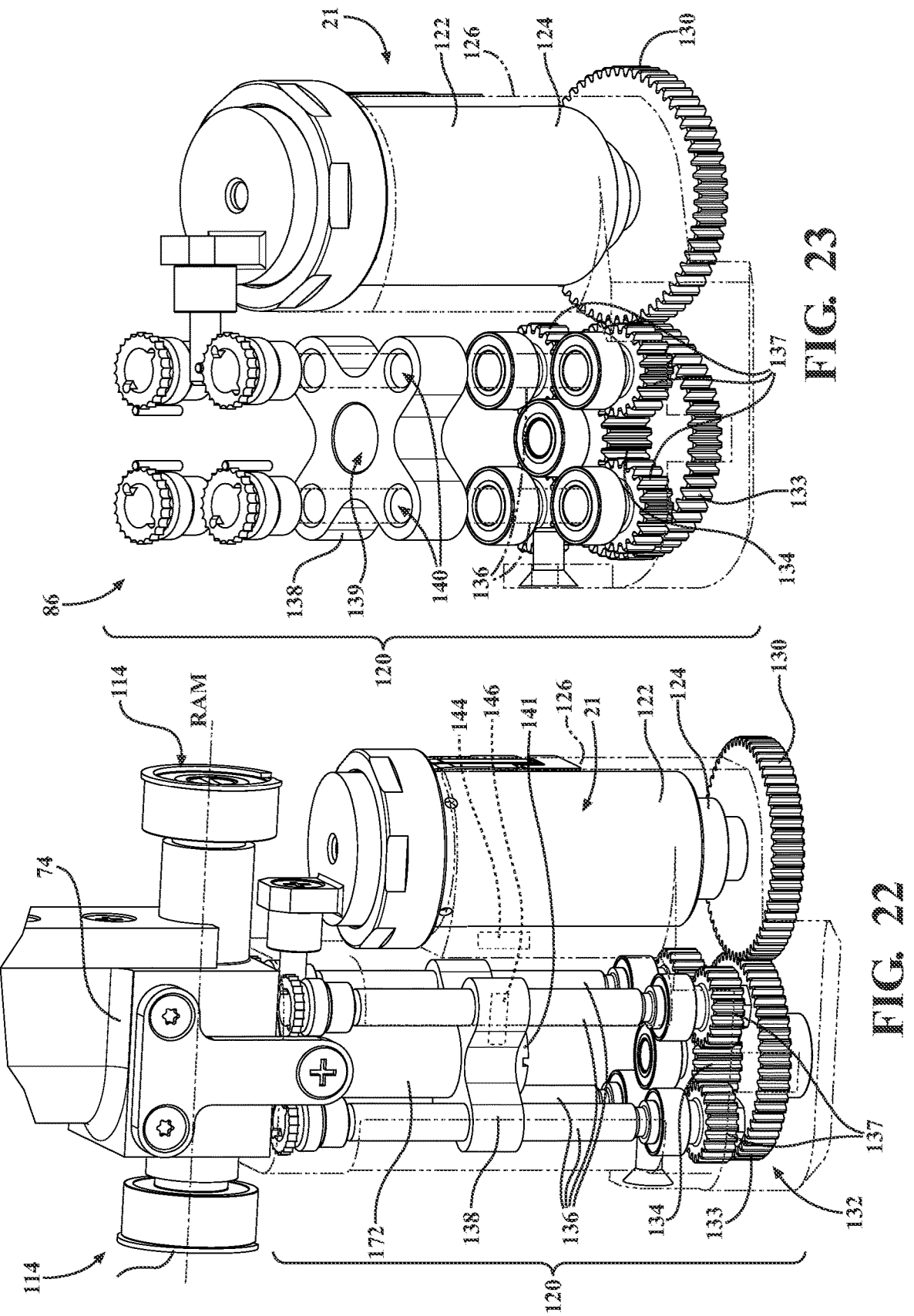
FIG. 22 illustrates a partial view of the hand-held portion with the housing removed to illustrate the lift assembly and remote axis of motion of the first configuration of the robotic instrument.
FIG. 23 illustrates a partial perspective view of the lift assembly of the first configuration of the robotic instrument.
Figure 24:
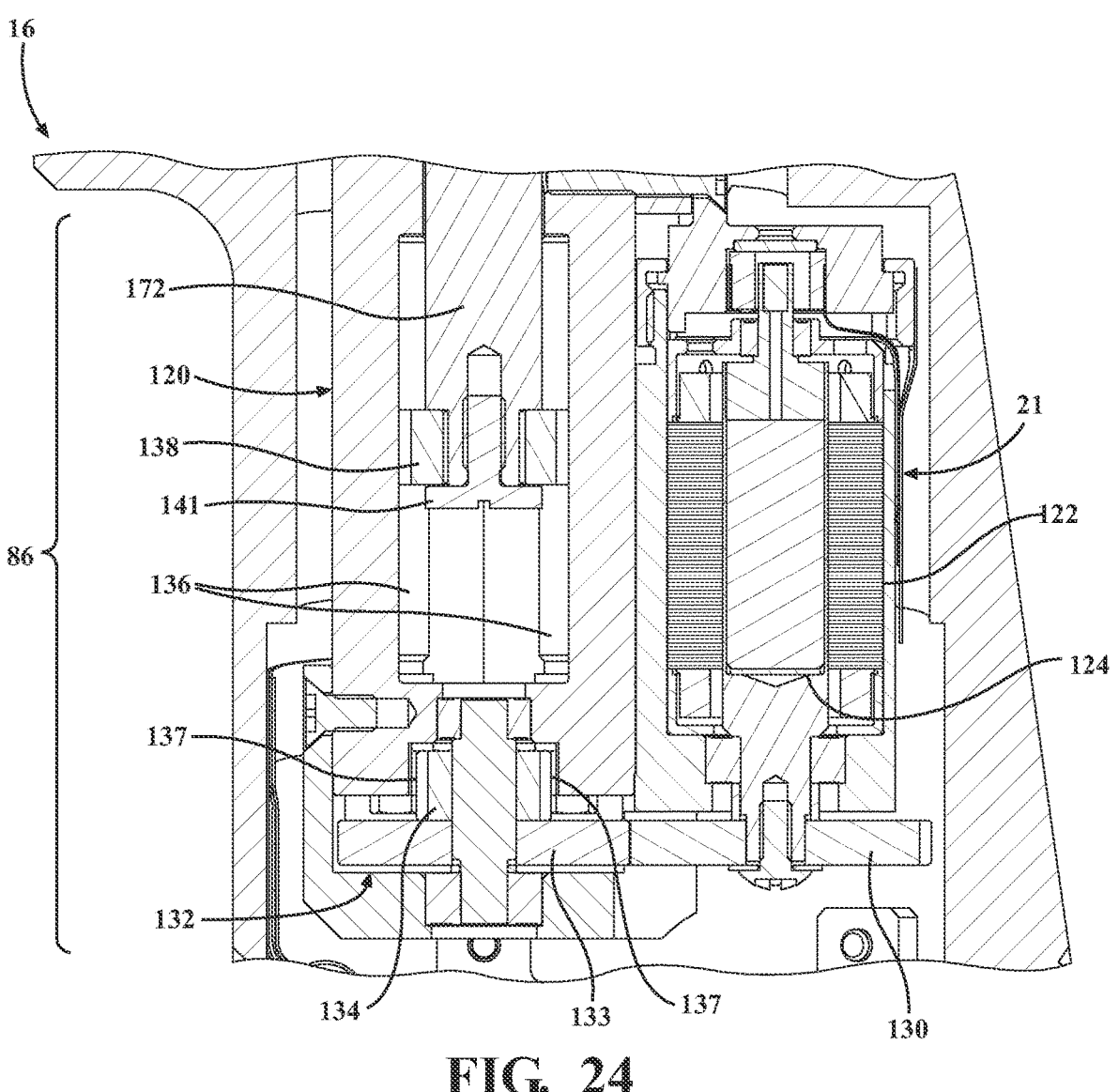
FIG. 24 illustrates a cross-sectional view of the lift assembly within the hand-held portion in accordance with a first configuration of the robotic instrument.

Turning to FIG. 16, the distal linkage 26 is shown operatively connected with the lift assembly 86 including actuator 21, an angular movement assembly 90 including actuator 22, a base support 74, and anchor post 172. The anchor post 172 is attached with the tool support 18 with the tool support 18 configured to pivot about a pivot axis PA defined by a yoke 176 of the anchor post 172. Anchor post 172 defines active axis AA1. FIGS. 16 and 18 illustrate the anchor post 172 at the tool support 18. Pins 156 are inserted through the yoke 176 to pivotably couple and mount the tool support 18 to the yoke 176. The tool support 18 may define one or more receiving pockets 158 to receive pins 156. After the pins 156 pass through the yoke 176, the tool support 18 may rotate about the pins 156 as the pins include a smooth portion that form a rotational interface with the aperture in the tool support 18. The pins 156 may feature geometries to prevent them from falling out of the yoke 176 once inserted, such as threads, opposite the smooth portion. In other words, the pins 156 and the receiving pockets on the tool support define the pivot axis PA. The length of the pins 156 are selected such that the distal end of the pin does not engage the motor shaft 250, or components rotatably coupled thereto. In other words, there is sufficient clearance between the pins 156 in the tool support 18 for the motor shaft 250 to pass through the tool support 18 adjacent the pins 156. FIG. 20 is a partial perspective view of the distal linkage 26 including actuator 22, the lift assembly 86, and the angular movement assembly 90. FIG. 21 illustrates the hand-held portion 16 with the mounting aperture 142 for the distal linkage 26. FIGS. 22 and 23 illustrate the lift assembly 86 for moving the anchor post 172 along AA1. The distal linkage 26 may be partially enclosed by the housing of the hand-held portion 16, such as seen in FIGS. 15 and 24. Both the lift assembly 86 and the angular movement assembly 90 work in conjunction with the proximal linkage 27 and its corresponding actuators 23, 24 to adjust the pose of the tool support, including but not limited to, the trajectory of the tool axis TA towards the target trajectory TTRAJ.

Figure 25:
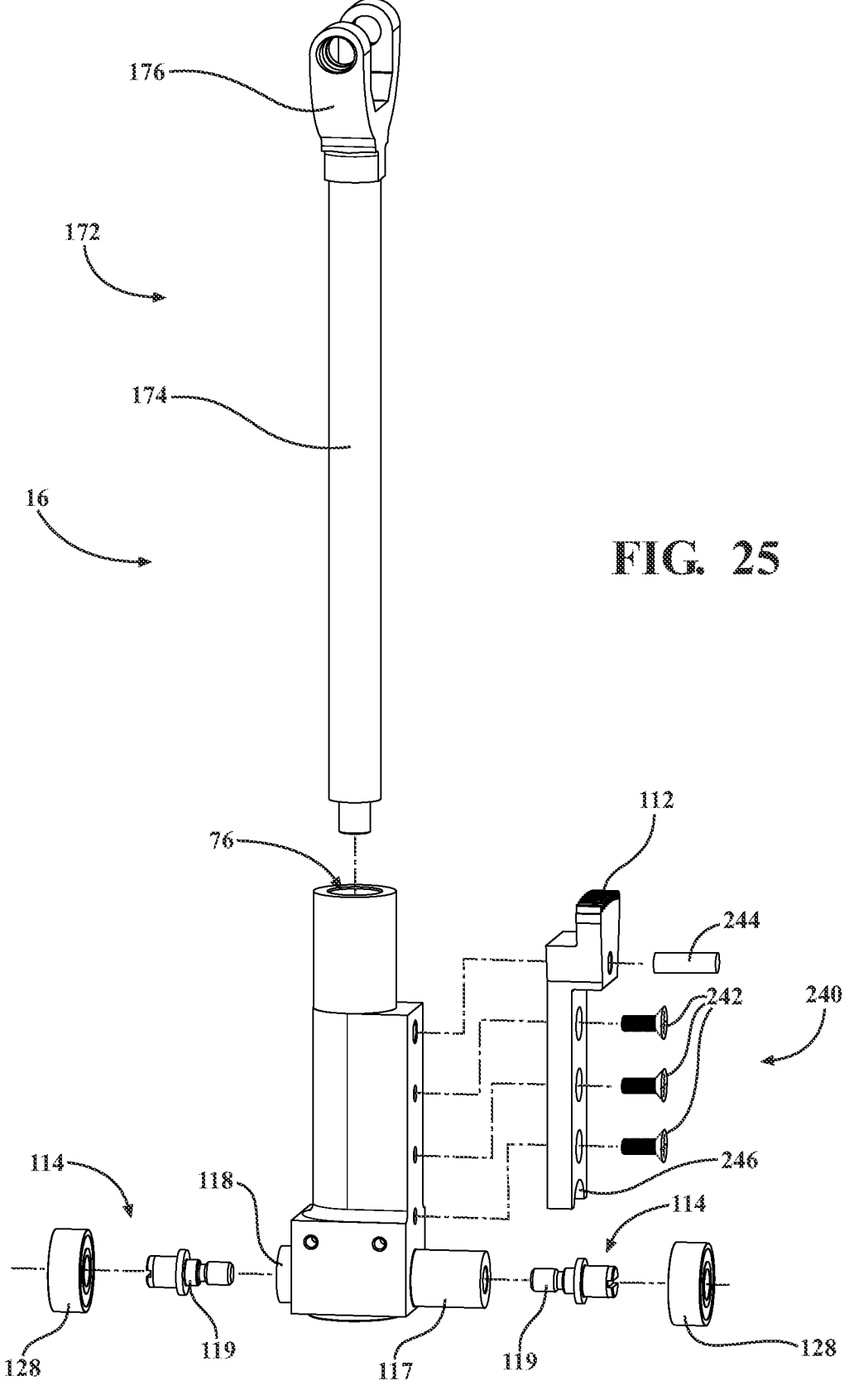
FIG. 25 illustrates an exploded view of the distal linkage in accordance with the first configuration of the robotic instrument.

The distal linkage 26 includes the base support 74. The base support 74 mounts the lift assembly 86 to the hand-held portion 16 with pivots 114. Pivots 114 are received in the hand-held portion 16 at handle apertures 142 (See FIGS. 15 and 21). The pivots 114 may comprise pivot pins 119 with bearings 128 which are received in the handle apertures 142. The pivot pins 119 are coupled with the base support 74 at pivot mounts 117, 118. Retaining rings are used on both sides of the pivot bearings to capture and position the distal linkage within the hand-held portion 16. The base support 74 may define a sleeve 76 for receiving the anchor post 172 and allowing the anchor post 172 to be moved axially through the base support 74 by the lift assembly 86, as best seen in FIG. 25. The anchor post 172 is free to rotate within the sleeve 76 of the base support 74. The lift assembly 86 is coupled to the base support 74. The base support 74 forms part of the angular movement assembly 90, including the sector gear 112 and anchor post 172, which are described further below.

During operation, the tool support 18 is moved by the actuators 21, 22, 23, 24 towards the target trajectory axis TTRAJ by the control system 60, changing the pose of the tool support 18 relative to the hand-held portion 16 and the patient. In some examples, during operation of the instrument 14 on the patient, the tool 20 is in contact with and/or within a tissue of the patient 12. As the user is performing the surgical procedure (e.g. cutting tissue, pre-drilling holes, driving implants, etc.), the control system 60 determines a pose of the tool support 18 such as described in PCT/US2021/049440 filed Sep. 8, 2021, titled "Systems And Methods For Guiding Movement Of A Handheld Medical Robotic Instrument" which is incorporated herein by reference. The control system 60 determines a commanded pose of the tool support 18 relative to the hand-held portion 16 and the patient 12 which would move the tool support 18 towards the target trajectory axis TTRAJ, and then controls the actuators 21, 22, 23, 24 to adjust the tool support 18 to the commanded pose toward the target trajectory axis TTRAJ. When the tool is in the tissue of the patient 12, such as spine SPN, and the control system commands the actuators 21, 22, 23, 24 to adjust the pose of the tool support 18, the tool 20 may be "grounded" within the tissue and an adjustment of the tool 20 by the movement of the tool support 18 by the actuators 21, 22, 23, 24 may place additional torque on the tool 20 within the tissue, particularly when the tool support 18 is rotated to maintain the target trajectory axis TTRAJ as the tool 20 is in the patient. As described above, the tool support 18 may be moved about the remote axis of motion RAM To minimize the additional torque applied to the tool 20 within the tissue, the drive motor M is controlled by the control system 60 based on an input signal from a position sensor 150 and the commanded pose. In some examples, the control system is configured to determine a commanded joint position and/or a commanded joint angle for each of the actuators 21, 22, 23, 24 based on the commanded pose, and to control each of the actuators 21, 22, 23, 24 based on the commanded joint position and/or commanded joint angle for each actuator. As the tool support 18 is rotated relative to the hand-held portion 16 and/or the patient anatomy, the drive motor M is commanded to compensate for the rotational change of the tool support 18 and tool 20 relative to the hand-held portion 16 and/or the patient anatomy by controlling the rotation of the tool 20 by drive motor M. The control system 60 may control the tool drive motor M based on an input signal from the position sensor or a previous input signal from the position sensor, and the commanded joint position of at least one actuator, a measured position of at least one actuator, a previous commanded position of at least one actuator, a previous measured position of at least one actuator, commanded joint angle of at least one actuator 21, 22, 23, 24, a measured joint angle of at least one actuator 21, 22, 23, 24, a previous commanded joint angle of at least one actuator 21, 22, 23, 24, a previous measured joint angle of at least one actuator 21, 22, 23, 24 or combinations thereof.

FIG. 20 depicts one example of a portion of the distal linkage 26. The anchor post 172 is connected to the tool support 18, via threaded pins 156 disposed through yoke 176 into the tool support at receiving pockets 158, and guided by the base support 74 (best seen in FIGS. 16 and 18). The anchor post 172 moves the tool support 18 when the lift assembly 86 and/or the angular movement assembly 90 is actuated. The anchor post 172 includes a rod 174 and a yoke 176. The rod 174 of the anchor post 172 is operatively coupled with a carriage 138 of the lift assembly 86 which moves the anchor post 172 through the sleeve 76 of the base support 74 between a minimum and a maximum position, defining the first active axis AA1. The anchor post 172 is fixed to the tool support 18 such that the tool support 18 is only able to rotate about a pivot axis PA relative to the anchor post 172 and its yoke 176. The anchor post 172 is free to rotate within the sleeve 76 of the base support 74, which by extension allows the tool support 18 to rotate about a second axis (the AA1 axis). The anchor post 172 is constrained by the sleeve 76 in the remaining four degrees of freedom. The anchor post 172 is free to rotate within the sleeve 76 of the base support 74 which allows the distal linkage 26 and proximal linkage 27 to move the tool support 18 to the commanded positions within the range of motion. A portion of the anchor post 172, has a smaller diameter, which is disposed through central aperture 139 of the carriage 138 and is retained to the carriage 138 by retainer 141. Retainer 141 may be threaded into the anchor post 172, or coupled in another suitable manner. The retainer 141 prevents the anchor post from translating relative to the carriage 138, but the retainer 141 allows the anchor post 172 to rotate relative to the carriage. By constructing the lift mechanism to allow for relative rotation between the carriage 138 and the anchor post 172, the anchor post 172 is permitted to rotate within the sleeve 76 while the lift assembly 86 simultaneously translates. The minimum and maximum positions may be defined by software and/or using mechanical stops.

The lift assembly 86 utilizes actuator 21 which may be configured as a drive motor and a movement mechanism generally indicated at 120 cooperating with actuator 21 to translate the anchor post 172 along the elevation axis (also known as the first active axis AA1).

Referring to FIGS. 22-24, actuator 21 includes an electromagnetic coil 122 and a rotor 124. The rotor 124 can include at least one or more bearings engaging the outer casing 126 via the electromagnetic coil 122. The actuator 21 also includes a drive gear 130 at one end of the rotor 124 to engage the receiving gear assembly 132 on the movement mechanism 120 of the lift assembly 86. It should be appreciated that the electromagnetic coil 122 rotates the rotor 124 spinning the drive gear 130. The rotor 124 and coil 122 may be collectively referred to as the lift motor. The drive gear 130 of actuator 21 interfaces with a receiving gear assembly 132. The receiving gear assembly 132 comprising a primary receiving gear 133 which in turn spins a secondary gear 134.

Referring to FIGS. 22-24, the movement mechanism 120 includes a plurality of lead screws 136 extending axially and spaced circumferentially. In the configuration illustrated, there are four (4) lead screws 136. Each of the lead screws 136 has a plurality of threads therealong. Each of the lead screws 136 includes a driven pinion gear 137 at one end thereof. The pinion gears are fixed to the ends of the lead screws 136 for transmitting torque from the receiving gear assembly 132 to the lead screws 136. The pinion gear 137 includes a plurality of teeth to engage the teeth of the secondary gear 134 of the receiving gear assembly 132.

The movement mechanism 120 also includes a carriage 138 to move linearly and/or axially along the lead screws 136. The carriage 138 provides a mechanical interface between the lead screws and the anchor post 172. Again, the carriage 138 and the anchor post 172 are separate components. During actuation, the anchor post 172 may rotate within the sleeve 76 and relative to the carriage 138 as the tool support 18 is moved through a plurality of positions and orientations. The carriage 138 includes threads to interface with the threads of the lead screws 136.

Turning to FIG. 23, the carriage 138 may include a central aperture 139 extending axially therethrough to receive a portion of the anchor post 172. The carriage 138 also includes a plurality of secondary apertures 140 spaced radially from the central aperture 139 and circumferentially and extending axially therethrough. The secondary apertures 140 of carriage 138 each include threads therein to engage the threads of the lead screws 136. It should be appreciated that all four pinion gears 137 engaged with the secondary gear 134 results in coordinated motion of the four lead screws 136 as actuator 21 rotates drive gear 130, turning the receiving gear assembly 132.

The carriage 138 may be axially captured at the end of the anchor post 172 opposite the yoke 176 using retainer 141. The carriage 138 and the anchor post 172 may be configured to exhibit tight axial compliance such that the carriage 138 does not wobble relative to the anchor post 172 along AA1.

On the other hand, the anchor post 172 and the carriage 138 may be configured to enable relatively large radial compliance to adjust for tolerances. The radial compliance may be much greater than the axial compliance between the carriage 138 and the anchor post 172. Such radial compliance may be implemented in various manners. In one potential implementation, an inner diameter of the central aperture 139 of the carriage 138 is deliberately larger than the outer diameter of the anchor post 172 to provide a gap therebetween and allow the carriage 138 to move radially with respect to the anchor post 172. Additionally, or alternatively, the secondary apertures 140, when present, may include an inner diameter being deliberately larger than the outer diameter of the lead screws 136. Furthermore, biasing members, such as springs, may be incorporated into the carriage 138, and/or coupled between the carriage 138 and the anchor post 172. In other examples, the carriage 138 and/or anchor post 172 may be comprised of or have coupled thereto deformable materials for accommodating the radial movement.

In some examples, the movement mechanism 120 may include a translation encoder, such as a translation sensor 144 disposed about the outer casing 126 to sense the linear position of the carriage 138. It should be appreciated that the translation encoder senses a position of the carriage 138, which provides one method for the position of the anchor post 172 and tool support 18 to be determined. The translation sensor 144 could be accomplished by placing a magnet 146 on the carriage 138 and use one or more hall-effect sensors as the translation sensor 144, and position the one or more hall-effect sensors 144 along the outer casing 126 of the hand-held portion 16, such as on or along the base support 74. In other examples, directly tracking the tool support 18 will determine the linear position of the carriage 138 based on the relationship between the movement mechanism 120 and the range of motion of the tool support 18. Other techniques for measuring or determining the position of the anchor post 172 and tool support 18 may be utilized, such as electromagnetic sensors, or the like. In some examples, the position of the carriage 138 is tracked via an encoder or sensor located within actuator 21 using the known properties of the mechanism (i.e. gear ratios, lead screw thread pitch, etc.) to calculate position of the carriage 138 as a function of rotor position.

Figure 26A:
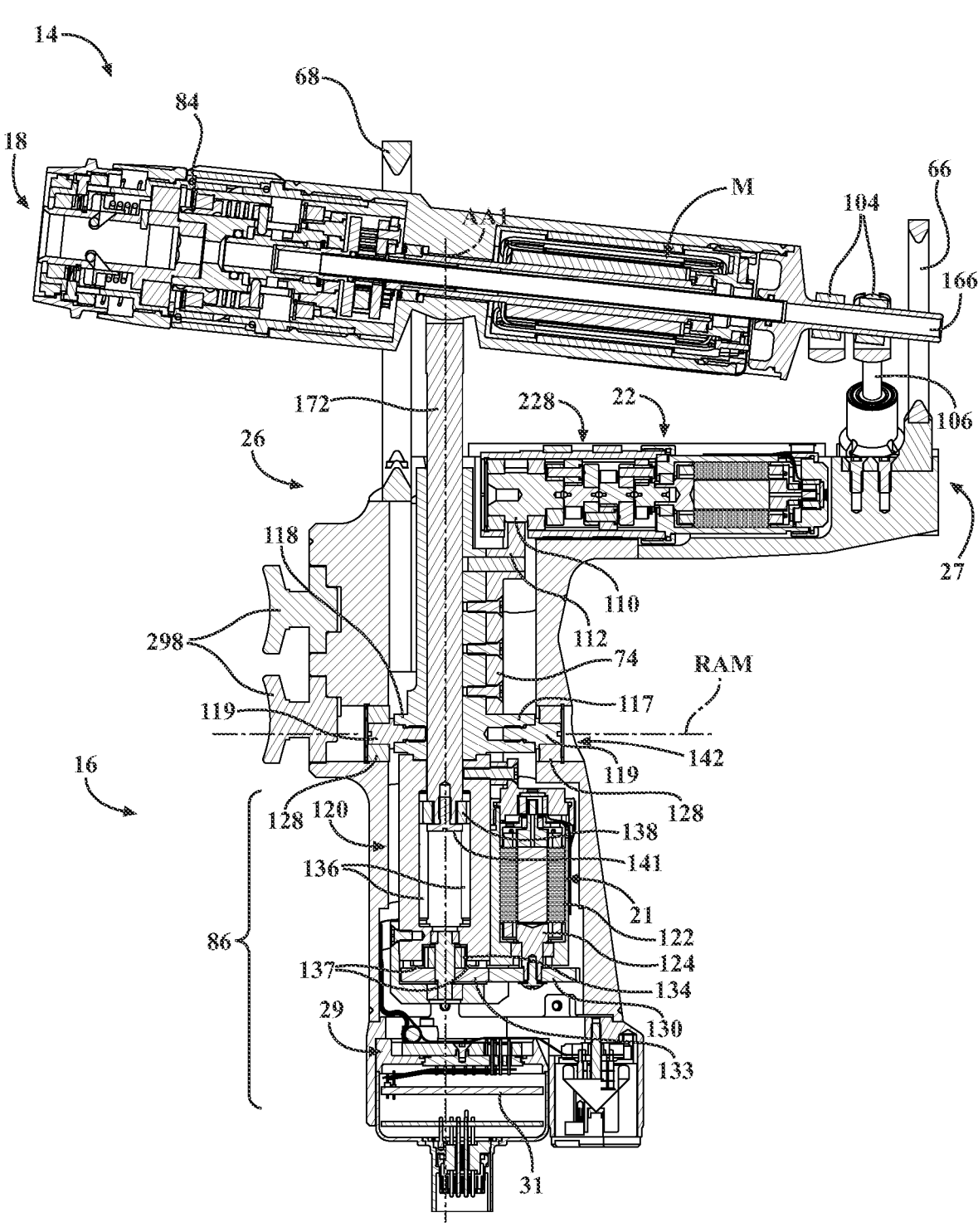
FIG. 26A depicts a cross-sectional view of the first configuration of the robotic instrument with the lift mechanism fully extended.
Figure 26B:
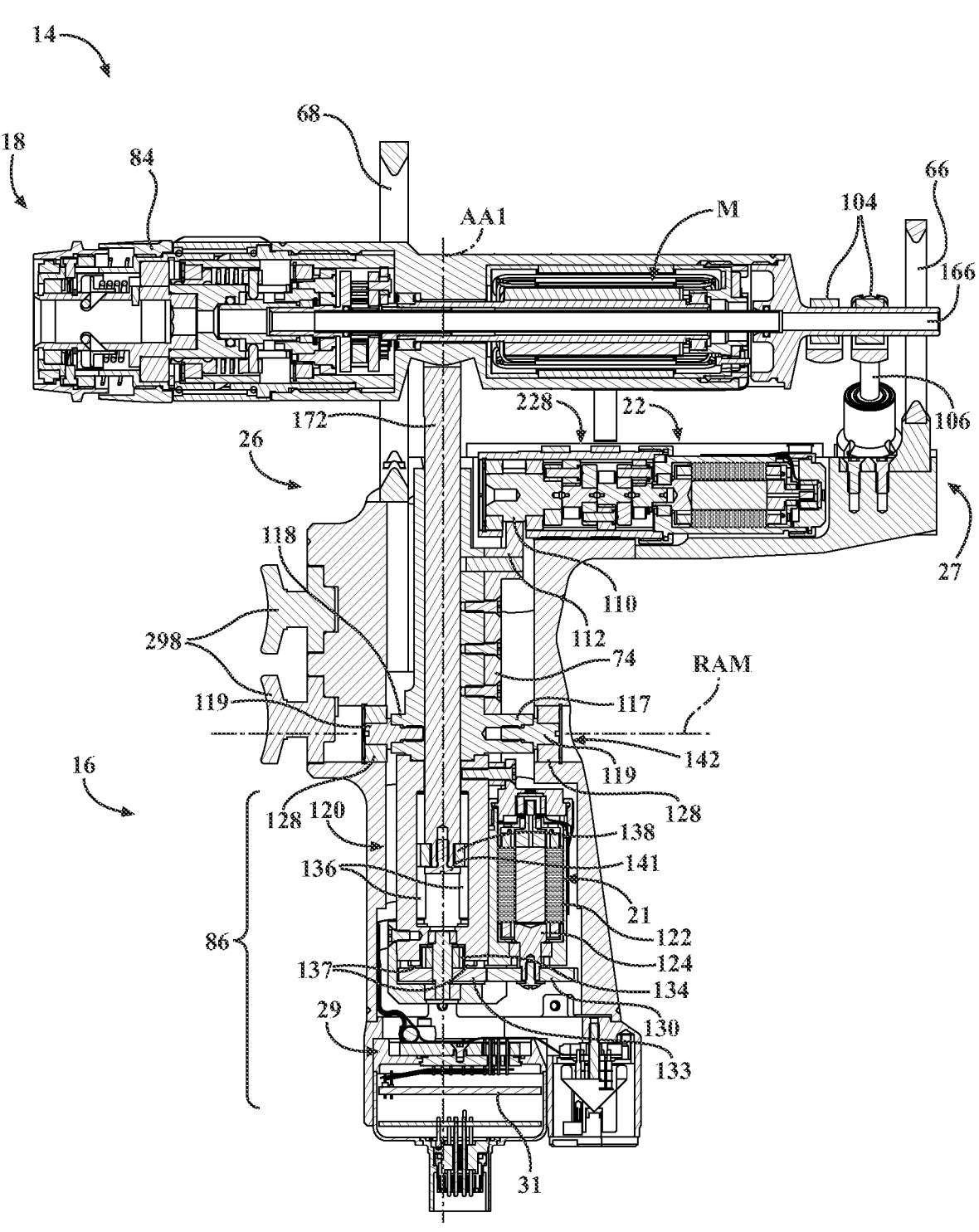
FIG. 26B depicts the cross-sectional view of the first configuration of the robotic instrument with the lift mechanism at a home position.
Figure 26C:
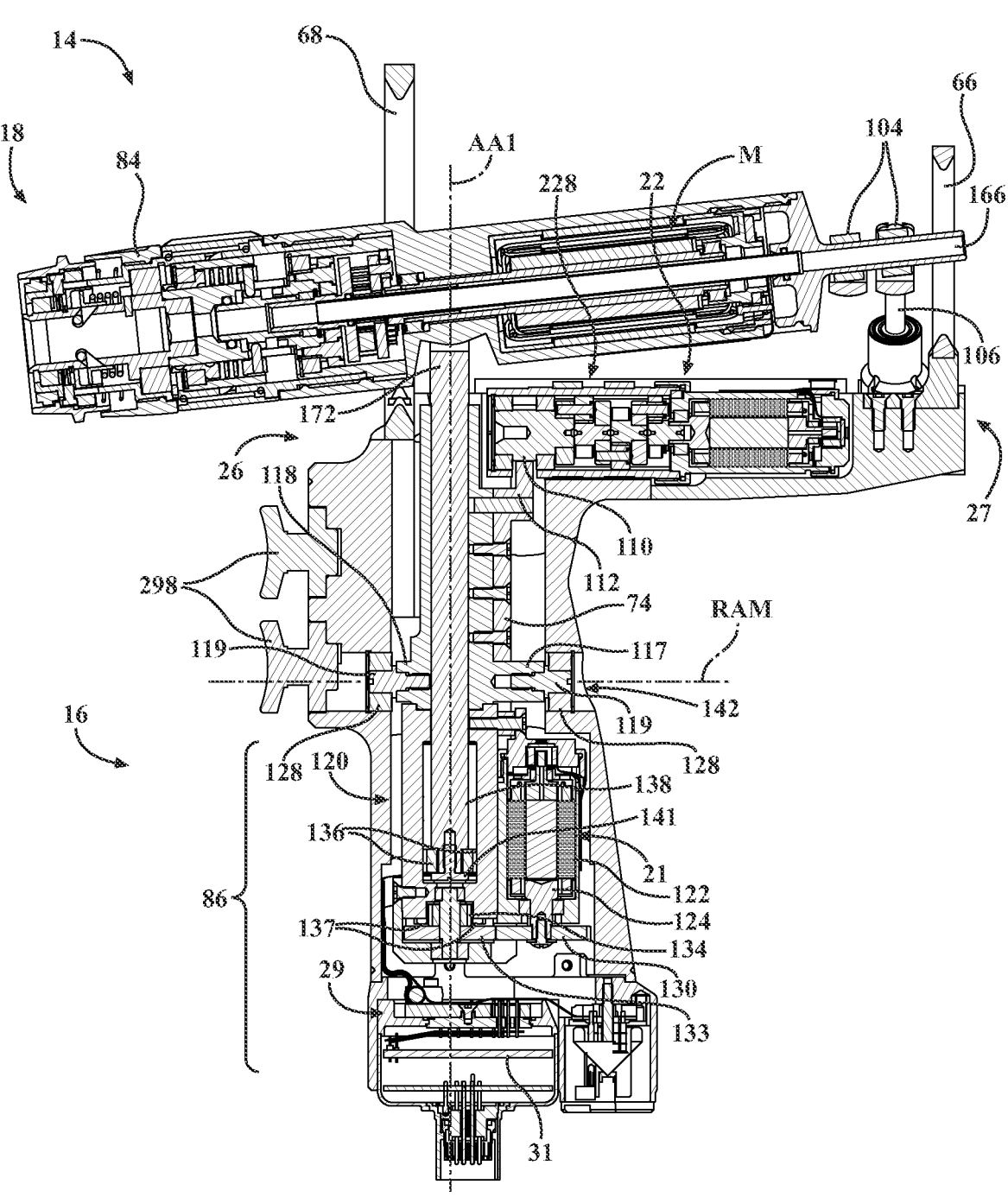
FIG. 26C depicts a cross-sectional view of the first configuration of the robotic instrument with the lift mechanism at a retracted position.

Turning to FIGS. 26A-26C, the robotic instrument 14 is shown with the tool support 18 moved relative to the hand-held portion 16 by the lift assembly 86. FIG. 26A depicts the tool support 18 extended away from the hand-held portion 16 in an upward pitched position when the lift assembly 86 has moved the carriage 138 upward away from the circuit boards 31 of the control housing 29 towards a top stop, causing the carriage 138 to lift the anchor post 172. FIG. 26B illustrates a home position where the carriage 138 has the greatest travel distance along the length of the lead screws 136 in either direction. FIG. 26C illustrates the tool support 18 pitched downward when the lift assembly 86 has moved the carriage 138 towards a bottom stop. By moving the carriage 138 down along the lead screws 136, the anchor post is moved and causes the tool support 18 to the pitched down position. The anchor post 172 is secured to the carriage 138 by retainer 141. The retainer 141 allows the anchor post to rotate relative to the carriage 138 but constrains the movement of the anchor post 172 in all other degrees of freedom relative to the carriage 138.

Figure 27:
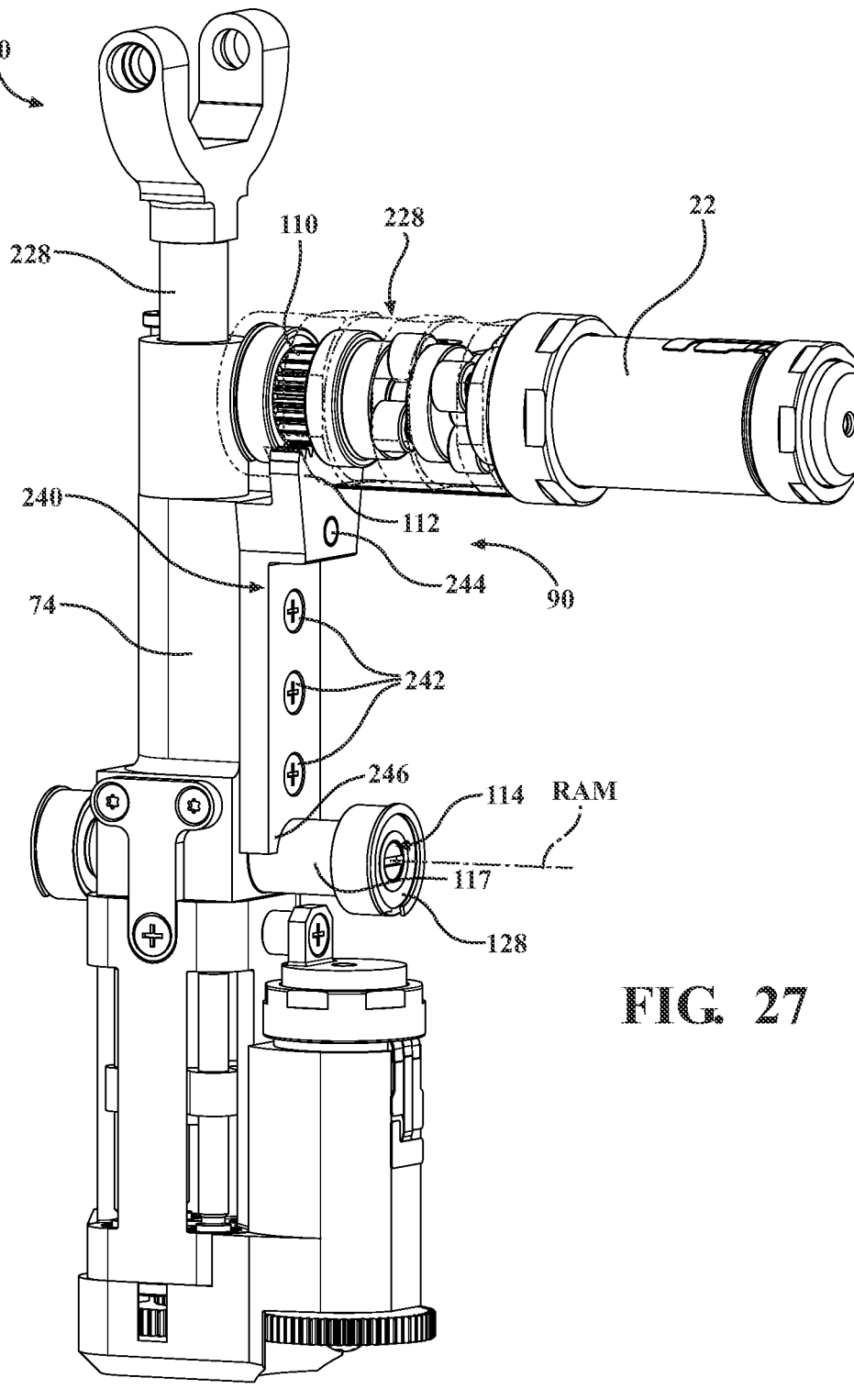
FIG. 27 illustrates a partial perspective view of the angular movement assembly and the remote axis of motion of the first configuration of the robotic instrument.
Figures 28, 29:
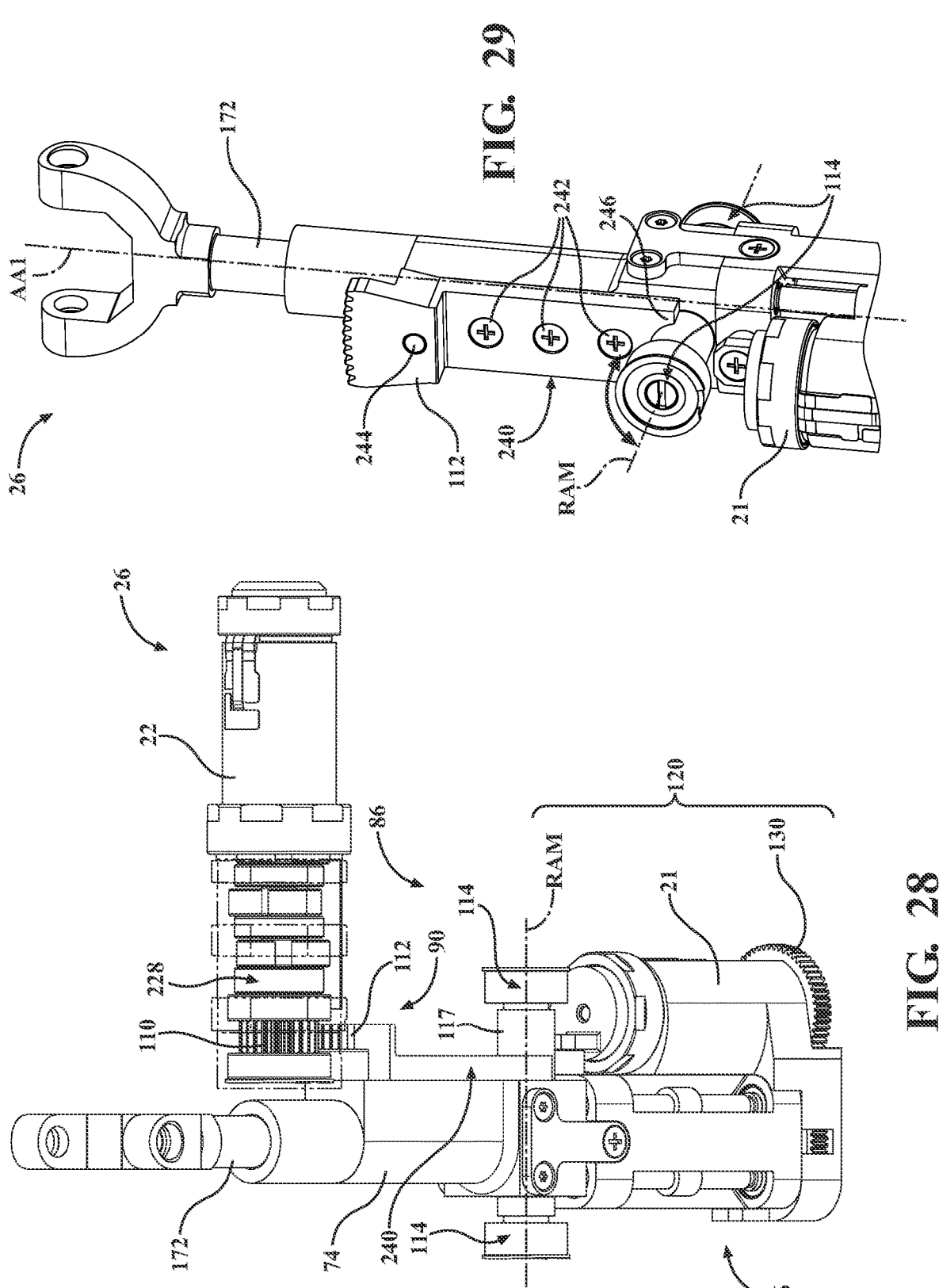
FIG. 28 illustrates a top front perspective view of the distal linkage and the rotary actuator of the first configuration of the robotic instrument.
FIG. 29 illustrates a partial rear perspective view of the distal linkage of the first configuration of the robotic instrument.

As mentioned above, the distal linkage 26 includes an angular movement assembly 90 comprising actuator 22. The actuator 22 is configured as a rotary actuator including a drive gear 110 in communication with sector gear 112 on the base support 74. The drive gear 110 and the sector gear 112 are complimentary to each other. Actuator 22 may include a gear set 228 for increasing or decreasing forces/torques from the actuator 22 to the sector gear 112 and base support 74. The sector gear 112 is a portion of the sector mount 240 which is connected with the base support 74 by fasteners 242 and pin 244. In the examples shown throughout the present application, actuator 22 is positioned longitudinally, generally parallel to the tool support 18 at the home position. FIGS. 27-29 illustrate the angular movement assembly 90. The angular movement assembly 90 may function to adjust the tool support 18 along a radius of a remote axis of motion RAM of the tool support 18, which may be defined by pivots 114. As described above, pivots 114 are the locations that the base support 74 is rotatably connected with the housing of hand-held portion 16. As the angular movement assembly 90 is actuated, the rotary actuator 22 spins the drive gear 110, moving the base support 74 along the sector gear 112 and pivoting the distal linkage 26 about the pivots 114. As a result, the tool support 18, which is connected to the hand-held portion 16 by the anchor post 172, is moved along a path of the remote axis of motion RAM changing the angular position of the tool support 18 relative to the hand-held portion 16. The radius is defined by the length of the anchor post 172, which, as described above, is adjustable relative to the base support 74 by the lift assembly 86. The base support 74 is connected to the housing of the hand-held portion 16 through the pivots 114. The pivots 114 are received on the housing of the hand-held portion 16.

FIGS. 28 and 29 illustrate the pivots 114 defining the remote axis of motion RAM. The sector gear 112 has a circumference concentric to the remote axis of motion RAM. The sector mount 240 includes a curved cutaway which partially surrounds the pivot mount 117, which, during use, assists with the transfer of torque between actuator 22 and the base support 74. When actuator 22 is actuated, rotating drive gear 110, the sector gear 112 is moved, pivoting the distal linkage 26 causing the tool support 18 to be moved along an adjustable concentric path defined by the remote axis of motion RAM and determined by length of extension of the anchor post 172 along AA1. FIGS. 30A, 30B and 30C show a lateral cross section view of the robotic instrument 14 in different positions commanded by the angular movement assembly 90. As can be seen in FIGS. 30A-30C, the lift assembly 86 maintains the position of the carriage 138 relative to the movement mechanism 120, keeping the radius defined by the distance between the remote axis of RAM and the tool support 18 constant. FIG. 30A illustrates the distal linkage 26 rotated counterclockwise (relative to the view shown). In the view of FIG. 30A, the tool support 18 is moved to the left while actuator 21 and the movement mechanism 120 are moved to the right. As indicated by the positioning of the tool support 18, the anchor post 172 is rotated. FIG. 30B shows the angular movement assembly 90 and the lift assembly 86 at a home position, centering the tool support 18 within alignment guide 66. FIG. 30C shows the tool support 18 moved clockwise relative to the hand-held portion 16. In the view of FIG. 30B, the tool support 18 is moved to the right while actuator 21 and the movement mechanism 120 are moved to the left. Similar to FIG. 30A, the anchor post 172 appears rotated since the tool support 18 is rotated. When the angular movement assembly 90 is actuated, the entire distal linkage is rotated. Similar to FIGS. 30A-30C, FIGS. 31A-31C illustrate a lateral cross section of the robotic instrument 14 moved between a plurality of positions, however, in FIGS.

Figures 31A, 31B, 31C:
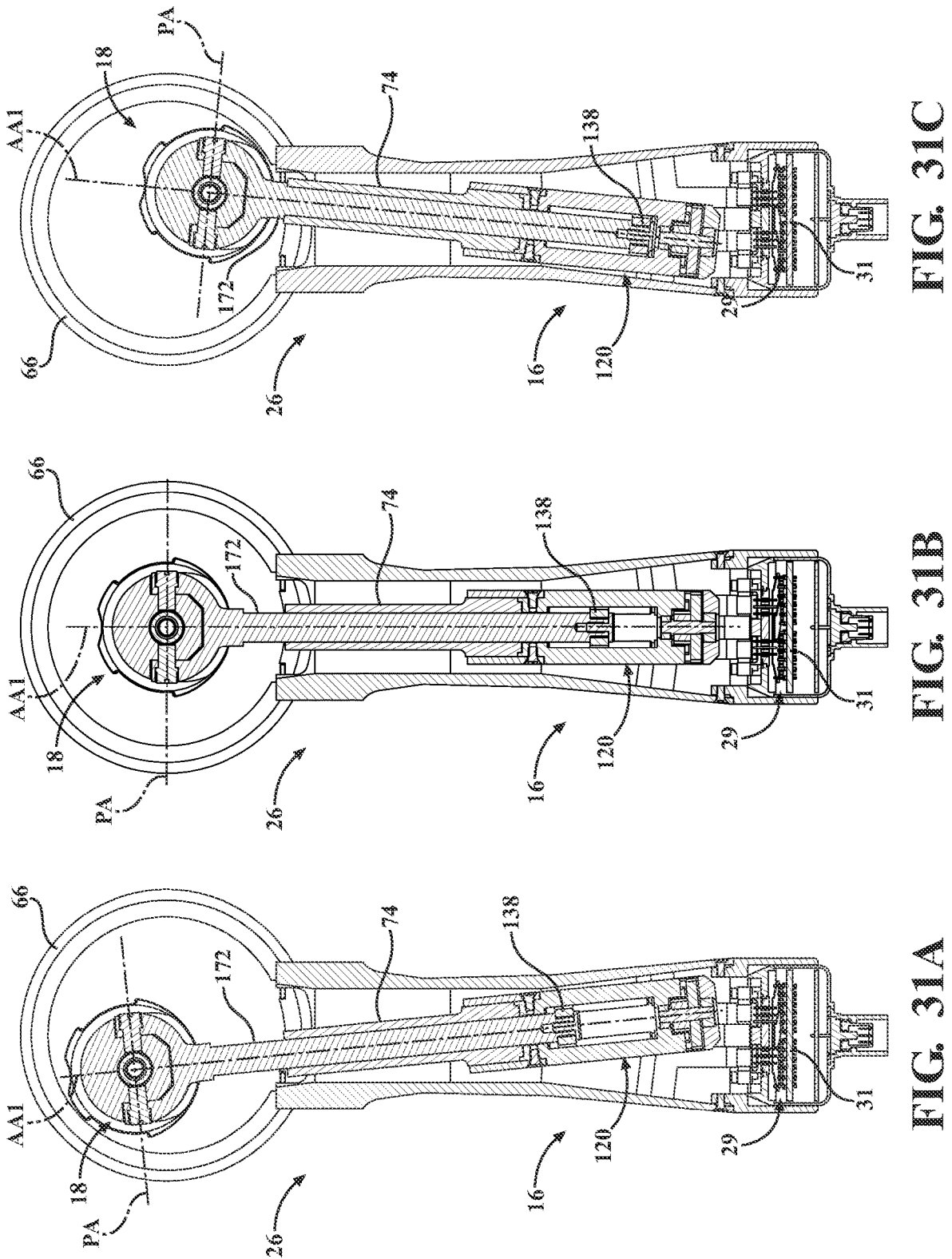
FIGS. 31A, 31B, and 31C illustrate cross-sectional views of the first configuration of the robotic instrument with the angular movement assembly and the lift mechanism in three different poses.

31A-31C, the carriage 138 of the lift assembly 86 is shown moving between positions, changing the radius between the remote axis of motion RAM and the tool support 18. Since anchor post 172 is adjustable, the radius which the tool support 18 travels along changes but is always concentric to the remote axis of motion RAM. In FIG. 31A, the instrument 14 is shown with the anchor post 172 partially extended and the tool support 18 rotated counterclockwise to the left. The anchor post 172 is partially extended, and the angular movement assembly 90 has pivoted the distal linkage 26 to the left, moving the distal portion of the tool support 18 to the left rotating the movement mechanism 120 to the opposite side. FIG. 31B illustrates the instrument 14 at a home position. FIG. 31C shows the tool support 18 moved clockwise with the anchor post 172 retracted and the moved to the right, moving the distal portion of the tool support 18 to the right, and rotating the lift movement mechanism 120 to the left. FIGS. 31A and 31C show several example poses within the range of movement relating to the compound movement of the lift assembly 86 and angular movement assembly 90. As shown in FIGS. 31A-31C, the tool support 18 is moved in a plurality of degrees of freedom by the concerted actuation of the lift assembly 86 and the lift movement mechanism 120. By extending and retracting the anchor post 172 with the lift assembly 86, the distance from the remote center of movement to the tool support 18 is changed along AA1 but will always be concentric to the remote axis of motion RAM.

Figures 32, 33:
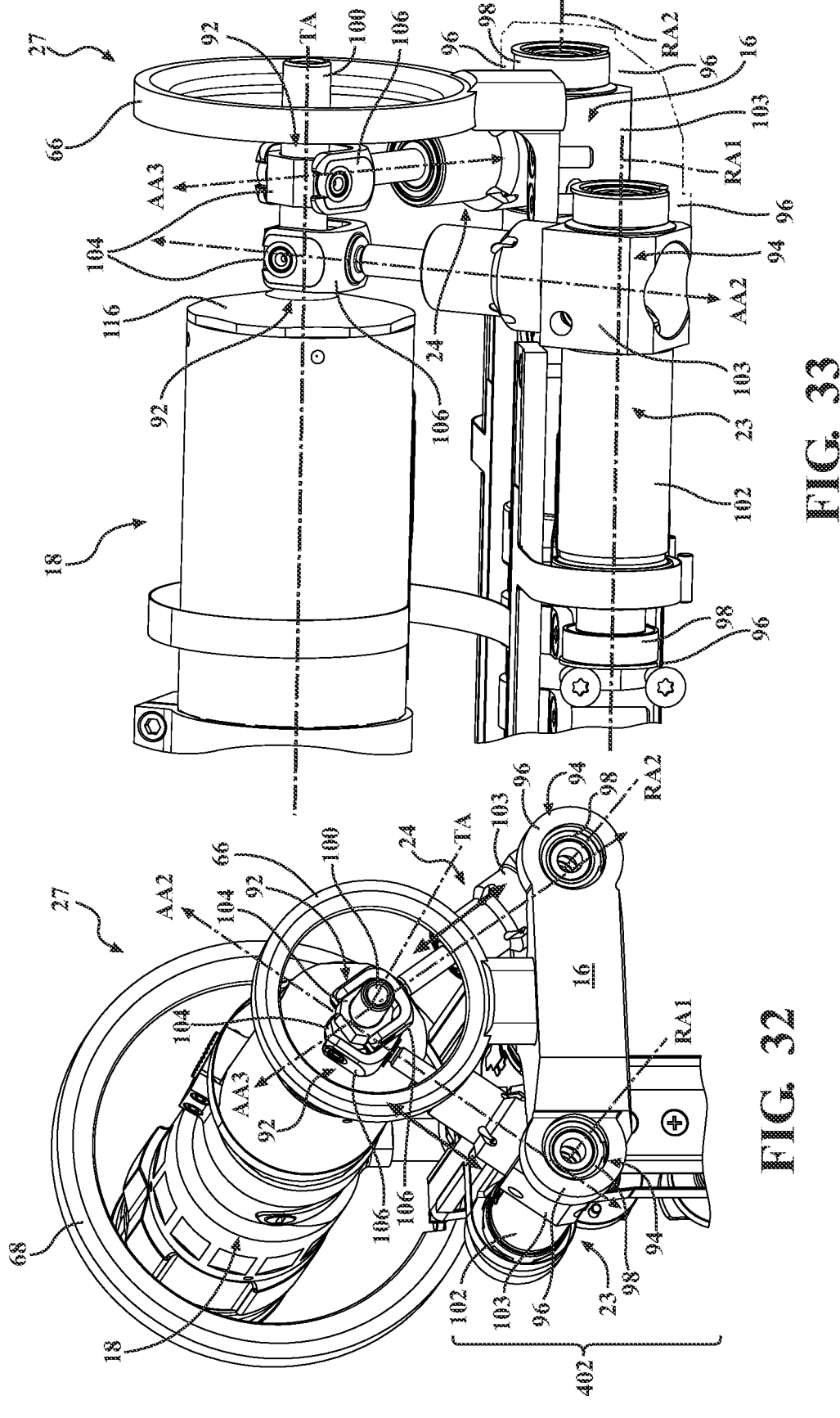
FIGS. 32 and 33 are rear partial perspective view of a proximal actuator assembly including the second set of actuator assemblies in accordance with the first configuration of the robotic instrument.
Figure 34:
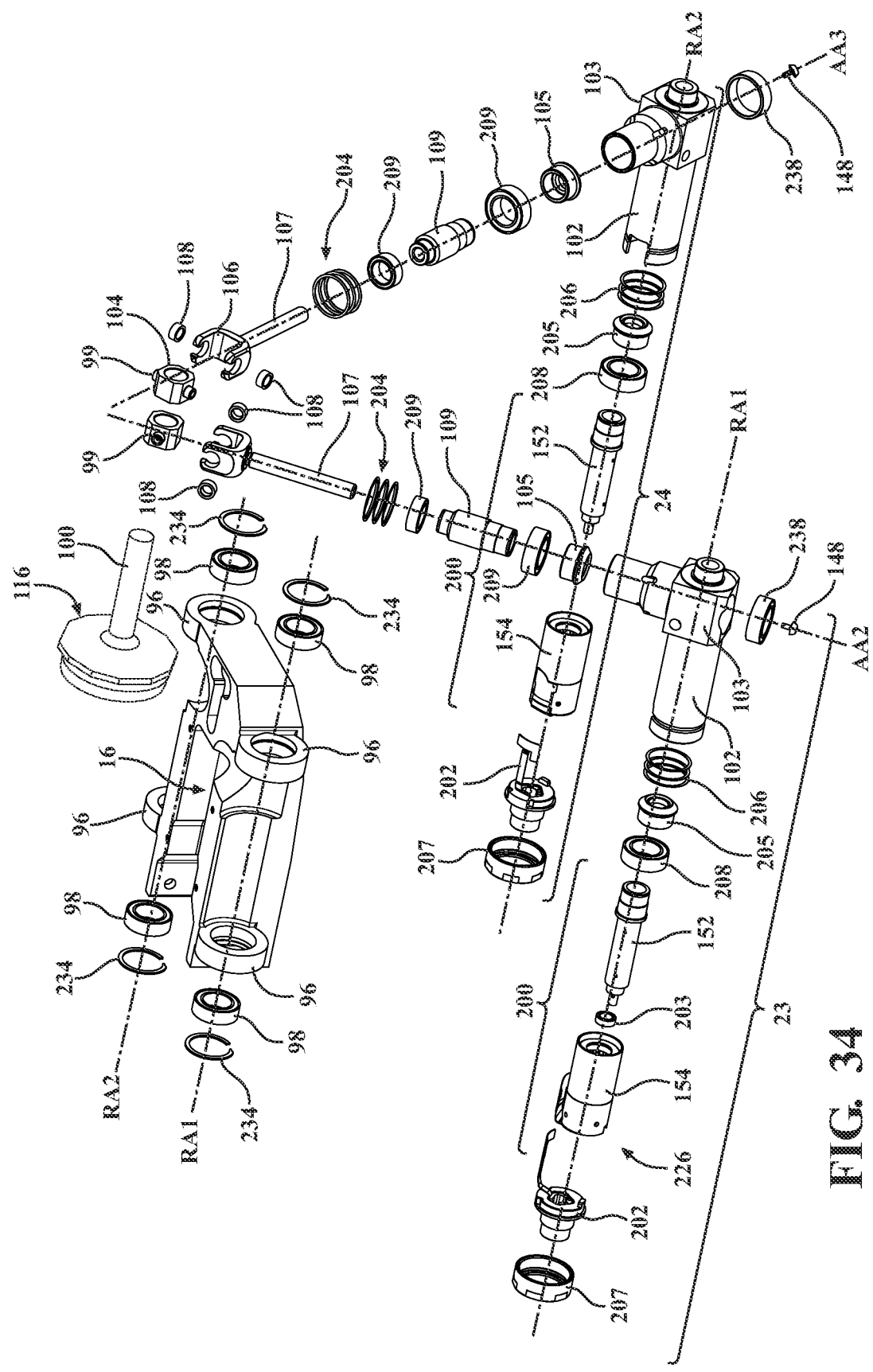
FIG. 34 is an exploded view of the second set of actuator assemblies in accordance with the first configuration of the robotic instrument.

Turning now to FIGS. 32 to 37C, the proximal linkage 27 and corresponding actuator assembly 402 including actuators 23, 24 are shown. In this version, such as shown in FIGS. 32 and 33, the actuators 23, 24 are coupled to the hand-held portion 16 and the tool support 18 via two sets of joints 92, 94. The first passive joint 92 couple the actuators 23, 24 to the tool support 18 at a positioning post 100. The first passive joints 92 comprises post slides 104 which are disposed along the positioning post 100 of the tool support 18. The positioning post 100 extends from the tool support 18, such as extending from a proximal end cap 116. Each of the post slides 104 has a throughbore disposed through the post slide 104 for receiving the positioning post 100 of the tool support 18. The first passive joint 92 are defined by pivot yokes 106 connected to post slides 104 disposed on the positioning post 100. Each of the actuators 23, 24 includes a pivot yoke 106 and a post slide 104. The post slides 104 include protrusions 99 which are received by the pivot yokes 106. Bushings 108 surround the protrusions 99 of the post slides 104 in the pivot yokes 106. The post slides 104 pivotally connect to the pivot yokes 106.

Referring to FIG. 34 and FIGS. 37A-37C, the pivot yokes 106 are coupled with a threaded rod 107 extending into the elbow 103 of base 102. Each of the actuators 23, 24 are configured to linearly move the threaded rods 107 connected with pivot yokes 106 along AA2 and AA3. In this example, actuators 23, 24 are configured as linear actuators 23, 24 extending threaded rods 107 relative to base 102 of the actuators 23, 24. Each of the threaded rods 107 define a rod axis. The rod axis is along AA2, AA3, respectively. In some examples, the pivot yoke 106 and threaded rod 107 are a single component. The base 102 and/or elbow 103 may house a gear set including bevel gears 105, 205 for transferring rotational movement from actuator 23, 24 to the hollow drive shaft 109. As shown in FIGS. 32-36, the bevel gears 105, 205 are placed approximately 90 degrees relative to each other, corresponding with the angular difference between actuator motor 200 and the hollow drive shaft 109 and threaded rod 107. The hollow driveshaft 109 is threaded to receive the threaded rod 107. The hollow driveshaft 109 is positioned in the elbow 103 running along the active axis AA2, AA3, and positioned within the elbow 103 by washer stack 204 and bearings 209 disposed on either end of the hollow driveshaft 109. The bevel gear 105 is connected and fixed to the hollow driveshaft 109. The hollow driveshaft 109 and bevel gear 105 are secured in the elbow 103 of the base 102 by press ring 238. The threaded rod 107 is retained with the hollow driveshaft 109 by stop 148. The bevel gear 105 is rotatably communication with a drive bevel gear 205 within the base 102 along the rotational axis RA1, RA2.

The base 102 of each actuator 23, 24 includes an electromagnetic coil 154 which rotates a rotor 152 connected with the drive bevel gear 105 for actuating the bevel gear 105 which, in turn, rotates the hollow driveshaft 109 and the threaded rod 107, thereby moving the pivot yoke 106 between positions along the active axes AA2, AA3, respectively. The actuator 23, 24 include encoder 202 connected to the distal end of the coil 154, with rotor 152 axially disposed through the coil 154. Bearing 203 positions and/or centers the distal end of the rotor 152 within the encoder 202 and coil 154. The proximal end of the rotor 152 is placed in communication with a bearing 208 and drive bevel gear 205. The rotor 152 and drive bevel are positioned within base 102 with washer stack 206 providing the appropriate clearance between the bevel gears 105, 205. On the other end of the base 102, end cap 207 connects with the base 102 to maintain the assembly of the actuator 23, 24.

The bevel gear 105 and the drive bevel gear 205 mesh at the intersection of the radial axis RA1, RA2 and the active axis AA2, AA3 within the elbow 103, respectively. As the rotor 152 of the actuator 23, 24 spins, the drive shaft 109 spins in the same direction, but at a 90-degree angle from the rotor 152. A gear ratio between the rotor 152 and the hollow driveshaft 109 is defined by the number of teeth on each respective bevel gear 105, 205. In one example, each of the bevel gears 105, 205 have a 1:1 drive ratio. In other examples, the gear ratio may be set accordingly to increase or decrease the speed and/or torque transmitted to the hollow drive shaft 109 as desired. The hollow driveshaft 109 rotation results in the pivot yoke 106 and threaded rod 107 extending (or retracting) along axis AA2, AA3, respectively. This resulting linear movement along axes AA2, AA3 is due to the pivot yoke 106 rotationally coupling to the positioning post 100 of the proximal end cap 116 via the post slides 104. The post slides 104 are configured to move along the positioning post 100, allowing the tool support 18 to move smoothly relative to the hand-held portion 16.

The actuators 23, 24 are rotatably coupled with the hand-held portion 16 at actuator mounts 96. The distal end and the proximal end of the actuator 23, 24 are placed through and support by bearings 98 in each of the actuator mounts 96 and axially retained by snap rings 234. The actuator 23, 24 are free to rotate when the threaded rods 107 are actuated to extend or retract, changing the angular position of the actuator 23, 24 about the rotation axis RA1, RA2.

Figure 37A:
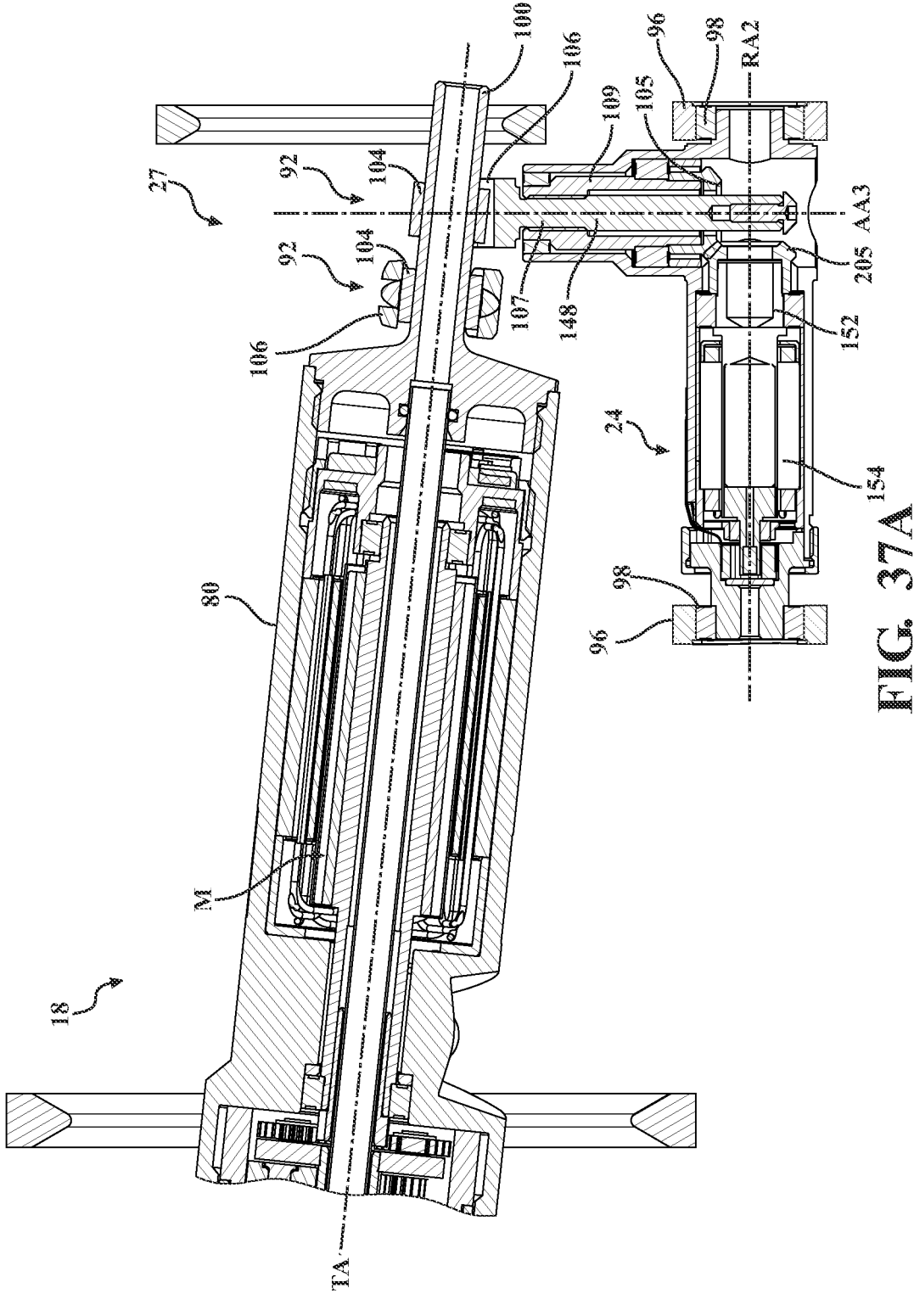
FIG. 37A-37C illustrates partial cross section views of the proximal actuator of the proximal actuator assembly and tool support in various degrees of extension in accordance with the first configuration of the robotic instrument.
Figure 37B:
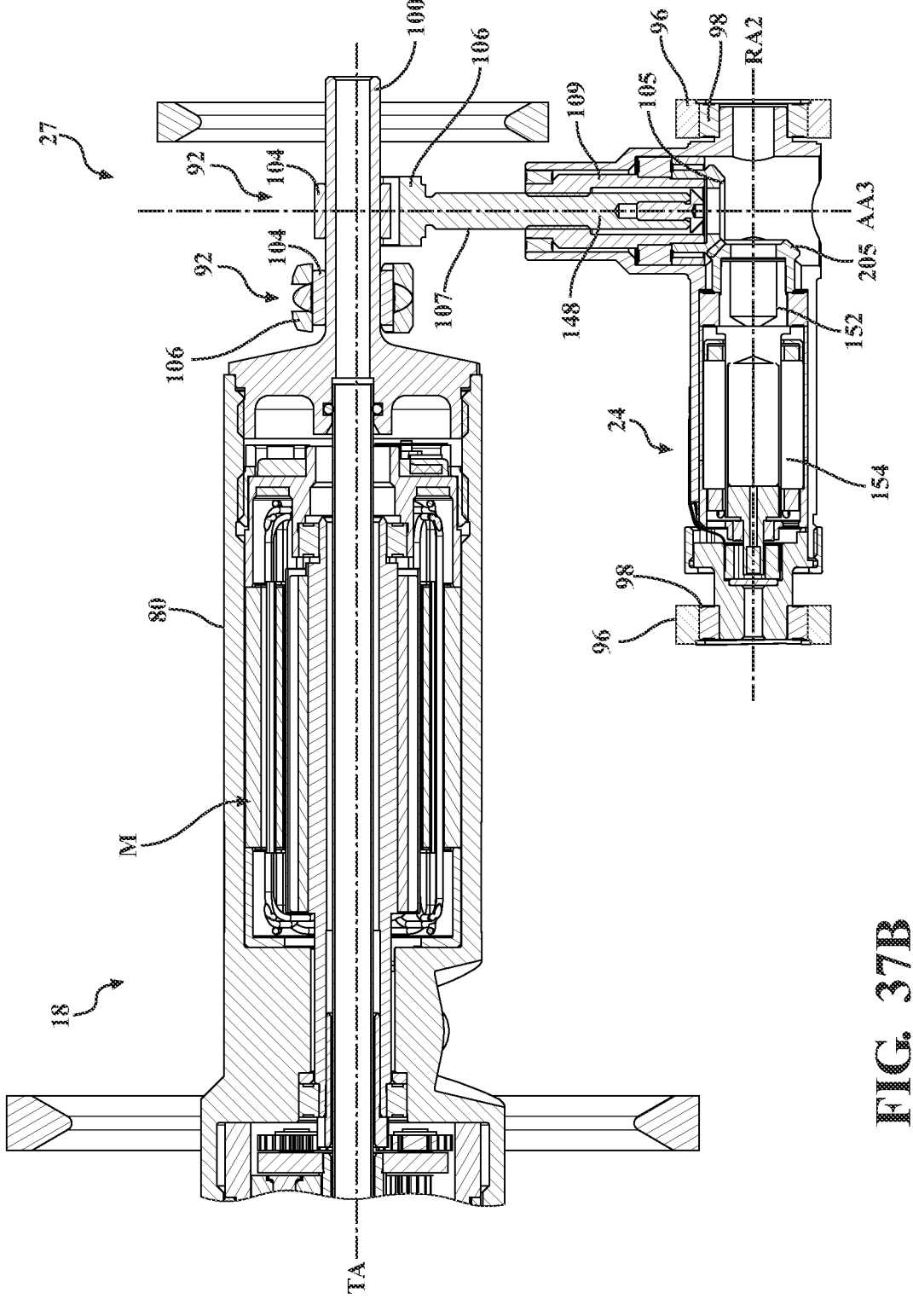
Figure 37C:
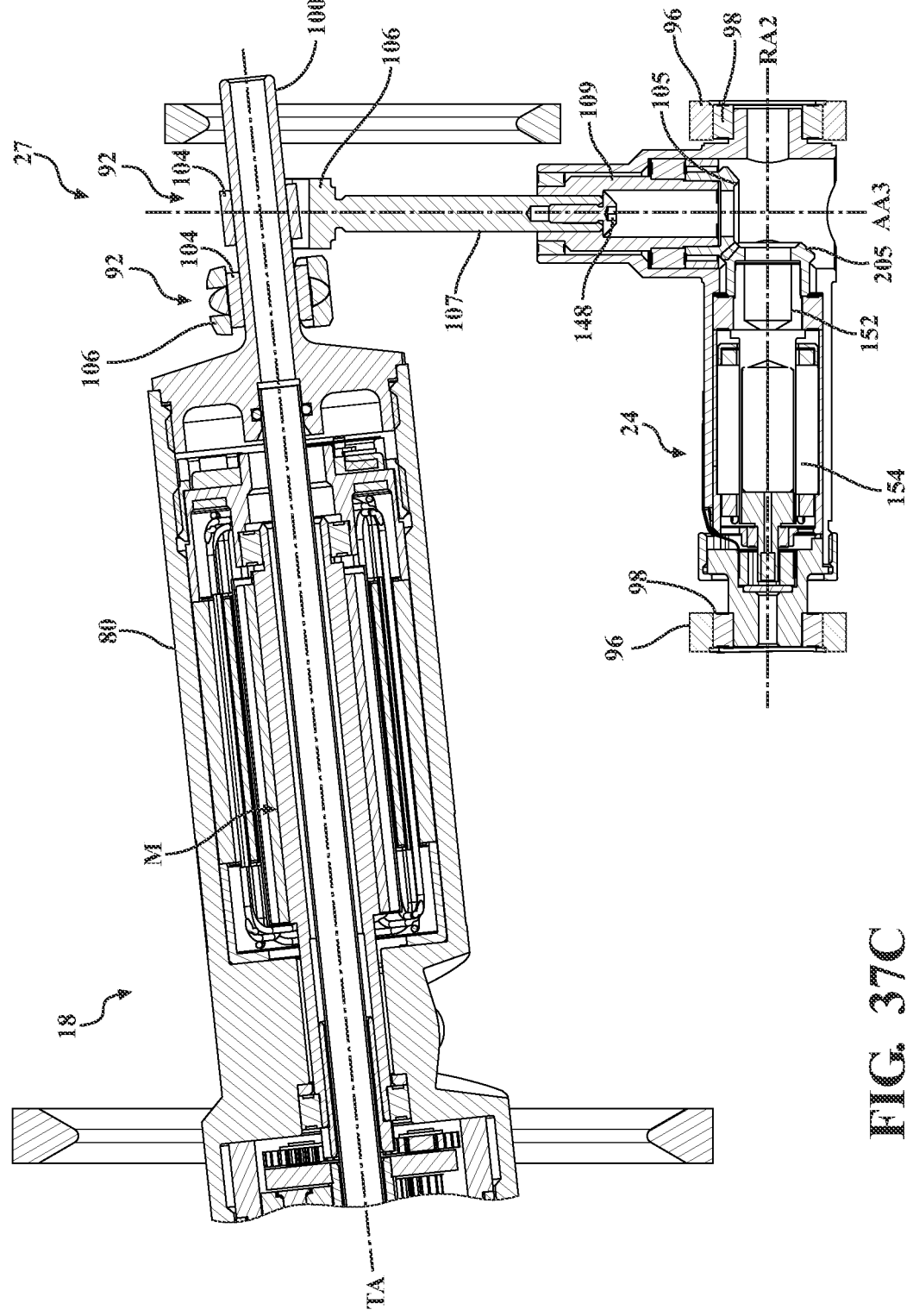

FIGS. 37A to 37C illustrate partial cross sections of actuator 24 and various positions of the tool support 18 as the pivot yoke 106 is translated via the actuator 24. FIG. 37A depicts the tool support 18 pitched upwards in the distal direction in the present view. The pivot yokes 106 are retracted showing the threaded rod 107 through the hollow driveshaft 109 and bevel gear 105. FIGS. 37A-37C display the pivot yoke 106 and threaded rod 107 of the proximal actuator 24, hiding distal actuator 23 and the corresponding pivot yoke 106 and threaded rod 107 to better show the change in movement of the actuator 24 as the tool support 18 is moved. Although distal actuator 23 is hidden in these views, the pivot yoke 106 and threaded rod 107 of actuator 23 adjusts in substantially similar manner as proximal actuator 24. In FIG. 37A, the pivot yoke 106 is in contact or near contact with the hollow driveshaft 109 representing a physical mechanical stop on one end of the range of travel of actuator 24. FIG. 37B shows the tool support 18 at a relative level position where the pivot yoke 106 is extended by threaded rod 107, and driven by drive shaft 109 when the bevel gears 105, 205 are rotated by actuator 24. FIG. 37C depicts the tool support 18 pitched distally downward with the proximal pivot yoke 106 and threaded rod 107 of actuator 24 fully extended in the present view. The threaded rod 107 is stopped from passing through the hollow driveshaft 109 by stop 148. In this example, stop 148 is a threaded member that is received by the threaded rod 107. The stop 148 includes a retention feature, seen here as a widened head, to prevent the threaded rod 107 and the connected pivot yoke 106 from passing completely through the hollow driveshaft 109. The stop 148 interfaces with a narrowed portion of the hollow driveshaft 109, physically preventing the threaded rod 107 from translating any further. Although not shown in FIGS. 37A-37C, actuator 23, along with the distal pivot yoke 106, threaded rod 107, and hollow drive shaft 109 are similarly moved.

Figure 36:
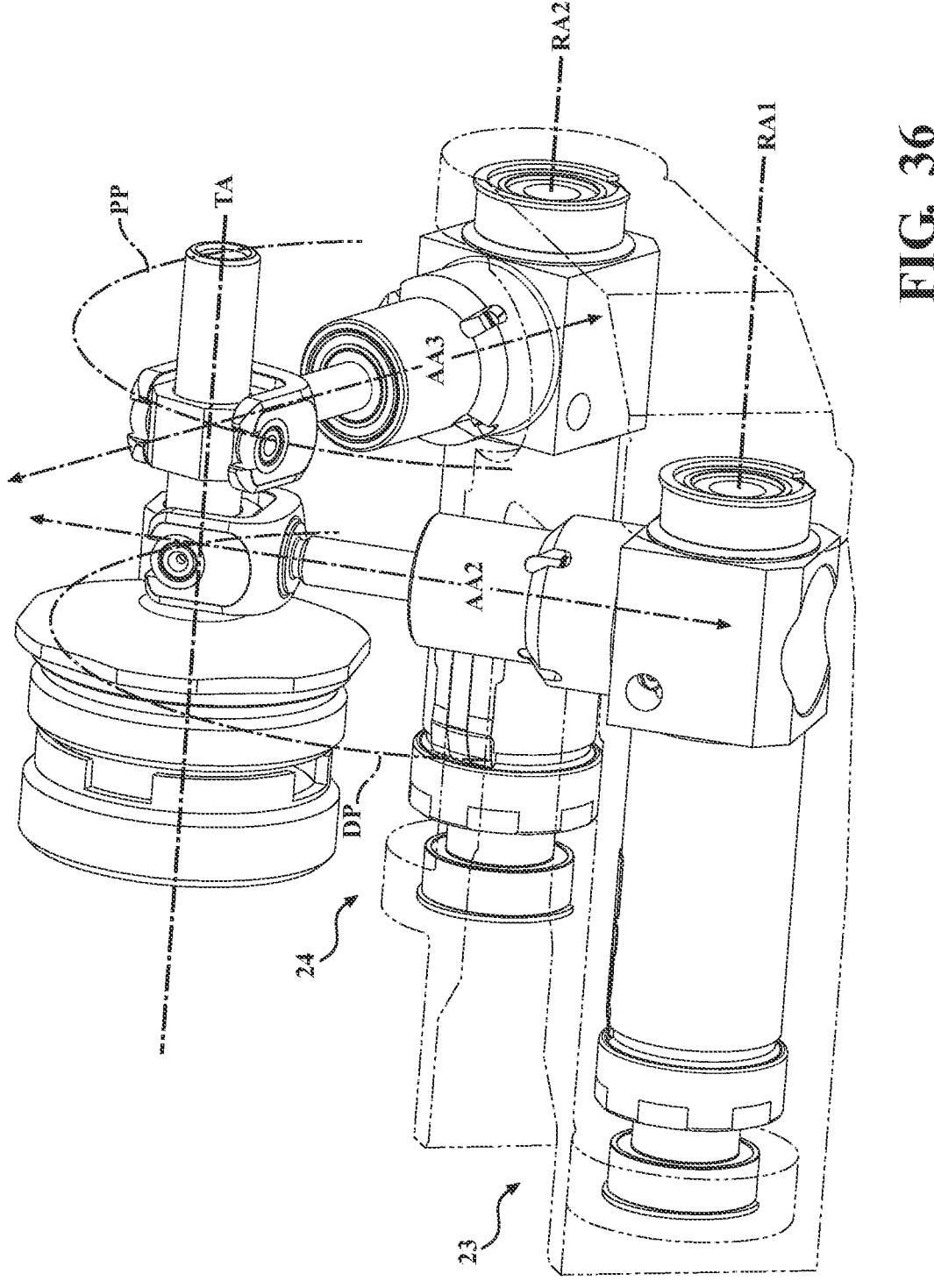
FIG. 36 illustrates a partial rear perspective view of the tool support with the distal actuator plane and proximal actuator plane portrayed in accordance with the first configuration of the robotic instrument.

The proximal linkage 27 connects with the hand-held portion 16 at the second passive joints 94. The second passive joints 94 connect actuators 23, 24 to the hand-held portion 16 at actuator mounts 96. Each of the actuators 23, 24 include a base 102 which forms a portion of the second passive joints 94. Each base 102 is connected to the hand-held portion 16 at actuator mounts 96. The actuator mounts 96 is configured to receive a portion of the actuator 23, 24. The actuator mounts 96 may function to anchor the actuator 23, 24 to the hand-held portion 16, while allowing actuators 23, 24 to spin freely about RA1 and RA2, respectively. One or more bearings 98 may be positioned within a bore of the actuator mounts 96 to receive the actuators 23, 24, allowing the actuators 23, 24 to rotate relative to the hand-held portion 16, changing the length and the angle of the pivot yokes 106 as the actuators 23, 24 are adjusted, moving the tool support 18 between positions. The actuator mounts 96 position each of the actuators 23, 24. Actuator motors 200 are aligned with the actuator mounts 96 defining the radial axes RA1, RA2 which the actuators 23, 24 rotate about when the yokes are extended and retracted to position the tool support 18. The second passive joints 94 rotate about rotational axes RA1, RA2. Rotational axes RA1 and RA1 are parallel to the remote axis of motion RAM. As can be seen in FIGS. 33 and 36, actuators 23, 24 are positioned in offset parallel planes. Furthermore, rotational axes RA1 and RA2 are offset from either side of the mid-plane of the hand-held portion. In some configurations, AA2 and AA3 may be substantially perpendicular when the instrument is in the home position. This ensures that the radii of the distal and proximal actuators 23, 24 will sufficiently intersect each other. As seen best in FIGS. 33 and 36, actuator 23 is mounted distal to actuator 24. Actuator 23 may also be referred to as the distal actuator 23. A distal actuator plane DP is defined by the radius formed from the threaded rod 107 extending from the distal actuator 23. Actuator 24 may also be referred to as the proximal actuator 24. A proximal actuator plane PP is defined by the radius formed from the threaded rod 107 extending from the proximal actuator 24. The actuators 23, 24 are axially fixed within actuator mounts 96 of the hand-held portion 16, allowing the actuators 23, 24 to rotate but remain stationary in a longitudinal direction, maintaining their location in offset planes. As best seen in FIG. 33 and FIG. 36, active axes AA2 and AA3 each extend from radial axes RA1 and RA2 along threaded rods 107. The plane in which actuator 23 rotates about RA1 (corresponding to AA2) is the distal plane DP, which is normal to RA1. The plane in which actuator 24 rotates about RA2 (corresponding to AA3) is the proximal plane PP, which is normal to RA2. The actuator mounts 96 may be apertures in certain configurations.

Figure 35:
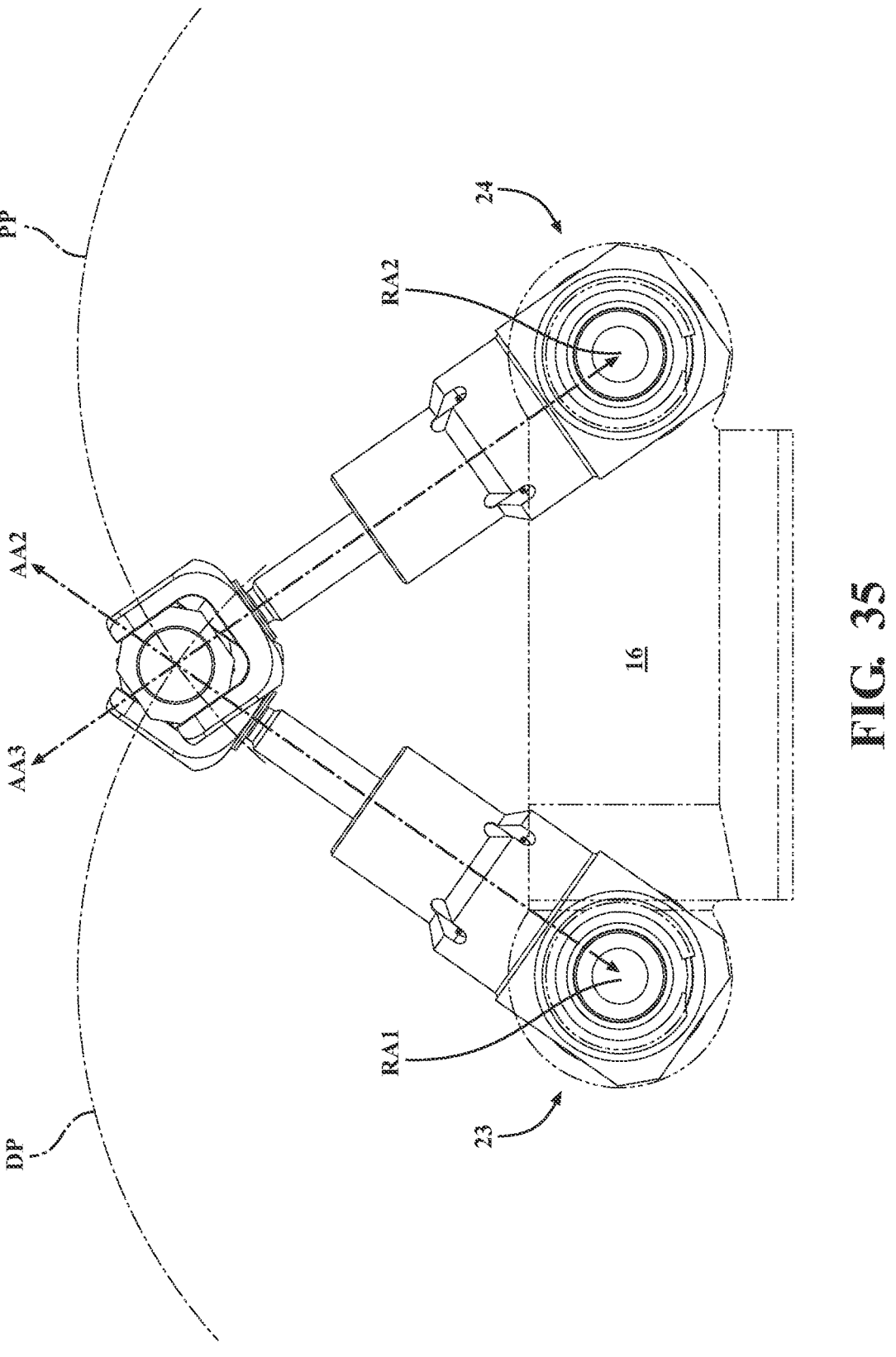
FIG. 35 illustrates a partial rear view of the tool support with the distal actuator plane and proximal actuator plane portrayed in accordance with the first configuration of the robotic instrument.

The actuators 23, 24 work to move the proximal linkage 27, which moves the proximal end of the tool support 18 in a plurality of degrees of freedom. As actuators 23, 24 adjust the length of their respective threaded rods 107 along active axes AA2, AA3, the tool support 18 is moved, changing the tool axis TA. As the actuators 23, 24 are commanded to adjust the threaded rods 107 to different lengths or radii, the bases 102 of the actuators 23, 24 are rotated about RA1 and RA2, rotating the elbow 103, threaded rod 107, and yoke 106. Since actuators 23, 24 are spaced apart on different axes and lay in different planes longitudinally, each actuator 23, 24 has their own path of movement which intersects at the positioning post 100 (FIGS. 35 and 36). Each of the active axes AA2 and AA3 each have a radius of movement defined by the threaded rod 107 about their respective radial axis RA1, RA2, and thereby the threaded rods 107 extend and retract along the distinct axes AA2, AA3 relative to RA1, RA2. Actuators 23, 24 each adjust the length/radius of the threaded rods 107 from RA1, RA2, which results in movement of the pivot yokes 106 along AA2, AA3. The instrument controller 28 adjusts the threaded rods 107 and pivot yokes 106 to different intersections of the radii extending along AA2 and AA3 from RA1 and RA2 to position the tool support 18 at the commanded position. As can be seen in FIGS. 35 and 36, the intersection of AA2, AA3 with the positioning post 100 (corresponding to the tool axis TA) is dependent on the lengths which each actuator 23, 24 extends their respective threaded rod 107. In this view, the actuators 23, 24 are at a home position with each threaded rod 107 and pivot yoke 106 extended the same length. The length the threaded rod 107 extends directly corresponds to a radius from RA1, RA2. As the pivot yokes 106 are extended and retracted by the threaded rods 107 along AA2 and AA3, respectively, the positioning post 100 is moved, positioning and orienting the tool support 18. Positioning post 100 extends along the tool axis TA. As actuators 23, 24 are actuated, the positioning post 100 and corresponding tool axis TA position and/or orientation is changed. The extension and retraction of the threaded rods 107 along AA2 and AA3 relative to the base 102 moves each pivot yokes 106, moving the post slides 104. The post slides 104 are re-positioned as a result of the pivot yokes 106 moving. The movement of the post slides 104 result in movement of the positioning post 100, causing the tool support 18 to change position and/or orientation. As a result of the threaded rods 107 extending and/or contracting, the actuators 23, 24 are rotated about RA1, RA2, changing the angular position of each actuator 23, 24 as the tool support 18 is moved relative to the hand-held portion 16.

Figures 6A, 6B, 6C:
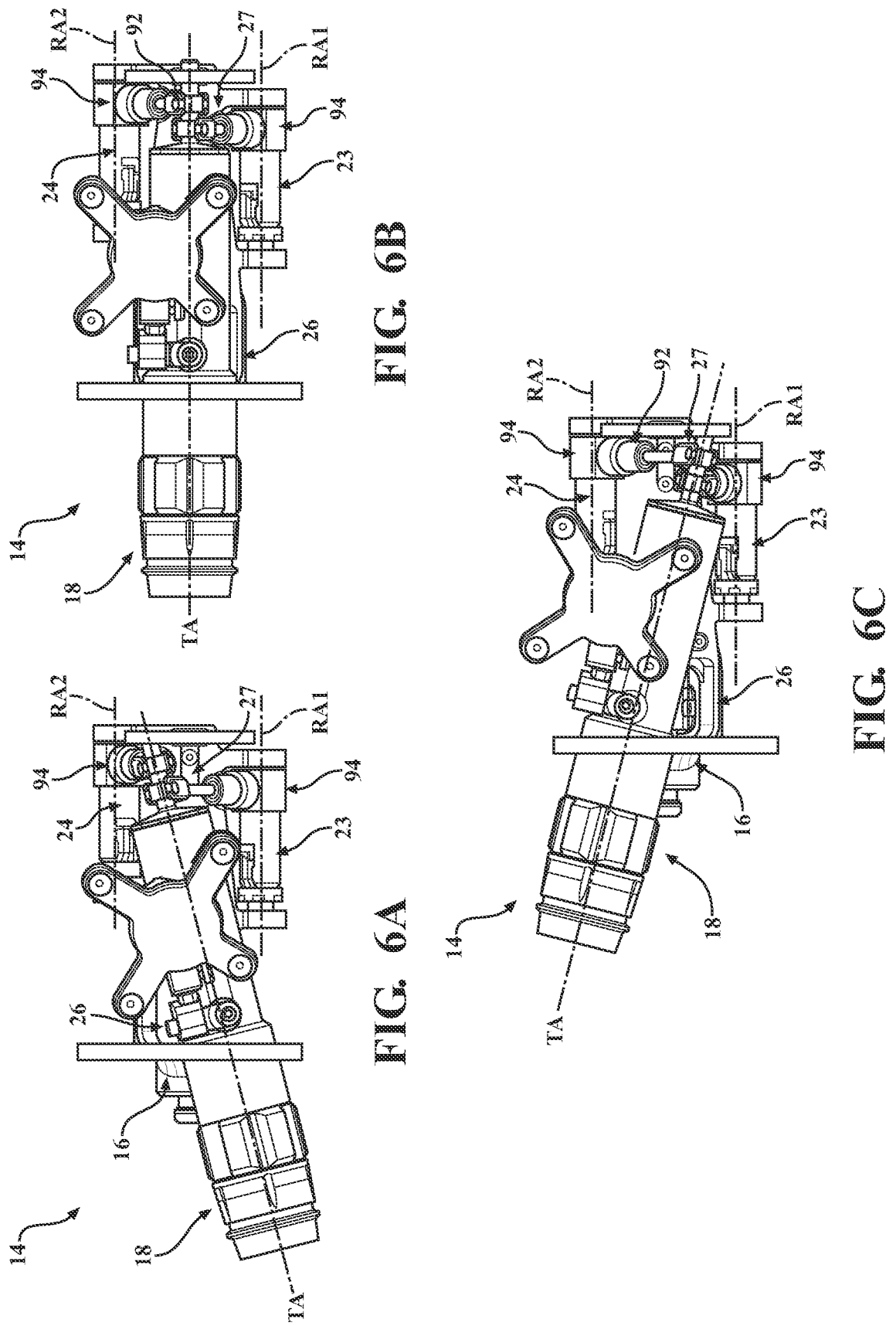
FIGS. 6A-6C are illustrations of various yaw orientations of the first configuration of the robotic instrument.
Figures 7A, 7B, 7C:
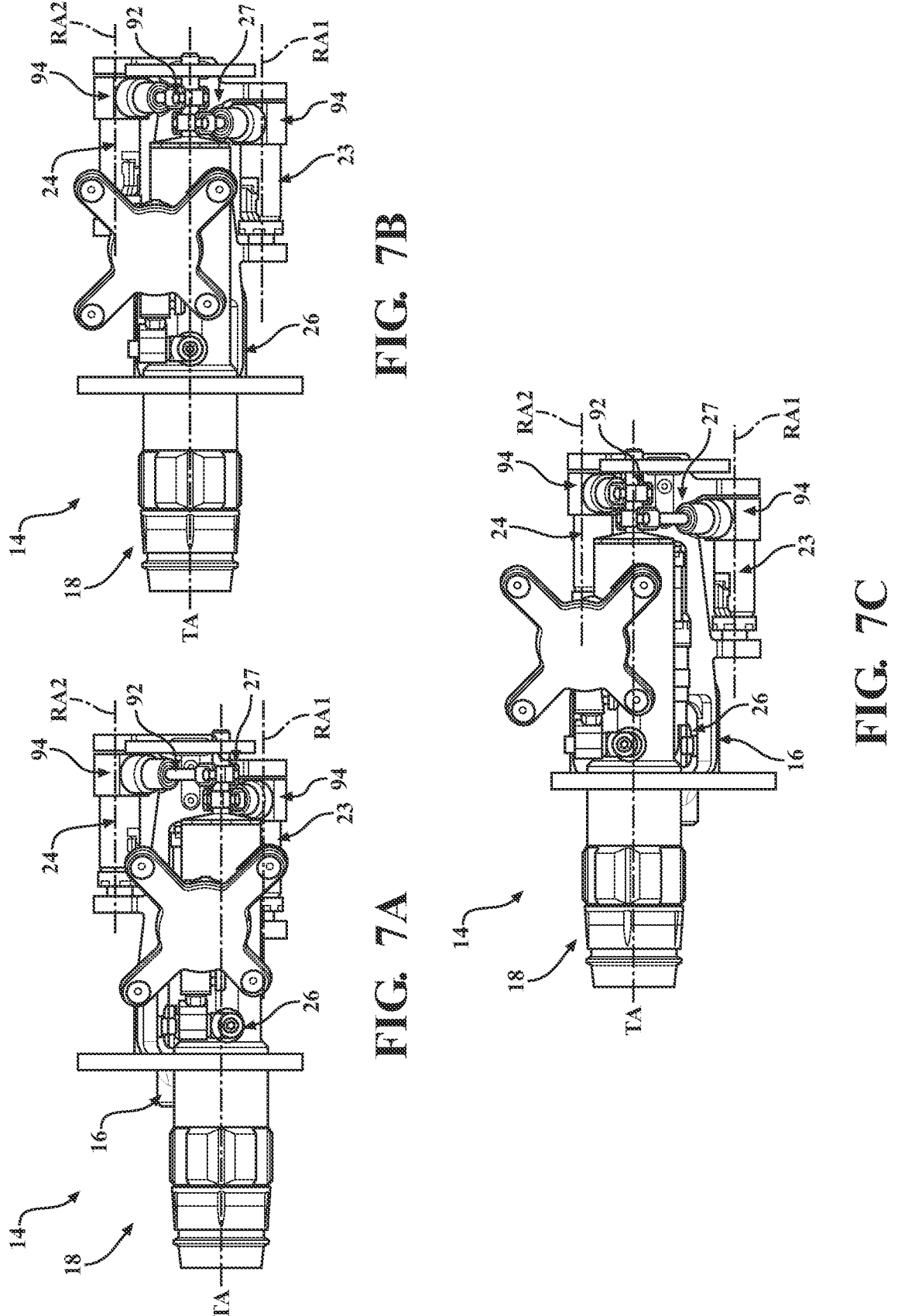
FIGS. 7A-7C are illustrations of various side-to-side translation positions of the first configuration of the robotic instrument.

By extending or retracting actuators 23, 24, the positioning post 100 moves the tool support 18. Similar to the distal linkage 26, as the actuators 23, 24 are actuated, the tool support 18 is positioned as a result of the individual movement of the actuators, working in concert. As shown in one example, turning back to FIGS. 6A-6C, the instrument 14 is shown transitioning between positions with a yaw movement. FIG. 6A illustrates the robotic instrument 14 with the distal end to left and the proximal end positioned to the right. In order to achieve this movement, the proximal linkage 27 must extend actuator 23 and retract actuator 24, rotating each actuator 23, 24 about axes RA1, RA2, in order to move the positioning post 100 to the right. Conversely, in order to achieve the yaw movement of FIG. 6C, the proximal linkage 27 must retract actuator 23 and extend actuator 24, rotating each actuator 23, 24 about axes RA1, RA2, in order to move the positioning post 100 to the left.

Figures 4A, 4B:
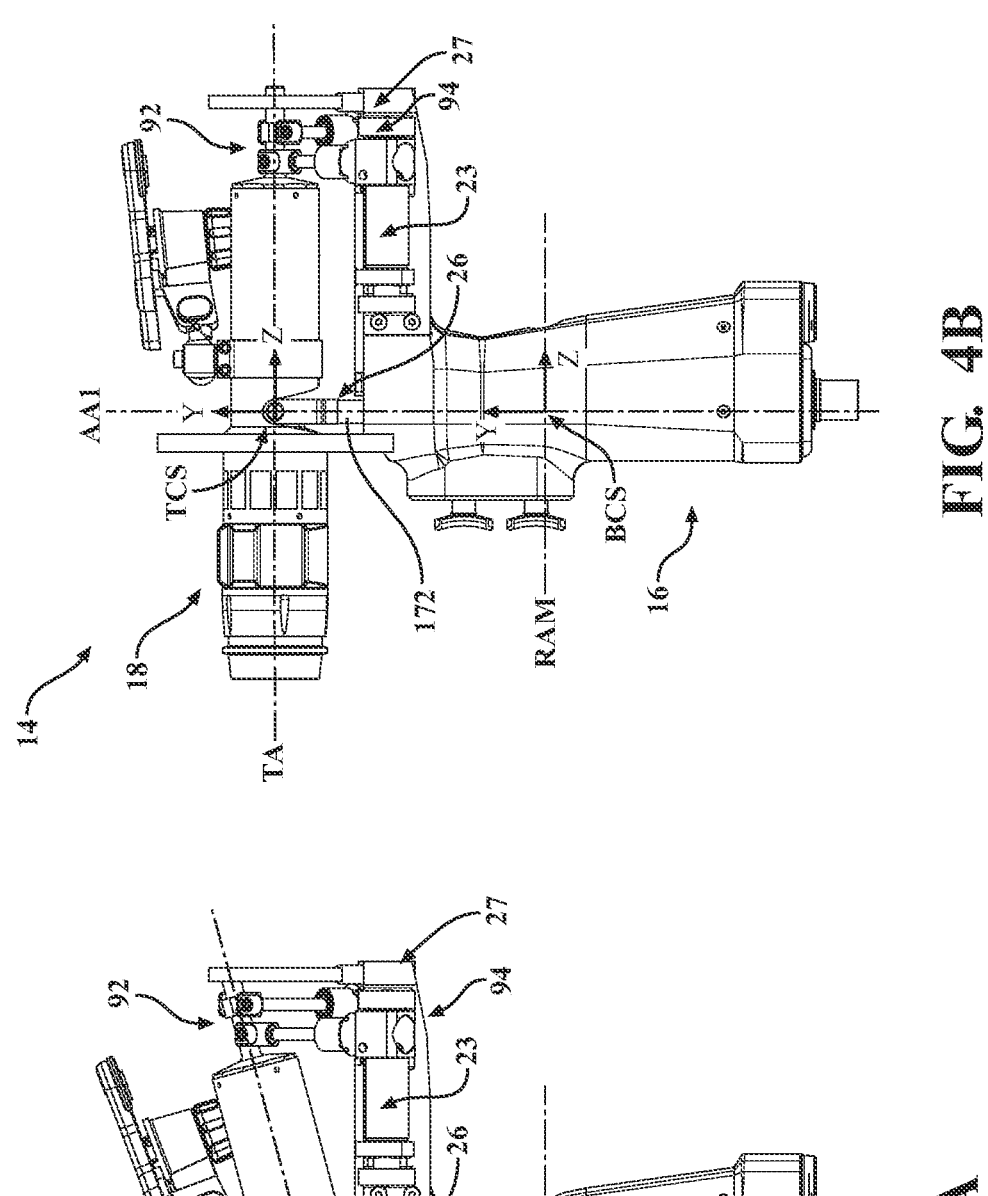
FIGS. 4A-4C are illustrations of various pitch orientations of the first configuration of the robotic instrument.
Figures 4C, 5A:
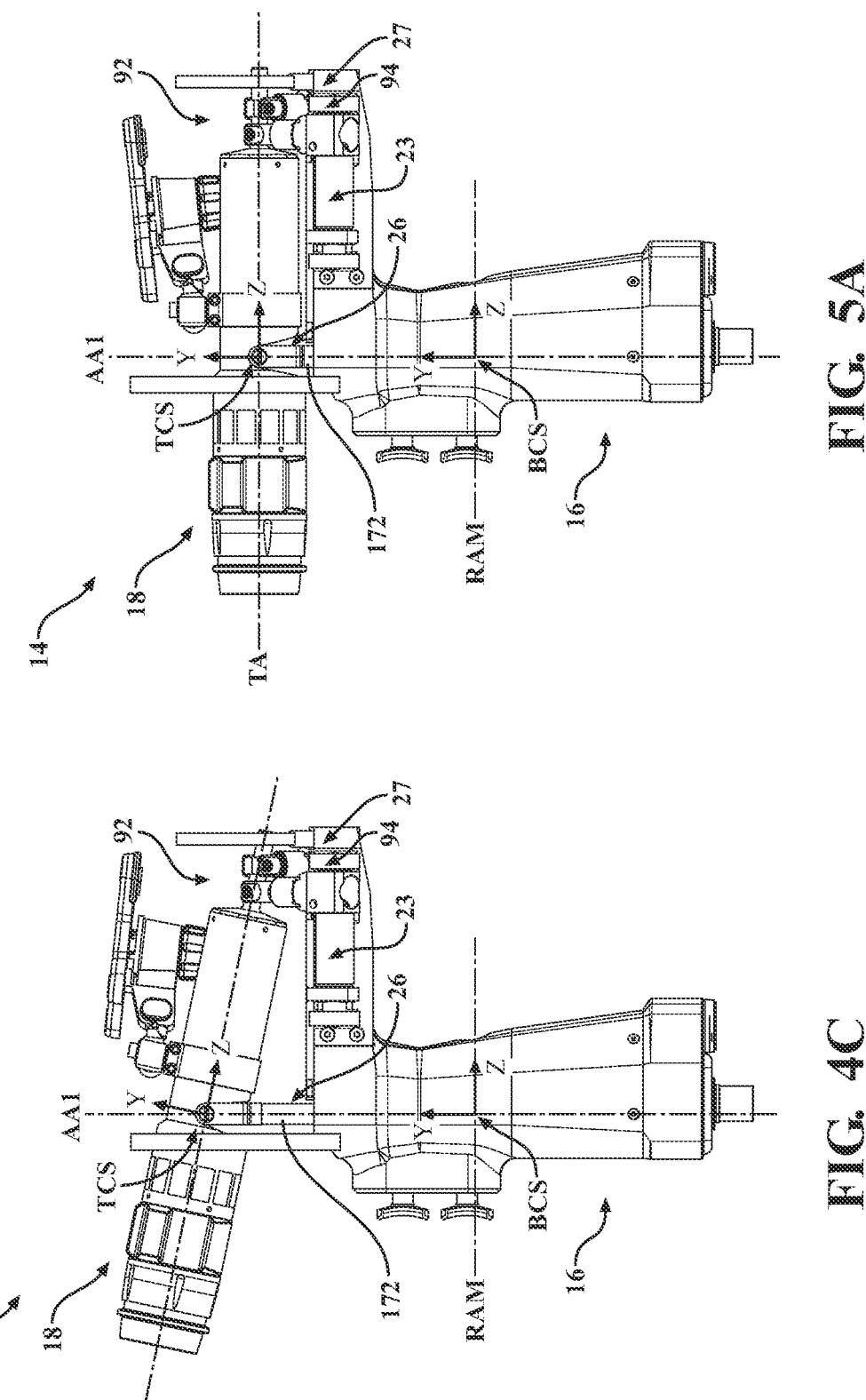
FIGS. 5A-5C are illustrations of various elevation translation positions of the first configuration of the robotic instrument.
Figures 5B, 5C:
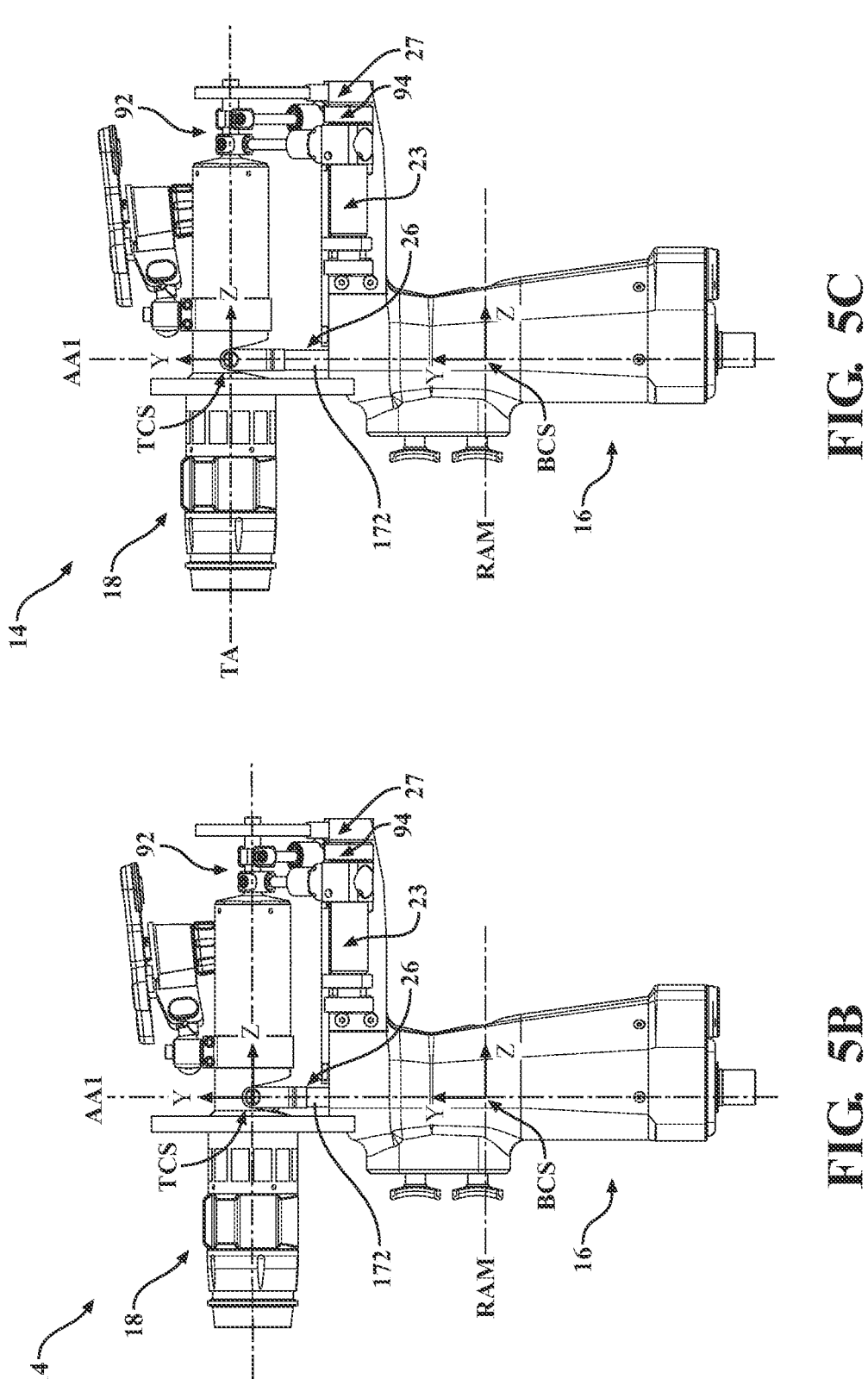

The distal linkage 26 and the proximal linkage 27 work in concert with one another to move the tool support 18 relative to the hand-held portion 16 in order to adjust the tool axis TA. As mentioned above, the robotic instrument 14 is configured to be controlled to maintain a target trajectory. In order to maintain the target trajectory TTRAJ, the distal portion and the proximal portion of the tool support 18 must be adjusted in unison. Compound, cooperative movements of all the actuators 21, 22, 23, 24, such as shown in FIGS. 4A-8C are required. For example, in order to achieve a pitch movement such as seen in FIGS. 4A, the lift assembly 86 of the distal linkage 26 has retracted the anchor post 172, whereas the proximal linkage 27 has actuators 23, 24 extended. Conversely, FIG. 4C illustrates a pitch movement in the opposite direction, having the lift assembly 86 of the distal linkage 26 extending the anchor post 172, whereas the proximal linkage 27 has actuators 23, 24 at least partially retracted. As each actuator 21, 22, 23, 24 is commanded, the tool support 18 is moved in response. Additionally, as the actuators 21, 22, 23, 24 move the tool support 18, the positioning post 100 is moved relative to the post slides 104. This slight movement of the tool support 18 relative to the proximal linkage 27 allows the tool support 18 to move smoothly between positions and orientations. This slight movement is best shown in FIGS. 4A-4C and FIGS. 6A-6C.

Figure 38:
FIG. 38 is a rear view of the first configuration of the robotic instrument, illustrating the alignment guides.

Turning now to FIG. 38 which depicts a proximal end view of the robotic instrument 14. The instrument 14 includes alignment guides 66, 68 attached to the hand-held portion 16 and surrounding the tool support 18. The alignment guides 66, 68 provide an operator with visual indication of the pose of the tool support 18 relative to the hand-held portion 16 during operation of the hand-held robotic instrument 14. Accordingly, the alignment guides 66, 68 provides visual indication to the operator of required changes in pitch, yaw, elevation translation, and side-to-side translation of the hand-held portion 16 to achieve the desired pose of the tool 20 while affording the plurality of actuators 21, 22, 23, 24 with maximum adjustability to maintain the tool 20 on the target trajectory TTRAJ. Particularly, when in the home position, the amount of adjustability of the actuators 21, 22, 23, 24 is maximized to keep the tool 20 at a desired pose. The alignment guides 66, 68 are coupled to the hand-held portion 16 and at least partially surround the tool support 18 for guiding the user as to how to move the hand-held portion 16 to provide the instrument 14 with sufficient adjustability by keeping the actuators 21, 22, 23, 24 near their home positions or other predetermined positions. In some configurations, at least a portion of the tool support 18 is relatively centered within the alignment guides 66, 68 when the actuators 21, 22, 23, 24 are in their respective home positions, such as shown in FIG. 38, indicating to a user that the instrument 14 has an optimal range of motion.

The alignment guides 66, 68 provide an operator a visual indication that the tool support 18 (and thus the tool axis TA) has a desired range of motion relative to the hand-held portion 16. Particularly, when in the home position, the amount of adjustability of the actuators 21, 22, 23, 24 is maximized to keep the tool 20 at a desired pose. The tool support 18 may be axially aligned with the first alignment guide and the second alignment guide when the tool support is within the optimal range of motion. The tool support 18 (and corresponding tool axis TA) and the first alignment guide 66 and second alignment guide 68 may be misaligned when the hand-held portion 16 is in a pose that does not provide the optimal range of motion, the alignment guides 66, 68 providing visual indication that the hand-held portion 16 is in a pose that does not provide the tool support with the optimal range of motion.

The alignment guides 66, 68 are a first alignment guide 66 and a second alignment guide 68. In some examples, such as shown in FIG. 38, the first alignment guide 66 extends from a first portion of the hand-held portion 16 and surrounds at least a first portion of the tool support 18, and the second alignment guide 68 extends from a second portion of the hand-held portion 16 a second portion of the tool support 18. The first alignment guide 66 and second alignment guide 68 are spaced axially from each other. The first alignment guide 66 and the second alignment guide 68 are arranged and sized relative to the tool support 18 such that the first alignment guide 66 and the second alignment guide 68 do not collide with the tool support 18 at any point between the first position and the second position of each of the plurality of actuators 21, 22, 23, 24. As shown throughout the Figures, alignment guides 66, 68 have a ring shape, however, other shapes are contemplated. The first alignment guide 66 has a larger diameter than the second alignment guide 68. In some examples, such as in FIG. 38, the alignment guides 66, 68 have a ring shape. In some examples, the first alignment guide 66 and the second alignment guide 68 are coaxial. In some examples, the first alignment guide 66 is positioned distal to the first actuator assembly 400.

Figure 39:
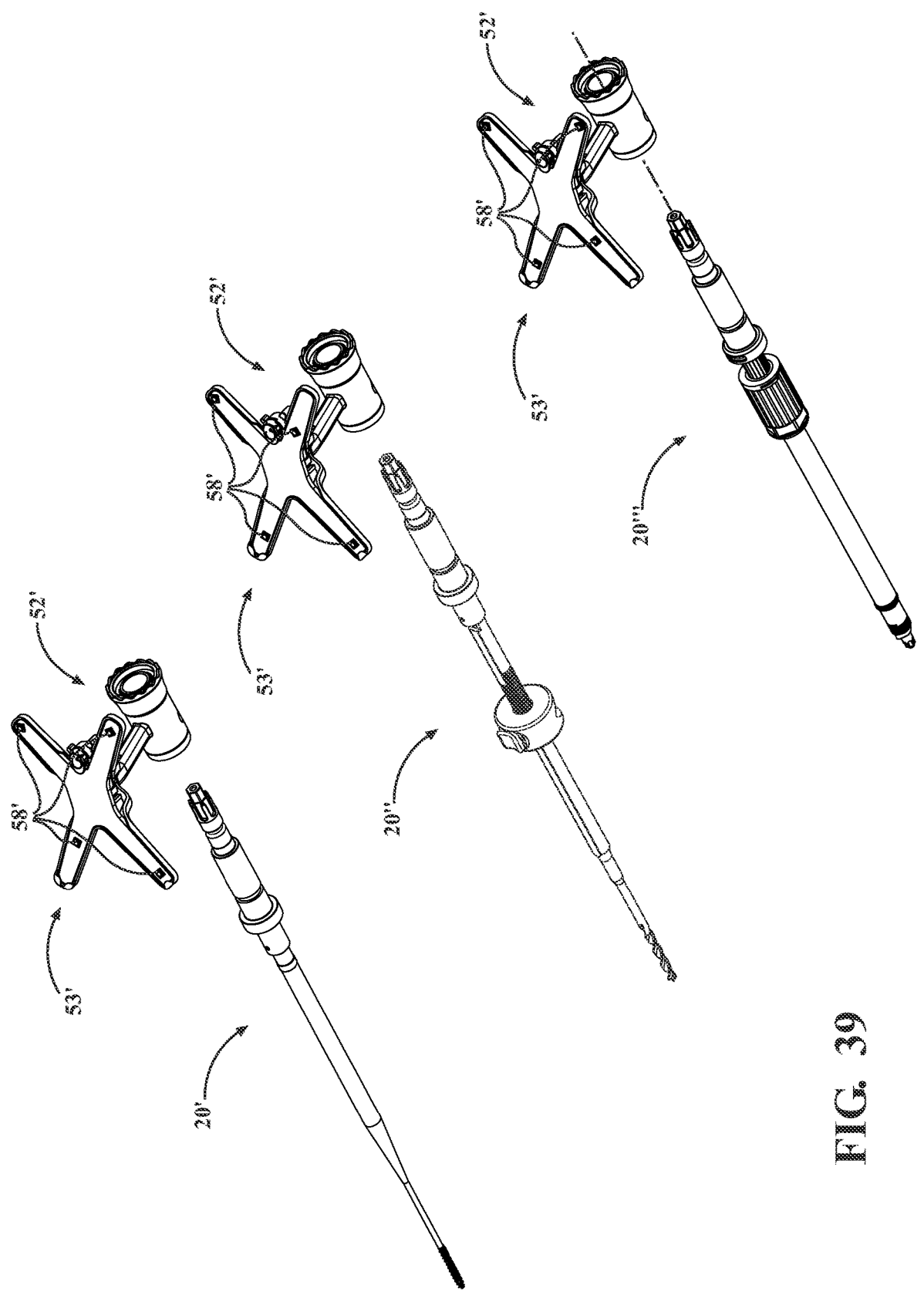
FIG. 39 is a perspective view of a surgical kit including a plurality of different end effectors, each of the end effectors including a rotational adapter and a tracker that is associated with the end effector and identifiable by the navigation system.

Referring to FIG. 39, as mentioned, the tool tracker 52' may be affixed to any suitable component of the instrument, such as to the tool 20', 20", 20'", and may be considered a rotational tracking adapter. The tool 20' is depicted as a tap; tool 20" depicted as a twist drill; and tool 20'" depicted as a screwdriver. The tool tracker 52' includes an array 53' that may rotate relative to the longitudinal axes of the tools 20', 20", and 20'". This allows the tools 20', 20", and 20'" to be rotated by the instrument without causing rotation of the array 53'. The tool tracker 52' may also be coupled to instrument by virtue of the proximal end of the tools 20', 20", and 20'" being engaged by the tool coupler assembly 84 of the instrument. In other words, the tool tracker 52' may be kept in position relative to the tools 20', 20", 20'". The array 53' can include the active markers 58', which may be active. The active markers 58' may include light emitting diodes (LEDs). Alternatively, the array 53' may have passive markers, such as reflectors, which reflect light emitted from the camera unit 46. Printed markers, or other suitable markers not specifically described herein, may also be utilized.

Alternative Configurations

Turning now to FIG. 40 to FIG. 43C, the present teachings provide for several examples of alternative actuator arrangements for moving the tool support 18 relative to the hand-held portion 16.

FIG. 40 and FIGS. 41A-41C illustrate a second exemplary configuration of a robotic instrument 14', including a third configuration of the proximal linkage 27'. The robotic instrument 14' includes a hand-held portion 16 connected with the tool support 18 through a distal linkage 26 and a proximal linkage 27'. The distal linkage 26 of the example shown in FIG. 39 incorporates the same distal linkage as described throughout the present disclosure including the lift assembly

86 and the angular movement assembly 90. In this version, the proximal linkage 27' includes the actuators 323, 325 are coupled to the hand-held portion 16. Actuator 323 is configured to control the length of the threaded rod 107 along axis AA2, thus controlling the length of the radius from RA1. Actuator 325 is configured to control the angular position of actuator 323 and, subsequently the threaded rod 107 about RA1. In this example, actuators 323, 325 are operatively coupled with the tool support 18 through a threaded rod 107 connected with a single pivot yoke 106 to post slide 104 engaged with the positioning post 100. Post slide 104 is disposed along the positioning post 100 of the tool support 18. Actuator 323 includes a pivot yoke 106 coupled to the post slide 104. The post slide 104 is pivotally connected to the pivot yoke 106. The post slide 104 has a throughbore disposed through the post slide 104 for receiving the positioning post 100 of the tool support 18. The post slide 104 is coupled with the pivot yoke 106.

Figure 40:
FIG. 40 is perspective view of a second configuration of the robotic instrument, with a second configuration of a proximal actuator assembly.
Figure 41:
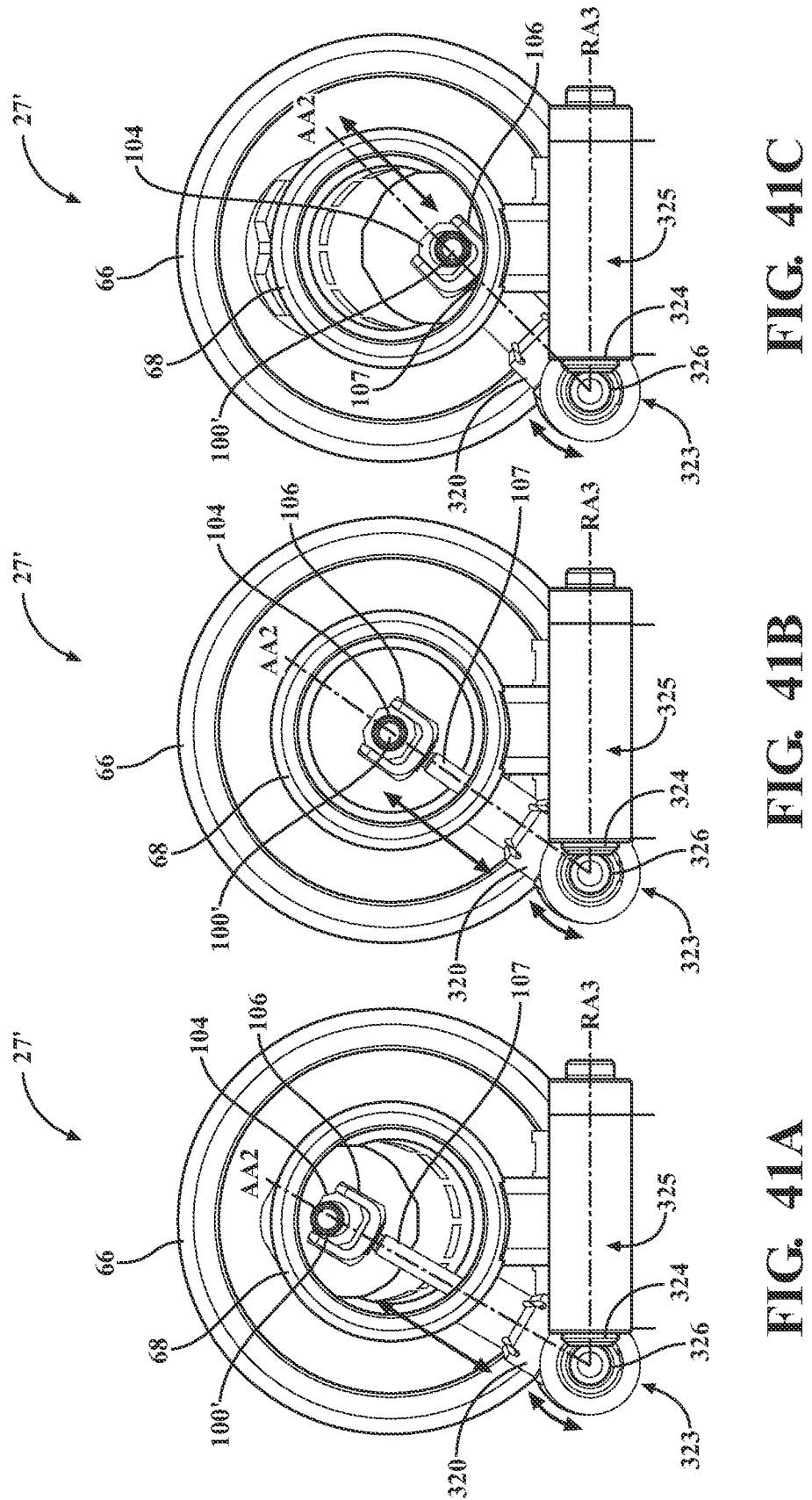
FIGS. 41A-41C illustrates rear views of the second configuration of the proximal actuator assembly as the tool support is placed in different poses.

Pivot yoke 106 extends from a threaded rod 107 extending into the base 320. The base 320 may house a gear set as described above with respect to FIGS. 37A-37C. In this example, the gear set may include a bevel gear which rotates about RA1 and a bevel gear which rotates around AA2 placed. As seen in FIG. 40, the threaded rod 107 defines active axis AA2. The second bevel gear may be positioned approximately 90 degrees relative to the bevel gear. The first and second bevel gear cooperate to transmit rotational movement from actuator 323 to axial movement of the threaded rod 107 along AA2. Although the bevel gears within base 320 are not shown, the arrangement is substantially similar to bevel gears 105, 205 shown in FIGS. 34 and FIGS. 37A-37C. The motor 200' of actuator 323 may positioned to one side of the hand-held portion 16. The motor 200' of actuator 323 defines the rotational axis RA1. The rotational axis RA1 may be parallel to a longitudinal axis of the tool support 18 and parallel to the remote axis of motion RAM at the home position. As the motor of actuator 323 spins the bevel gear about RA1, it causes rotation of the bevel gear about AA2 to extend and retract the threaded rod 107. As the threaded rod 107 is extended and retracted along AA2, the positioning post 100 is moved, changing the position and/or orientation of the tool support 18. The arrangement of actuator 323 may be substantially similar to actuator 23 as described above. With reference to FIG. 40 and FIGS. 41A-41C, an additional actuator 325 is included. Actuator 325 includes a motor 200' comprising a coil and a rotor (similar to actuators 23, 24 described above) and is connected with gear set 327. The motor 200' of actuator 325 may be positioned perpendicular to the longitudinal axis of the tool support at the home position. The motor 200' of actuator 325 defines a rotation axis RA3 perpendicular to rotation axis RA1.

Actuator 325 is operatively connected with the threaded rod 107 through actuator 323. Gear set 327 of actuator 325 may include a bevel gear 326 which is coupled with the first bevel gear 324 coupled with actuator 323. Actuation of actuator 325, in the present example, is configured to rotate base 320 to a plurality of angular positions about rotational axis RA1. When actuator 325 is commanded by the control system 60 to actuate, the actuator 325 rotates the second bevel gear 326, which rotates bevel gear 324, articulating actuator 323 and base 320 between a plurality of angular positions, such as in FIGS. 41A-41C. The gear set 327 may further include one or more additional gears for increasing or decreasing rotational force and/or speed.

As described above, actuators 323, 325 include a coil and a rotor, the coil and rotor forming an actuator motor. Each of the actuators 323, 325 include an actuator motor 200'. In some examples, actuators 323, 325 may have a multi-stage planetary gear set to provided sufficient torque. The actuator motors 200' of actuators 323, 325 each define a motor axis. In FIGS. 40 and 41A-41C, the motor axes correspond with rotational axis RA1 and RA3. The motor axis corresponding to RA1 is perpendicular to the axis defined by threaded rod 107 corresponding to AA2. Particularly, the motor axis of actuator 323 corresponds with RA1, and the motor axis of actuator 325 corresponds with RA3. Similarly, the actuator motor of actuator 325 is connected with a gear set comprising a first bevel gear 324 configured to rotate about RA3. The first bevel gear 324 is in communication with the second bevel gear 326, which is connected to and fixed with actuator 323 and base 320 and configured to rotate about RA1, rotating actuator 323 and base 320 when the second bevel gear 326 is actuated. The motor axis of actuator 323 is perpendicular to the motor axis of actuator 325. Similarly, the first bevel gear 324 is positioned approximately 90 degrees relative to the second bevel gear 326, the first bevel gear 324 configured to transfer rotational force from actuator 325 to the second bevel gear 326. The second bevel gear 324 rotates actuator 323 and base 320 about RA1 when actuated by actuator 325, rotating the actuator 323 and base 320 relative to the actuator mounts 96, moving the positioning post 100' and the tool support 18 to a desired pose. The motor axis of actuator 323 may be parallel to the remote axis of motion RAM.

Turning now to FIG. 41B, the proximal linkage 27' is illustrated with the tool support 18 at the home position with each of the actuators 323, 325 at their home position. To move from FIG. 41B to FIG. 41C, the threaded rod 107 is articulated about RA1 clockwise by actuator 325. Furthermore, actuator 325 is controlled to cause rotation of the first bevel gear 324 which rotates about RA3, subsequently rotating the second bevel gear 326 connected with actuator 323 and base 320 which rotate about RA1 relative to the actuator mounts 96. Furthermore, actuator 323 is actuated to retract the threaded rod 107, spinning the bevel gears located within base 320, retracting the threaded rod 107 relative to base 320, causing the positioning post 100' and the tool support 18 to move to the desired pose.

Turning to FIGS. 42 and 43A-43C, a third configuration of the robotic instrument 14" is shown. The third configuration of the instrument includes positioning links 330, 332 which are respectively coupled with actuators 423 and 424, keyed to their outputs. Each positioning link 330, 332 include a slot 334, 335 having a length and a concave surface defining the slot 334, 335. Riding within the slot 334, 335 may be a gimbal 336 having a generally spherical shape with an aperture for receiving the positioning post 100" configured to translate along a length of the slot 334, 335 as the tool support 18 is moved between a plurality of degrees of freedom relative to the hand-held portion 16. The gimbals 336 are positioned on the positioning post 100" and move the positioning post 100" (and the tool support 18) when the positioning links 330, 332 are moved. The positioning post 100" is configured to slide relative to the gimbals 336 and corresponding positioning links 330, 332 as the positioning links 330, 332 are moved by actuators 423, 424.

Each of the actuators 423, 424 include a base 430 connected to the hand-held portion 16 at actuator mounts 96. The actuators 423, 424 are selectively actuated, which causes articulation of the links about RA1. As the one or more of the positioning links 330, 332 are articulated, the gimbals 336 may slide within the slots 334, 335 defined by the of the positioning links 330, 332. Because the gimbals

336 are disposed about the positioning post 100", the sliding of the gimbals results in movement of the positioning post 100", which results in movement of the tool support 18 between positions. The actuators 423, 424 are mounted to the hand-held portion 16, and each of the actuator motors 200" defining radial axes RA1, RA2. In some examples, motors 200" of actuators 423, 424 may include a multi-stage planetary gear set to provided sufficient force and/or torque. The actuators 423, 424 are configured to rotate the positioning links 330, 332 about rotational axes RA1, RA2, which may be parallel to the remote axis of motion RAM. As can be seen in FIGS. 42 and 43A-43C, the positioning links 330, 332 are positioned in offset planes defining AA2 and AA3. Furthermore, rotational axes RA1 and RA2 are offset from one another such that AA2 and AA3 are substantially perpendicular when the instrument is in the home position. The offset of RA1 and RA2 ensures that the radii of the distal actuator 423 and proximal actuators 424 will sufficiently intersect each other. As best seen in FIG. 41A-41C, active axes AA2 and AA3 each extend from radial axes RA1 and RA2. The plane in which actuator 423 rotates about RA1 (corresponding to AA2) is the distal plane, which is normal to RA1. The plane in which actuator 424 rotates about RA2 (corresponding to AA3) is the proximal plane, which is normal to RA2.

Figure 42:
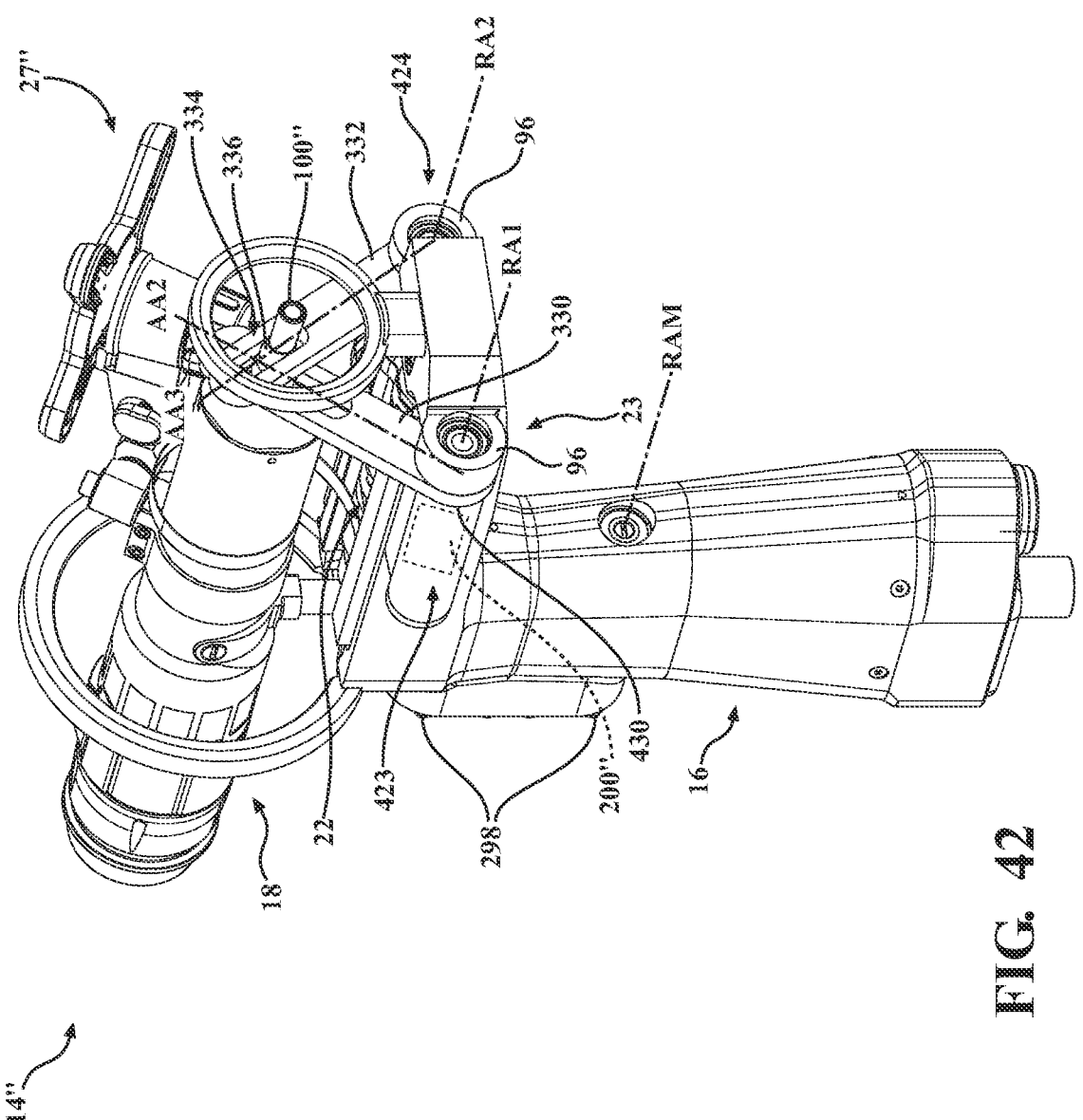
FIG. 42 is a rear perspective view of a third configuration of the robotic instrument with a third configuration of the proximal actuator assembly.
Figures 43A, 43B, 43C:
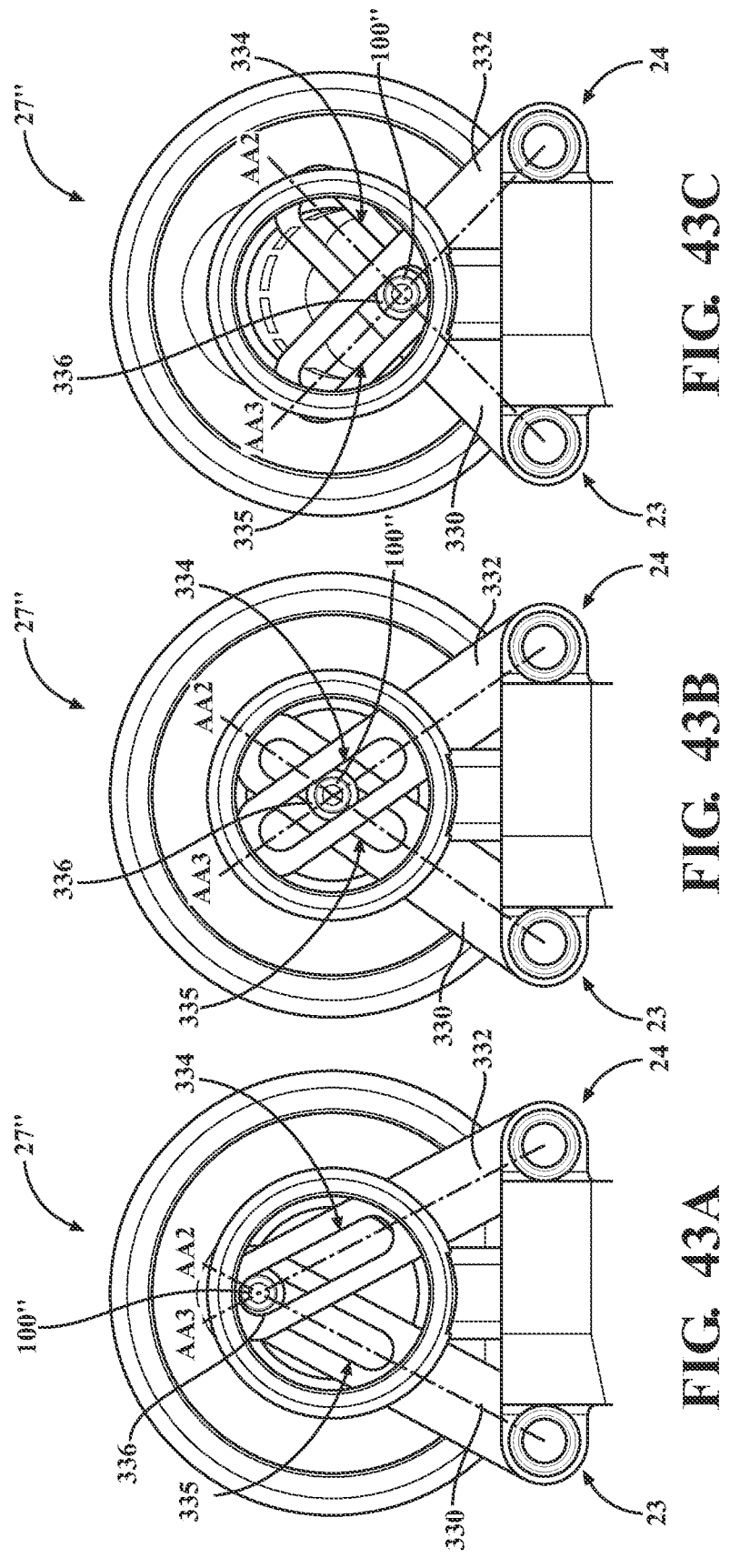
FIGS. 43A-43C illustrates rear views of the third configuration of the proximal actuator assembly as the tool support is placed in different poses.
Figure 44:
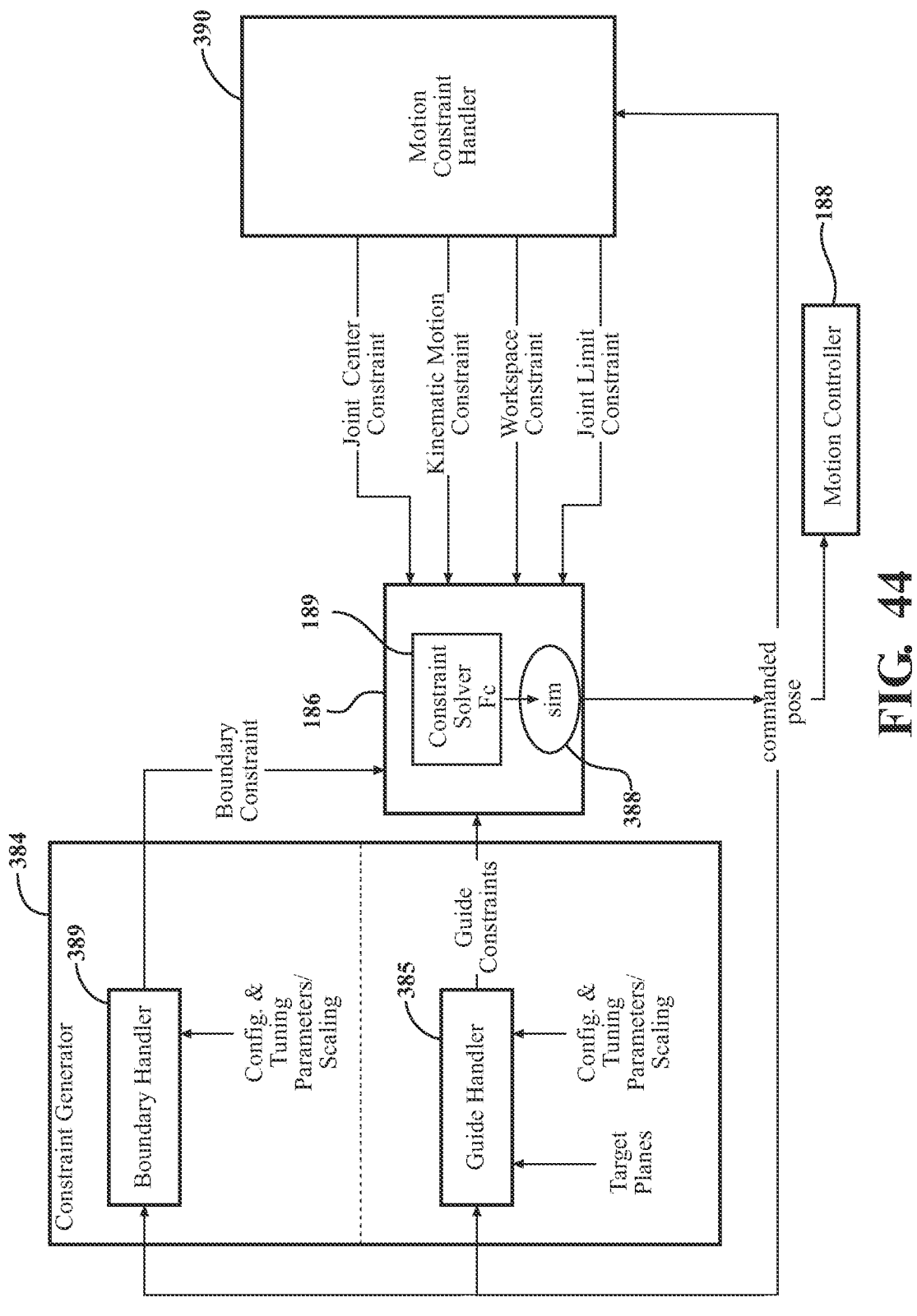
FIG. 44 is a block diagram of particular modules operable by the control system.

The actuators 423, 424 work to move the proximal linkage 27', which moves the proximal end of the tool support 18 in a plurality of degrees of freedom. As actuators 423, 424 are adjusted, which results in articulation of the linkages, and movement of the positioning post along active axes AA2, AA3, the tool support 18 is moved, changing the tool axis TA. As the actuators 423, 424 are commanded to different angles, the actuators 423, 424 rotate their respective rotors about RA1 and RA2, turning links 330, 332. Since actuators 423, 424 are spaced apart on different axes and the positioning links 330, 332 lay in different planes longitudinally, each actuator 423, 424 has their own path of movement which intersects at the positioning post 100" (FIGS. 42 and 43A-43C). Each of the active axes AA2 and AA3 each have a radius of movement about their respective radial axis RA1, RA2, and thereby translate the gimbals 336 along the slots 334, 335, corresponding with the distinct axes AA2, AA3 relative to RA1, RA2. Actuators 423, 424 each adjust the angular position of the respective positioning links 330, 332 about RA1, RA2, which results in movement of the gimbals 336 along AA2, AA3. The instrument controller 28 adjusts the actuators 423, 424 to move each gimbal 336 (and the positioning post 100") to different intersections of the slots 334, 335 along AA2 and AA3 from RA1 and RA2 to position the tool support 18 at the commanded pose. As can be seen in FIGS. 43A, 43B, and 43C, the intersection of AA2, AA3 with the positioning post 100 (corresponding to the tool axis TA) is dependent on the angular position of the positioning links 330, 332, which results in translation of the gimbals 336 to a commanded position. In FIG. 42B, the actuators 423, 424 are at a home position, the positioning post 100" located in the middle of slots 334, 335 of the positioning links 330, 332. The length of each of the slots 334, 335 of the positioning links 330, 332 corresponds to a radius from RA1, RA2. As the positioning post is moved along the length of the slots 334 of the positioning links 330, 332 along AA2 and AA3, respectively, the positioning post 100" is moved, positioning and orienting the tool support 18. Positioning post 100" extends along the tool axis TA. As actuators 423, 424 are actuated, the positioning post 100" and corresponding tool axis TA position and/or orientation is changed. The movement of the gimbals 336 along each slot

334, 335 result in movement of the positioning post 100", causing the tool support 18 to change position and/or orientation.

By changing the angle of each of the positioning links 330, 332 with actuators 423, 424, the positioning post 100" moves the tool support 18. Similar to the distal linkage 26, as the actuators 423, 424 are actuated, the tool support 18 is positioned as a result of the individual movement of the actuators, working in concert. As shown in one example, turning to FIGS. 42A and 42C, the instrument 14" is shown transitioning between positions with a pitch movement. FIG. 42A illustrates the robotic instrument 14 with the distal end of the tool support pointing downward and the proximal end positioned upward. In order to achieve the pitched movement of FIG. 42A, the proximal linkage must move the positioning post 100" upward by rotating positioning link 330 counterclockwise about RA1 and rotating positioning link 332 clockwise about RA2 to slide the positioning post 100" up along the slots 334, 335. Conversely, in order to achieve the pitched movement of FIG. 42C, the proximal linkage 27" must move the positioning post 100" downward by rotating positioning link 330 clockwise about RA1 and rotating positioning link 332 counterclockwise about RA2 to slide the positioning post 100" down along the slots 334, 335.

Controls

Figure 45:
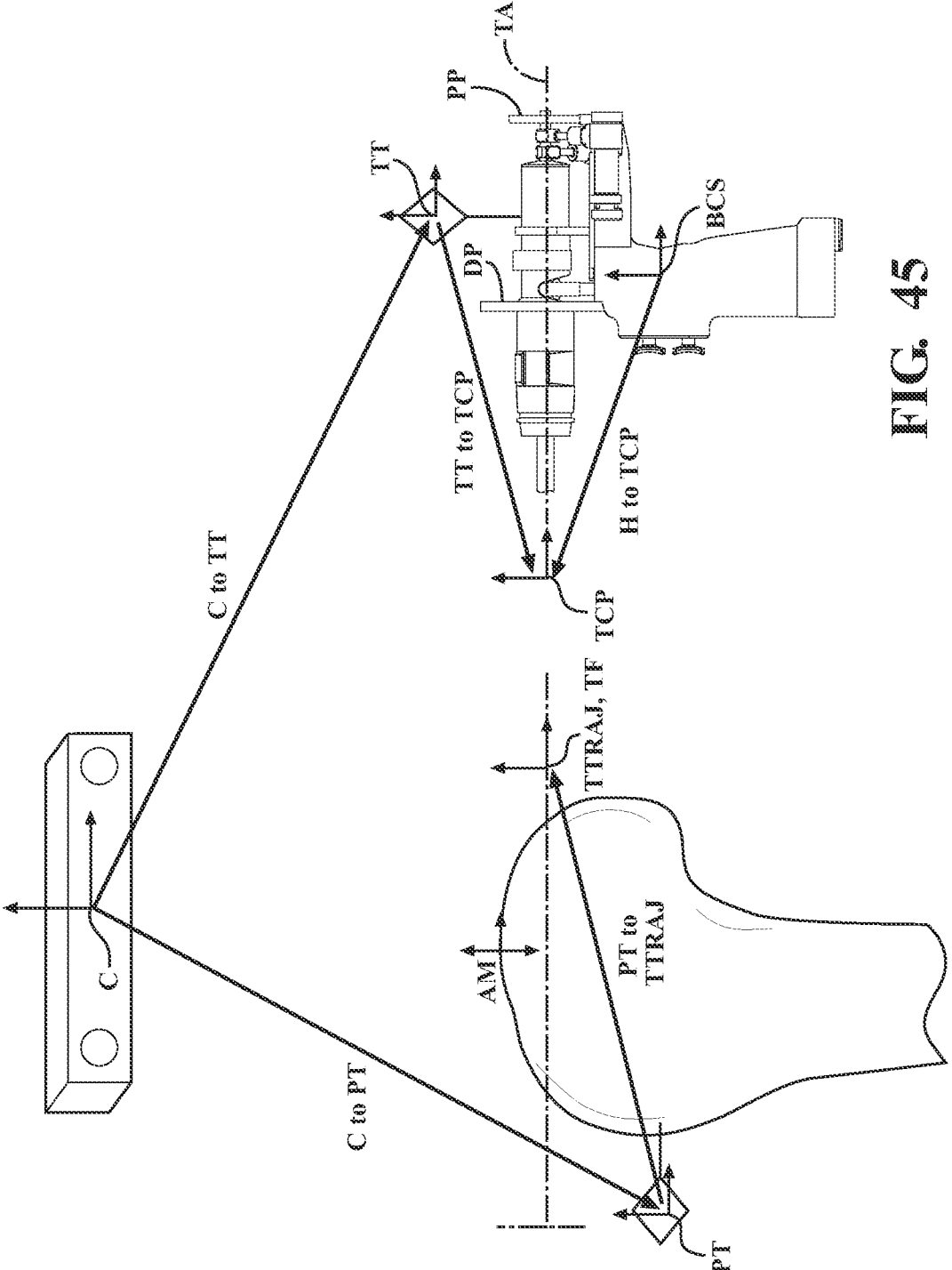
FIG. 45 is an example of a portion of the navigation system relative to the patient anatomy and a surgical robotic instrument, and the potential transform calculations related to a target trajectory.

Referring to FIG. 9, a behavior controller 186 and a motion controller 188 may be run on the instrument controller 28 and/or the navigation controller 36. The control system 60 computes data that indicates the appropriate instruction for the plurality of actuators. In one implementation, the behavior controller 186 functions to output the next commanded position and/or orientation (e.g., pose) for the tool relative to the hand-held portion. During operation, the tool 20 is effectively moved toward the target state using the plurality of actuators. These effects may be generated in one or more degrees of freedom to move the tool 20 toward the target state. Thus, the target state may be defined such that the tool 20 is being moved in only one degree of freedom, or may be defined such that the tool 20 is being moved in more than one degree of freedom. Accordingly, the target state may comprise a target position, target orientation, or both, defined as a target coordinate system TF (also referred to as a target frame TF). The target coordinate system TF may be defined with respect to the coordinate system of an anatomy tracker or target bone(s), however, other coordinate systems may be used. As shown in FIG. 45, the target position may comprise one or more position components with respect to x, y, and/or z axes of the target coordinate system TF with respect to a reference coordinate system, such as the anatomy tracker or bone, e.g., a target x position, a target y position, and/or a target z position. In some cases, the target position is represented as the origin of the target coordinate system TF with respect to a reference coordinate system, such as the anatomy tracker or bone. It should be appreciated that the reference coordinate system and the patient coordinate system may be the same or different. In some instances, the reference coordinate system may be identical to the reference coordinate system. The target orientation may comprise one or more orientation components with respect to the x, y, and/or z axes of the target coordinate system TF with respect to a reference coordinate system, such as the anatomy tracker or bone, e.g., a target x orientation, a target y orientation, and/or a target z orientation. In some cases, the target orientation is represented as the orientation of the x, y, and z axes of the target coordinate system TF with respect to a reference coordinate system, such as the anatomy tracker or bone. Target pose means a combination of the one or more position components and the one or more orientation components. In some cases, the target pose may comprise a target position and target orientation in less than all six degrees of freedom of the target coordinate system TF. For example, in one specific configuration, the target pose may be defined by a two position components and two orientation components. In some cases, the target position and/or target orientation may also be referred to as starting position and/or starting orientation. In another configuration, the target pose may be defined as an axis anchored relative to the known coordinate system.

Referring to FIG. 9, the target state is an input to the behavior controller 186. The target state may be a target position, target orientation, or both where the tool 20 is adjusted to a target plane or target trajectory. In some cases, only the position of the TCP is output from the behavior controller 186, while in other cases, the position and orientation of the tool 20 is output. In some examples, the commanded pose output of the behavior controller 186 may include position, orientation, or both. In some examples, output from a boundary generator 182 and one or more sensors, such as an optional force/torque sensor, may feed as inputs into the behavior control 186 to determine the next commanded position and/or orientation for the tool relative to the hand-held portion. The behavior controller 186 may process these inputs, along with one or more virtual constraints described further below, to determine the commanded pose.

The motion controller 188 performs motion control of the plurality of actuators. One aspect of motion control is the control of the tool support 18 relative to the hand-held portion 16. The motion controller 188 receives data from the behavior controller 186, such as data that defines the next commanded pose. Based on these data, the motion controller 188 determines a commanded joint position of each of the plurality of actuators coupled to the tool support 18 (e.g., via inverse kinematics) so that the tool 20 is positioned at the commanded pose output by the behavior controller. In other words, the motion controller 188 processes the commanded pose, which may be defined in Cartesian space, into commanded joint positions of the plurality of actuators coupled to the tool support 18, so that the instrument controller 28 can command the actuators 21, 22, 23, 24 accordingly, to move the tool support 18 to commanded joint positions corresponding to the commanded pose of the tool relative to the hand-held portion. In one version, the motion controller 188 regulates the joint positions of the plurality of actuators and continually adjusts the torque that each actuator 21, 22, 23, 24 outputs to, as closely as possible, ensure that the actuators 21, 22, 23, 24 lead the instrument to assume the commanded pose. Alternately, and/or additionally, the motion controller 188 can output the commanded joint positions to a separate set of motor controllers (e.g., one for each actuator 21, 22, 23), which handle the joint-level position control. In some examples, the motion controller 188 (or motor controllers) may use feed-forward control to improve the dynamic tracking and transient response. In such a case, in addition to commanded joint positions, the motion controller 188 may also compute feed-forward joint velocities (or rather commanded joint velocities) and potentially feed-forward joint torques (and/or motor currents). This data is then used within the control loop of the motor controllers to more optimally drive the actuators 21, 22, 23, 24.

It should be appreciated that while position control is described in detail, similar control implementations may be used with joint angle control. Furthermore, the motion controller may use joint angle control and joint position control. In some examples, joint angle may interchanged with joint position. Depending on the joint type, actuator type, or both on the instrument, joint angle, joint position, or both may be used. For example, the motion controller may determine a commanded joint angle based on the commanded pose for one or more actuators.

Referring to FIG. 9, the software employed by the control system 60, and run on the instrument controller 28 and/or the navigation controller 36 may include a boundary generator 182. The boundary generator 182 is a software program or module that generates a virtual boundary 184 for constraining movement and/or operation of the tool 20. The virtual boundary 184 may be one-dimensional, two-dimensional, three-dimensional, and may comprise a point, line, axis, trajectory, plane, or other shapes, including complex geometric shapes. The virtual boundary could also be a plane or line defined perpendicular to a planned trajectory. The virtual boundaries 184 may also be referred to as virtual objects. The virtual boundaries 184 may be defined with respect to an anatomical model AM, such as a 3-D bone model, in an implant coordinate system. The anatomical model AM is associated with the real patient anatomy by virtue of the anatomical model AM being mapped to the patient's anatomy via registration or other process.

The virtual boundaries 184 may be represented by pixels, point clouds, voxels, triangulated meshes, other 2D or 3D models, combinations thereof, and the like. U.S. Patent Publication No. 2018/0333207 and U.S. Pat. No. 889,843 are incorporated by reference, and any of their features may be used to facilitate planning or execution of the surgical procedure. One example of a system and method for generating the virtual boundaries 184 is described in U.S. Pat. No. 9,119,655, entitled, "Surgical Manipulator Capable of Controlling a Surgical Instrument in Multiple Modes," the disclosure of which is hereby incorporated by reference. In some examples, the virtual boundaries 184 may be generated offline rather than on the instrument controller 28 or navigation controller 36. Thereafter, the virtual boundaries 184 may be utilized at runtime by the instrument controller 28.

There are a variety of options for how the location and/or shape of the boundary can be determined, including the boundary that provides the depth protection. As mentioned, the boundary could be 'implant specific', a predefined shape that is stored in a databased based on the type/size of implant for each of planned screws, with its pose relative to the bone being adjusted based on surgeon input as part of the implant positioning workflow (i.e., the boundaries may be defined in the implant coordinate system and moves with the implant placement). Alternatively, the boundary could be 'patient-specific", i.e., computed automatically or manually based on pre-operative imaging, such as a CT scan. The boundary could be 'drawn' by the user (via touch screen or mouse) as an overlay superimposed on a representation of bone (real or generated) on the GUI, either pre-operatively or intraoperatively. Another option is that the boundary is a fixed shape that is placed or generated interactively by the surgeon. Alternatively, still, the boundary could be tool specific, a predefined position based on the type/size of tool.

The anatomical model AM and associated virtual boundaries 184 are registered to the one or more patient trackers 54, 56. Thus, the anatomical model AM (and associated real patient anatomy) and the virtual boundaries 184 fixed to the anatomical model AM can be tracked by the patient trackers 54, 56. The virtual boundaries 184 may be implant-specific, e.g., defined based on a size, shape, volume, etc. of an implant and/or patient-specific, e.g., defined based on the patient's anatomy. The virtual boundaries 184 may be boundaries that are created pre-operatively, intra-operatively, or combinations thereof. In other words, the virtual boundaries 184 may be defined before the surgical procedure begins, during the surgical procedure, or combinations thereof. In any case, the control system 60 obtains the virtual boundaries 184 by storing/retrieving the virtual boundaries 184 in/from memory, obtaining the virtual boundaries 184 from memory, creating the virtual boundaries 184 pre-operatively, creating the virtual boundaries 184 intra-operatively, or the like. In other words, one or more virtual boundaries may be obtained from the planned pose of the implant, and planned size, shape, volume, etc. of the implant. The implant coordinate system and the anatomical model coordinate system may be considered interchangeable throughout this description.

The virtual boundaries 184 may be used in various ways. For example, the control system 60 may: control certain movements of the tool 20 to stay inside the boundary; control certain movements of the tool 20 to stay outside the boundary; control certain movements of the tool 20 to stay on the boundary (e.g., stay on a point, trajectory, and/or plane); control certain operations/functions of the instrument 14 based on a relationship of the instrument 14 to the boundary (e.g., spatial, velocity, etc.); switch control modes of the instrument (i.e., switch from 4-DOF mode to 2-DOF mode, or switch from one 2-DOF mode to another 2-DOF mode; and/or control energization to the drive motor M of the instrument 14. Other uses of the boundaries 184 are also contemplated. In one potential implementation, the virtual boundary 184 may comprise a generally planar mesh located perpendicular to the planned trajectory, a depth boundary, such as line perpendicular to the planned trajectory, DB. Other examples may be seen in FIG. 49. This virtual boundary 184 may be associated with the 3-D bone model. This virtual boundary may be used to control the drive motor M. In other examples, the boundary generator 182 provides virtual boundaries 184 for purposes of controlling the plurality of actuators. Virtual boundaries 184 may also be provided to delineate various operational/control regions as described below for either control of the tool drive motor or for control of the plurality of actuators. The virtual boundaries 184 may be one-dimensional (1D), two-dimensional (2D), three-dimensional (3D), and may comprise a point, line, axis, trajectory, plane (an infinite plane or plane segment bounded by the anatomy or other boundary), volume or other shapes, including complex geometric shapes.

Figure 50:
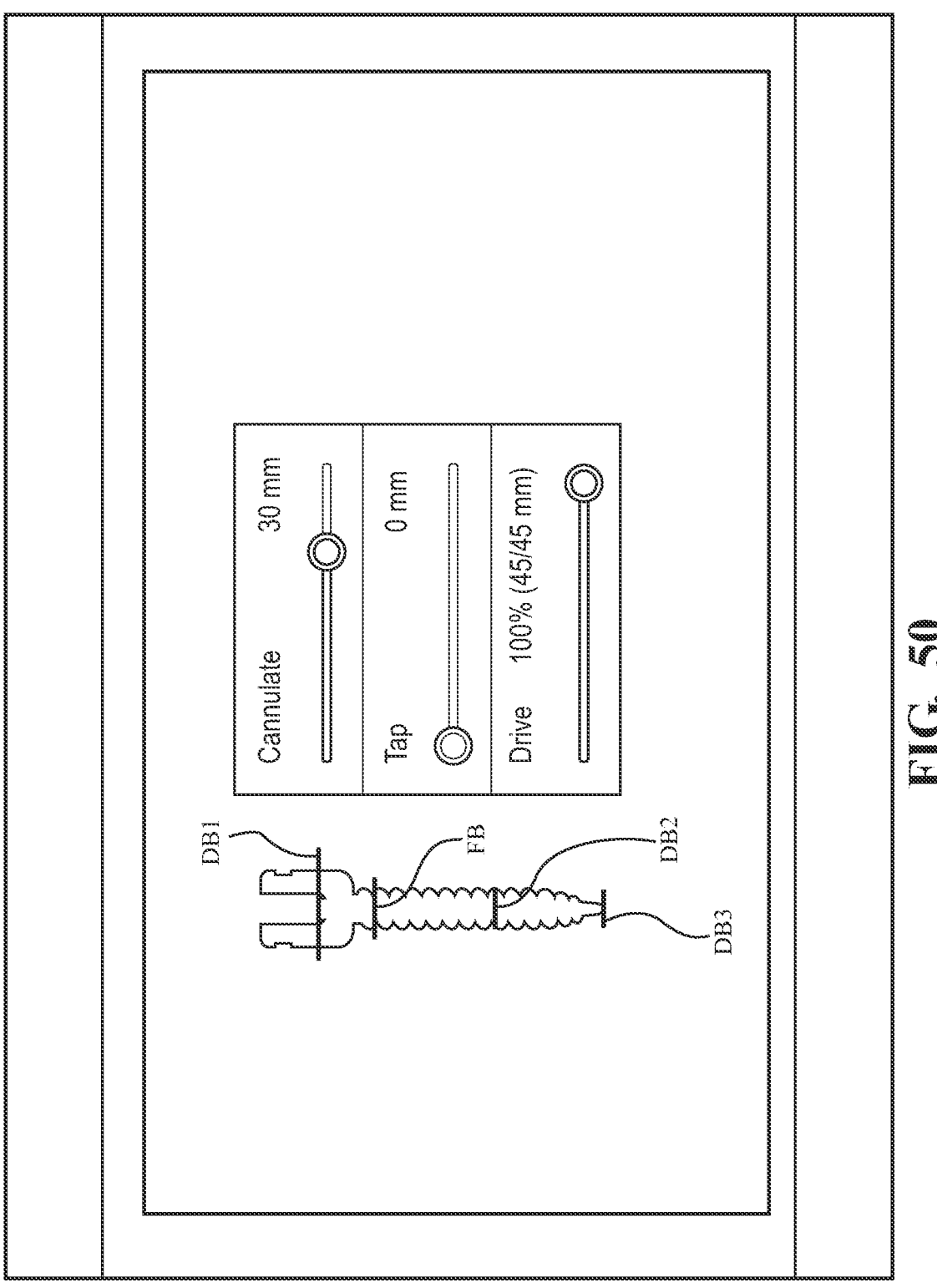
FIG. 50 illustrates a display with one example of an implant with associated user-settable depth boundaries.
Figure 61:
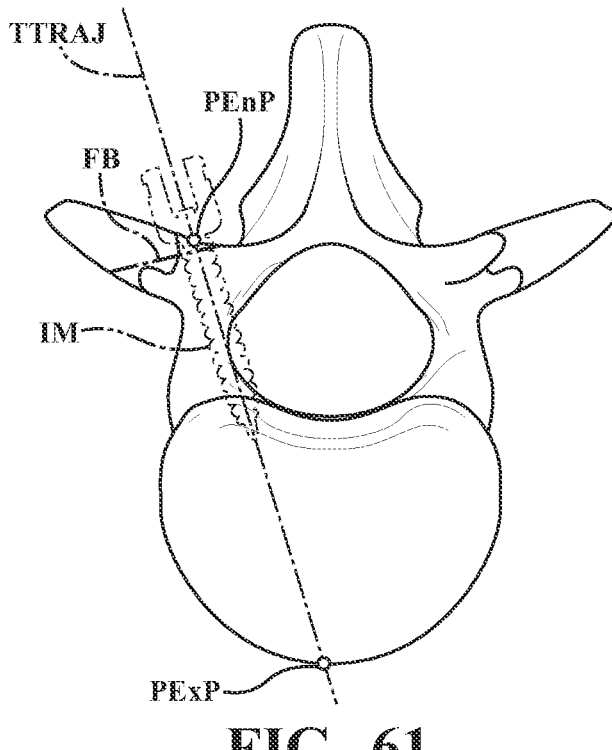
FIGS. 61 and 62 illustrate boundaries associated with a target bone based on a selected implant and the target trajectory associated with the boundaries.
Figure 62:
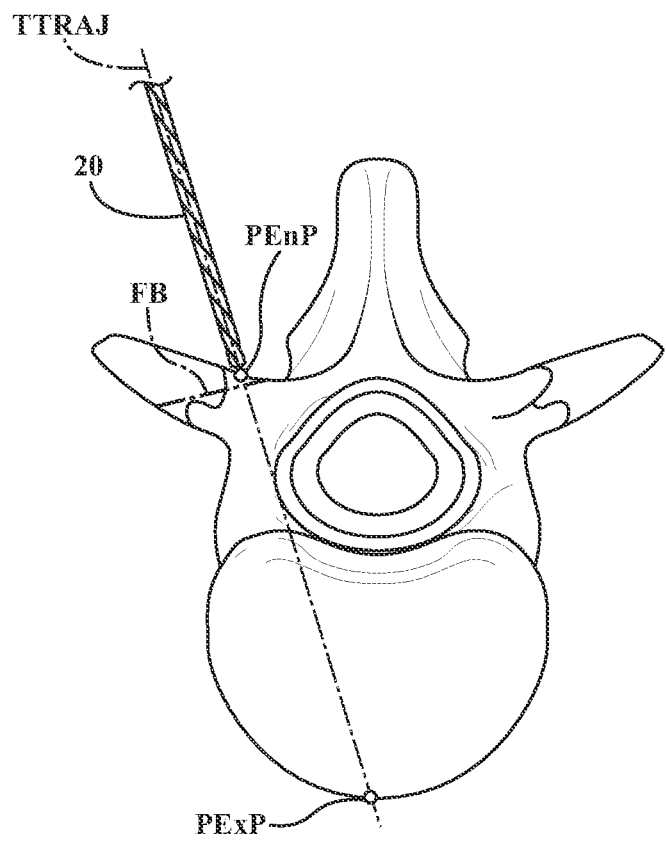

Referring to FIGS. 50, 61 and 62, the pose of the implant (IM) may be planned relative to the bone, such as a vertebra, in the implant coordinate system. This planned pose of the implant may be then defined relative to the one of the patient trackers 54, 56 through various navigation transforms, and the pose of the implant may be the basis of planned virtual objects, such as the target trajectory (TTRAJ), or the virtual boundaries. The target trajectory may be a representation of what hole needs to be made relative to bone to achieve the planned implant pose. In other words, the target trajectory (TTRAJ) may be aligned with the axis where the planned implant intends to be inserted into bone. The target trajectory TTRAJ may be generated as a form of the virtual boundary that may be used to control the plurality of actuators. Furthermore, it should be appreciated that the target trajectory for applications other than for drilling bone and/or for applications beyond vertebra. For example, the target trajectory may be used for controlling the instrument relative to a tumor in the skull, and the second point may not necessarily be aligned with the cortical wall of the bone, but rather a location a tumor based on segmentation data, or a point distal the bone to be drilled.

The control system 60 will ultimately function to urge the tool 20 towards the desired trajectory in some versions. The virtual boundary 184 that may be used control the plurality of actuators may also be a volumetric boundary, such as one having a diameter equal to and/or slightly larger than the diameter of the cutting tool to constrain the drill bit to stay within the boundary and on the desired trajectory. Therefore, the desired trajectory can be defined by a virtual axis, a virtual volumetric boundary, or other forms of virtual boundary. Virtual boundaries 184 may also be referred to as virtual objects.

The virtual boundaries 184 may be implant-specific, e.g., defined based on a size, shape, volume, etc. of an implant and/or patient-specific, e.g., defined based on the patient's anatomy. The implant-specific boundaries may be larger or smaller than the physical dimensions of the implant. The virtual boundaries 184 may be boundaries that are created pre-operatively, intra-operatively, or combinations thereof. In other words, the virtual boundaries 184 may be defined before the surgical procedure begins, during the surgical procedure (including during tissue removal), or combinations thereof. The virtual boundaries 184 may be provided in numerous ways, such as by the control system 60 creating them, receiving them from other sources/systems, or the like. The virtual boundaries 184 may be stored in memory for retrieval and/or updating.

In some cases, such as when preparing the spine for receiving various pedicle screws, the virtual boundaries 184 comprise multiple axes that can be used to delineate multiple target trajectories for each of the screws to be inserted. These multiple virtual boundaries 184 and/or target axes can be activated, one at a time, by the control system 60 to control the plurality of actuators to drill one hole at a time. Each of these trajectories may be a target trajectory for the control system. Example virtual boundaries FB, DB1, DB2, DB3 are shown in FIG. 50, for illustrative purposes.

Figure 49:
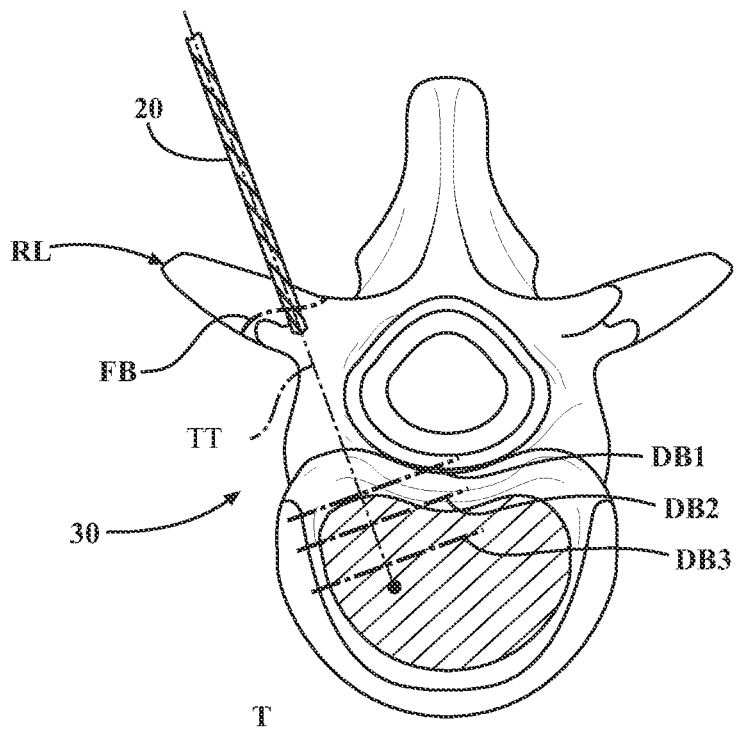
FIG. 49 illustrates is a schematic view of the instrument positioned relative to bone with respect to virtual boundaries.

In cases wherein the virtual boundaries are used to control the tool drive motor and referring to FIG. 49, the virtual boundaries may represent boundaries that can be used delineate on-trajectory drilling or driving depths. The on-trajectory depths may be features of a 3D boundary model rather than distinct boundaries. Those depth boundaries DB may be generally perpendicular to the target trajectory. Additional boundaries may be present, which are contoured to the patient's anatomical features (vertebra, femur, ligaments, arteries, soft tissue, etc.). This may avoid inadvertent cutting of a critical structure. The virtual boundaries 184 used to control the drive motor may include one or more lateral boundaries. These lateral boundaries may serve to prevent cutting beyond a target depth in a lateral direction. In some examples, the cutting cylinder defined by the depth boundaries and lateral boundaries in the 3D boundary may be used for a secondary error mitigation feature, such as to turn off the drive motor M if the cutting tool does not sufficiently stay on trajectory (in the case of sudden fast motion of the instrument and/or bone or as a mitigation against another system malfunction). The boundaries for controlling the tool drive motor may be selectively activated based on the selected target axis.

In some cases, the virtual boundaries that delineate cutting depths may be based on a pose of a planned virtual object, such as a fixed boundary offset, such as 5 mm offset from the distal end of the planned screw and perpendicular to each target trajectory. In some versions, the control system 60 evaluates whether the tool will violate the depth boundary DB by more than a threshold amount, and may command the instrument controller 28 to cease operation of the drive motor M. In some examples, the instrument controller 28 may not cease operation of the drive motor M, but rely on user-controlled starting, stopping, and/or speed control of the drive motor M.

In some cases where virtual boundaries are not utilized, the instrument controller 28 controls a motor parameter of the drive motor M at a first value and a second value, such that the first value is different than the second value and the instrument controller 28 may change operation from the first value to the second value based on the position of the tool 20 and the position of a reference location associated with bone, such as the virtual boundary, or based on a computed distance parameter. For example, with reference to FIG. 49, as the tool 20 proceeds into a hole of the bone, the control system using navigation data of the tool 20 relative to the reference location RL or based on the pose of the tool associated with the bone, may allow activation of the drive motor M. Further, the control system may turn off the drive motor M based on whether the tool 20 has reached a certain pose, distance parameter value or position relating to the reference point or boundary associated with the bone. In some cases, the user may find difficulty in perceiving the depth of the tool 20 within the bone while performing the surgical procedure because of limited line of sight due to soft tissue, and other surgical apparatuses used in the procedure. By controlling the drive motor M based on the pose or position of the tool 20, the user may be able to control with more accuracy the depth of the hole or driven tool.

In some examples, when the instrument controller 28 changes the operating mode by changing a parameter of the drive motor M, the instrument 14, the input device, the navigation system 32, the instrument controller 28, or a combination thereof may provide an audible indication, a tactile indication, or both that the mode has been changed. In one instance, the input device may be a footswitch, and when the mode of the instrument is changed, controlling the speed of the drive motor M, the footswitch may vibrate. In another example, when the mode and/or control behavior is changed speeding up or slowing down the drive motor M, a user may perceive an audible indication such as the motor speed of the drive motor M changing volume, pitch, vibration, or a combination thereof, indicating that the mode and/or control behavior of the instrument has changed.

As described above, the instrument controller 28 and/or the navigation controller 36 track the state of the tool 20, such as the position and/or orientation of the tool relative to the virtual boundaries. In one example, it can be described as monitoring the state of the TCP is measured relative to the virtual boundaries for purposes of controlling the tool drive motor M. In other words, the control system may control the tool drive motor M based on the state of the TCP measured relative to the virtual boundaries, such as slowing down or stopping the drive motor M when any aspect of the instrument virtual model VM violates the virtual boundary by more than a threshold amount. In some examples, the pose of the tool (TCP coordinate system) may be utilized to evaluate whether any aspects of the tool 20 would violate the virtual boundary 184 by more than a threshold amount. The control system may have a model of the tool (e.g., a CAD model or a simplified model using geometric primitives) that may be evaluated for violations of the virtual boundaries.

Further, the virtual boundary may be an open-ended surface or a closed surface. When the virtual boundary 184 is configured as a closed surface, the virtual boundary 184 may function as a "keep out" boundary where the instrument 14 may be actuated "outside" of the virtual boundary but shut off after crossing the virtual boundary by a threshold amount. Similarly, the closed surface virtual boundary may function as a "keep in" boundary, where the drive motor may only operate within the virtual boundary 184, shutting off the drive motor when the instrument "leaves" the virtual boundary by more than a threshold amount.

In another example, the state of the TCP is measured relative to the virtual boundaries for purposes of determining forces to be applied to a virtual rigid body model via a virtual simulation so that the tool 20 remains in a desired positional relationship to the virtual boundaries (e.g., not moved beyond them). The results of the virtual simulation are processed when controlling the plurality of actuators coupled to the tool support 18. The boundary generator 182 may be implemented on the instrument controller 28. Alternatively, the boundary generator 182 may be implemented on other components, such as the navigation controller 36.

The boundary generator 182, the behavior controller 186 and motion controller 188 may be sub-sets of a software program 378. Alternatively, each may be software programs that operate separately and/or independently in any combination thereof. The term "software program" is used herein to describe the computer-executable instructions that are configured to carry out the various capabilities of the technical solutions described. For simplicity, the term "software program" is intended to encompass, at least, any one or more of the boundary generator 182, behavior controller 186, and/or motion controller 188. The software program 378 can be implemented on the instrument controller 28, navigation controller 36, or both, or may be implemented in any suitable manner by the control system 60.

A clinical application 190 may be provided to handle user interaction. The clinical application 190 handles many aspects of user interaction and coordinates the surgical workflow, including pre-operative planning, implant placement, registration, bone preparation visualization, and post-operative evaluation of implant fit, etc. The clinical application 190 is configured to output to the displays 38. The clinical application 190 may run on its own separate processor or may run alongside the navigation controller 36. In one example, the clinical application 190 interfaces with the boundary generator 182 after implant placement is set by the user, and then sends the virtual boundary 184 and/or target trajectory returned by the boundary generator 182 to the instrument controller 28 for execution. The instrument controller 28 executes the target trajectory as described herein. The instrument controller 28 may also process the virtual boundaries 184 to generate corresponding virtual constraints, if utilized.

Turning to FIGS. 2 and 45, the exemplary control is described with respect to the various transforms. The TCP is located by tracking the tool 20 with the tool tracker 52 (TT) with respect to the localizer coordinate system LCLZ (LCLZ-TT transform), and determining a transform between tool tracker 52 and the TCP of the tool 20 (TT-TCP transform), using registration data or calibration data. Similarly, the patient is tracked using the patient tracker (shown as PT), resulting in the transform from the localizer coordinate system LCLZ to the patient tracker coordinate system (LCLZ-PT transform).

As described with respect to FIGS. 9 and 45, through a bone registration process or automatic image registration process, a transform from bone to the patient tracker 54, 56 is established (bone to patient tracker). Through the implant planning process, a bone to implant/anatomical model transform is determined (bone to IM transform). Then, a patient tracker 54 to planned implant (patient tracker to IM) transform is computed. The planned implant (IM) may be related to the target trajectory (IM to TTRAJ transform), given the locations of the chosen implant component and size, or may be related to a target trajectory. A transform is then computed between the patient tracker PT and each planned virtual object, such as each target trajectory (PT—trajectory transform) using the combination of registration data and planning information.

The position and/or orientation of the tool support 18, and therefore TCP, may be related to the tool tracker 52 (tool support to tool tracker transform, computed via registration or calibration process). As described above, in some implementations, a transform between the hand-held portion 16 and the TCP (BCS-TCP) is computed based on the positions of each actuator. The transform between BCS and TCP is utilized to relate the various coordinate systems back to the hand-held portion 16, since the commanded pose may be determined relative to the BCS for certain control implementations. Conceptually, the commanded pose, is an update to the BCS to TCP transform which results in the TCP being aligned with the planned virtual object (the target trajectory TTRAJ) in this example. As an alternative, the pose of the hand-held portion 16 may be determined directly in some instances by using a hand-held portion tracker 53 coupled directly to the hand-held portion 16. This may eliminate the need to utilize the TCP coordinate system and perform a transform between BCS and TCP based on the positions of each actuators.

An initial pose of the TCP with respect to the base coordinate system BCS can be determined based on a known geometric relationship between the tool support and the hand-held portion 16 when the actuators 21, 22, 23, 24 are at their home position/center point or other predetermined position. This relationship changes when the actuators 21, 22, 23, 24 are adjusted and the associated changes can be determined based on the kinematics of the robotic system 10 (e.g., which establishes a dynamic transformation between these coordinate systems). Thus, the robotic system 10 knows the pose of the tool 20, such as in the home position and its relation to the pose of the hand-held portion 16. Accordingly, when the tool 20 is moved by the user and its pose is tracked using the tool tracker 52, the robotic system 10 also tracks the pose of the hand-held portion 16 and its base coordinate system BCS. In some examples, as a result of prior calibration processes, the position of the tool 20 relative to the tool support 18 is assumed to be known. After the home position/center point and maximum travel of each of the actuators 21, 22, 23, 24 is established, control is based on the position and/or orientation data from the navigation controller 36 and the measured position data of the actuator (s). The home position could also be computed in other manners. When all of the actuators are in their home positions, this collectively defines the home state of the instrument. The home state may involve a pose of the hand-held portion relative to a pose of the tool support, i.e., defined in cartesian space, or the home state of the instrument may be defined in actuator space (position) or joint space (angles) of the plurality of actuators and/or joints.

Since both the patient tracker 54, 56 and the tool tracker 52 are each reported by the localizer 44 with respect to the localizer coordinate system LCLZ, providing LCLZ-to-PT and LCLZ-to-TT, these transforms may be processed together to determine a transformation between the tool tracker 52 and the patient tracker 54, 56 (TT-to-PT). From there, a base coordinate system to patient tracker (BCS-to-PT) transformation can be calculated by the control system 60, computing the location of the patient tracker 54, 56 with respect to the hand-held portion 16. Since the target trajectory with respect to the patient tracker 54, 56 is known, the control system 60 may calculate a base coordinate system BCS to target trajectory TTRAJ (BCS-to-TTRAJ) transformation, resulting in the pose of the target trajectory in the coordinate system of the hand-held portion 16 (BCS). In one example, the BCS-to-TP may be used directly to compute the commanded pose BCS-to-TCP which puts the TCP on the target trajectory TTRAJ, which may then be commanded to the actuators 21, 22, 23, 24 to move the tool 20 to the desired pose. In some examples, the BCS-to-TCP calculation may be used to generate constraints to attract the TCP to TTRAJ within a virtual simulation VM.

The instrument controller 28 may control the one or more actuators 21, 22, 23, 24 by sending command signals to each actuator 21, 22, 23, 24 to adjust the tool 20 towards a target state in at least one degree of freedom. The instrument controller 28 may send command signals to each actuator 21, 22, 23, 24 to move the actuators 21, 22, 23, 24 from a first set of positions to a set of commanded positions which will place the tool 20 into the target state. In some examples, the commanded position may be determined by the instrument controller 28 in conjunction with the navigation system 32 based on the pose of hand-held portion 16 and a target state in a known coordinate system (i.e. defined relative to the patient tracker 54, 56), such as the pose of the virtual object (target trajectory), and send a signal to the actuators 21, 22, 23, 24 to adjust to the commanded position.

The second software module is a motion controller 188. One function of the motion controller 188 is the control of the instrument 14. The motion controller 188 may receive data defining the target state of the tool, such as the next commanded pose from the behavior controller 186. Based on these data, the motion controller 188 determines the next commanded joint position of each actuator 21, 22, 23, 24 (e.g., via inverse kinematics) so that the instrument 14 is able to position the tool 20 as commanded by the behavior control 186, e.g., controlling instrument to the commanded pose. In other words, the motion controller 188 processes the commanded pose, which may be defined in Cartesian space, into actuator positions (such as commanded joint positions) of the instrument 14, so that the instrument controller 28 can command the motors accordingly, to move the actuators 21, 22, 23, 24 of the instrument 14 to commanded positions, such as commanded joint positions corresponding to the commanded pose. In one version, the motion controller 188 regulates the joint position of each motor of each actuator 21, 22, 23, 24 and continually adjusts the torque that each motor outputs to, as closely as possible, ensure that the motor drives the associated actuator 21, 22, 23, 24 to the commanded joint position. In another version, the instrument controller regulates the joint position of each motor and continually adjusts the torque that each motor outputs to, as closely as possible, ensure that the motor drives the associated actuator 21, 22, 23, 24 to the commanded joint position.

In some versions, the instrument controller 28, for each actuator 21, 22, 23, 24, determines the difference between a commanded position and a measured position of the actuator. The instrument controller 28 outputs a target current (proportional to a torque of the actuator), changing the voltage to adjust the current at the actuator from an initial current to the target current. The target current effectuates a movement of the actuators 21, 22, 23, 24, moving each actuator 21, 22, 23, 24 towards the commanded joint position, and, as a result, moving the instrument towards the commanded pose. This may occur after the commanded pose is converted to joint positions. In one example, the measured position of each joint may be derived from the sensors S described above, such as an encoder.

Throughout this description, unless otherwise noted, any instance of pose may be a current commanded pose, a current measured pose, a past measured pose, or a past commanded pose. While each of these poses may be different from one another, due to the frequency of control cycles, the difference in position and/or orientation between these poses may be minimal in each control iteration. Furthermore, any instance of position may be a current commanded position, a current measured position, a past measured position, or a past commanded position.

Different control methodologies may be used to control the plurality of actuators to place the tool at a desired location, such as the target trajectory, including but not limited to impedance control, admittance control, position control, or a hybrid control using multiple different control implementations. In an admittance control mode, the control system accepts force input (virtual or measured) and commands position (or motion) output. For example, for admittance control, the system models a force and/or torque at a particular location on a virtual mass and acts to modify the pose of the virtual mass to achieve the desired target state of the tool. In an impedance control mode, the control system accepts position (or motion) input and commands a force or torque output. For example, the impedance control system measures, senses, and/or calculates a position (i.e., position, orientation, velocity, and/or acceleration) of the instrument and may apply an appropriate corresponding torque to each of the actuators to achieve the desired target state of the tool. Position control may also be used to control the plurality of actuators towards implementing certain behaviors. It should be appreciated that changes to both the behavior controller and the motion controller would be needed implement these control schemes.

In some versions, once treatment begins, the instrument controller 28 may mitigate the effects of the user's ability to place the tool 20 away from the desired pose (e.g., outside or off of the virtual boundary or planned virtual object (TTRAJ). For example, in some implementations, as soon as the navigation system 32 provides an indication that the tool 20 is moving off the desired trajectory, the instrument controller 28 immediately terminates the application of energization signals to the drive motor M, preventing the tool 20 from drilling in an undesired direction. In other examples, the drive motor M may be slowed down or stopped using motor braking, for example, as described in U.S. Pat. No. 7,998,157 entitled "Surgical tool system with a powered handpiece and a console, the console able to provide energization signals to the handpiece in either a motor drive mode or a direct drive mode" which is hereby incorporated by reference. In some implementations of this feature, the acceptable misalignment of the tool 20 with the desired trajectory may vary as the depth of the penetration into bone increases.

As described above, to control the plurality of actuators, a commanded pose is often set. This commanded pose may be a desired relationship between the BCS and the TCP, i.e., a desired relationship between the tool support and the hand-held portion. The commanded pose is determined based on the pose of the hand-held portion 16 in a known coordinate system and a target state in the same coordinate system (e.g., the coordinate system associated with the patient tracker 54, 56), such as a pose of a planned virtual object, e.g., a target pose of the tool deduced from the pose of the planned implant. The commanded pose may result in the tool 20 aligned with the planned virtual object, such as a planned trajectory. As mentioned above, the instrument controller 28 may convert the commanded pose to a commanded position for each of the plurality of actuators using inverse kinematics, then send command instructions to the actuators 21, 22, 23, 24 to move to a commanded position, thereby changing the relative poses of the tool support 18 and tool 20.

An initial pose of the TCP with respect to the base coordinate system BCS can be determined based on a known geometric relationship between the tool support and the hand-held portion 16 when the actuators 21, 22, 23, 24 are at their home position/center point or other predetermined position.

Since both the patient tracker PT, 54, 56 and the tool tracker 52 are each reported by the localizer 44 with respect to the localizer coordinate system LCLZ, providing LCLZ-to-PT and LCLZ-to-TT, these transforms may be processed together to determine a transformation between the tool tracker 52 and the patient tracker 54, 56 (TT-to-PT), such as seen in FIG. 45. From there, a base coordinate system to patient tracker (BCS-to-PT) transformation can be calculated by the control system 60, computing the location of the patient tracker 54, 56 with respect to the hand-held portion 16. Since the target trajectory TTRAJ with respect to the patient tracker 54, 56 is known, the control system 60 may calculate a base coordinate system BCS to target trajectory TTRAJ (BCS-to-TTRAJ) transformation, resulting in the pose of the target trajectory in the coordinate system of the hand-held portion 16 (BCS). In one example, the BCS-to-TTRAJ may be used directly to compute the commanded pose BCS-to-TCP which puts the TCP on the target trajectory TTRAJ, which may then be commanded to the actuators 21, 22, 23 to move the tool 20 to the desired pose. In some examples, the BCS-to-TCP calculation may be used to generate constraints to attract the TCP to TTRAJ within a virtual simulation VM.

The instrument controller 28 may control the one or more actuators 21, 22, 23, 24 by sending command signals to each actuator 21, 22, 23, 24 to adjust the tool 20 towards a target state in at least one degree of freedom. The instrument controller 28 may send command signals to each actuator 21, 22, 23, 24 to move the actuators 21, 22, 23, 24 from a first set of positions to a set of commanded positions which will place the tool 20 into the target state, aligning the tool 20 with the target trajectory. In some examples, the commanded position may be determined by the instrument controller 28 in conjunction with the navigation system 32 based on the pose of hand-held portion 16 and a target state in a known coordinate system (i.e. defined relative to the patient tracker 54, 56), such as the pose of the virtual object (target trajectory), and send a signal to the actuators 21, 22, 23, 24 to adjust to the commanded position. Other control systems and methods are contemplated, such as described in PCT application PCT/US2021/49440 filed Sep. 8, 2021 and PCT application PCT/US2022/054115 filed Dec. 28, 2022, both of which are incorporated by reference herein.

In some implementations, the control system uses one or more virtual constraints to compute the commanded pose. Generally, virtual constraints are restrictions and/or enhancements on the motion of rigid bodies in certain directions that are considered by the control system 60, along with other motion-related information, as part of a virtual simulation. Each virtual constraint may be considered to act along a particular direction, called the direction of the constraint. These one-direction constraints can be combined to produce multi-degree-of-freedom constraints that may, for example, work to align or repel two coordinate systems from each other in the virtual simulation. A virtual constraint may both restrict motion or enhance motion in a certain direction. A constraint 'restricts' the motion, but not in a directional sense (attract/repel), but rather the constraint does not allow free (unconstrained) motion by influencing movement in a certain way based on the relative motion or pose of two tracked objects/coordinate systems in the virtual simulation. The active virtual constraints are all added into a constraint solver where the constraint solver determines a set of parameters which account for each virtual constraint and compute a force. This resulting force may be represented as a 6-DOF force/torque vector which represents a balance or equilibrium of the various virtual constraints, each acting along potentially separate constraint directions. It should be noted in the present teachings that the term "force" is used, it may refer to a generalized force/torque vector, in which components of linear force and/or rotational torques are specified in one or more degrees of freedom. For example, "force" may refer to a single force in a single direction, a single torque about a single axis, or any combination thereof, e.g., a 6-DOF force/torque vector in a given coordinate system defining a force consisting of x, y, and z components and a moment consisting of torque components about an x, y, and z axis. The system may utilize the various constraints described in PCT application PCT/US2021/49440 filed Sep. 8, 2021, and PCT/US2022/054115 filed Dec. 28, 2022, which are hereby incorporated by reference.

The joint centering position may be the location at which each actuator 21, 22, 23, 24 has a relatively high amount of travel. In other words, the joint centering position may be considered the 'home' or 'idle' position of each of the actuators as described above. By setting the joint centering position to the home position, a median position for each actuator 21, 22, 23, 24, the tool support may achieve maximum range of motion. Alternatively, the joint centering position may be set to a position other than the home position for one or more of the plurality of actuators. This may be considered a secondary joint centering position. The secondary joint centering position may be different for each of the actuators 21, 22, 23, 24. It should be understood that the when the actuator is located at the secondary joint centering position, the one or more actuators 21, 22, 23, 24 may only be capable of a fraction of the travel in one direction that the same actuator may have had when the joint centering position was the home position. In one example, a first joint centering position is the 'home position' and a second joint centering position is a position other than the home position. Without being particularly limited, when the actuator is in the secondary joint centering position, the actuator may have less than 50 percent, less than 40 percent, or less than 30 percent of the range of motion in a particular direction than that same actuator would have had when set in the joint centering position equivalent to home. However, for certain surgical procedures or for certain users, it may be helpful to bias a joint centering position away from the actuator's median position in order to provide more travel in a certain (potentially challenging) direction, to improve ergonomics or to account for how the instrument is held. It should be appreciated that each actuator may have a multitude of different joint centering positions, or presets for preferred balance arrangements. Groups of joint centering positions may be aggregated together (sets of joint centering positions for all of the actuators) which correspond to preferred grips/balance scenarios. These centering positions may be selectable by a user using one or more user input devices.

When each actuator 21, 22, 23, 24 is at the home position, the amount of adjustability of the actuators 21, 22, 23, 24 is typically symmetrically maximized to make it easier for the user to keep the tool 20 at a desired pose, i.e., the joint centering position is typically set to the median position or 'home' position of the actuator. Various levels of adjustment are possible depending on the particular geometry and configuration of the instrument 14.

The control system may be used to 'freeze' the one or more actuators into a free-hand/unguided mode at the position of the one or more actuators to prevent unnecessary actuation and movement, preventing the actuators from generating excessive heat from movement, such as when the instrument 14 is a substantial distance away from the target bone. The free-hand/unguided mode may be useful to perform some types of treatment. When the actuators 21, 22, 23, 24 are frozen from further movement in the free-hand/unguided mode, then the instrument 14 behaves much like a conventional drilling and/or driving instrument, without any movement of the tool support 18 relative to the hand-held portion 16. The virtual boundaries 184 may also be deactivated in the unguided mode. The free-hand/unguided mode may be engaged by any suitable input device of any suitable user interface (e.g., push-button, foot switch, etc.). In some versions, the user may select this tool behavior (i.e., activate the joint centering behavior with a particular joint centering position and/or change the joint centering position) by actuating an input device, and selecting the free-hand/unguided mode where the instrument controller 28 commands a tool pose to be held or frozen in position. In some examples, to freeze the tool 20 at a particular pose, the instrument controller 28 may set centering positions for each actuator 21, 22, 23, 24 to the joint positions which correspond to the desired tool pose (e.g., by performing inverse kinematics on the desired tool pose to get the corresponding joint positions). Alternately, in another example, the joint centering positions may be left at or reset to zero (i.e., a home position). Further, the joint centering positions may be set to the current positions of the actuators, as determined using encoders or other actuator position feedback, at the time the mode is requested by the user. As described above, the joint centering position is adjustable. The secondary joint centering position may be set using a user input device, or may be set automatically.

The instrument controller 28 may automatically control a state of the joint centering behavior. For example, the state of the joint centering constraint may be controlled based on a state of the tool and the target state. Alternatively, the state of the joint centering constraint may be controlled based on the position of the tool 20 and the position of a reference location associated with bone in a known coordinate system. The state of the joint centering behavior could include a value of the joint centering position for each of the plurality of actuators 21, 22, 23, 24.

The instrument controller 28 may be configured to control the state of the joint centering behavior based a distance parameter (e.g. distance; magnitude) calculated between the position of the tool 20 and the position of the reference location associated with the bone. The distance parameter may be a direction, a magnitude, or both. In some cases, when the distance parameter has a direction away from bone and a magnitude greater than a first threshold value, such as 15 cm, the controller may switch to a different state.

As described above, the joint centering position is adjustable. The secondary joint centering position may be set using a user input device, or may be set automatically. In certain configurations, the secondary joint centering position and activation of joint centering behavior may be based on the state of an axis defined by the tool relative to a plurality of planned trajectories in the known coordinate system.

More particularly, the secondary joint position of and activation of the joint centering behavior may be based on angles between a current orientation of the tool and a plurality of target orientations of the tool, a distance between a current position of the tool and a plurality of target positions of the tool, or both the angles and the distances, and determining the one of the plurality of the plurality of target trajectories selected by the user based on the values of the angles, values of the distances, or both the values of the angles and the values of the distances. Thus, a particular secondary centering position for each of the actuators may be selected to optimize the pose of the tool support relative to the hand-held portion for purposes of improved usability. Similar implementations could be used for trajectories for other types of surgical tools.

A workspace limit may used by the control system 60 to implement a particular restriction in the motion of tool support 18 that is intended to prevent the tool 20 from traveling outside its workspace. The workspace limit may defined in Cartesian coordinate space or Polar coordinate space, rather than in joint space. The workspace limit may be used by the control system 60 to prevent the movement of the tool support 18 and the tool 20 into various locations outside a defined workspace.

The workspace limit may be based on a pose or state of the tool and one or more predetermined Cartesian/Polar spaces, typically defined with respect to the BCS coordinate system. The pose of the instrument 14 may be calculated as described above.

Figures 70, 71:
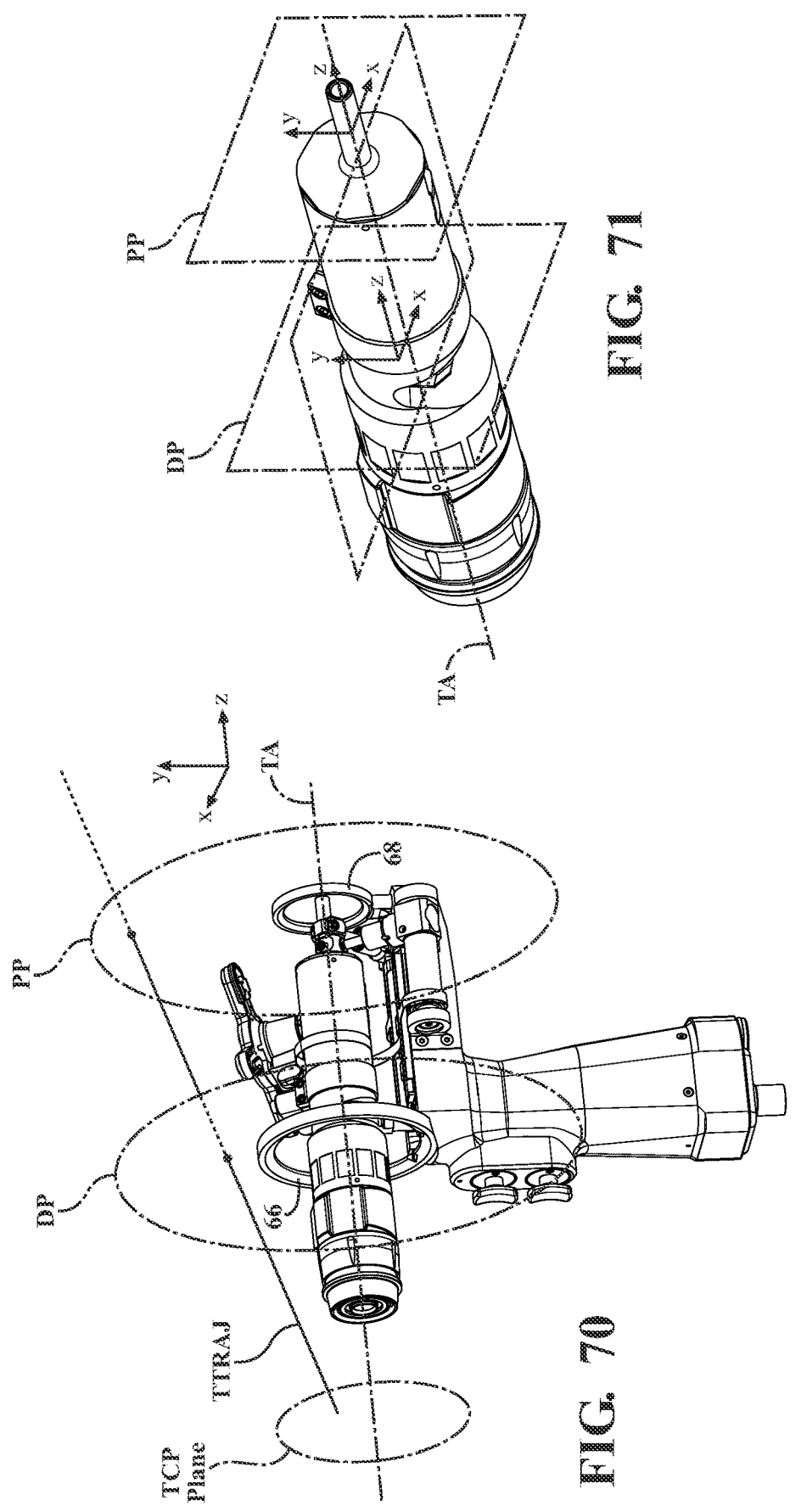
FIG. 70 is a perspective view of the instrument in its home state relative to its exemplary proximal and distal planes and a target trajectory.
FIG. 71 is an alternative view of the tool platform of FIG. 70 relative to the proximal and distal planes.

As best shown in FIGS. 3A-8B, the plurality of actuators 21, 22, 23, 24 are capable of moving the tool support 18 and tool 20 relative to the hand-held portion 16 in at least four degrees of freedom including pitch, yaw, elevation translation (vertical translation) and side-to-side translation of the tool support 18 relative to the hand-held portion 16. These individual degrees of freedom are best shown in FIG. 4A-4C (pitch), FIGS. 5A-5C (elevation), and FIGS. 6A-6C (yaw) and FIGS. 7A-7C (side-to-side translation). FIGS. 70-71 shows one example of a predetermined Cartesian space, illustrated as a series of offset planes. Other shapes of the predetermined Cartesian space may be implemented as a volume, such as an octahedron, an asymmetrical octahedron, a sphere, a cuboid, a cylinder, etc. Alternatively, the predetermined Cartesian space may be defined in each degree of freedom separately. For example, the Cartesian space may be defined with a plurality of Cartesian points. The predetermined Cartesian space may also be defined by one or more orientations.

The use of workspace limits (may provide advantages with respect to control of the instrument, such as additional robustness in design by avoiding vulnerable poses that could cause damage to the one more flex circuits, and/or may provide additional options to avoid mechanical interference. For example, the control system 60 may implement workspace limits in order to limit the amount of yaw of the tool support 18 relative to the hand-held portion 16 by limiting the workspace constraint and the joint limit constraint more than the workspace constraint and joint limit constraints in side-to-side translation, elevation translation, pitch or a combination thereof. By setting the workspace limit on roll higher than in the other controlled degrees of freedom (pitch and elevation), the limited yaw may be less yaw than the mechanical capabilities. In some cases, the workspace constraint in the yaw direction may have the same amount or less mechanical movement as the other controlled degrees of freedom in the pitch, elevation, and side-to-side directions.

The workspace limits may be used to control one or more of the plurality of actuators, and/or the drive motor. The control system may control the tool drive motor based on a workspace limit, a pose of one of the surgical tool, hand-held portion, and the tool support, and optionally, in consideration of the motor status. Furthermore, the control system may change workspace limits based on one the pose of the surgical tool, hand-held portion, and the tool support and a boundary and/or the motor status. This can be viewed as an alternative of setting actuator limits based on similar factors. Such an implementation is control in the cartesian space, versus control in the joint space. Thus, it is contemplated throughout that discussion of joint limits can be replaced within workspace limits, and such alternatives are expressly contemplated.

In one version, the instrument 14 may be configured to calculate, estimate, or measure forces and torques placed on the instrument 14 by the user or by the bone in order to affect or influence the tool 20. For example, the instrument 14 may detect and measure the forces and torques applied by the user or by the bone onto the tool 20 and generates corresponding input used by the control system 60 (e.g., one or more corresponding input/output signals). The forces and torques applied by the user at least partially define an external force Fext that is used to determine and facilitate control of the plurality of actuators. By including an external force/torque measurement into the virtual simulation, the forces applied by the user or bone may be brought into the virtual simulation. This may allow the virtual constraints to have compliance against physically applied forces. For example, this external force may be used in computing the commanded pose by including the external force in the constraint solver in combination with the other virtual constraints described above, and then applying the external force to the virtual rigid body in the virtual simulation.

The external force Fext may comprise other forces and torques, aside from those applied by the user or by the bone, such as gravity-compensating forces, backdrive forces, other virtual forces, and the like, as described in U.S. Pat. No. 9,119,655, incorporated herein by reference. Thus, the forces and torques applied by the user at least partially define the external force Fext, and in some cases may fully define the external force Fext that influences overall movement of the tool 20. In some instances, the instrument may comprise a force/torque sensor S that is implemented as a 6-DOF force/torque transducer positioned on the hand-held portion, the tool platform, or between the two components. In other examples, a linear force sensors in each of the actuators 21, 22, 23, 24, or torque sensors in each of the actuator motor outputs may also be used. Additionally, motor current may be used as a lower-fidelity approximation of motor torque, in place of a force/torque sensor.

In an alternative implementation, the external force may be considered an amount of external effort applied to the tool support and the hand-held portion. The estimated amount of external effort may be a force or a torque. The estimated force or torque may be computed in one or more degrees of freedom. The control system may control the display screen 38 to display an indicator 300 based on the estimated amount of external effort applied. The indicator 300 may be seen in FIG. 45. Alternatively, the control system 60 may be configured to control the drive motor M based on the estimated amount of external effort applied. For example, the control system 60 may slow or disable the drive motor M based on the estimated amount of external effort applied.

The control system 60 may control the indicator 300 or drive motor M based on the estimated amount of external effort applied and a force threshold. For example, the control system 60 may control the indicator 300 or drive motor M when the estimated amount of external effort applied exceeds the force/torque threshold in one or more degrees of freedom. Furthermore, the control system 60 may control the indicator and/or the drive motor M based on the estimated amount of external force, a force threshold, and an error counter. The error counter is configured to trip for every instance of the estimated amount force exceeds the threshold for more than a de minimis time interval. Once the error counter exceeds a given number, such as an error counter threshold, such as three instances, the control system 60 may control the indicator 300 and/or the drive motor M so as to convey to the user than an excess amount of tool fighting is occurring.

Alternatively, the control system may control the indicator 300 and/or the drive motor M based on the estimated amount of force and a time threshold, such as 5 or 10 seconds. More particularly, the control system 60 may configured to control the indicator and/or the drive motor M when the estimated amount of external force exceeds the force threshold in one or more degrees of freedom for longer than the time threshold, such as longer than 5 or 10 seconds. The control system 60 may utilize different force thresholds, error counter thresholds, and/or time thresholds for each degree of freedom, such as different thresholds for the pitch degree of freedom, different thresholds for the elevation degree of freedom, and/or different thresholds for the roll degree of freedom.

The indicator 300 may be a visual indicator, tactile indicator, or audible indicator, and may be generated by a speaker, a display screen, a light, a vibration motor, or similar. The indicator may be mounted on the instrument 14 or located elsewhere, such as part of the navigation system 32 or console 33. The indicator 300 may take the form of a display screen or icon on an application associated with the user interface UI of the control system 60.

Control of the instrument 14 takes into account the latest positions and/or orientations of the anatomy (e.g., the one or more vertebra) and the instrument 14, which are transmitted from the navigation controller 36 to the instrument controller 28 over the data connection. Using these data, the instrument controller 28 determines the pose (i.e., position and/or orientation) of the target trajectory and/or virtual boundaries 184 in a desired coordinate system. The relative pose of the tool 20 (e.g., the TCP) to the target trajectory and/or virtual boundaries 184 is also computed. The instrument controller 28 updates the navigation system 32 (including the displays 38) with the position and/or orientation of the tool 20 relative to the anatomy to which the tool 20 is to be applied. An indication of the location of the target trajectory and/or virtual boundaries may also be presented.

The relative location of the tool 20 to the target trajectory and/or virtual boundaries is evaluated by the instrument controller 28 to determine if action needs to be taken, i.e., moving the tool 20, changing a speed (such as a rotational speed) of the tool 20, stopping operation of the tool 20, etc. Instructional data packets are sent, for example, to the motor controllers, such as from the instrument controller 28. These instructional data packets include the commanded positions or angles for each actuator 21, 22, 23, 24. Here, each commanded position may be a positive or negative number representative of a targeted cumulative encoder count relating to the number of rotations for each actuator 21, 22, 23, 24, or other representation of the actuator's position. Instrument controller 28 may also selectively regulate a cutting speed of the instrument 14 based on the relative location of the tool 20 to one or more of the virtual boundaries 184. For instance, the drive motor M that controls rotational speed of the tool 20 and corresponding cutting/burring/drilling, may be disabled by the instrument controller 28 any time the tool 20 is in an undesired relationship to the virtual boundaries, e.g., the tool 20 is off a target trajectory by more than a threshold value, the penetration of the tool 20 into the virtual boundary is greater than a threshold, etc. It is contemplated that the control system 60 may also control the drive motor M based on whether the optical tracking system retains line of sight for the tool tracker 52 and/or the patient tracker 54, 56. For example, the control system 60 may deactivate the drive motor M if line of sight has been compromised for a predetermined amount of time.

During use, in one potential implementation, the control system 60 determines a pose (a current pose) of the tool 20 with the navigation system 32 by virtue of the tool tracker 52 being located on the tool support 18. The instrument controller 28 may also determine a current position of each of the actuators 21, 22, 23, 24 based on an output encoder signal from the one or more encoders located on each of the actuators 21, 22, 23, 24. Once the current position of each of the actuators 21, 22, 23, 24 is received, the instrument controller 28 may calculate a current pose of the tool (TCP) with respect to the hand-held portion 16 (BCS) using forward kinematics. The localizer data may be used to determine the relative pose between the patient tracker 54, 56 and the tool tracker 52. The aforementioned poses may be combined, along with additional calibration and registration data, to compute the pose of the hand-held portion 16 (e.g., a current pose of the base coordinate system BCS) with respect to a desired coordinate system, such as the patient tracker coordinate system.

Once the instrument controller 28 has the pose of the hand-held portion 16 in the desired coordinate system, the instrument controller 28 may then control the plurality of actuators 21, 22, 23, 24. In one implementation, the instrument controller 28 may determine a commanded pose of the tool 20 based on the current pose of the hand-held portion 16 and based on a position and/or orientation of a planned virtual object, subject as a target trajectory. The instrument computes a pose (a commanded pose) of TCP with respect to BCS that results in the TCP aligned with the planned virtual object. This commanded pose may optionally be computed using the virtual constraints (guide constraints, joint centering constraints, joint limit constraints, workspace constraints). The instrument controller 28 may convert the commanded pose to a commanded position or commanded angle for each of the plurality of actuators 21, 22, 23, 24 using inverse kinematics, then send command instructions to the actuators 21, 22, 23, 24 to move to a commanded position/angle, thereby changing the pose of the tool support 18 and tool 20 relative to the hand-held portion.

Figure 46A:
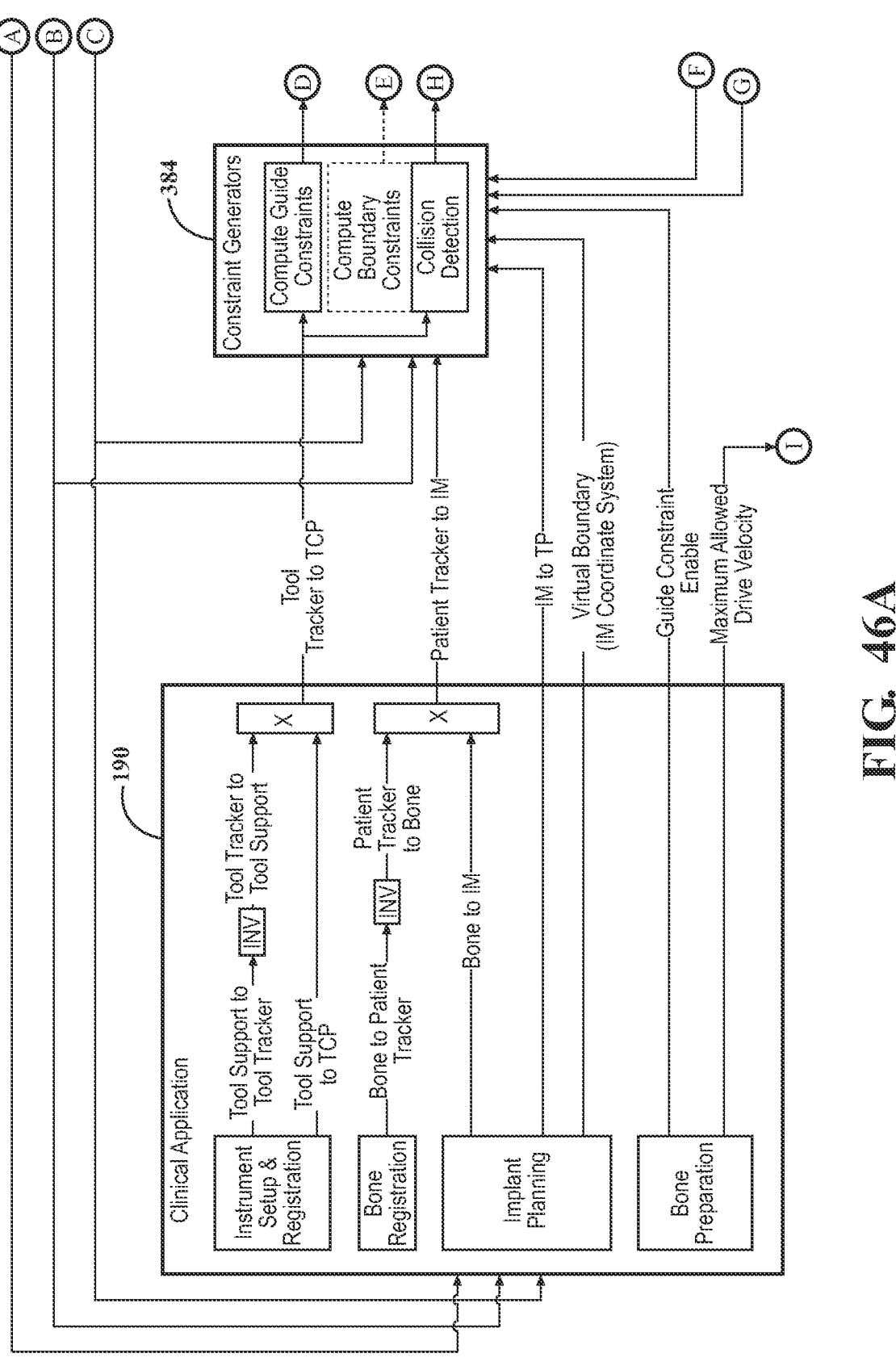
FIGS. 46A-46E are a block diagram of various portions of the control system.
Figure 46B:
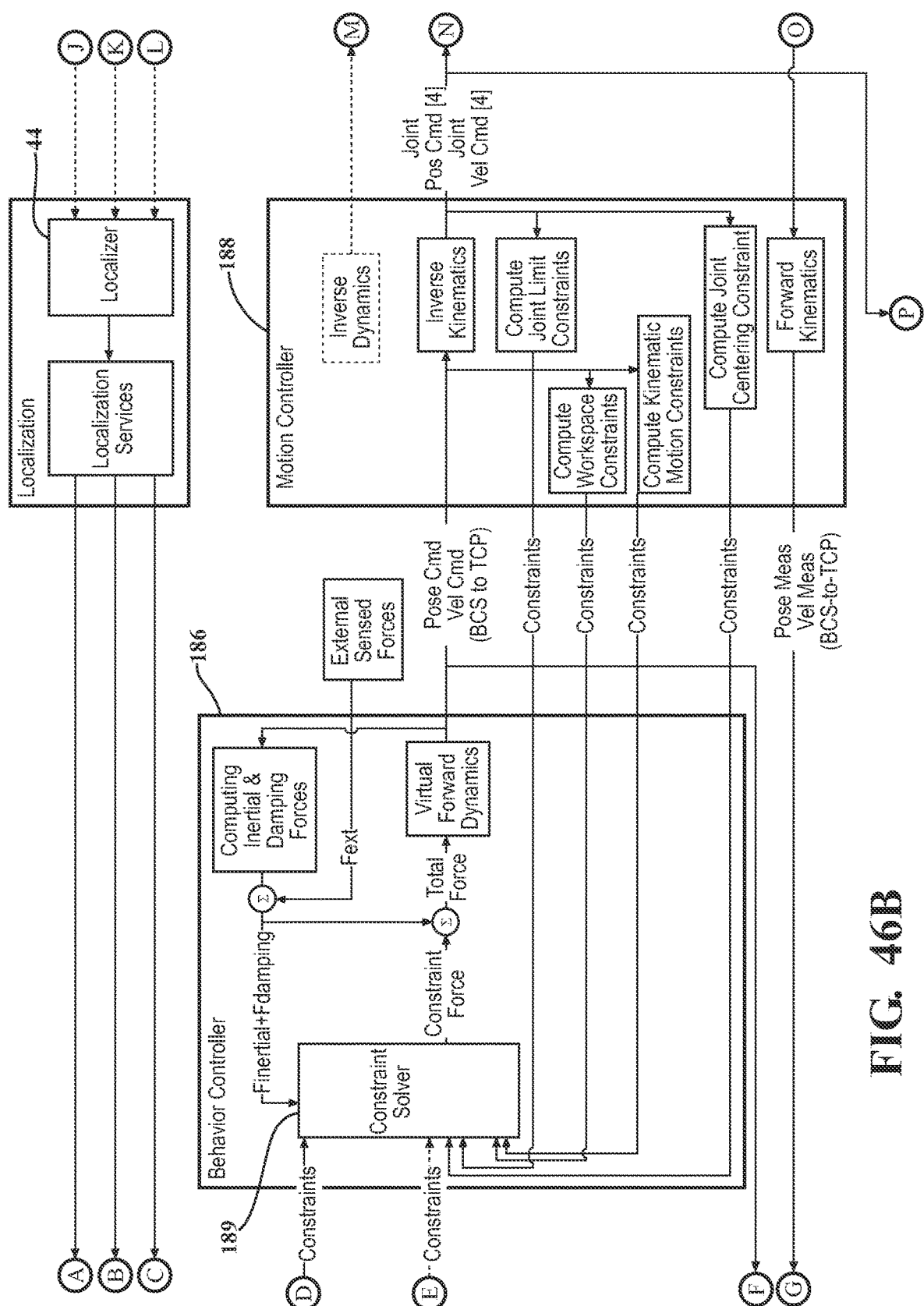

As can be seen in FIGS. 44 and 46A-46E, the control system determines the movements of the instrument and the energization of the drive motor M based on particular conditions and parameters. Starting at FIG. 46D, one or more trackers 54, 56 are placed on a patient's anatomy (e.g. one or more vertebra, femur, tibia, pelvis, glenoid, etc.) and one or more trackers 52 are placed on the instrument 14. The localizer 44 captures the position of each the trackers 52, 54, 56, and processes the position information into a common coordinate system (FIG. 46B).

The clinical application 190 is used to calculate registration and planning transforms used by the control system to command the tool. In FIG. 46A, the clinical application receives the pose information of the tool tracker 52 and the patient tracker(s) 54, 56 from the localizer 44. The clinical application 190 may also use the localizer data relating to the pointer tracker PT, tool tracker 52 and patient tracker 54, 56 to calculate device command transforms based on the hand-piece setup and registration, bone or patient registration, implant planning, and bone or tissue preparation.

Within the clinical application 190, the tool tracker 52 and pointer tracker PT information is processed with hand piece setup and registration information to create tool tracker-to-TCP (tool tracker-to-TCP) transform. This may be computed by combining results of two registration steps: 1) registration of the tool support 18 to the tool tracker 52, and 2) registration of the tool support 18 to the tool (TCP). The resulting tool tracker-to-TCP transform (i.e., the instrument registration result) is then forwarded to the constraint generator 384. The position information from the localizer 44 is used with the bone registration data to calculate a bone-to-patient tracker transform and then inverts to yield a patient tracker-to-bone transform, associating the location of the patient tracker with the bone. Utilizing one or more of the user interfaces UI, the user may adjust the size and positioning of the desired implant with respect to an on-screen bone model to allow the Clinical Application to create a bone-to-implant transform based on the location of the bone relative to the planned position and/or orientation of the implant. Based on the known geometry and size of the selected implant, the Clinical Application looks up the transform of the planned pose of the implant to a desired one or more target trajectories TTRAJ, an implant-to-target-trajectory transform. A virtual boundary may also be calculated based on the selected implant. The patient tracker-to-bone transforms and the bone to implant transform (B-to-IM) are combined to yield a patient tracker 54, 56 to implant pose transformation (patient tracker-to-IM), which is a combined result of bone registration and implant planning, which is forwarded to the constraint generator 384. The IM to TTRAJ transform may be used to generate the guide constraint and the boundary may be used to generate a boundary constraint (if used) with the boundary generator. The boundary information may also be sent to the drive command handler 192.

Three transforms are utilized to ultimately determine the hand-held portion to localizer transform: a) a hand-held portion to TCP transform, the forward kinematic result received from the motion controller 188; b) a tool support to TCP transform, the tool registration result received from the clinical application 190; and c) a tool tracker to localizer transform received from the localizer 44. A localizer to patient tracker(s) transform(s) may also be received from the localizer 44. Then, a hand-held portion to patient tracker transform may be computed based on: a) a hand-held portion to localizer transform; and b) a localizer to patient tracker(s) transform. It should be appreciated that the tool tracker coordinate system and the tool support coordinate system may be used interchangeable with one another as the pose of the tool support may be fixed relative to the TCP with a known, calibrated, and/or registered transform.

The motion controller 188 controls the motion of the tool support 18, and specifically the TCP coordinate system. The motion controller 188 receives data defining the next commanded pose from the behavior controller 186. Based on the data, the motion controller 188 determines the next position/angle of each of the actuators (e.g., via inverse kinematics and Jacobian calculators) so that the tool support can assume the pose relative to the hand-held portion as commanded by the behavior controller 186, e.g., at the commanded pose. In other words, the motion controller 188 processes the commanded pose of the tool support relative to the hand-held portion, which may be defined in Cartesian coordinates, into commanded joint positions/angles of the plurality of actuators 21, 22, 23, 24 so that the instrument controller 28 can command the actuators accordingly. In one version, the motion controller 188 regulates the position of the tool support with respect to the hand-held portion and continually adjusts the torque that each actuator 21, 22, 23, 24 outputs to, as closely as possible, ensure that the actuators 21, 22, 23, 24 move the tool support 18 relative to the hand-held portion 16 such that the commanded pose can be reached.

The joint position velocity controllers 194 are used to process the data from the motion controller 188 and process the commanded joint position command (Joint Pos Cmd) and the joint velocity command (Joint Vel Cmd) to determine a joint torque command (Joint Torque Cmd) for each of the actuators. The calculation of the joint torque command may be done through a closed-loop control algorithm, such as PID control. The joint torque command is sent into the surgical instrument where each of the current controllers corresponding to each actuator interprets the joint torque command into a current. The current controller then selectively applies voltage as needed to drive the commanded current to each actuator motor causing each actuator to move the tool support towards a commanded position. The applied torque (or current) may cause each of the actuators to move and accelerate in the corresponding direction. The amount of travel and the speed the actuators move/accelerate may depend on the mechanical load, friction, other outside factors, or a combination thereof. By monitoring each of the actuators position feedback over time, the commanded torque (current) is adjusted by the position-velocity controller so that the commanded position of each actuator is tracked closely. As the actuator motors are adjusting the tool support, each motor encoder is collecting rotational and/or positional data for each rotor and sending the joint position data back to the current controller. The current controller then processes the joint position data of each actuator into a joint velocity measurement (Joint Vel Meas) and a joint position measurement (Joint Pos Meas) and sends the joint velocity measurement data and the joint position measurement data through the joint position-velocity controller to the motion controller 188. The motion controller 188 then transforms the joint position and velocity measurement data of each actuator with forward kinematics to generate pose and velocity relationships between the TCP and the hand-held portion 16.

Figure 47:
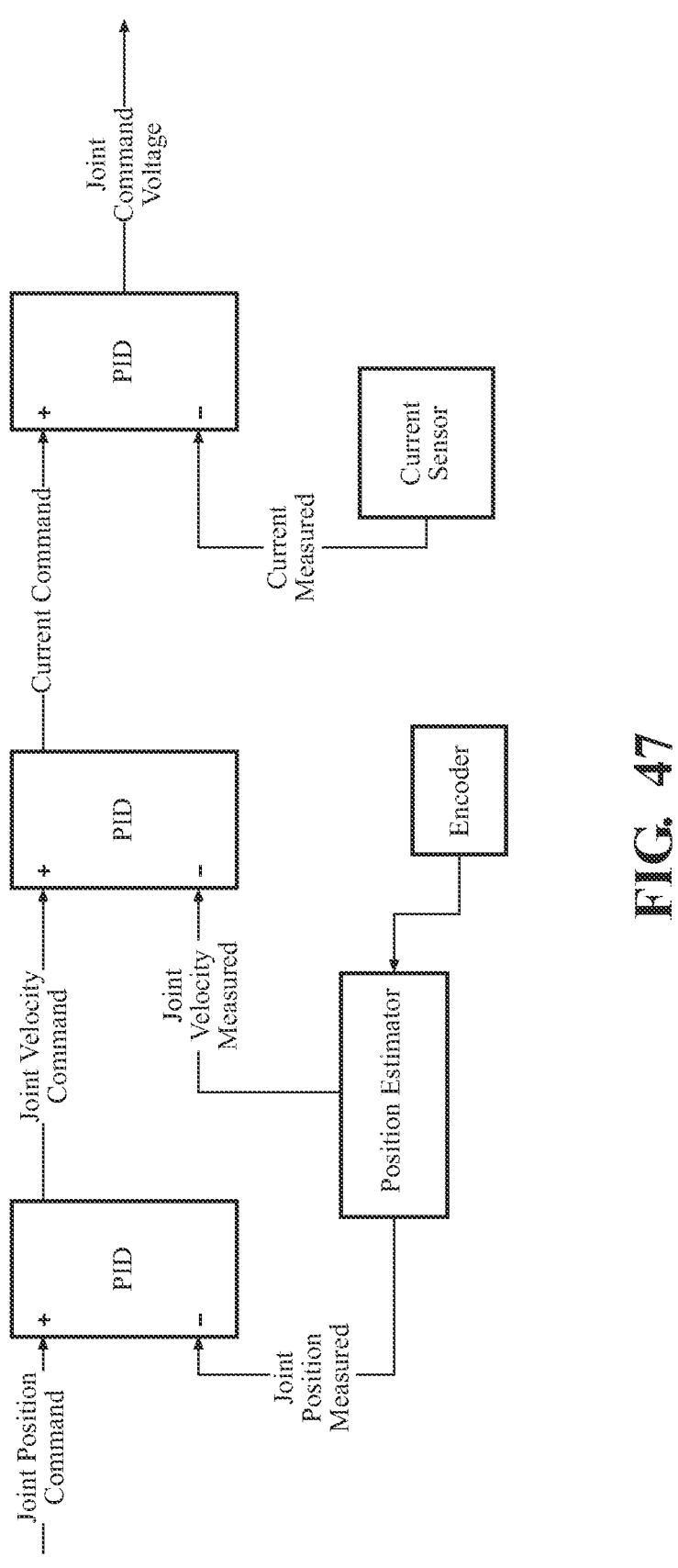
FIG. 47 is a block diagram of a control system.

In addition, with reference to FIG. 47 the joint velocity measurement and the joint position measurement may be used in the PID control loops. For example, PID loop may compute an error between the joint commanded position and the joint measured position, which may be used with a PID loop to control the joint commanded velocity. The commanded velocity of the joint may be compared versus the joint measured velocity to determine an error. That error may be used in a PID loop to control the commanded current. The commanded current may be compared versus the measured current to determine an error. That error may be used in a PID loop to output a commanded joint voltage.

Figure 46C:
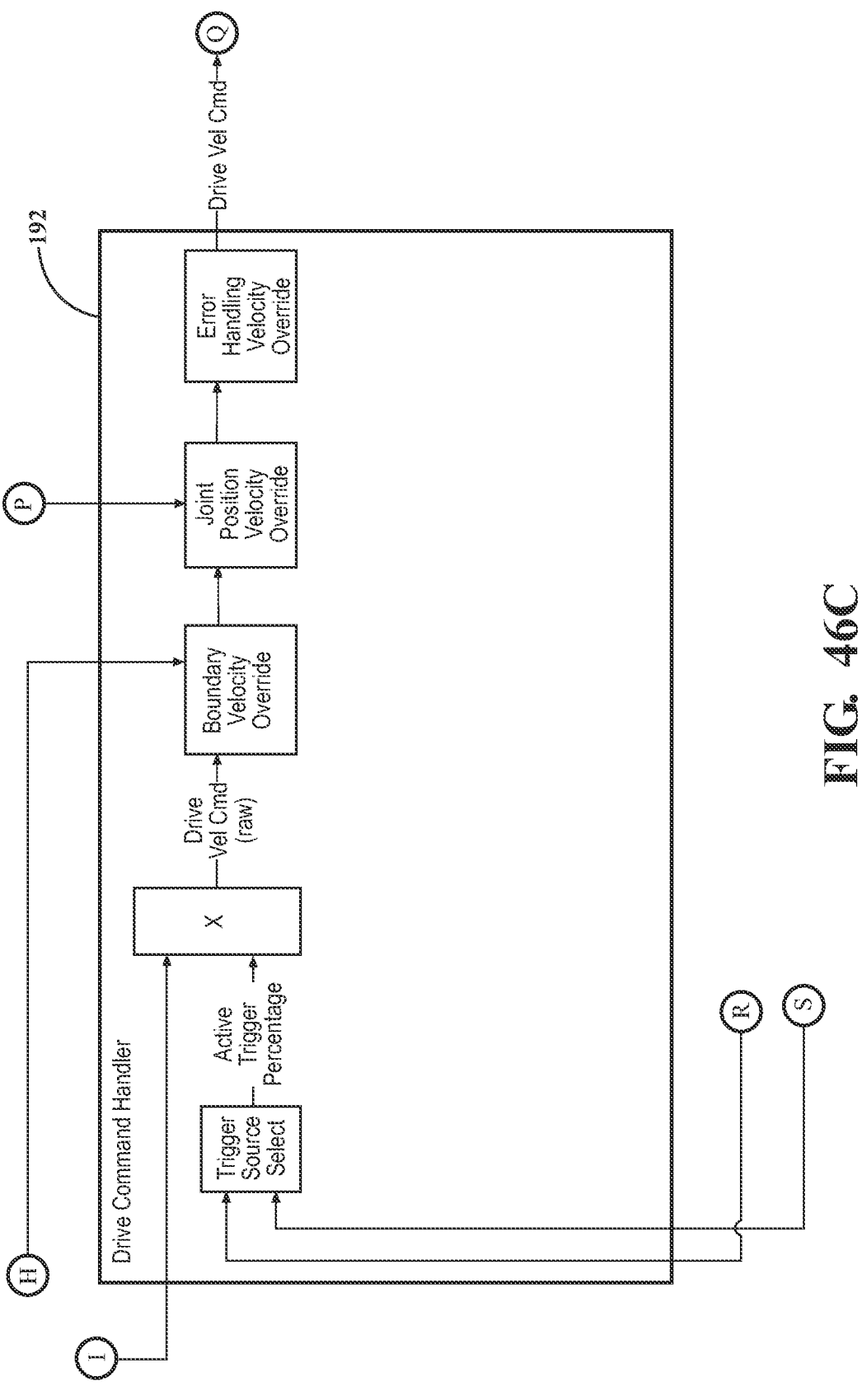
Figure 46D:
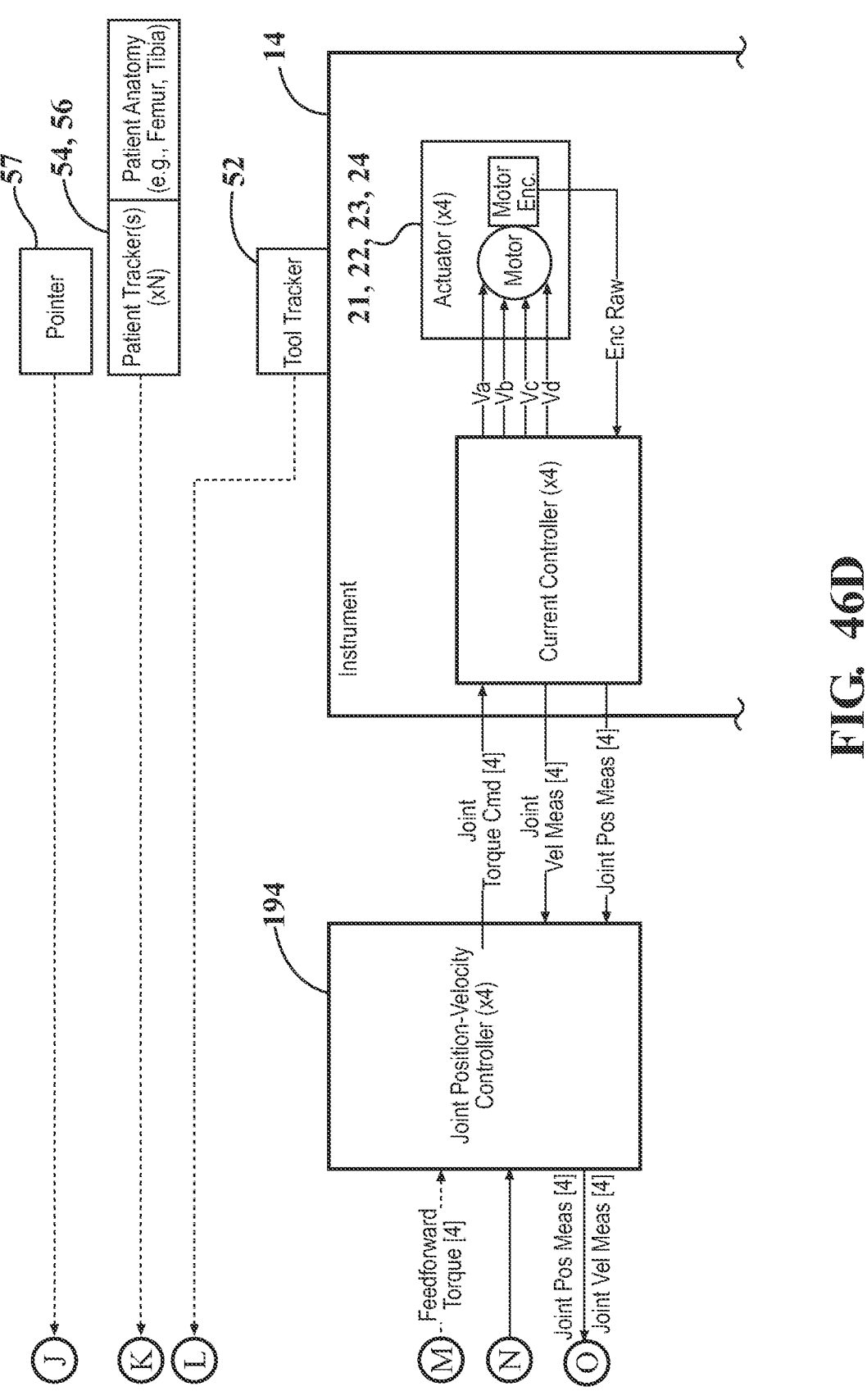
Figure 46E:
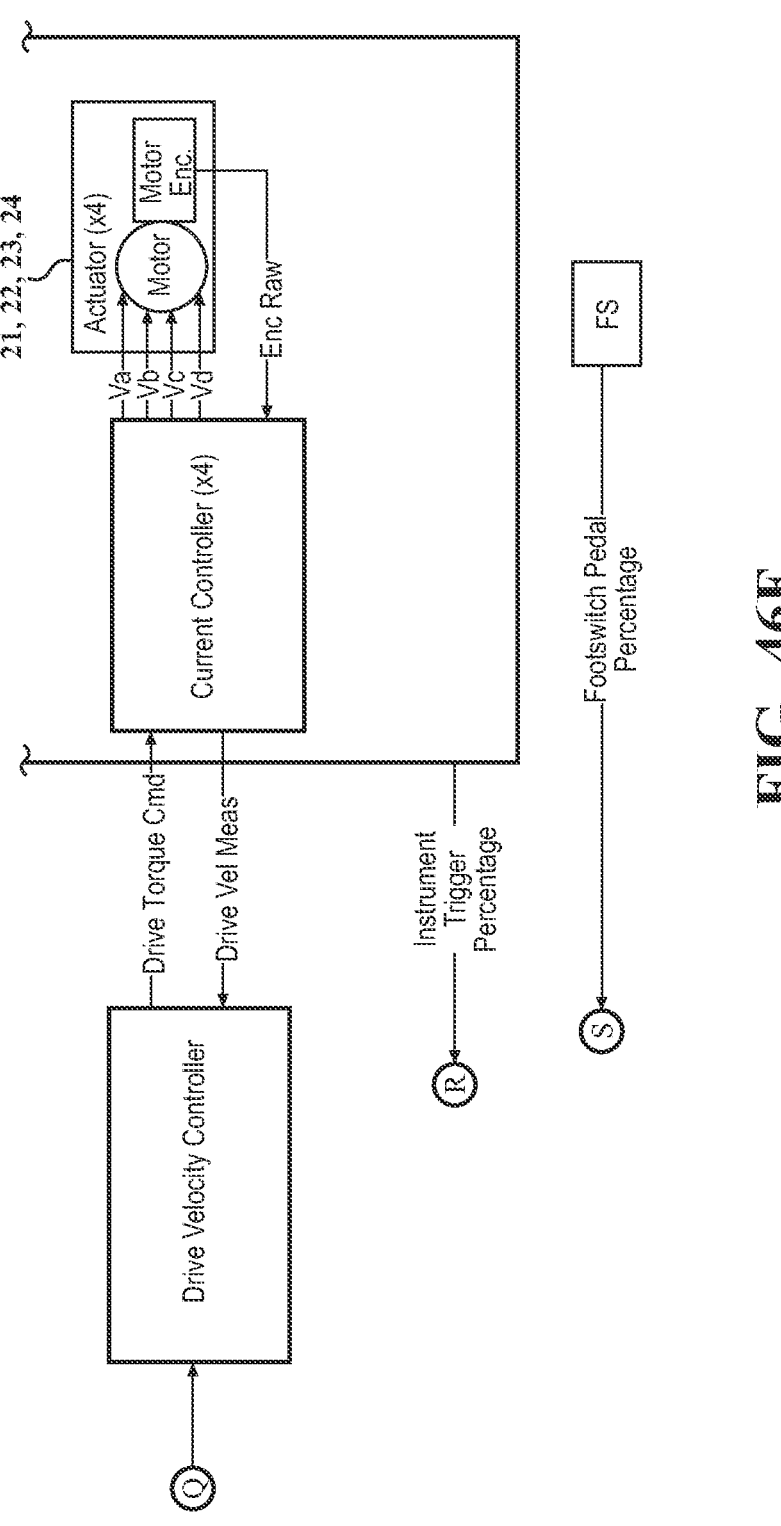

The drive command handler 192 is a part of the control system which calculates and determines particular parameters for controlling the drive motor M (FIG. 46C). The drive command handler 192 receives input command signals from one or more input devices to actuate the drive motor M. As can be seen in FIG. 46E, one example of an input device is a trigger on the hand-held portion of the instrument. Another example, also displayed in FIG. 46E is a foot switch. In another example, the drive command handler has a trigger source select, which may be used to multiplex between multiple user input devices (such as a button, a trigger, and a foot switch). In some examples, the trigger source select only evaluates a change in trigger source when both input devices are inactive, and then evaluates which input device becomes active first. The selected input device may then determines the active trigger percentage. In other examples, potentially one input device may have priority over the other. When one or more of the input devices are actuated, a command signal is sent to the drive command handler 192 which then analyzes the percentage which the input device was actuated (e.g. how far the trigger was squeezed by a user). The drive command handler 192 analyzes the command percentage with the maximum allowed velocity output from the bone preparation portion of the clinical application and modifies the command signal according to the data received.

The drive command handler 192 may also utilize results from the collision detection performed within constraint generator 384 or other component of the control system. In the illustrated configuration, the constraint generator 384 compares the position and/or orientation of the tool to a boundary. Specifically, as described previously, collision detection determines whether the tool is violating the boundary by more than a threshold amount. Further, the collision detection step processes this location information to determine a boundary velocity override signal. As mentioned above, any number of suitable boundaries may be used for this collision detection step, such as the depth boundaries. Based on this comparison, the instrument controller 28 may alter a motor parameter, which may be used to slow or stop the drive motor M.

Figure 48:
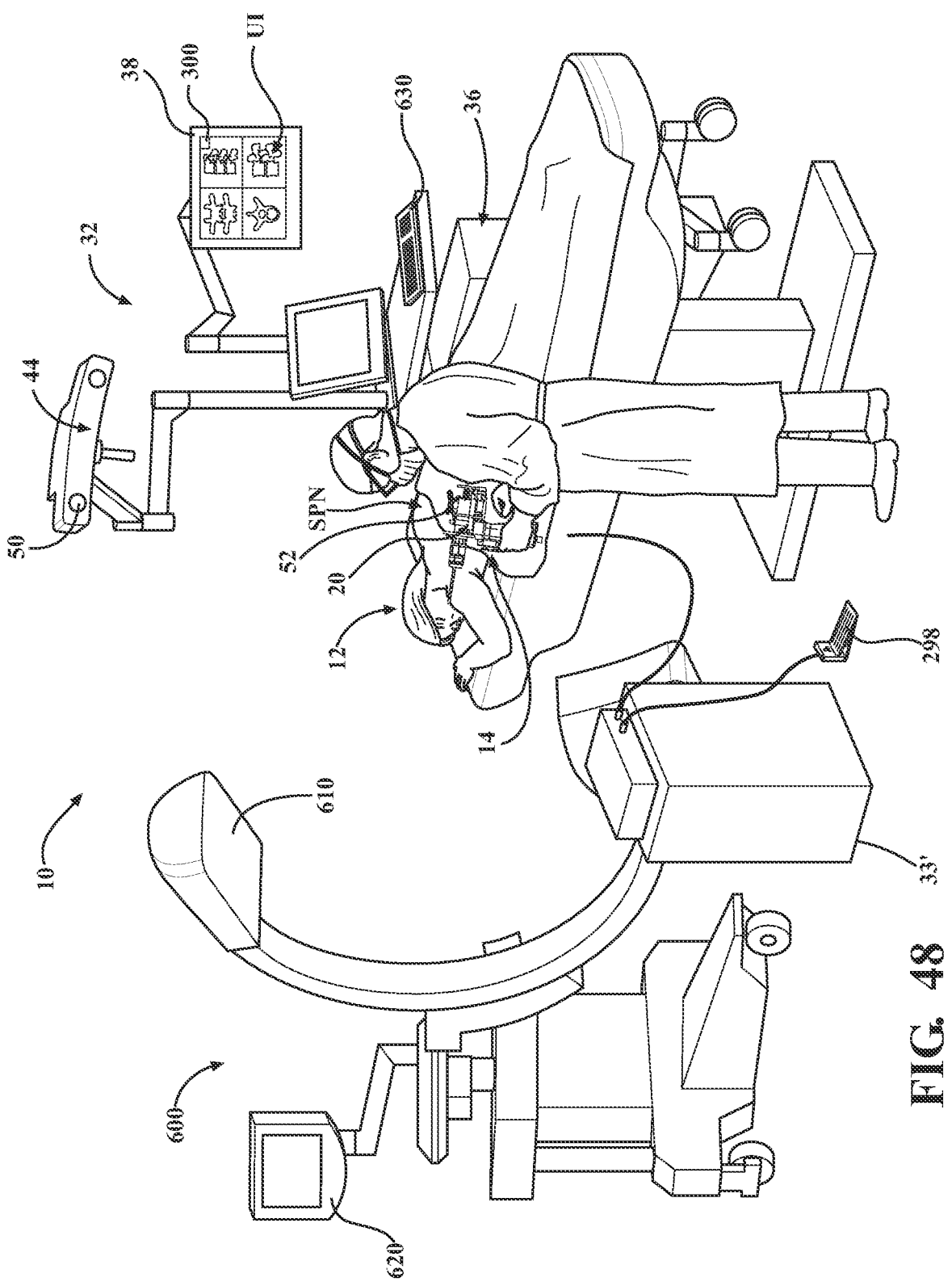
FIG. 48 is another perspective view of a surgical robotic system.

FIG. 48 illustrates another example of the surgical robotic system 10 further including an imaging system 600, such as CT or MRI imaging device. The imaging system 600 may comprise a scanner 610 and a display unit 620. The scanner 610 may be utilized to take an image of the surgical site on the patient 12 and display it on the display unit 620. For example, the scanner may comprise a C-arm configured to be rotated about the patient 12 to produce a plurality of images and/or models of the surgical site (e.g. the spine SPN). In other examples, the scanner may be a CT machine capable of helical scans and scout scans. The imaging system 600 may also comprise a processor (not shown) including software, as is known by those skilled in the art, which is capable of taking the plurality of images captured by the scanner 610 and producing a 2-D image and/or a 3-D model of the surgical site. The display unit 620 may be configured to display the resulting 2-D image and/or 3-D model.

The imaging system 600 may also be in communication with the navigation controller 36 of the surgical navigation system 32. The imaging system 600 may be configured to communicate via a wired and/or a wireless connection with the navigation controller 36. For example, the imaging system 600 may be configured to provide pre-operative and/or intraoperative image data, such as the resulting 2-D image and/or 3-D model of the surgical site, to the navigation controller 36. The navigation controller 36 may then be configured to provide the resulting 2-D image and/or 3-D model to the navigation display unit 38, where the surgeon, using the user input 630 or using algorithms, may identify and/or define the corresponding regions and/or zones around critical anatomical structures. For example, the surgeon may utilize the user input 630 of the surgical navigation system 32 to define an alert zone around a vertebral body, a nerve or a blood vessel that the surgeon wishes to avoid during execution of the medical procedure. The surgeon may utilize the user input 630 of the surgical navigation system 32 to input and/or modify the planned surgical trajectory, boundaries, or alert zones to be utilized in executing the medical procedure.

Referring to FIGS. 67-69 and 73A-74B, once a hole is established, the control system 60 may automatically adjust values of one or more motion parameters of the tool 20 relative to the hand-held portion 16 as the user drills or drives the tool into bone. In one example, while approaching the cut, the tool is automatically aligning to the target trajectory TTRAJ. For one implementation, the control system 60 maintains the active state of the guide constraints as the tool contacts bone and enters beyond a specified depth boundary FB, distance parameter relative to a reference location/reference coordinate system. At the moment the tool passes the specified depth FB, the control system 60 senses the current positions/angles of the actuators, and sets the current position/angles of the actuators as the new joint centering positions, enabling the joint centering constraints and disables the guide constraints. This causes the system to enter a free hand mode with the 'tool to handle' alignment frozen as it was when it first entered and proceeded into the bone. The user may continue drilling or driving, but the control system 60 does not automatically correct for alignment while the tool remains within the bone beyond the specified depth because the guide constraints are inactive. Even though the instrument is frozen in a fixed pose, the tool may still stay approximately on the target trajectory TTRAJ, since the hole in the bone formed by the initial actuation of the tool is mechanically constraining the motion of the tool to stay in that hole. As the user starts to move the tool towards the bone exit, the system returns to a mode where the guide constraints are active once the depth is less than the earlier configured value (e.g., the pose of the tool relative to a reference location/reference coordinate system is at a threshold value). At this point, joint centering constraints are disabled and the guide constraint is reenabled to resume aligning the tool to the trajectory. By disabling the guide constraints and enabling joint centering constraints, the tool is prevented or less likely to bind the tool within bone. Once a certain depth of hole is reached in hard bone, the drill bit or other tool is effectively constrained by bone recess formed during the initial drilling. If the accuracy of the tool alignment has any small errors (due to calibration inaccuracy, etc.), the robotic system may be prevented from restoring the tool to the target trajectory, and the walls of already drilled hole of the bone may block the tool from returning to the target trajectory. As a result, the control system is limited in restoring the alignment of the tool when deep into the bone, and, if binding occurs, cause the user to have to apply increased force to complete the hole. Such an approach may ensure that the guide constraints are enabled upon bone approach (within a threshold value of a reference location/reference coordinate system) and hole drilling, to ensure that the initial drill entry performed in the bone is as accurate as possible, and to continue this alignment until a certain depth is reached sufficient to mechanically constrain further (deeper) motion of the tool.

Figures 74A, 74B:
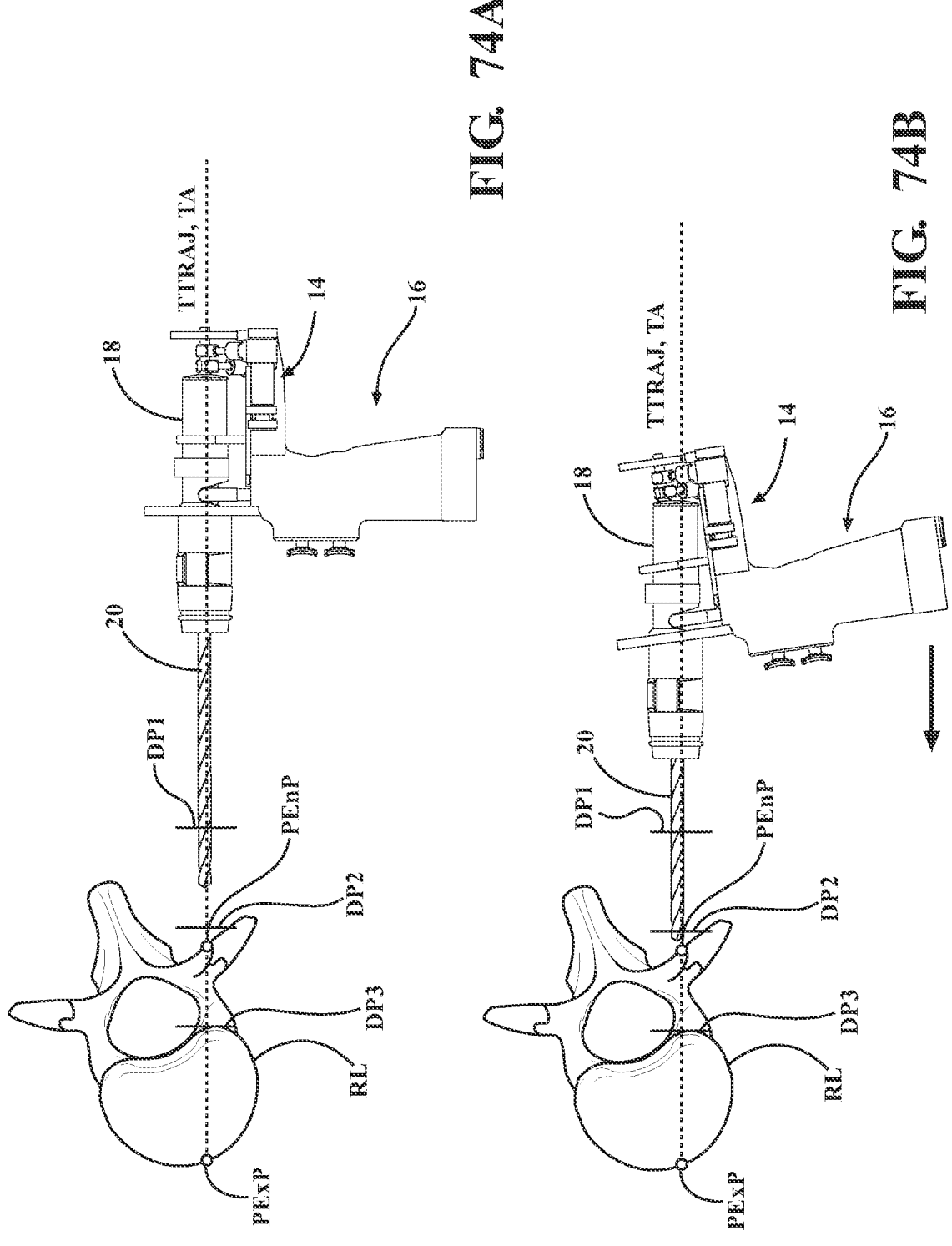
FIGS. 74A and 74B illustrate schematic views of the instrument approaching the target bone relative to various distances.

With reference to FIGS. 74A and 74B, one exemplary way of controlling the plurality of actuators is described. When the position of the tool (TCP) is spaced from the reference location associated with bone with a first distance parameter (DP1), the instrument is controlled such that the tool support is moved relative to the handheld portion, e.g., a motion parameter with a magnitude greater than zero is used. This is because the hole has not yet been sufficiently established. In this instance, the guide constraints have a value greater than zero and have a high stiffness value, actively adjusting and commanding the tool support 18 to stay on the desired trajectory.

With reference to FIG. 74B, when the position of the tool (TCP) is spaced from the reference location associated with bone with a second distance parameter (DP2), the instrument is controlled such that a motion parameter has a lower magnitude, such as a magnitude of greater than zero and less than the magnitude associated with DP1 is utilized or the movement of the tool support relative to the hand-held portion is slowed. When the position of the tool (TCP) is spaced from the reference location associated with bone with a third distance parameter (DP3), the instrument is controlled such that a motion parameter has a lower magnitude, such as a magnitude of zero is utilized or the movement of the tool support relative to the hand-held portion is stopped. This is because the hole has been sufficiently established. In this instance, the guide constraint force value is reduced or inactive and the joint centering constraint force value is also reduced and/or disabled. Alternately, the joint centering constraint may be re-set to hold this fixed relative pose between the tool support 18 and hand-held portion 16.

The various distance parameter thresholds may be used to transition the instrument between other modes than that which is described with respect to FIG. 74B, such as transitioning the instrument from unguided mode to trajectory mode, or trajectory mode to various 2-DOF modes, such as 2-DOF translation mode or 2-DOF orientation mode.

In general, wherein the instrument 14 is far from the patient anatomy, such as far from the vertebra or far from the target trajectory, guided mode of the instrument should be disabled. In other words, the guide constraint should be deactivated and/or the trajectory mode should be disabled. In instances where the instrument 14 is near the vertebra or the target trajectory (within a given spatial region, boundary, or distance parameter), the guided or trajectory mode should be enabled.

Figures 73A, 73B:
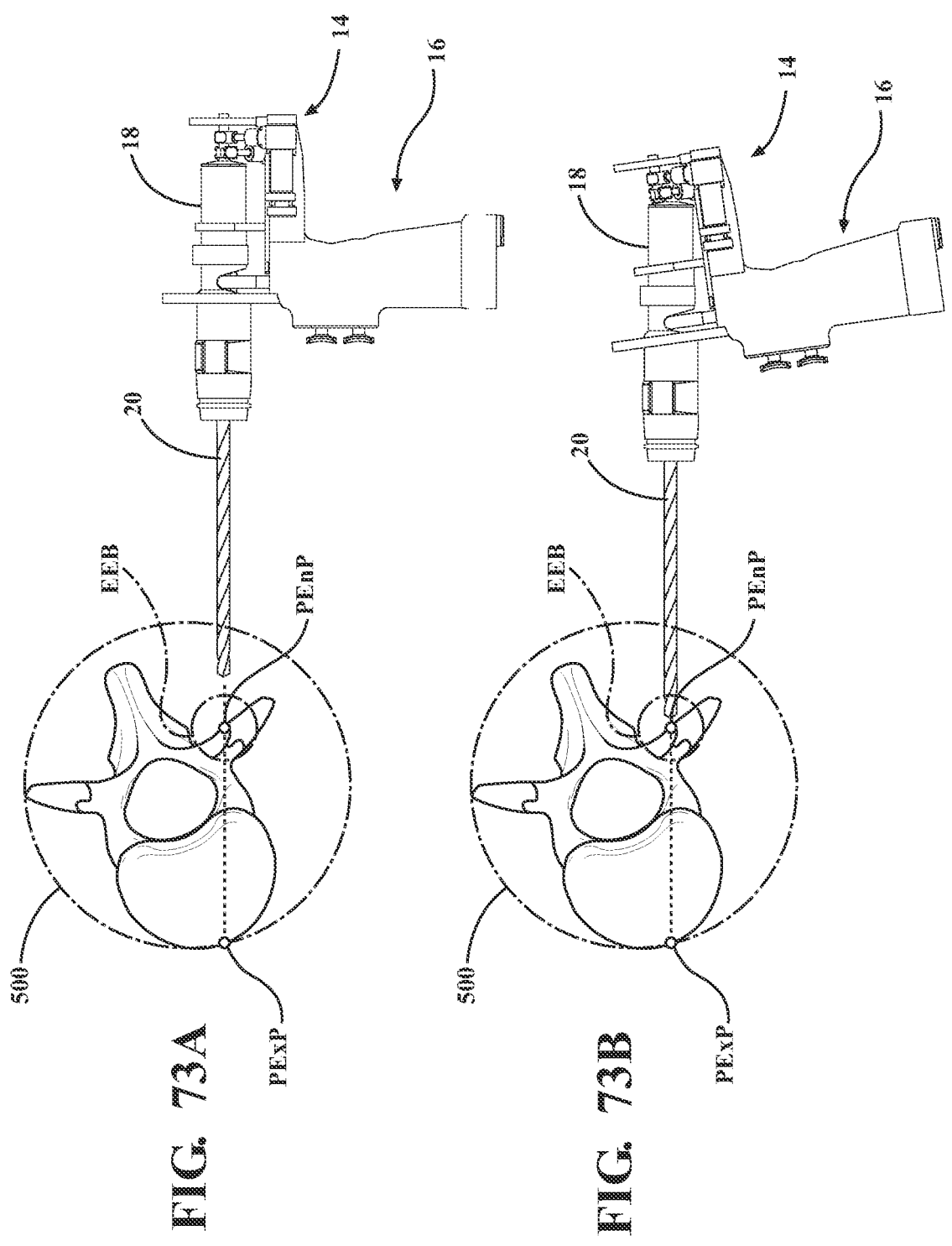
FIGS. 73A and 73B are schematic views of the instrument approaching bone relative to various control zones.

Referring now to FIGS. 73A-73B, one way for the system 10 to determine which region the instrument 14 is in is by monitoring the position of the TCP of the tool 20 relative to the patient anatomy, such as relative to a virtual object 500 defined relative to the patient or relative to a reference location that is known relative to the patient anatomy. As such, the control system 60 may determine a state of the surgical tool 20 in the known coordinate system. As described above, the state of the TCP of the surgical tool may be determined based on tracking one of the tool support 18 and/or the hand-held portion, along with CAD data or a tool registration process. In certain instances, the user may position the instrument 14 such that the TCP of the tool 20 or other tool is on the edge of the different spatial regions, such as frames, boundaries or distance parameters. There is frequently some deviation in the TCP position, either based on the steadiness of the user's hand and/or the noise in the measurements of the localizer. In this case, the TCP may move inadvertently back and forth between the two different spatial regions, which could cause the instrument 14 to transition between the mode where the instrument 14 is guided and the mode where the instrument 14 is unguided. This would likely be unpleasant to the user since they would feel the motors of the plurality of actuators rapidly engage and disengage, and flutter/chatter on/off as they move between the different spatial regions.

To rectify one or more of the issues, the control system may be configured to activate the guided mode or trajectory based on a first relationship criteria between the state of the surgical tool 20 and the reference system and the control system may be configured to deactivate the guided mode based on a second relationship criteria between the state of the surgical tool 20 and the reference coordinate system, where the first and second relationship criteria are different. Alternatively, the control system need not utilize a reference coordinate system, but rather activate and deactivate the guided or trajectory mode based on relationships between the state of the surgical tool and the patient coordinate system, i.e., one defined relative to a tracker coupled to a portion of the patient's anatomy. The reference coordinate system may also be based on the target pose of the surgical tool. Similar approaches may be used for other mode transitions beyond the guided/unguided mode transitions, such as transition between pointing mode and trajectory mode and/or trajectory mode to 2-DOF mode and/or 2-DOF orientation mode to 2-DOF translation mode.

In this instance, guided or trajectory mode may be defined as a mode operable to control the plurality of actuators to align the surgical tool with a virtual object, such as the target trajectory. Guided mode is not limited to use of the guide constraint to align the surgical tool to the virtual object, but guided mode may include activation of the guide constraint in some instances. In some instances, the state of the tool may be characterized as the pose of the surgical tool. Virtual object 500 may be configured as a small sphere and could be used as a basis to enable the guided or trajectory mode when the control system 60 is in the unguided mode.

Once the tool 20 establishes the hole, the instrument controller 28 may set the value of the motion parameter to a lower magnitude or zero and/or control the state of the virtual constraints, to stop or reduce the actuators 21, 22, 23, 24 from adjusting the tool support 18 relative to the hand-held portion 16. Once the tool 20 has established a hole within the bone, the tool 20 may flex and move off course a small amount (e.g. skive), pushing back onto the hand-held portion 16 as the control system attempts to adjust for the error. The user may perceive this force as a push-back, since a drill bit is not typically designed to remove hard bone in the direction necessary to adjust pitch and/or roll, for example, once embedded into bone. The sense of "push-back" or "fighting" the hand-held portion is created by the control system controlling the actuators 21, 22, 23, 24 while the tool 20 is in the drilling hole 290 (See FIGS. 67-69). Thus, the only movement that is caused by controlling the actuators to move towards the desired trajectory is movement of the hand-held portion 16. This means that the control system may cause forces to be applied to the hand-held portion 16, which are then transferred to a user's hand. These forces may result in fatigue and/or discomfort during the drilling process. By changing the motion parameter, the tool 20 may provide less resistance further in the hole. A user may find that by setting the motion parameter value to 0 or by otherwise stopping the movement of the hand-held portion 16 relative to the tool support 18 allows the hole to be finished without struggling against the hand-held portion 16 when the tool 20 is within the drilling hole 290, the drilling hole 290 serving as a natural drill guide. More particularly, the instrument controller 28 may actively change values of the motion parameter relating to force, velocity, acceleration, or other states of each of the virtual constraints, so that the further the tool 20 enters into the target anatomy, the actuators 21, 22, 23, 24 adjust towards the target trajectory with a relatively lower force, velocity and/or acceleration than when the hole was first initiated, eventually stopping actuator movement when the tool 20 is mid-hole, utilizing the hole drilled into the bone as the guide. In some examples, an external force/torque sensor may allow the user's applied force to be considered in the virtual simulation. In such cases, the stiffness of the guide constraint may be reduced once the tool is sufficiently into the bone and the hole is established. With reduced guide stiffness and sensing of the user applied force, the constraint solver may find an equilibrium in which the user is able to balance out the guide forces with a small magnitude of applied force. This may give the user haptic feedback indicating to the user that the tool 20 is not perfectly aligned on trajectory, but at a magnitude such that it does not create fatigue or cause the hand-held portion 16 to push back excessively to the point that the joint limits of the actuators 21, 22, 23, 24 are exhausted.

In addition, in another exemplary configuration, based on the magnitude of sensed external force, either from a force/torque sensor or derived via actuator motor currents, the control system may trigger the joint centering mode, or transition to one of the contemplated 2-DOF mode, such as transition from the trajectory mode to the 2-DOF translation mode or 2-DOF orientation mode, or transition from the 2-DOF translation mode to 2-DOF orientation mode. This allows the control system to detect 'fighting' and go into 'fixed handle'/free-hand/unguided mode when detected. Such a method would also typically be utilized in conjunction with drive motor boundary control, see exemplary DB1, DB2, DB3 or control frame FR1, discussed further below, to ensure that the tool stays sufficiently on trajectory when the handle is fixed (and hopefully being guided by the established bore hole) to allow the drilling to continue. If the boundary or frame gets violated due to the tool drifting too far off trajectory, either feedback could be given to the user through a suitable indicator or the drive motor parameter may be adjusted (e.g., the drive motor may be turned off).

As will be described in detail below, in some examples, the instrument 14 may be in a first control mode, referred to as trajectory mode. In trajectory mode, the control system may control actuators 21, 22, 23, 24 to adjust the instrument 14 in a plurality of degrees of freedom. In some examples, with reference to FIGS. 70 and 71, the first control mode may adjust the position of the tool axis both in the proximal plane PP and the distal plane DP. The compound movement of actuators 21, 22, 23, 24 allows the instrument 14 to be adjusted in at least four degrees of freedom. The first control mode may be selected by a user manually, or based on the location of the instrument 14 relative to a virtual object, such as a boundary 500, a reference location, or a combination thereof as will be described in further detail below.

In some examples, the instrument may be placed in the first control mode (trajectory mode) and the second control mode (one of the 2-DOF modes) based on the state of the surgical tool and based on a boundary 500, FB. In some examples, the boundary is set relative to an anatomical feature (e.g., cortical surface), a planned implant (e.g., pedicle screw), or both. The trajectory control mode may adjust the instrument 14 in at least two translation degrees of freedom and at least two orientation degrees of freedom as illustrated in FIGS. 3A-8B. In this example, the control system 60 monitors the position of each actuator 21, 22, 23, 24 and the location of the TCP of the tool 20 relative to the preplanned boundaries, such as the target trajectory TTRAJ. As the instrument 14 is approaching the bone, the control system 60 controls the actuators 21, 22, 23, 24 in a first control mode, such that the tool support is manipulated in at least four degrees of freedom. As the instrument 14 approaches the target bone, one or more of the actuators may be nearing or at the maximum amount of adjustment relative to the workspace limits, depending on the position the user is holding the instrument 14 relative to the target trajectory TTRAJ and the location of the TCP relative to the target bone. The state of the surgical tool 20 may correspond to the state of each of the actuators 21, 22, 23, 24 and how much range each of the actuators 21, 22, 23, 24 has to adjust the tool 20 relative to the target trajectory TTRAJ. In addition to monitoring the state of the actuators 21, 22, 23, 24 and the instrument 14, the position of the tool 20 and corresponding TCP is monitored relative to the target trajectory TTRAJ and/or one or more boundaries.

While in trajectory mode, in one example, when the TCP is substantially misaligned with the target trajectory TTRAJ (see discussion of control frame FR1 below), the actuators 21, 22, 23, 24 and the drive motor M may be shut off so that the user does not enter the bone at the wrong location or trajectory.

Referring to FIGS. 61 and 62, the target trajectory TTRAJ may include a target axis extending between a bone entry point, which can be designated as a planned entry point PEnP and a second point PExP, such as planned bone exit point PExP or a point distal the planned bone exit point or a point distal of the targeted anatomical structure. The entry point PEnP may be a point located on tissues other than bone, or the planned entry point may be a point not actually on the patient's body. While illustrated that that second point is the PExP which is on the surface of the bone, the second point of the trajectory may be a point located on tissues other than bone, or the second may be a point not actually on the patient's body or may be distal the target anatomical structure. As such, any instance of the planned entry point could be replaced with planned first point, and any instance of planned exit point could be referred as a planned second point such that the trajectory need not be defined by planned entry and exit points. The target trajectory TTRAJ can be based on the axis of a planned implant IM, as illustrated in FIG. 61 or based on a target anatomical location, such as a biopsy location or tumor location.

Referring to FIGS. 70 and 71, the control system may be operable to control the instrument by controlling the plurality of actuators relative to one or more of a first virtual plane DP, a second virtual plane PP, and a third virtual plane, TCP Plane. The first virtual plane DP may be referred to as the distal plane and the second virtual plane PP may be referred to as the proximal plane. While it is contemplated that these virtual planes DP, PP are aligned with the ring-shaped alignment guides 66, 68 in the known coordinate system, the ring-shaped alignment guides are optional and not needed to implement the described control methodology. The control system may be understood as operating to control the trajectory of the tool by controlling the plurality of actuators 21, 22, 23, 24 in two separate pairs. One pair of actuators 21, 22 is for controlling the position of the tool in the first virtual plane, DP, and the other pair of actuators 23, 24 is for controlling the position of the tool in the proximal plane PP. With respect to the instrument described above, actuators 21, 22 can be understood as the first pair of actuators for controlling the position of the tool in the distal plane DP, and actuators 23, 24 can be understood as the second pair, for controlling the position of the tool in the proximal plane PP. The position of the distal end of the tool can also be visualized as a plane, referred to herein as the TCP plane. This represents the position of the distal end of the tool in a plane.

With reference to FIG. 70, the target trajectory TTRAJ can be understood as virtually penetrating the proximal plane PP and distal plane DP and TCP plane. The control system controls the plurality of actuators to move the tool platform to the location of the trajectory TTRAJ on each of the planes DP, PP, TCP plane respectively. In the known coordinate system, the proximal, distal, and TCP planes are all parallel to one another. The positions of the proximal, distal, and TCP planes may be considered fixed relative to the base coordinate system BCS described above, i.e., fixed relative to the hand-held portion of the instrument.

Figure 72:
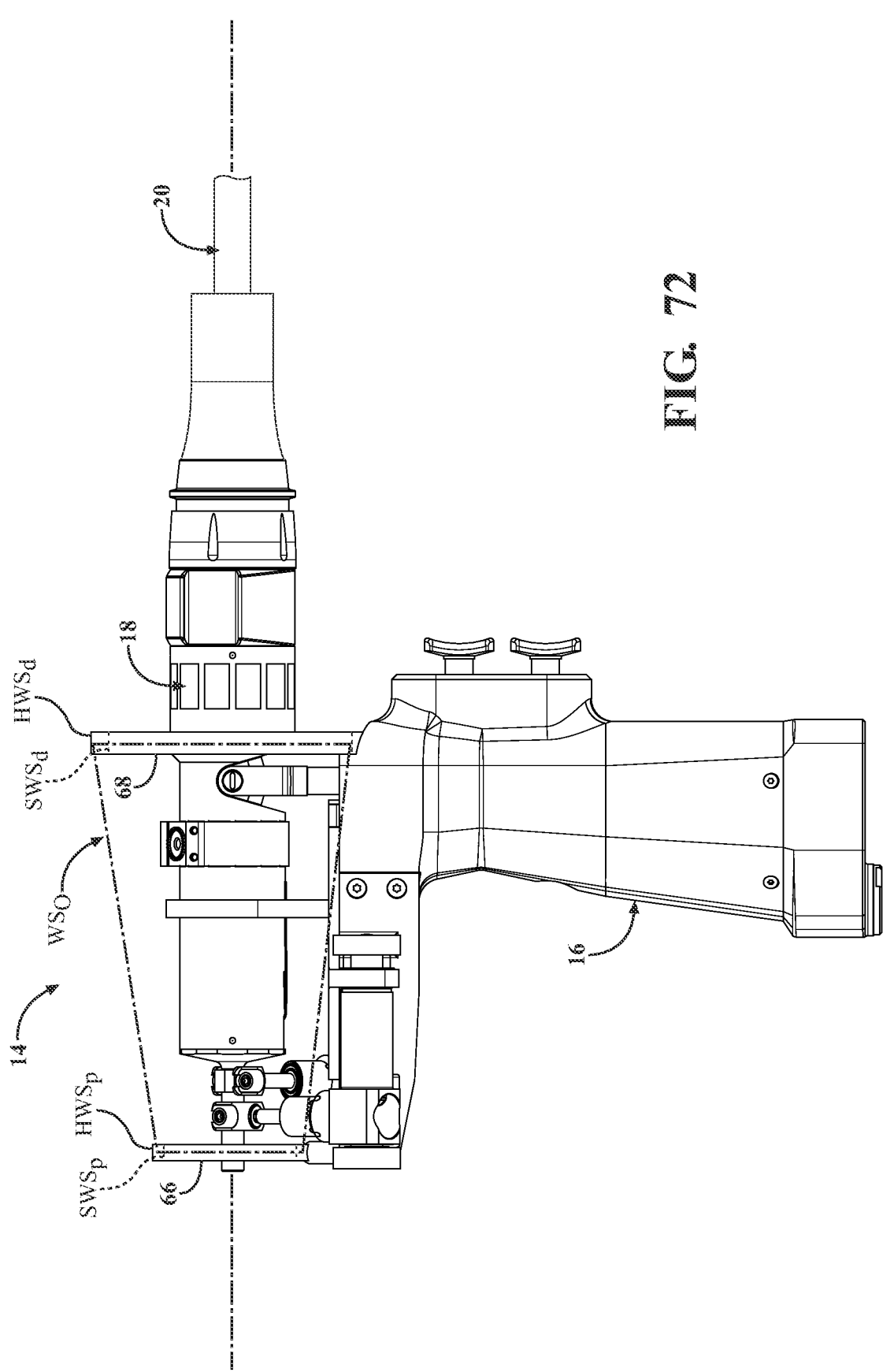
FIG. 72 is side perspective view of the instrument with the workspace limit defined by a 3-D object.

In certain implementations, the virtual planes DP, PP, and/or the TCP Plane may also be used to define the workspace of the instrument. For example, with reference to FIG. 56B, the proximal plane and the distal plane may each define a hard workspace limit $HWS_P$, $HWS_D$ and a soft workspace limit $SWS_P$, $SWS_D$. The hard workspace limits $HWS_P$, $HWS_D$ represent the mechanical constraints of the system, whereas the soft workspace limits $SWS_P$, $SWS_D$ are associated with software that ensures that the plurality of actuators do not engage the mechanical constraints of the system. Similar workspace limits may also be defined in the TCP plane, such as $SWS_{TCP}$. The workspace limits $SWS_P$, $SWS_D$ are defined in the described implementation as circular shapes in the distal plane DP and proximal plane PP. However, it is contemplated that the workspace limits may be defined in other ways, such as by 2-D shapes other than circles, by 3D objects that include the proximal and distal planes. For example, with reference to FIG. 72, see $WS_O$, which is one exemplary virtual object that could define the workspace limit. It is illustrated as a flat-bottom cone in the exemplary implementation. In instances where the workspace limit is defined by a circle, each of the virtual planes define an origin, i.e., proximal plane origin, and a distal plane origin. In instances where the workspace limit(s) are defined by a three-dimensional object, the three-dimensional object is positioned to encompass an axis of the tool when the instrument is in the home state. More particularly, the three-dimensional object may be coaxial with an axis of the tool when the instrument is in the home state. It should also be understood that the workspace limits may be different in shape or dimension between the proximal, distal, and/or TCP plane. Furthermore, it is contemplated that in certain implementations, the control system may utilize only one or only two of the planes to control the plurality of actuators, or may control the plurality of actuators without utilizing the planes for purposes of control. It should be appreciated that the workspace limit for the TCP plane may not be active at all times, particularly during certain control modes, such as pointing mode.

Figure 63:
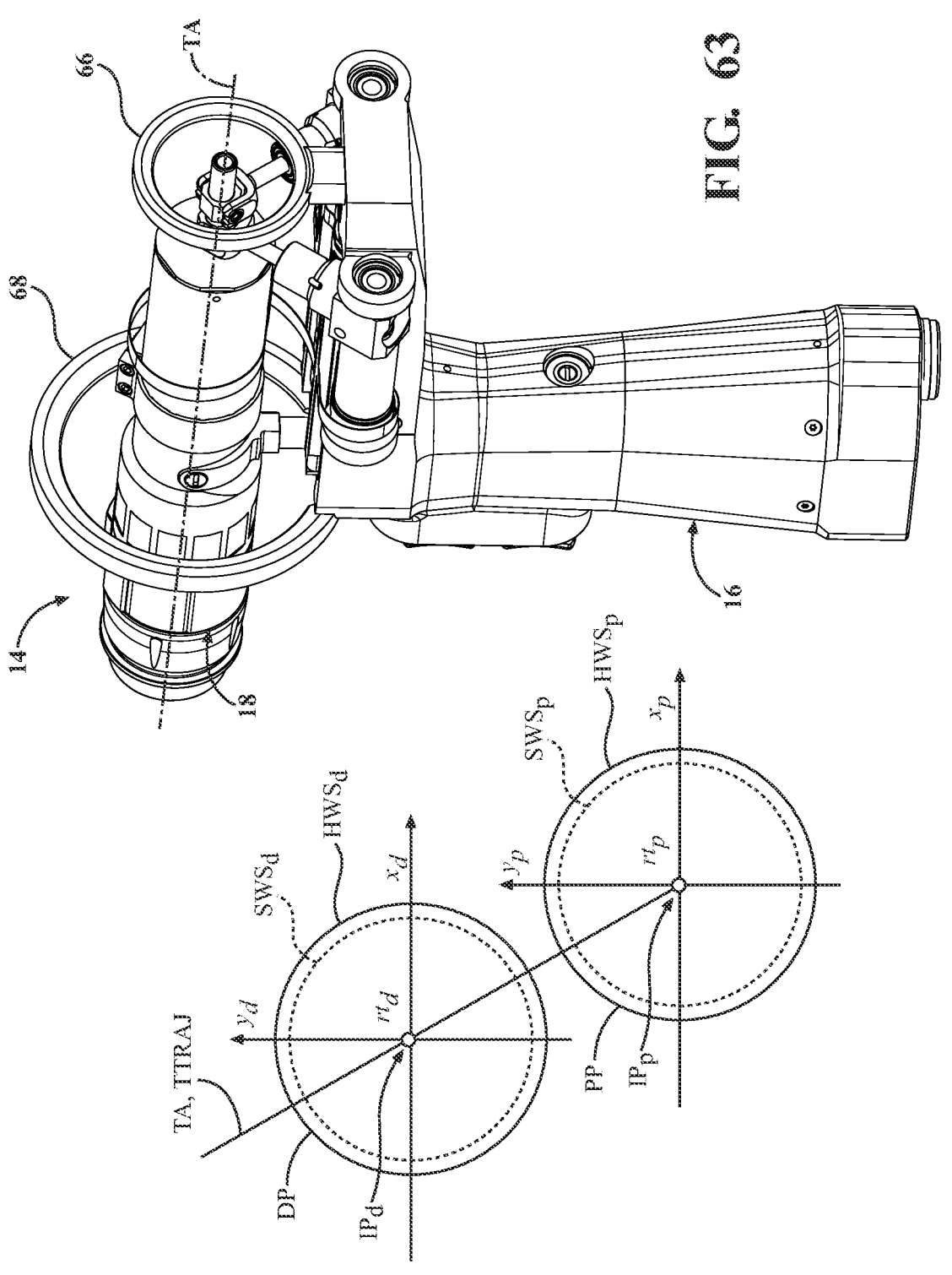
FIG. 63 shows the pose of the instrument in the home state relative to schematic views of the proximal and distal planes.

Referring to FIG. 63, the workspace limits $SWS_d$, $SWS_p$ may be defined based on the home state of the instrument 14. For example, the home state of the instrument 14 may result in the tool axis TA being centered with the workspace limits $SWS_p$, $SWS_d$ in the proximal plane PP and the distal plane DP. However, alternative ways of defining the workspace are also contemplated. The workspace limit(s) $SWS_p$, $SWS_d$ may be fixed relative to the hand-held portion 16 and move with the hand-held portion 16 as the user utilizes the instrument, and as the tool support 18 moves relative to the hand-held portion 16.

The target trajectory TTRAJ can be specified in each of the planes by a plurality of parameters, including a plurality of coordinates in the coordinate system of each of the virtual planes. For example, the control system may define a Yd, Xd associated with the X, Y coordinates of the distal intersection point IPN of the target trajectory TTRAJ in the distal plane DP. Similarly, the control system may define a Xp, Yp associated with the X, Y coordinates of the proximal intersection point $IP_p$ of the target trajectory in the proximal plane PP.

Figure 64:
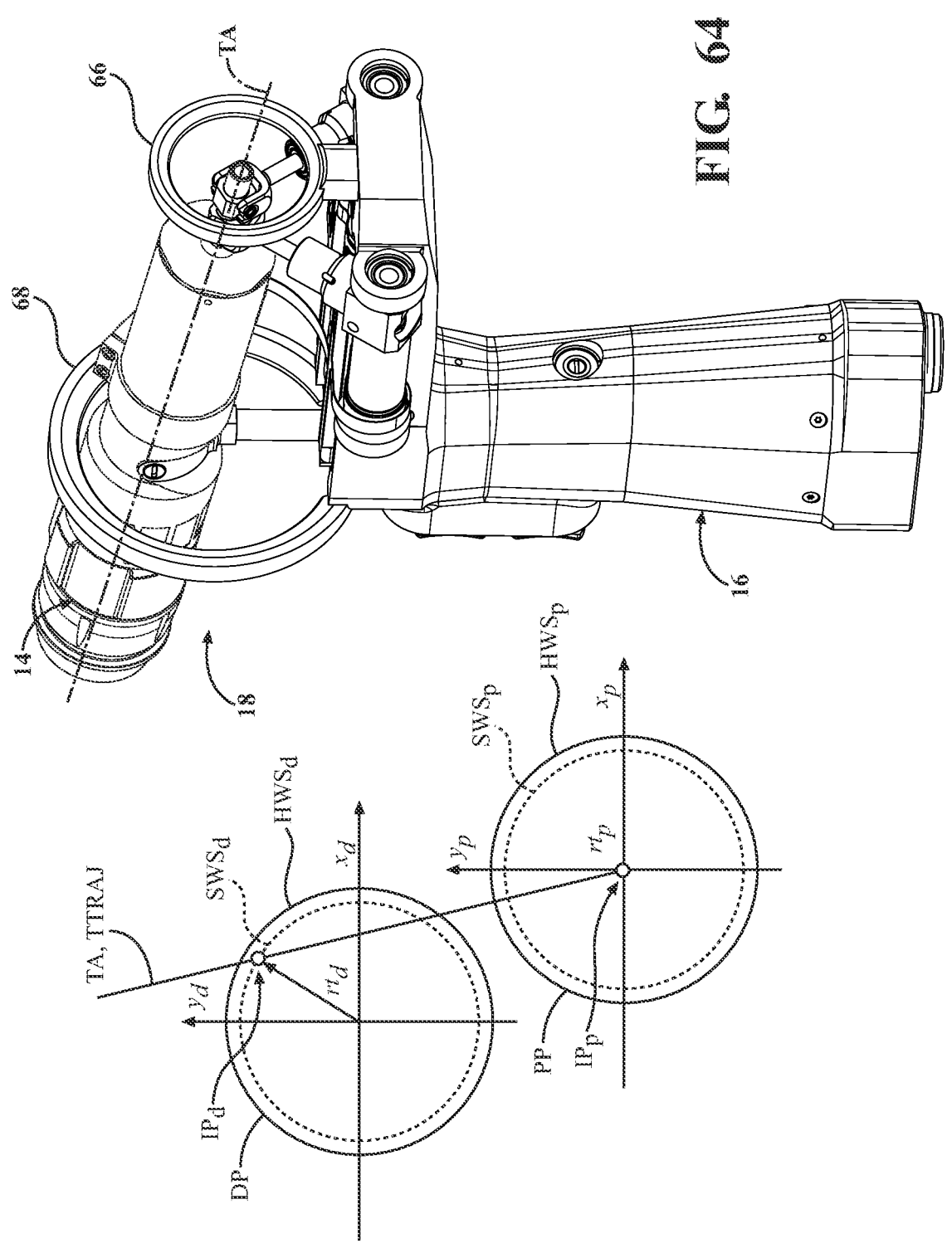
FIG. 64 shows the pose of the instrument in the relative to schematic views of the proximal and distal planes when the tool axis engages the workspace limit in only the distal plane and the tool axis is the origin of the proximal plane.

The origin of each plane DP, PP and the X, Y coordinates may be used to define a radius of the intersection of the target trajectory TTRAJ in the planes DP, PP. For example, with reference to FIG. 64, the radius in the distal plane ($rt_d$) is defined between the origin of the distal plane DP and the distal intersection point IPN. Also similar to the distal plane, the origin of the proximal plane and these coordinates may be used to define a radius in the proximal plane ($rt_p$) between the origin of the PP and the proximal intersection point $IP_p$. Similarly still, with reference to FIG. 56B, the control system may identify the coordinates of the target trajectory in the TCP plane, Xtcp, Ytcp, and a radius in the TCP plane $rt_{tcp}$.

Figure 65:
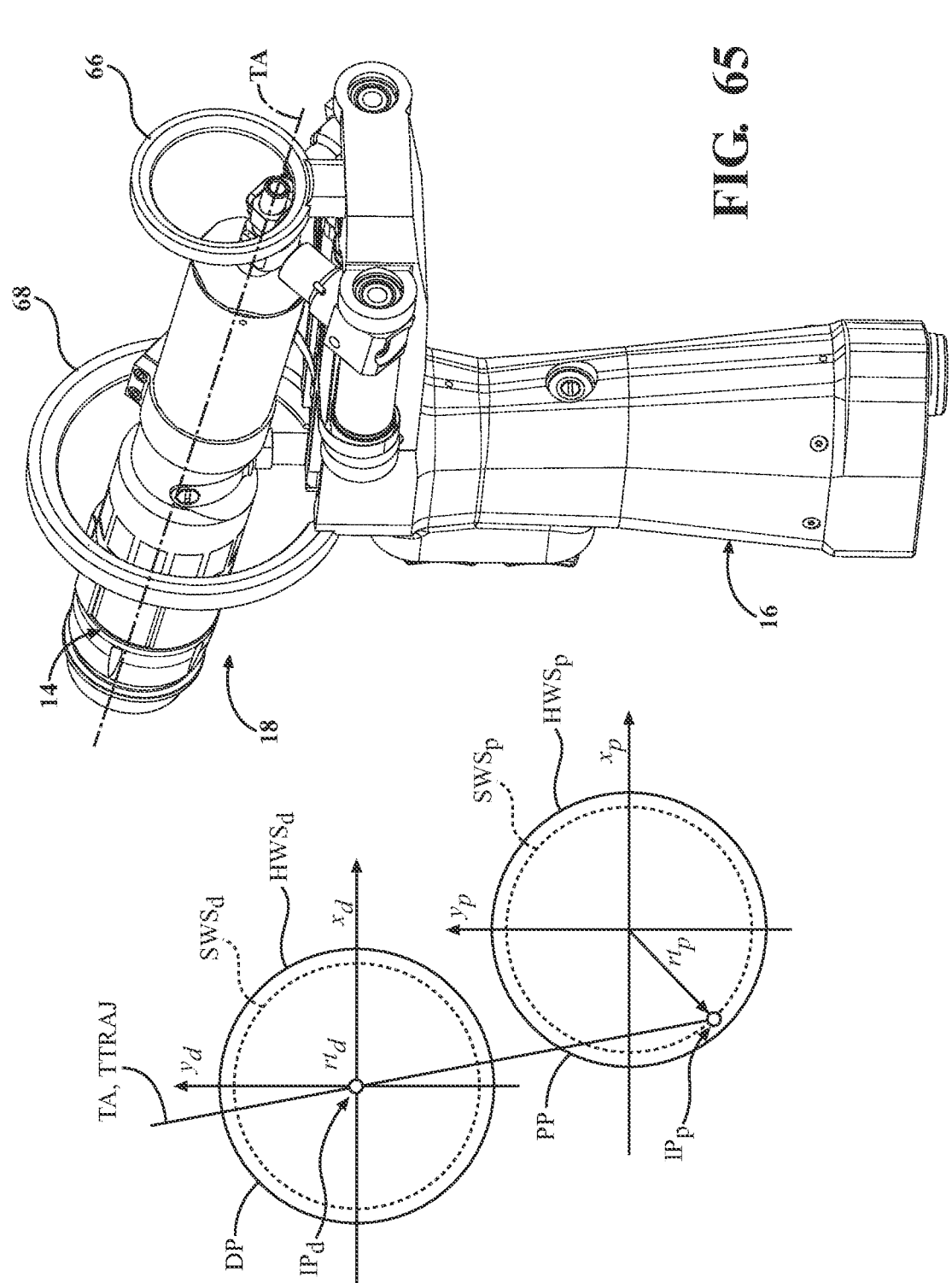
FIG. 65 shows the pose of the instrument in the relative to schematic views of the proximal and distal planes when the tool axis engages the workspace limit in only the proximal plane and the tool axis is the origin of the distal plane.

With reference to FIG. 65, the radius of the tool axis in distal plane $rt_d$ passes through the origin of the distal plane DP, which correlates to tool axis passing through the center of the distal guide ring 68. On the other hand, the radius of the tool axis in the proximal plane $rt_p$ engages the software workspace limit in the proximal plane $SWS_p$. This correlates to the tool axis TA being located at the inner periphery of the proximal guide ring 66.

Figure 66:
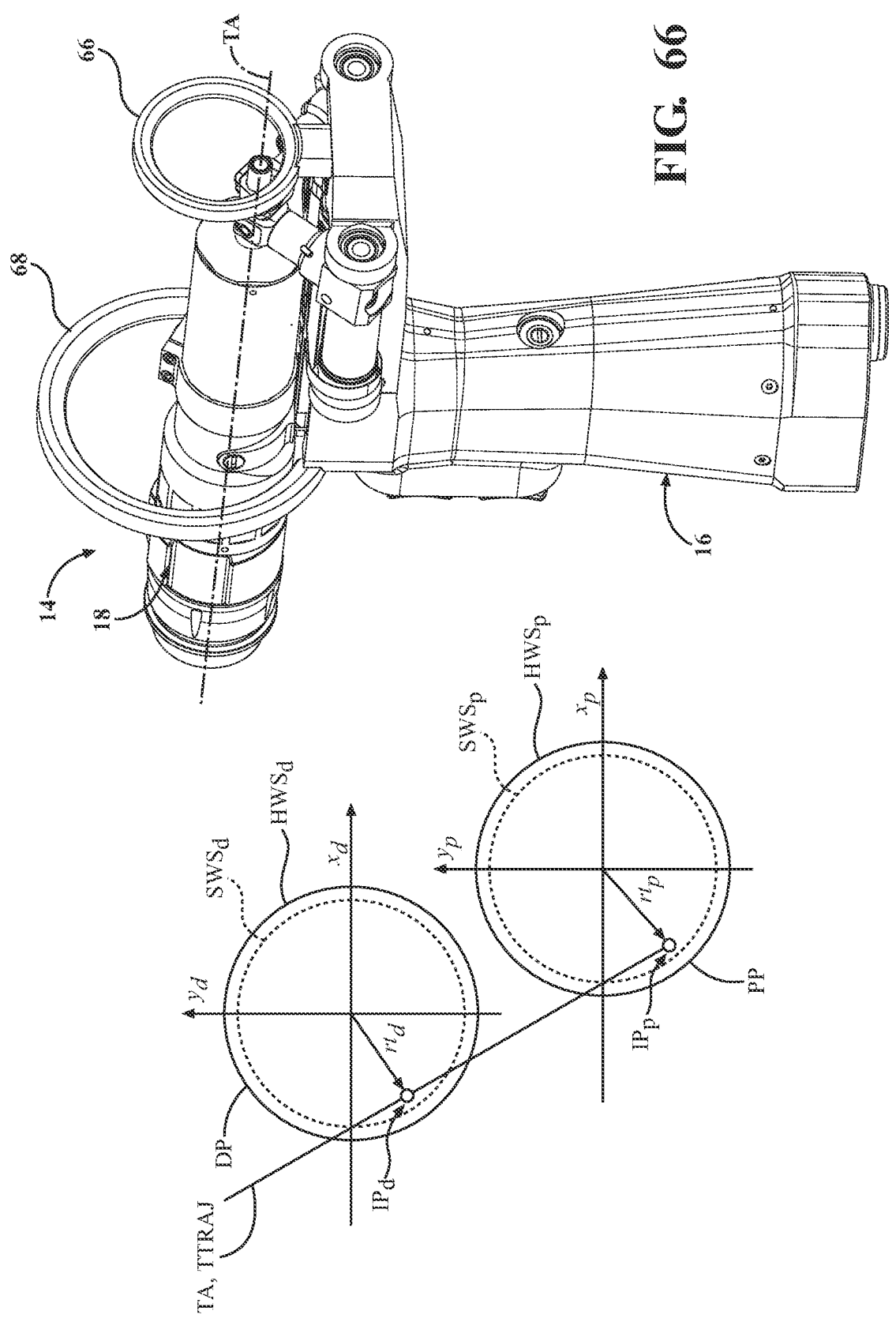
FIG. 66 shows the pose of the instrument in the relative to schematic views of the proximal and distal planes when the tool axis engages the workspace limit in both the proximal plane and the distal plane.

With reference to FIG. 66, the radius of the tool axis in distal plane $rt_d$ passes through a location offset from the origin if the distal plane DP, which correlates to tool axis passing through the lower left quadrant distal guide ring 68. Similarly, the radius of the tool axis in the proximal plane $rt_p$ is offset from the origin but does not engage the software workspace limit in the proximal plane $SWS_p$. This correlates to the tool axis TA being located in the lower left quadrant of the proximal guide ring 66.

As seen in FIG. 45, the control system utilizes various transforms to transfer the data from the localizer into a known coordinate system C. For example, the control system identifies the position of the tool axis TA in the proximal plane PP, the position of the tool axis TA in the distal plane DP, and the position of the tool axis TA in the TCP plane. The control system may utilize the pose of the patient tracker PT, and the tool tracker TT coupled to the instrument, along with the kinematics of the plurality of actuators to accomplish this transformation.

The inventors of the subject application have surprisingly identified a way to control the plurality of actuators of the hand-held robotic system to improve the user-experience. In particular, the inventors have recognized that there are certain usage scenarios where it makes sense to control the plurality of actuators in different degrees of freedom for different clinical scenarios. For example, there may be usage scenarios where the control system operates in a control mode to control the plurality of actuators to move in at least four degrees of freedom, or exactly four degrees of freedom. There may also be an alternative control mode where the control system is configured to control the plurality of actuators to move the tool in two or fewer degrees of freedom, such as only in two orientation degrees of freedom or only in two translation degrees of freedom. In still a further control mode, the control system may control the plurality of actuators such that they move the in zero degrees of freedom, i.e., the actuators are essentially frozen.

The control system 60 may switch the instrument 14 from the trajectory mode controlling the instrument 14 in four degrees of freedom, to a second mode which reduces and/or stops adjustment of the actuators 21, 22, 23, 24 in one or more degrees of freedom. In another example, when the TCP of the tool 20 is aligned with the target trajectory TTRAJ and is drilling into the bone, the actuators 21, 22, 23, 24 may be reduced to adjusting the tool support 18 relative to the hand-held portion 16 in two degrees of freedom when fixation occurs or when the tool reaches the boundary FB shown in FIG. 62. In another example, if the tool violates the boundary FB, one or more of the actuators 21, 22, 23, 24 may be reduced in movement or stopped to allow the user drill along the natural guide created in the bone to reduce instrument 14 from "fighting" the user.

The two-degree of freedom control modes can be very useful when the tool is inflexible, such as a stiff twist drill or tap or driver. Similarly, this is useful when one or more of the motors of the plurality of actuators are not backdriveable. These two degree of freedom control modes may also be useful when the instrument does not include any computation of the force applied by the user to the hand-held portion. These two-degree of freedom control modes may be useful when the distal end of the tool is fixed, which results in the inability of the plurality of actuators to correct the error in trajectory Referring now to FIGS. 73A and 73B, the system may define different spatial regions to specify where guided mode of instrument 14 should be enabled. These spatial regions may be defined in a number of different ways, such as using or more different virtual objects (FIGS. 73A-73B) or using various distance parameters (FIGS. 74A-74B). In one example, the spatial regions may be specified in a reference coordinate system, where the control system is configured to determine the position and/or orientation of the reference coordinate system relative to the known coordinate system. In another example, the virtual objects are representative of various distance parameters. These virtual objects may be used relative to the position of the tool, to select one of the described control modes, such as trajectory mode, pointing mode, off-target mode, on-target mode, or any of the two degree of modes described.

Beyond simply reducing the degrees of freedom during transition between control modes, the control system is capable of maintaining the same number of degrees of freedom, but changing those degrees of freedom without changing the number of controlled degrees of freedom. For example, when the control system is operating in a mode where the actuators are moving in a first set of two degrees of freedom, such as controlling the plurality of actuators to move in two orientation degrees of freedom, the control system may transition to controlling the plurality of actuators in a second set of degrees of freedom, such as controlling the plurality of actuators in two translation degrees of freedom. The first set of degrees of freedom differs from the second set of degrees of freedom in a least one degree of freedom. However, it is contemplated that any suitable degree of freedom may be changed.

By changing the degrees of freedom between control modes, the hand-held robotic system changes how the hand-held portion of the instrument moves relative to the tool platform. This can result in different feelings to the user throughout the surgical procedure. This transition between control modes, and the resultant differing degrees of freedom, can provide a tactile cue to the user that a certain usage scenario or stage of the surgical procedure has been reached. Furthermore, the control of the plurality of actuators in particular modes can result in maintaining a predictable orientation and/or positions of the hand-held portion relative to the tool platform when a particular control mode has been adopted. For example, in the control mode where control system controls the plurality of actuators in only two translation degrees of freedom, the tool may be maintained in a generally perpendicular relationship with the hand-held portion even as the control system continues to adjust the position and/or angle of one or more of the plurality of actuators to achieve distinct poses of the tool platform relative to the hand-held portion. This relationship can be advantageous to a user who is comfortable with a pistol-style grip.

Within certain control modes, the user may find it easier to align their hand into the desired position as they only need to monitor one mechanical alignment guide, such as one of the guide rings to keep the hand-held portion in the appropriate location to avoid reaching range of motion limitations of the instrument. The transition in control modes may create a user feeling for identifying that the tool is aligned with the target trajectory or that create a user feeling for identifying that the tool is not aligned with the trajectory.

In some aspects of the control system, the control system may optionally be configured to control the plurality of actuators to return to the home state before being controlled in the selected mode. For example, in situations where the control system transitions the system from a control mode where the plurality of actuators are being controlled in four or more degrees of freedom to a control mode where plurality of actuators are being controlled in only two degrees of freedom, the control system may set the instrument to a home state via controlling the plurality of actuators in up to four degrees of freedom in order to reach the home state of the instrument. Upon reaching the home state of the instrument, the control system may subsequently control the instrument in only two degrees of freedom. Similarly, the control system may transition the instrument to the home state when switching from a first set of two degrees of freedom to a second set of two degrees of freedom. The return to a home state may provide the instrument with greater range of motion when operating in the selected control mode.

When the control system is operating the plurality of actuators in a mode having four or more degrees of freedom, the control system may control the plurality of actuators such that the surgical tool is aligned with a target trajectory. As described above, this may involve controlling the actuators 21, 22, 23, 24 to provide motion to assist in placing the tool at the desired position or orientation, such as aligned with a target trajectory, while the user holds the housing of the hand-held portion.

Referring now to FIGS. 56A-60B, during usage of the instrument, there may be instances where the user has not positioned the instrument close enough to the target trajectory such that the tool cannot be completely aligned with the target trajectory in all of the controlled degrees of freedom. In this scenario, one or more of the plurality of actuators may be limited from adjusting to an extent that would allow complete alignment of the tool with the target trajectory OTTRAJ, OTTRAJ1. For example, with reference to two exemplary trajectories OTTRAJ and OTTRAJ1, the instrument does not have sufficient range of motion to adjust in order to place the tool aligned with either of these two target trajectories. This can be understood because these two trajectories OTTRAJ, OTTRAJ1 do not pass through the proximal plane PP and distal plane DP. To accommodate the limitations in the range of motion of the instrument, the control system may transition between the trajectory sub-mode and a pointing-sub mode. The transition between these modes provides for a predictable behavior of the instrument such that the user can easily move their hand into a position that would allow them to transition from the pointing-sub mode to the trajectory sub-mode before the tool encounters tissue. In other words, by controlling the instrument in a pointing sub-mode in instances where the instrument does not have the range of motion to fully align the tool with the target trajectory, the user is cued by virtue of the movement pattern of the actuators to reposition their hand until the instrument is positioned in a location that the plurality of actuators are capable of adjusting the tool platform such that the tool can be fully aligned with the target trajectory.

When the control system is operating in the trajectory mode, the control system is configured to control the plurality of actuators such that an axis of the tool is aligned with both the bone entry point and the second point of the target trajectory. When the control system is operating in the pointing-sub mode, the control system is configured to control the plurality of actuators such that an axis of the tool is aligned with the bone entry point and a portion of the axis of the tool engages the workspace limit. As an alternative, when joint limits are used to control the plurality of actuators, the control system may operate in pointing sub-mode to control the plurality of actuators such that an axis of the tool is aligned with the bone entry point and at least one actuator of the plurality of actuators is coincident with the joint limit for that actuator. It should be understood that the control system may operate to control the plurality of actuators to move in at least four degrees of freedom while in the trajectory sub-mode, and at least three degrees of freedom while in the pointing sub-mode.

Figure 58B:
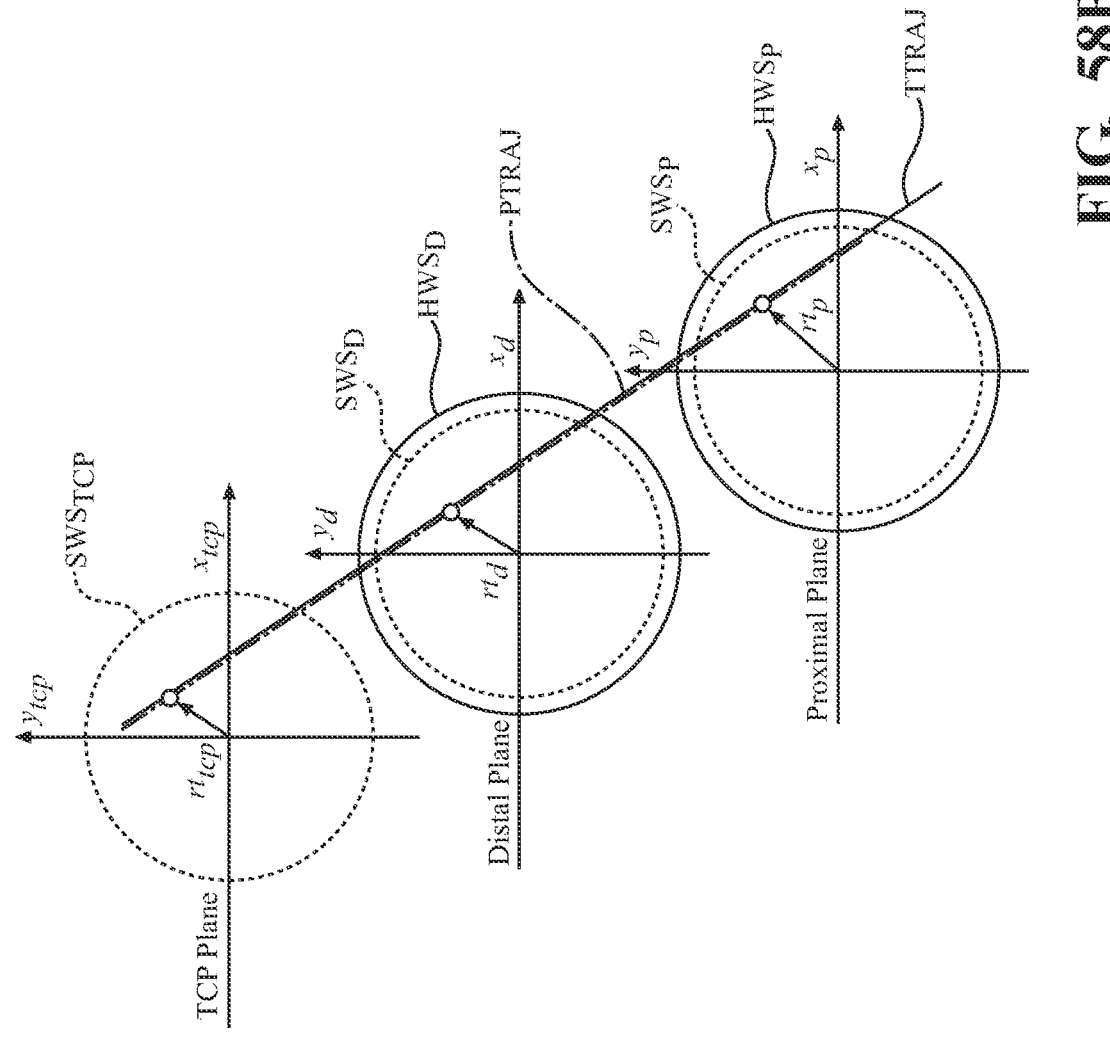
FIG. 58B illustrates a trajectory in the trajectory mode of FIG. 58A in the virtual planes.
Figure 58A:
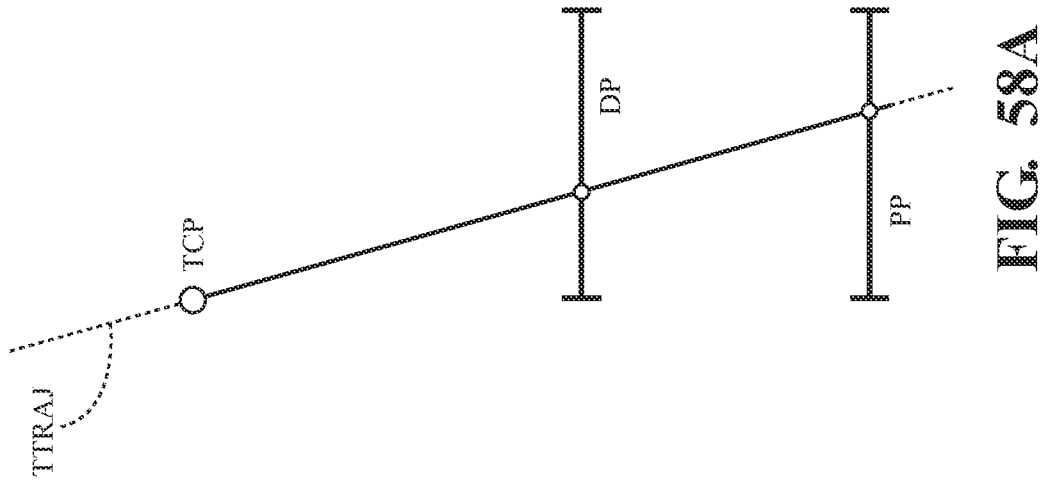
FIG. 58A illustrates a schematic view of the surgical instrument relative to trajectories set in a trajectory mode and a pointing mode when the tool axis does not engage the workspace limit in the proximal or distal plane.

While in trajectory sub-mode, with reference to FIGS. 58A and 58B, the control system is capable of setting a position of the tool axis with respect to the distal and proximal planes that is within the workspace limits $SWS_D$, $SWS_P$. The tool axis is shown as the broken line in FIG. 58A that is aligned with the target trajectory TTRAJ. With respect to FIG. 58B, the radius of the intersection point within the distal plane $rt_d$ is less than the radius of the workspace limit $SWS_D$ in the distal plane DP. Similarly, the radius of the intersection point with the proximal plane $rt_p$ is less than the radius of the workspace limit $SWS_P$ in the proximal plane PP. It should be also be appreciated that the drive motor may be permitted to run while the tool is in trajectory mode with the optional feature of shutting off the drive motor if the tool violates the distal boundary or one of the control frames described below.

The control system may be operable to automatically select one of the pointing sub-mode and a trajectory sub-mode based on the target trajectory, the workspace limit or joint limit, and the pose of one of the surgical tool, the tool support, and the hand-held portion. In other words, if the control system identifies that the current state of the tool, tool support, or hand-held portion is such that the plurality of actuators cannot position the tool to be aligned with the target trajectory without violating the workspace limit or without violating the joint limit for one or more of the plurality of actuators, the control system may automatically select the pointing sub-mode. One benefit of pointing mode is that the user can monitor only one set of actuators and/or one of the guide rings to understand how to best move their hand, i.e., the hand-held portion of the instrument, to achieve the desired trajectory.

Figures 57A, 57B:
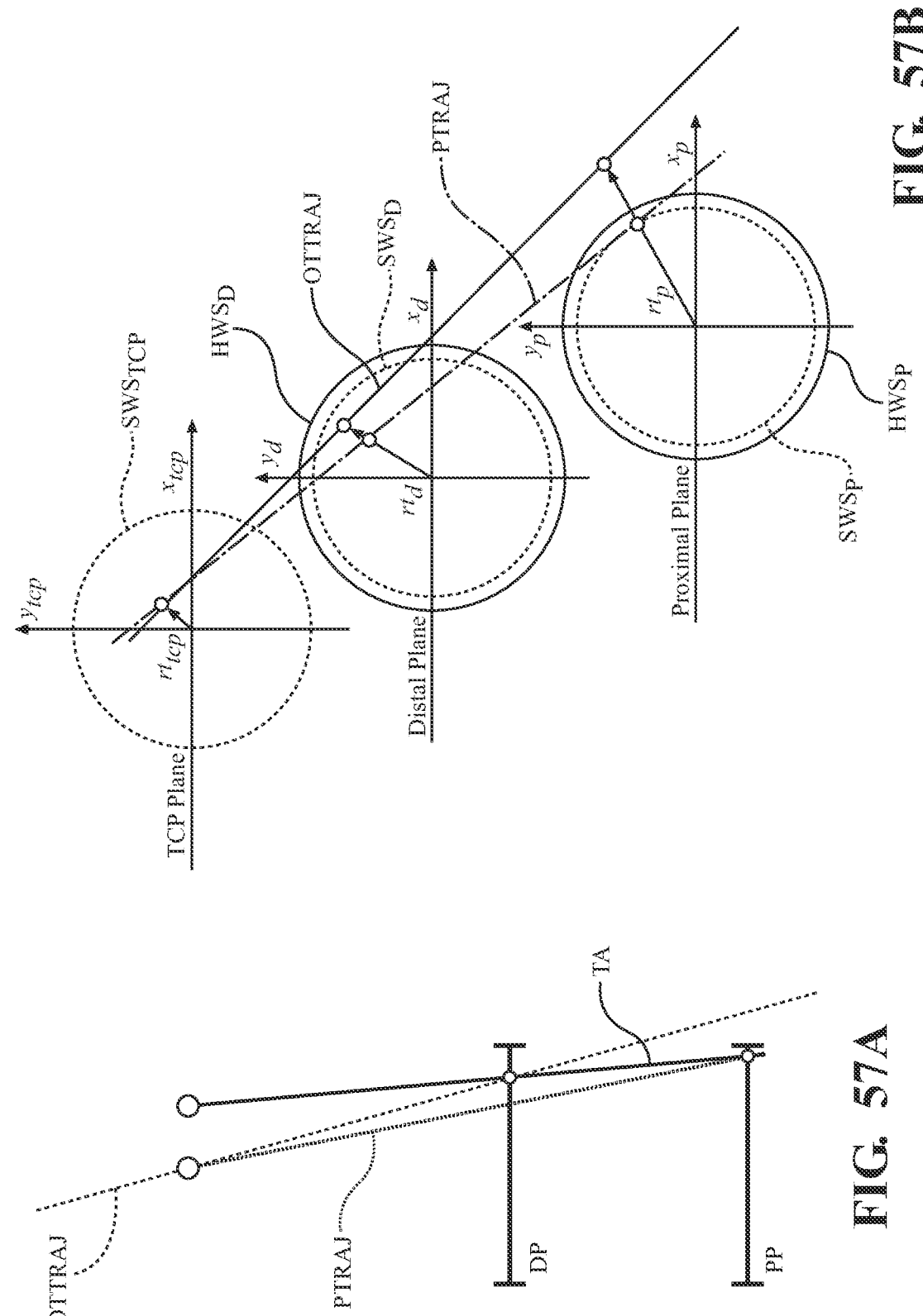
FIG. 57A illustrates a schematic view of the surgical instrument relative to trajectories set in a trajectory mode and a pointing mode when the tool axis engages the workspace limit in the proximal plane.
FIG. 57B illustrates a trajectory in the pointing mode of FIG. 57A in the virtual planes.

As described above, one way achieving the pointing mode of the instrument is by using various workspace limits, such as the workspace limits defined in the proximal plane, the distal plane, and/or the TCP plane. With reference to FIGS. 57A and 57B, the originally set target trajectory OTTRAJ would result in violation of the workspace limit defined in the proximal plane. This is shown in FIG. 57A as OTTRAJ does not pass through the proximal plane PP. This is also shown in FIG. 57B where the radius of the tool axis in the proximal plane $rt_p$ exceeds the radius of the workspace limit $SWS_P$ defined in the proximal plane PP, the control system controls the plurality of actuators such that the position of the tool axis is maintained in the proximal plane at the workspace limit, i.e., the radius of the workspace limit $SWS_p$. This point can be identified in FIG. 57B where the PTRAJ lines intersects the proximal plane PP. The control system may controls the plurality of the actuators such that the tool axis intersects the distal plane DP in a position that would ultimately result in the tool axis being aligned with a point disposed along the target trajectory, such as the bone entry point, the planned exit point, or the most proximal point along the target trajectory that can be reached with the tool axis being disposed at the workspace limit in the proximal plane. FIG. 57A shows TA which is the axis that the tool would assume if pointing mode were not enabled, and PTRAJ shows the axis that the tool would assume with pointing mode enabled with the tool axis being aligned with the most proximal point along the target trajectory.

Figures 59A, 59B:
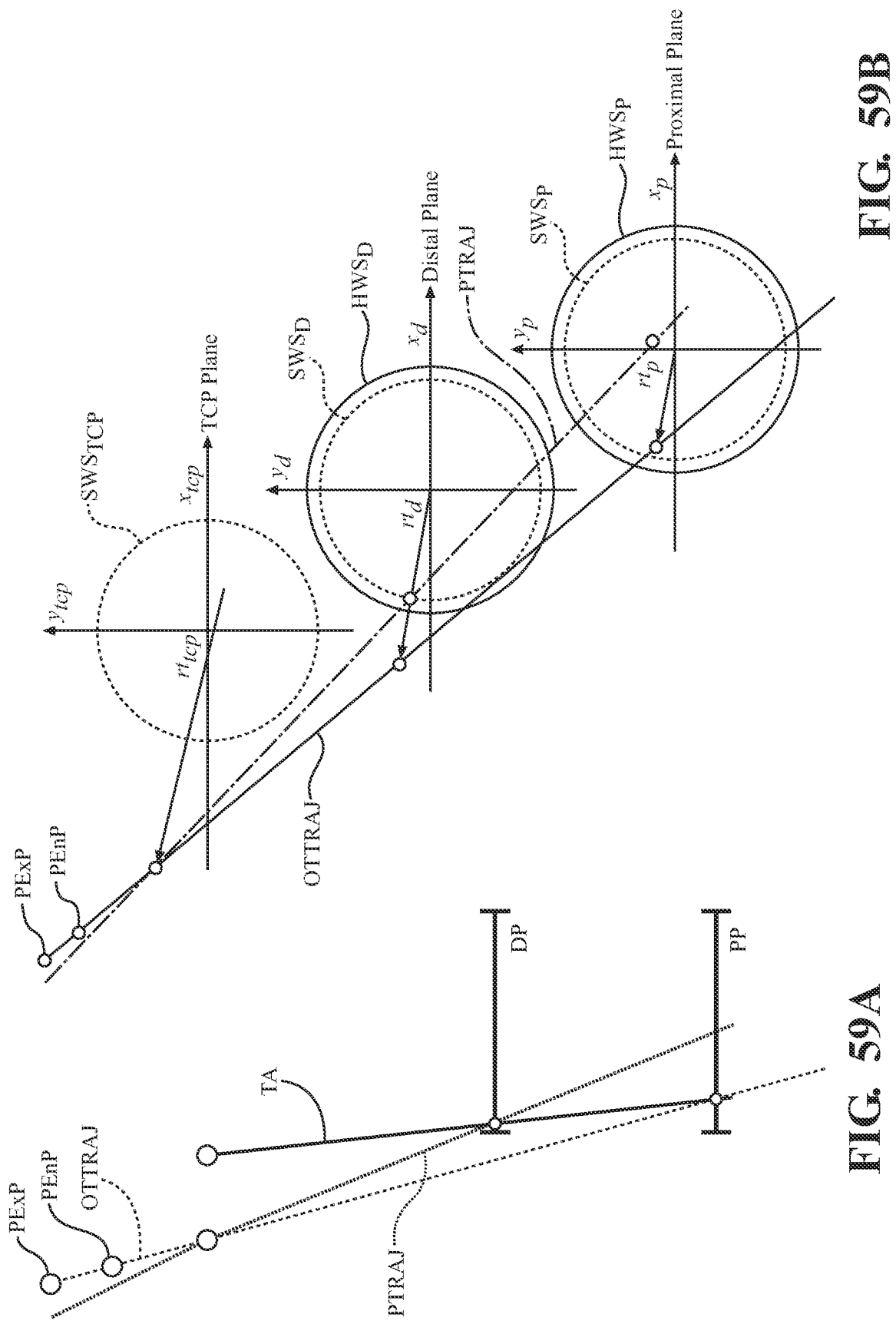
FIG. 59A illustrates a schematic view of the surgical instrument relative to trajectories set in a trajectory mode and a pointing mode when the tool axis engages the workspace limit in the distal plane.
FIG. 59B illustrates a trajectory in the pointing mode of FIG. 58B in the virtual planes.

With reference to FIGS. 59A-B, in some instances, the target trajectory OTTRAJ would result in violation of the workspace limit defined in the distal plane $SWS_D$, i.e., the target trajectory OTTRAJ does not intersect the distal plane DP. With reference to FIG. 59B, the radius of the tool axis in the distal plane $rt_d$ exceeds the radius of the workspace limit in the distal plane DP, the control system controls the plurality of actuators such that the position of the tool axis is maintained in the distal plane DP at the workspace limit, i.e., the radius of the workspace limit $SWS_D$. This is shown by the point at which PTRAJ intersects the distal plane DP. The control system may control the plurality of the actuators such that the tool axis PTRAJ intersects the proximal plane PP in a position that would ultimately result in the tool axis PTRAJ being aligned a point disposed along the target trajectory, such as the bone entry point, the planned exit point, or the most proximal point along the target trajectory that can be reached with the tool axis being disposed at the workspace limit in the distal plane. In FIG. 59A, the intersection of the tool axis and the target trajectory is at the most proximal point along the target trajectory that can be reached with the tool axis being disposed at the workspace limit in the distal plane.

It should be also be appreciated that the drive motor may be restricted from running while the tool is in pointing mode. Thus, the control system may disable or stop the tool drive motor when the control system transitions the instrument from the trajectory mode to the pointing mode. The unavailability of the drive motor may provide another cue to the user that they need to reposition his or her hand to reach the target trajectory.

With reference to FIGS. 56A-56C and FIGS. 60A-60B, in certain scenarios, it is contemplated that the instrument is incapable of positioning the tool to reach the target trajectories OTTRAJ, OTTRAJ1 without violating the workspace limits in both the distal plane DP and the proximal plane PP due to its limited range of motion. In these scenarios with reference to FIGS. 56A-56C and FIGS. 60A-60B, the control system may analyze the radius of the tool axis in various planes $rt_d$, $rt_{tcp}$, and $rt_p$, and select a pointing trajectory based on the analysis.

Figures 60A, 60B:
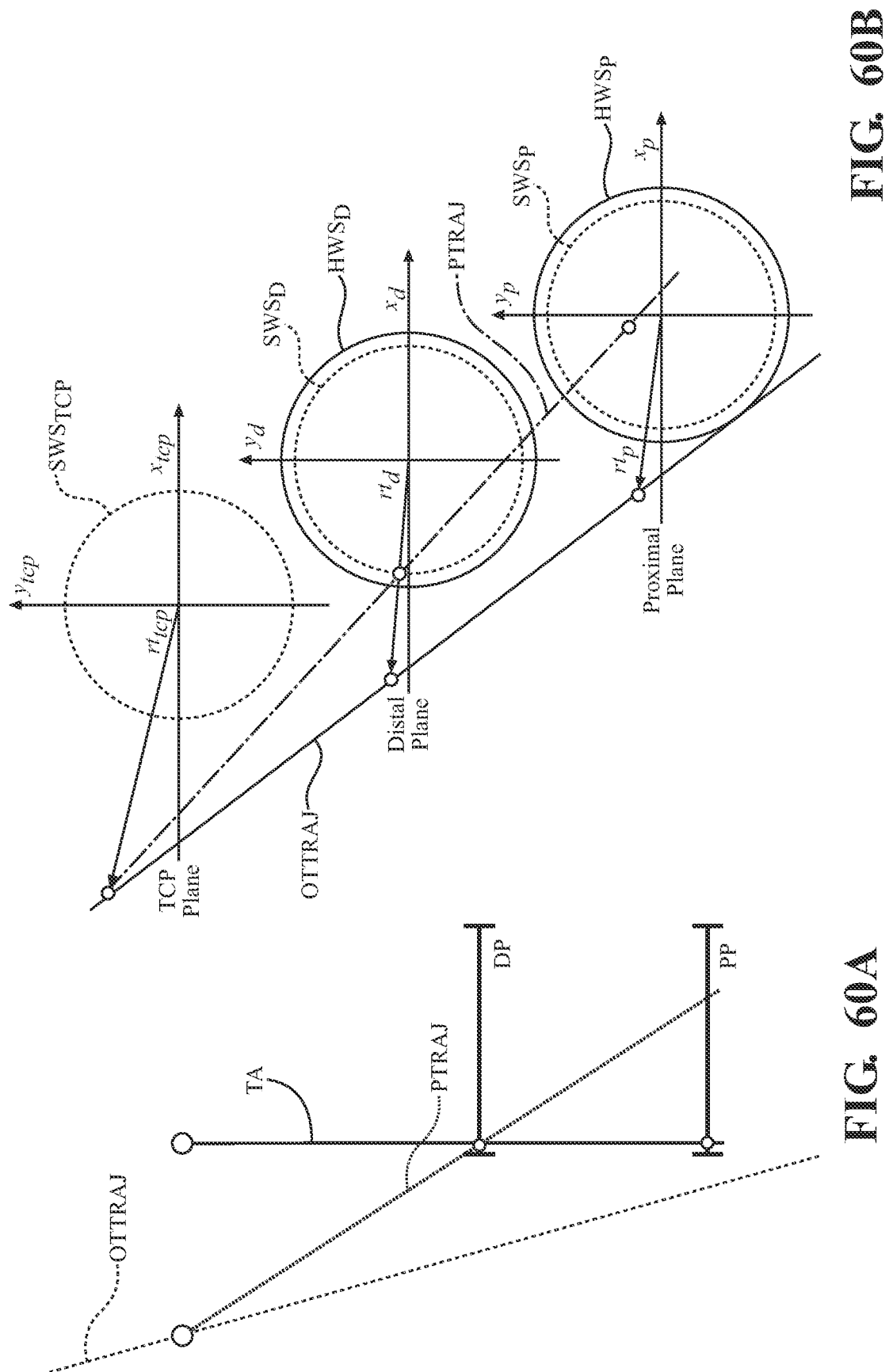
FIG. 60A illustrates a schematic view of the surgical instrument relative to trajectories set in a trajectory mode and a pointing mode when the tool axis engages the workspace limit in the distal and proximal planes.
FIG. 60B illustrates a trajectory in the pointing mode of FIG. 60A in the virtual planes.

First, with reference to FIG. 60A-60B, if the control system determines that the $rt_d$ is greater than $rt_p$, the control system may control the plurality of actuators such that the tool axis PTRAJ is maintained at the workspace limit $SWS_D$ in the distal plane DP. This is shown by the tool axis PTRAJ intersecting the distal plane DP in FIG. 60B. This is also shown in FIG. 60A where the pointing mode results in the tool assuming axis PTRAJ, whereas without pointing mode, the tool would be aligned with TA because the OTTRAJ is outside of the achievable range of motion in both the proximal and distal planes.

Figures 56A, 56B:
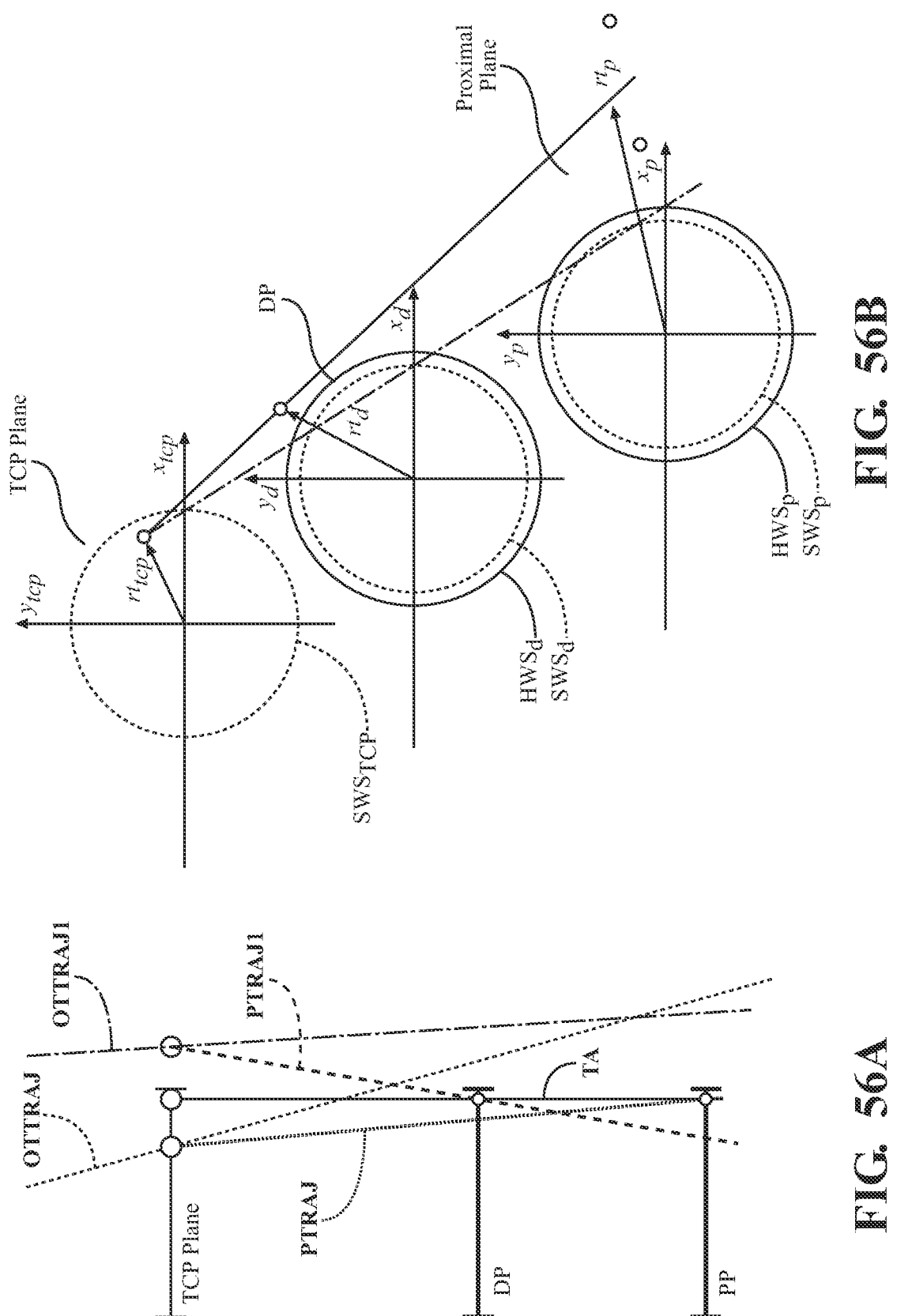
FIG. 56A illustrates a schematic view of the surgical instrument relative to trajectories set in a trajectory mode and a pointing mode when the tool axis engages the workspace limit in the distal plane.
FIG. 56B illustrates a first trajectory in the pointing mode of FIG. 56A in the virtual planes.
Figure 56C:
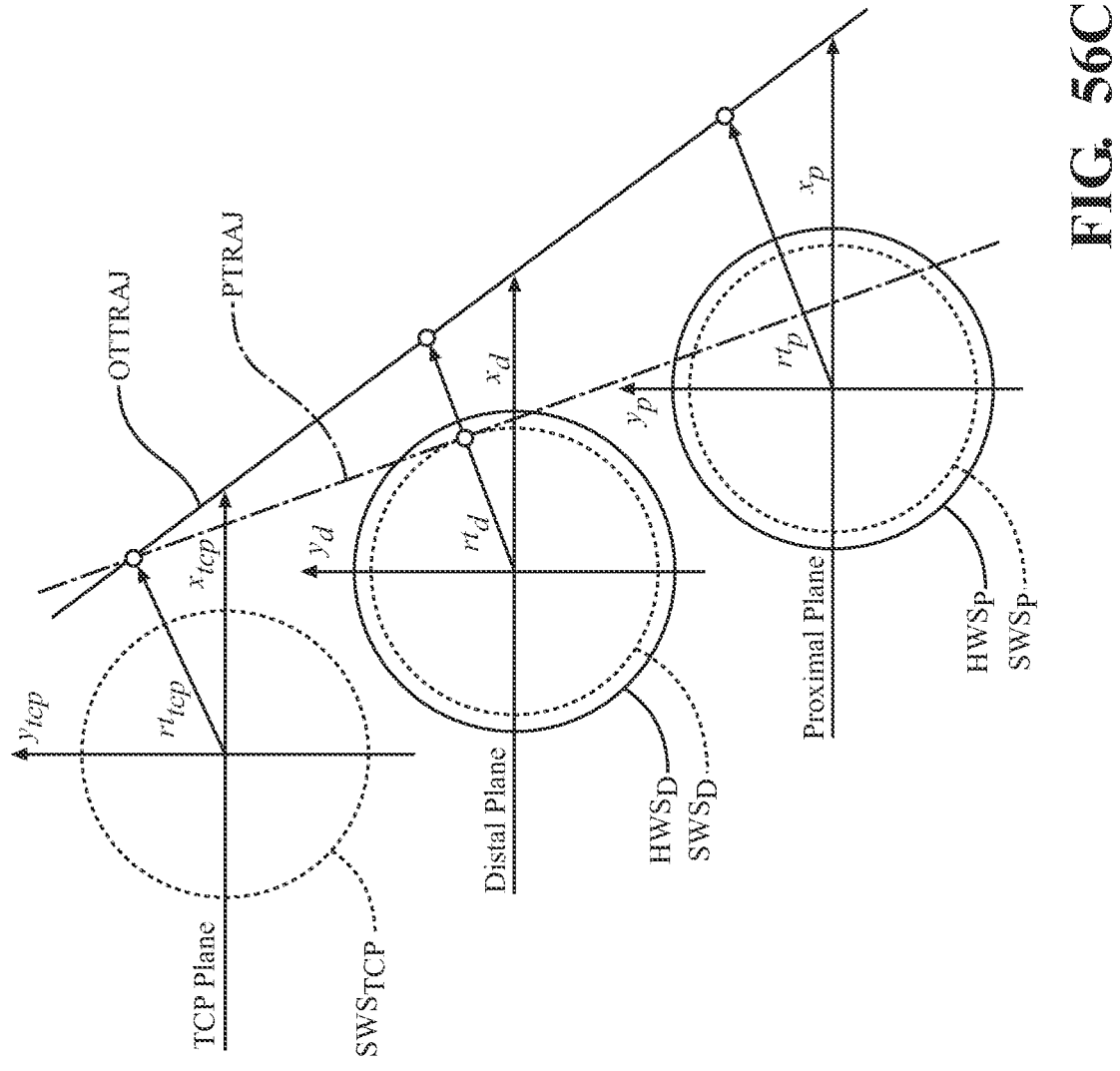
FIG. 56C illustrates a second trajectory in the pointing mode of FIG. 56A in the virtual planes

With reference to FIGS. 56A-56C, if the control system determines that the radius of the tool axis in the proximal plane $rt_p$ is greater than the radius of the tool axis in the distal plane $rt_d$, the control system may control the actuators based on the radius of the tool axis in the TCP plane $rt_{tcp}$ and a workspace limit defined the TCP plane $SWS_{TCP}$. With reference to FIG. 56C, if the radius of the tool axis in the TCP plane $rt_{tcp}$ is greater than the radius of the workspace limit in the TCP plane $SWS_{TCP}$, the control system may control the plurality of actuators such that the tool axis PTRAJ is maintained at the workspace limit in the proximal plane PP and moved in the distal plane DP such that the tool axis PTRAJ is aligned with the a point disposed along the target trajectory, such as the bone entry point, the planned exit point, or the most proximal point along the target trajectory that can be reached with the tool axis being disposed at the workspace limit in the proximal plane. FIG. 56C shows that the radius of the intersection point in the TCP plane is greater than the radius of the workspace limit in the TCP plane.

With reference to FIG. 56B, if the radius of the tool axis in the TCP plane $rt_{tcp}$ is less than the than the radius of the workspace limit in the TCP plane $SWS_{TCP}$, the control system may control the plurality of actuators such that the tool axis PTRAJ is maintained at the workspace limit in the distal plane DP and the control system control the plurality of actuators to move the tool axis PTRAJ in the proximal plane PP to align with the point disposed along the target trajectory, such as the bone entry point, the planned exit point, or the most proximal point along the target trajectory that can be reached with the tool axis being disposed at the workspace limit in the distal plane. FIG. 56B shows that the radius of the intersection point in the TCP plane is less than the radius of the workspace limit in the TCP plane.

Figures 51A, 51B:
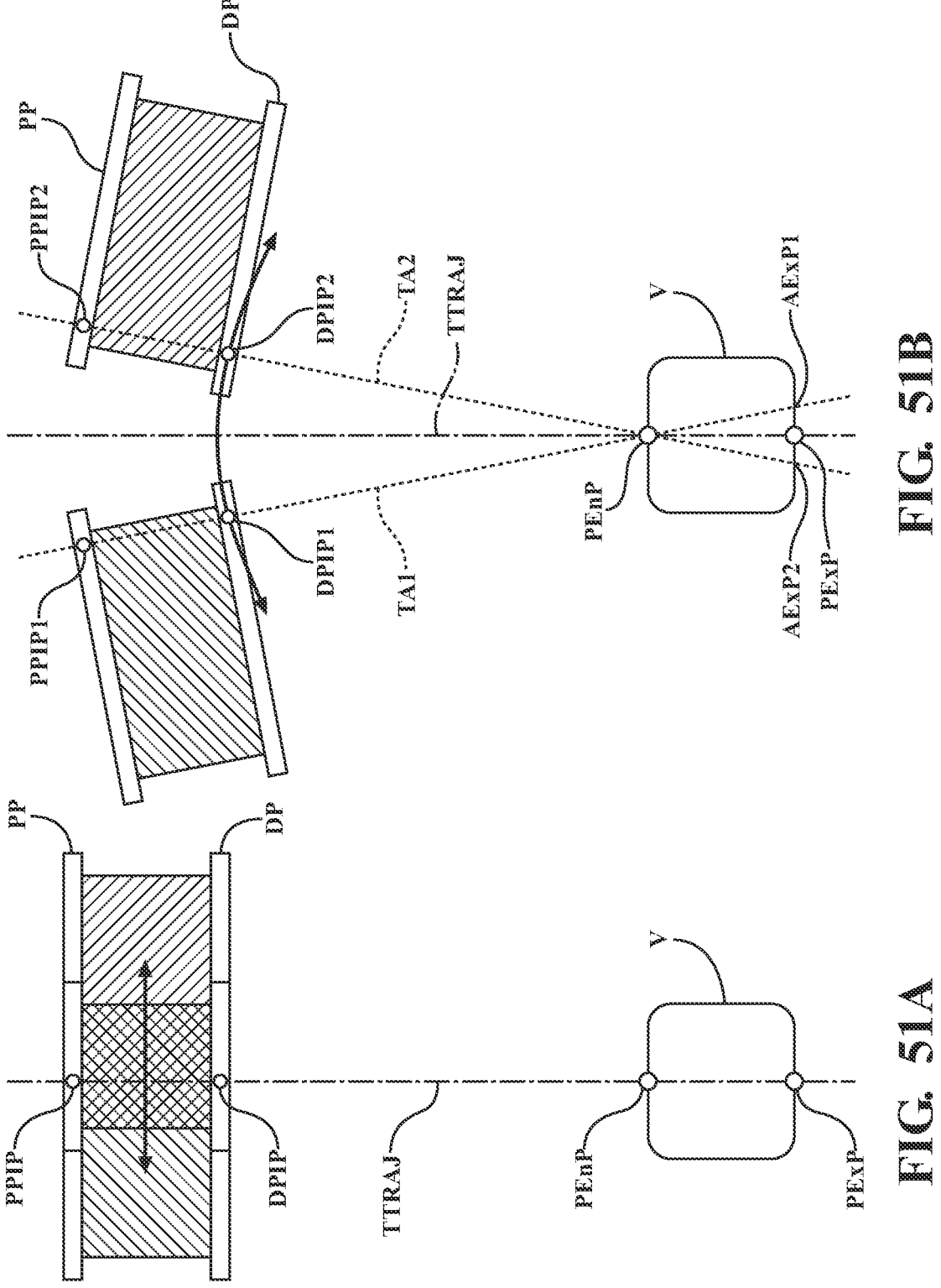
FIGS. 51A and 51B illustrate schematic views of the surgical instrument moving relative to proximal and distal planes in a two-degree of freedom mode.

As described above, the instrument is capable of assuming multiple control modes, including certain control modes where the instrument is controlled to move the plurality of actuators in only two degrees of freedom. With reference to FIGS. 51A-51B, in one potential control mode, the control system may control the plurality of actuators in two translation degrees of freedom. Such a control mode be achieved by controlling the plurality of actuators such that an axis of the surgical tool intersects the first plane PP and a second plane DP at the same position in a first degree of freedom and a second degree of freedom. More particularly, the control system may achieve such a two degree of translation mode such that the target pose passes through the first plane and the second plane with the same coordinates in at least two degrees of freedom. The first virtual plane may be a distal virtual plane DP, and the second virtual plane may be a proximal virtual plane PP. In the illustrated diagrams, the control system will control the plurality of actuators such that the tool axis TA will be positioned with the same X-Y coordinate position in the distal plane DP as in the proximal plane PP. The target trajectory TTRAJ defines an intersection point in the proximal plane PPIP where the target trajectory TTRAJ intersects the proximal plane PP. Similarly, the target trajectory TTRAJ defines an intersection point in the distal plane DPIP where the target trajectory TTRAJ intersects the distal plane DP. This can be shown with respect to FIG. 51A as the proximal plane intersection point PPIP is maintained at the same coordinates (X,Y) as distal plane intersection point DPIP. This 2-DOF control mode supports the weight of the handpiece on the tissue while enabling the hand-held portion of the instrument to be maintained in a generally perpendicular relationship to the axis of the tool. If the user moves their hand in attempt to pivot the tool about the distal end of the tool, TCP, the hand-held portion of the instrument will be translated in two degrees of freedom in an attempt to keep the tool on trajectory. This 2-DOF translation control mode can feel comfortable to the user and helps with visually keeping the instrument within the range of motion of the instrument. This 2-DOF translation mode does not allow the handle to 'flop', but instead supports the position of the hand-held portion relative to the tool support. However, this 2-DOF translation mode does not provide the user with a feeling of where the target trajectory is located without looking at the instrument, or more particularly, without looking at the mechanical alignment guide.

This control mode may be further understood with respect to FIG. 51B, which shows the actual tool axis locations TA1, TA2 as the instrument is positioned relative to the target trajectory TTRAJ. Despite the fact that TA1 is not aligned with target trajectory TTRAJ, this control mode operates the plurality of actuators to maintain the intersection point of the TA1 with the distal plane DP and the proximal plane PP such that the proximal plane intersection point PPIP1 and the distal plane intersection point DPIP1 have the same coordinates in the exemplary X-Y coordinate system. In this control mode, when the tool axis TA1 is located at its illustrated location, the tool axis TA1 still contacts the vertebra V at the planned entry point PEnP, but extends along an axis that does not intersect the planned exit point PExP, but rather extends along an axis that intersects the actual exit point AExP1. Similarly, although TA2 is not aligned with the target trajectory TTRAJ, this control mode operates to maintain the intersection point of the TA2 with the distal plane DP and the proximal plane PP such that the proximal plane intersection point PPIP2 and the distal plane intersection point DPIP2 have the same coordinates in the exemplary X-Y coordinate system. In this control mode, when the TA2 is located at its illustrated location, the tool axis TA2 still contacts the vertebra V at the planned entry point PEnP, but extends along an axis that does not intersect the planned exit point PExP, but rather extends along an axis that intersects the actual exit point AExP2.

To accomplish this 2-DOF translation control mode, the control system can determine the position of the target trajectory TTRAJ penetrating the proximal plane PP. The control system can control one of more of the plurality of actuators to align the tool axis to this point of penetration in the proximal plane PP. The control system may also simultaneously control one or more of the plurality of actuators to align the tool axis in the same position with respect to the distal plane DP. In instances where the control system is controlling the plurality of actuators to position the tool axis TA in the distal plane DP, the control system may be controlling only actuators 21, 22 to position the tool axis TA in the distal plane DP. Similarly, in instances where the control system is controlling the plurality of actuators to position the tool axis in the proximal plane PP, the control system may be controlling only actuators 23, 24 to position the tool axis TA in the proximal plane PP. As an alternative, it is contemplated that the control system could determine where the tool axis penetrates the distal plane PP, and control the plurality of actuators to position the tool axis in the distal plane DP to be aligned with this point of penetration, and control the plurality of actuators to position the tool axis TA in the proximal plane PP in the same position (e.g., X, Y position) in the proximal plane PP. It is also contemplated the control system could accomplish this control without determining points of intersections with the proximal and distal planes.

It is contemplated that the control system may automatically transition the instrument to the home state when the control system initiates control of the instrument in this 2-DOF translation control mode. This can provide the comfortable pistol-style grip with the tool axis being generally perpendicular to the hand-held portion. As the user positions the hand-held portion of the instrument in different locations relative to the patient, the control system determines various commanded poses, with those commanded poses being translated into various commanded positions and/or angles for the plurality of actuators. This ultimately results in the instrument assuming different poses of the tool platform relative to the hand-held portion, with the first pose of the tool support relative to the hand-held portion being different from the second pose of the tool support relative to the hand-held portion only in two or fewer translation degrees of freedom With reference to FIGS. 52A-53B, in potential alternative two DOF control modes, the control system can be configured to control the plurality of actuators to move only in two orientation degrees of freedom. In such implementations, the control system may be configured to control the plurality of actuators such that a location of an intersection of an axis of the tool in a first virtual plane is maintained and the control system controls the plurality of actuators to vary the location of the intersection of the tool axis in a second plane.

Figures 52A, 52B:
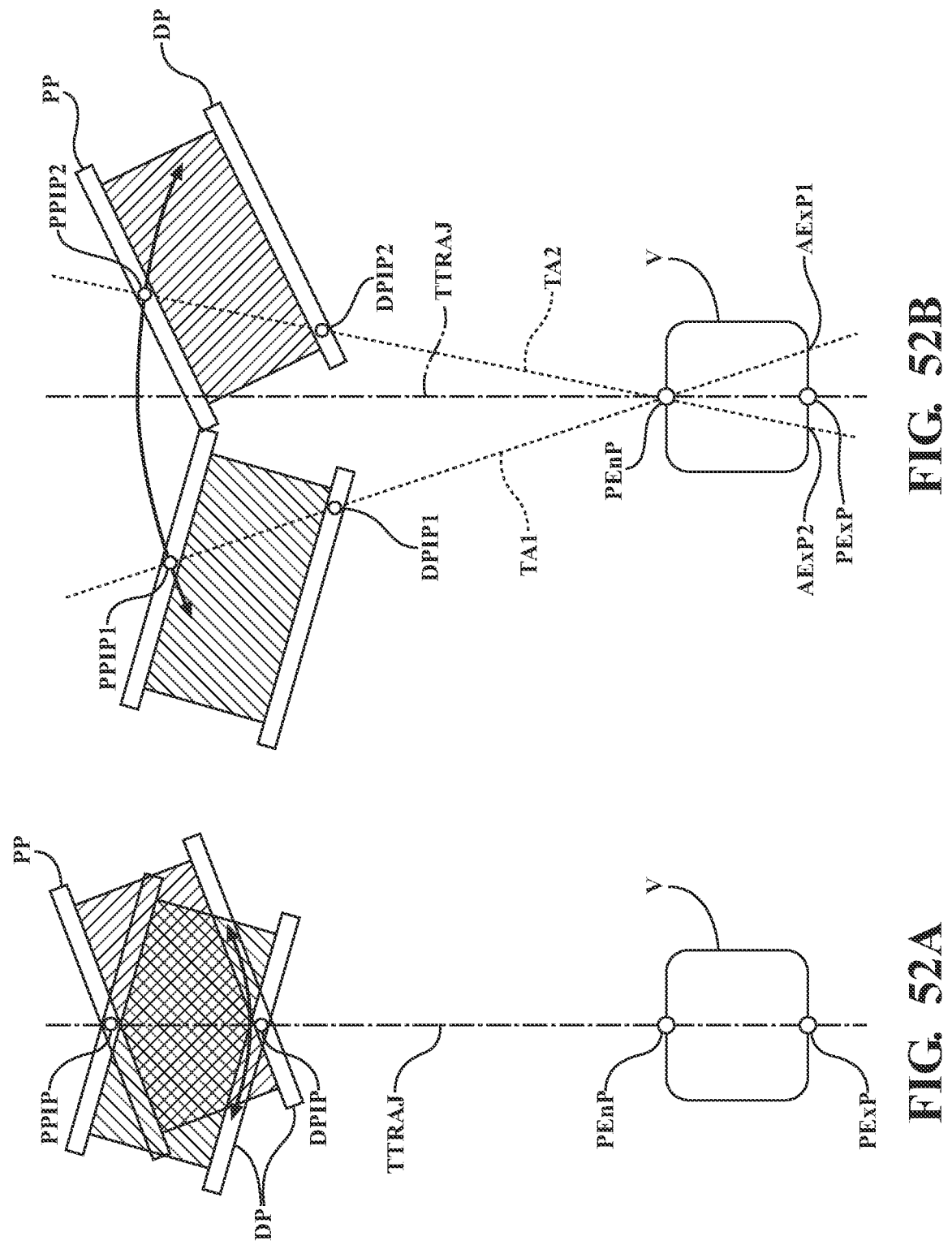
FIGS. 52A and 52B illustrate schematic views of the surgical instrument moving relative to proximal and distal planes in a second two-degree of freedom mode.

Specifically, with respect to FIGS. 52A-52B, in a first 2-orientation DOF mode, referred to as a pivot about proximal trajectory point control mode, the control system may control the plurality of actuators such that the location of the intersection of the tool axis TA in the proximal plane PP is maintained, and the control system controls the plurality of actuators to vary the position of the intersection of the tool axis in the distal plane DP. FIG. 52A can be understood by showing that the intersection point of tool axis in the distal plane DPIP can vary as the user repositions the hand-held portion with respect to the target trajectory, whereas the intersection point of the tool axis in the proximal plane PPIP is maintained. Similar to the other modes, it is contemplated that the control system may control the plurality of actuators such that the instrument transitions to the home state when the pivot about proximal trajectory point control mode is selected. In this manner, it is contemplated that the control system controls the plurality of actuators such that the tool axis TA is maintained in the center/origin of the proximal plane PP, but it could maintain the tool axis at other points other than the origin.

In this control mode, the fixation of the point in the proximal plane PP provides for a pivot point for the hand-held portion. As the target trajectory passes through both proximal plane PP and distal plane DP, the control system will control the plurality of actuators to move the tool axis TA1, TA2 in the distal plane DP. Because the tip of the tool may be fixed in the tissue of the patient when this mode is selected, the result of utilizing this control mode is that the instrument will be adjusted about two orientation degrees of freedom, rotation about X and Y axes.

With respect to FIG. 52B, it is shown that this control mode may result in the tool axis TA1, TA2 may differ from the target trajectory TTRAJ. As the hand-held portion is repositioned by the user such that the tool assumes various tool axes TA1, TA2, the intersection point in the proximal plane PPIP1, PPIP2 is maintained with respect to X and Y axes, while the intersection point in the distal plane DPIP1 and DPIP2 is adjusted. Similar to the previous control mode, this may result in the tool axis TA1, TA2 being aligned with the planned entry point PEnP, but be aligned with points other than the planned exit point PExP, such as the actual exit points AExP1, AExP2.

The proximal trajectory point control mode provides for a satisfying user experience by providing the user a sensation at they are pushing into a wall when the hand-held portion of the instrument is located in a position that results in the tool axis TA1, TA2 being off the target trajectory TTRAJ. This control mode also requires the user to hold to the target trajectory TTRAJ because the instrument would not adjust the position of the tool axis in the proximal plane. Instead, this control mode would give the user a feeling of where the correct alignment is and cue the user to move the hand-held portion into the correct position relative to the target trajectory TTRAJ.

Figures 53A, 53B:
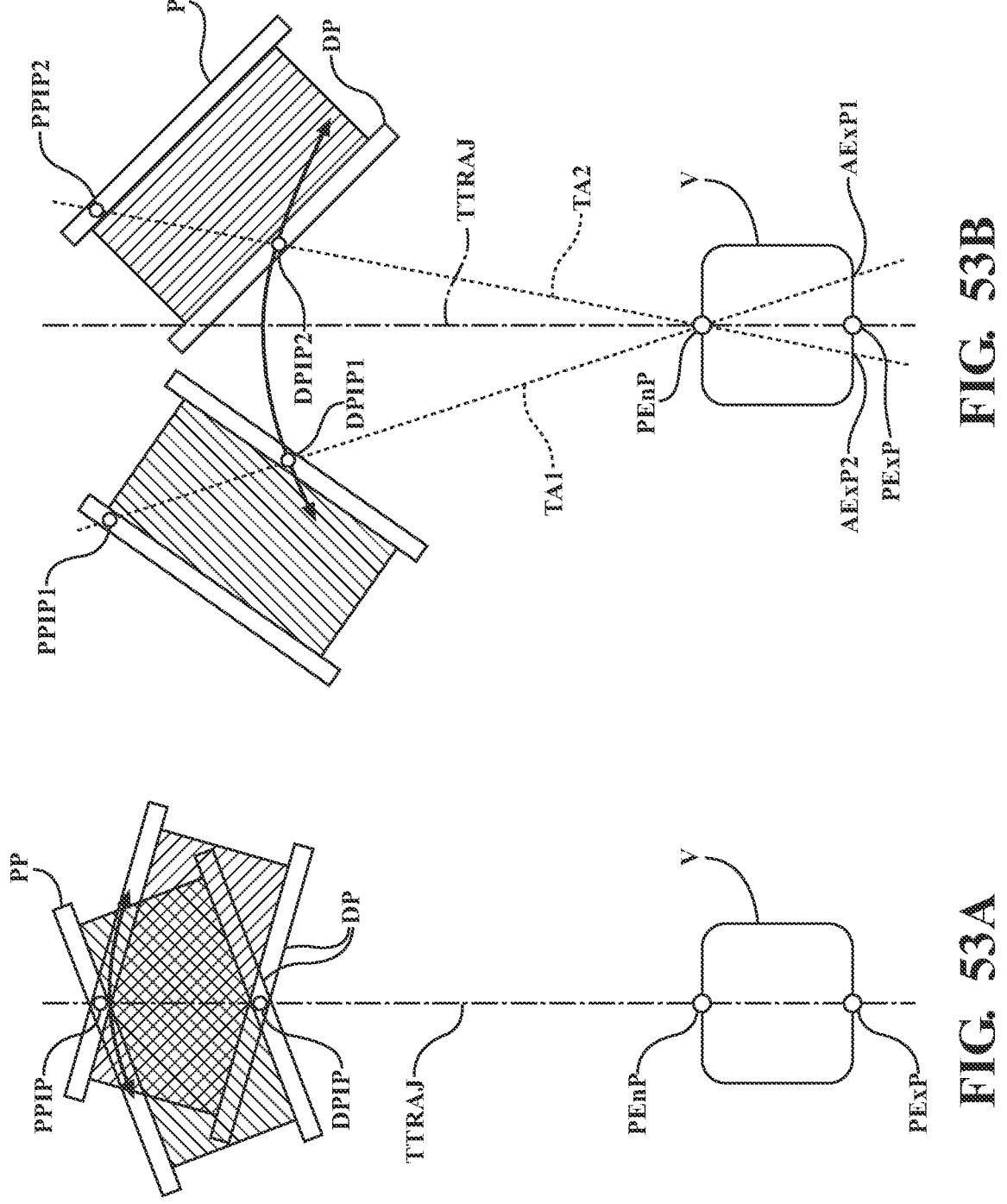
FIGS. 53A and 53B illustrate schematic views of the surgical instrument moving relative to proximal and distal planes in a third two-degree of freedom mode.

With respect to FIGS. 53A-53B, in an alternative orientation DOF mode, referred to as a pivot about the distal trajectory point control mode, the control system may control the plurality of actuators such that the location of the tool axis TA1, TA2 in the distal plane DP is maintained, and the control system controls the plurality of actuators to vary the position of the intersection of the tool axis TA1, TA2 in the proximal plane PP. Similar to the other modes, it is contemplated that the control system may control the plurality of actuators such that the instrument transitions to the home state when the pivot about the distal trajectory point control mode is selected. In this control mode, the fixation of the point DPIP1, DPIP2 relative to the X, Y axes, in the distal plane DP provides for a pivot point for the hand-held portion. Because the tip of the tool may be fixed in the tissue when this mode is selected, the result of utilizing this control mode is that the instrument will be adjusted two orientation degrees of freedom, X and Y axes.

FIG. 53A can be understood by showing that the intersection point of target trajectory in the proximal plane PPIP can vary as the user repositions the hand-held portion with respect to the target trajectory TTRAJ, whereas the intersection point of the target trajectory in the distal plane DPIP is maintained The distal trajectory point control mode requires the user to hold the instrument to the target trajectory because the instrument would not adjust the position of the tool axis in the distal plane. However, this control mode would provide a cue to where the correct alignment of the hand-held portion is with respect to the target trajectory. This control mode also provides for a feeling of being pushed off the target trajectory, which may be described as a sensation that the user is at the top of the hill. This can provide useful cues to the user to reposition his or her hand to an appropriate location to achieve the target trajectory.

With respect to FIG. 53B, it is shown that this control mode may result in the tool axis TA1, TA2 may differ from the target trajectory TTRAJ. As the hand-held portion is repositioned by the user such that the tool assumes various tool axes TA1, TA2, the intersection point in the distal plane DPIP1, DPIP2 is maintained with respect to X, Y axes, while the intersection point in the proximal plane PPIP1 and PPIP2 is adjusted. Similar to the previous control mode, this may result in the tool axes TA1, TA2 being aligned with the planned entry point PEnP, but be aligned with points other than the planned exit point PExP, such as the actual exit points AExP1, AExP2.

Figure 75A:
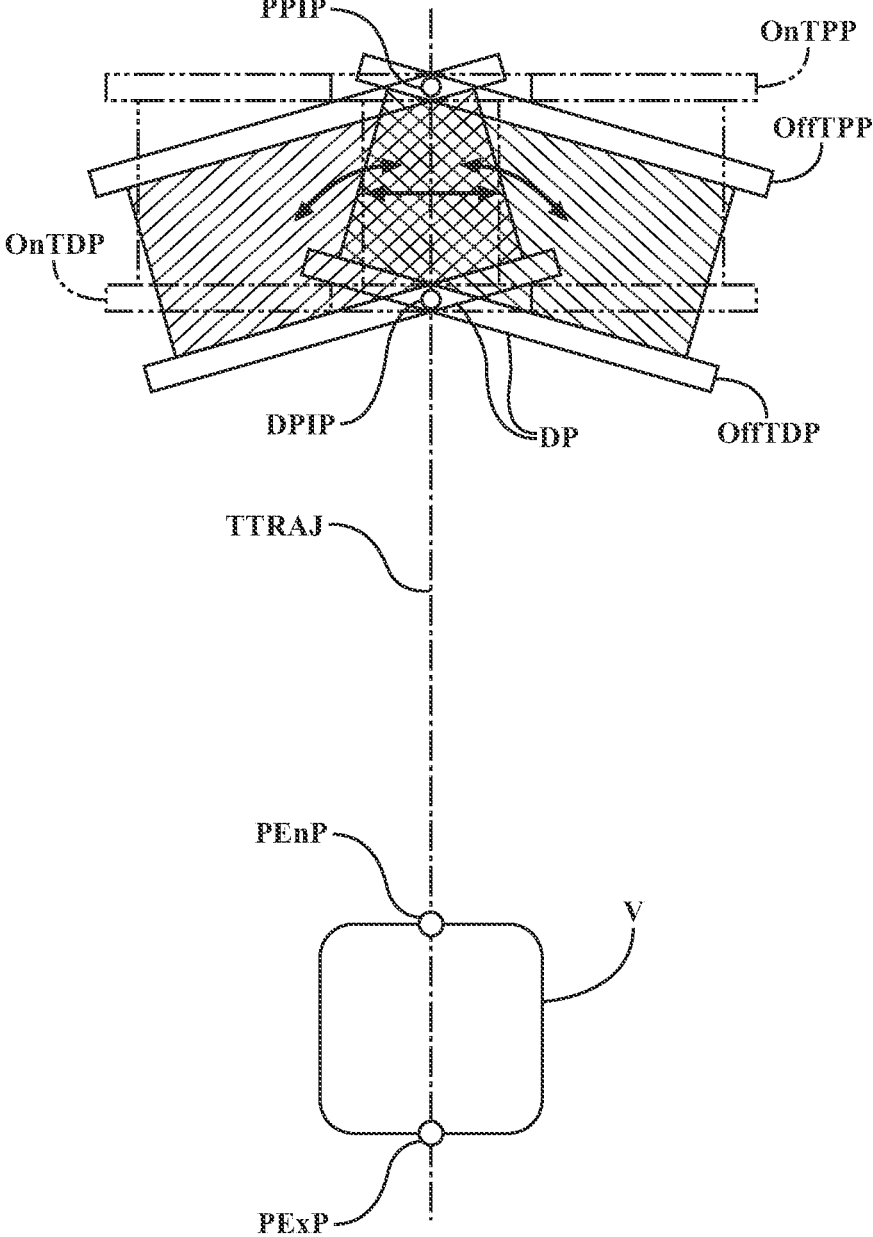
FIG. 75A illustrates a schematic view of the surgical instrument in one example of the instrument is in an on-target mode.
Figure 75B:
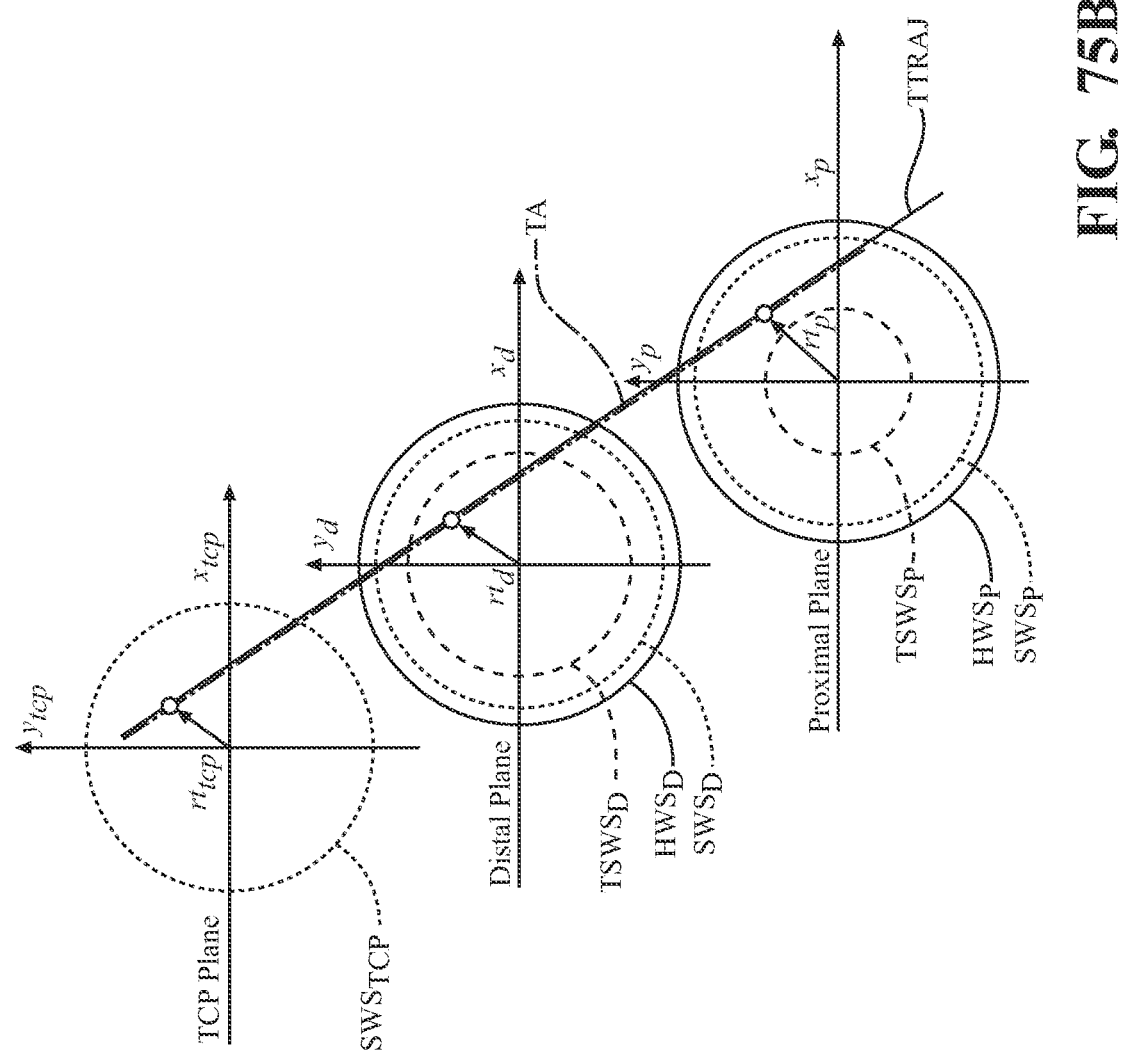
FIG. 75B illustrates the pose of the instrument relative to schematic view of the proximal and distal planes when the radius of the tool exceeds the transition workspace limit.

With reference to FIGS. 75A and 75B, it is also contemplated that the control system may switch between two different two degree of freedom control modes during operation. In such an implementation, the first 2-DOF control mode can be considered an on-target sub-mode and the second 2-DOF control mode can be considered an off-target sub mode. In the on-target sub-mode, the control system may be configured to control the plurality of actuators in a first and second degree of freedom, and in the off-target sub mode, the control system may be configured to control the plurality of actuators in a third and fourth degrees of freedom. It should be appreciated that the first degree of freedom is different from the second, third, and fourth degrees of freedom. In some implementations, the first and second degrees of freedom are translation degrees of freedom, and the third and fourth degrees of freedom are orientation degrees of freedom. In this implementation, when the instrument is centered near the target trajectory, the control system controls the plurality of actuators in two translation degrees of freedom, as described above. However, when the instrument is positioned away from the target trajectory and is approaching the range of motion limitations, the control system controls the instrument as described in the distal trajectory point control mode, I.e., controls the instrument in two orientation degrees of freedom. This particular combination of two degree of freedom control modes allows for some off trajectory adjustments while also providing the user a physical sense of when the instrument is near the range of motion limits to correct the alignment of the tool to the target trajectory. It should be appreciated that the instrument could alternatively transition between any of the other combinations of 2 or 4 degrees of freedom control modes based on similar criteria.

The diagram of FIG. 75B shows how the proximal plane PP and distal plane DP might move when the instrument is in the on-target mode, OnTPP, OnTDP. As it can be seen from the diagram, the X-Y coordinates of the tool axis TA in the proximal plane PP and the distal plane DP is maintained as identical when the instrument is in the on-target mode. In contrast, when the instrument is in the off-target mode, the proximal and distal planes may move as shown in the figure with reference to OffTPP, OffTDP, where the intersection point in the distal plane DP is maintained with respect to X axes and Y axes, and the intersection point in the proximal plane PP is varied with respect to X axes and Y axes.

The control system may be configured to transition between the on-target sub-mode and the off-target sub-mode based on various parameters and/or computations. For example, the control system may select from the on-target sub-mode and the off-target sub-mode based on the state of the tool, the tool support, the hand-held portion, or the state of at least one of the plurality of actuators.

In one particular implementation, referring now to FIG. 75B, the control system may be configured to select the on-target sub-mode and the off-target sub-mode based on the state of the tool and a transition workspace limit $TSWS_D$, $TSWS_p$. For example, the control system may compute where the tool axis TA is located in the proximal plane PP or distal plane DP relative to the location of the transition workspace limits $TSWS_D$, $TSWS_p$. For example, the control system may determine the $rt_d$ and compare to a transition radius for the distal plane, a radius extending from the origin of the distal plane to the transition workspace limit for the distal plane $TSWS_D$. If the $rt_d$ exceeds the transition radius for the distal plane $TSWS_D$, the control system may transition from the on-target sub-mode to the off-target sub-mode. The transition radius for the distal plane may be smaller than the radius of the workspace limits for the distal plane $SWS_D$, such as 80% or 90% of the workspace limit of the distal plane. In the exemplary scenario shown in FIG. 75B, the $rt_d$ is smaller than the transition radius in the distal plane, so the control system would not transition to the off-target mode based on the position of the tool axis TA in the distal plane DP.

In a similar implementation, the control system may determine the radius of the tool axis in the proximal plane $rt_p$ and compare to the transition radius for the proximal plane. The transition radius for the proximal plane is a radius extending from the origin of the proximal plane to the transition workspace limit in the proximal plane $TSWS_p$. If the $rt_p$ exceeds the transition radius for the proximal plane, the control system may transition from the on-target mode to the off-target sub-mode. The transition radius for the proximal plane TSWSp may be smaller than the radius of the workspace limits for the proximal plane, such as 80% or 90% of the workspace limit of the proximal plane $SWS_p$.

Figure 76B:
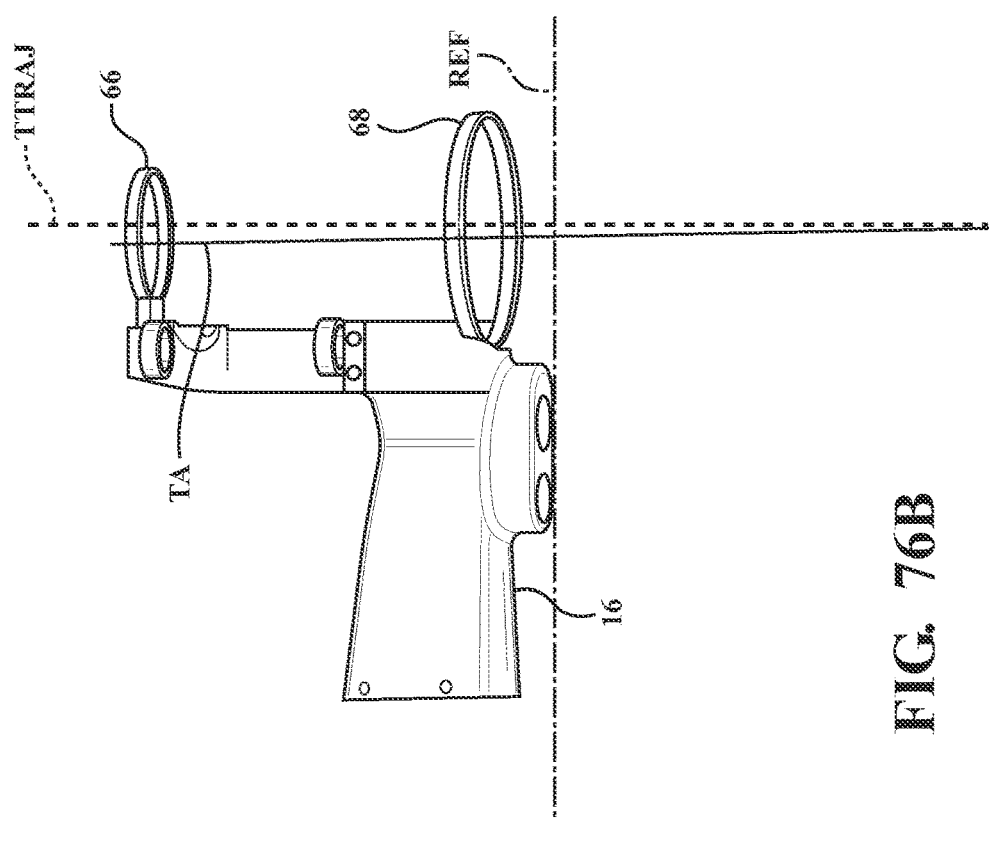
FIGS. 76A-76E shows schematic views of the surgical instrument transition between on-target mode and off-target mode.
Figure 76A:
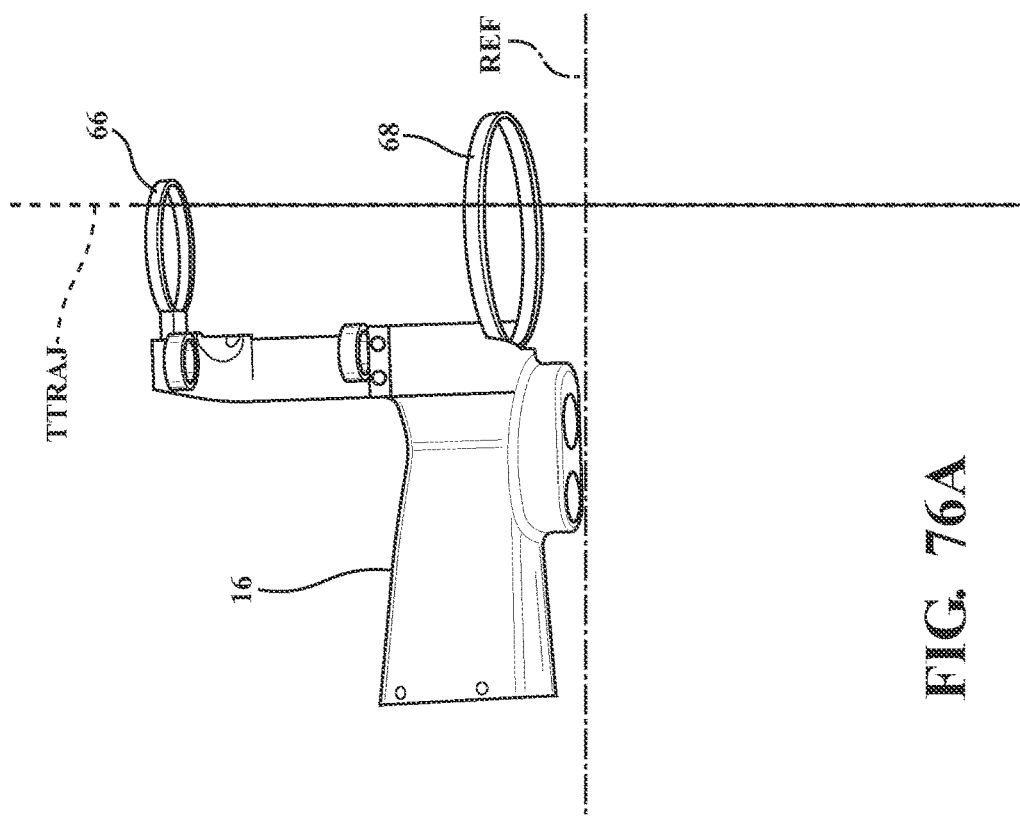
Figure 76D:
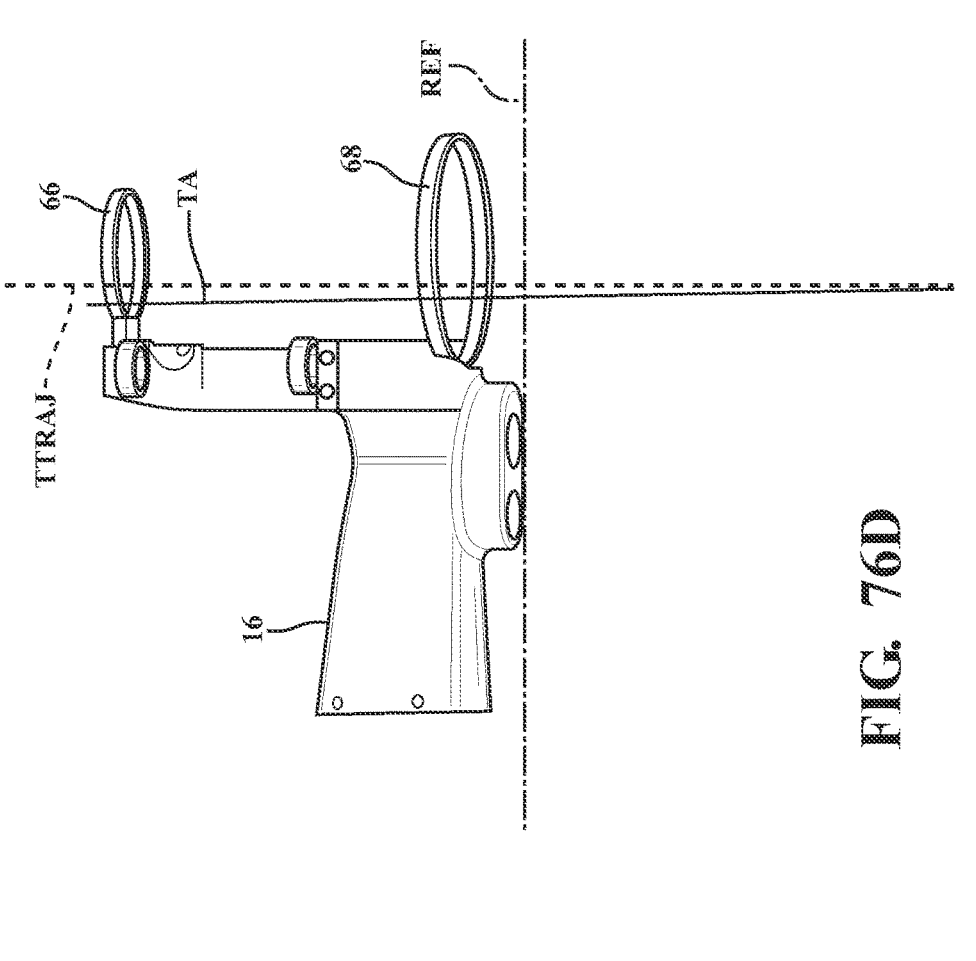
Figure 76C:
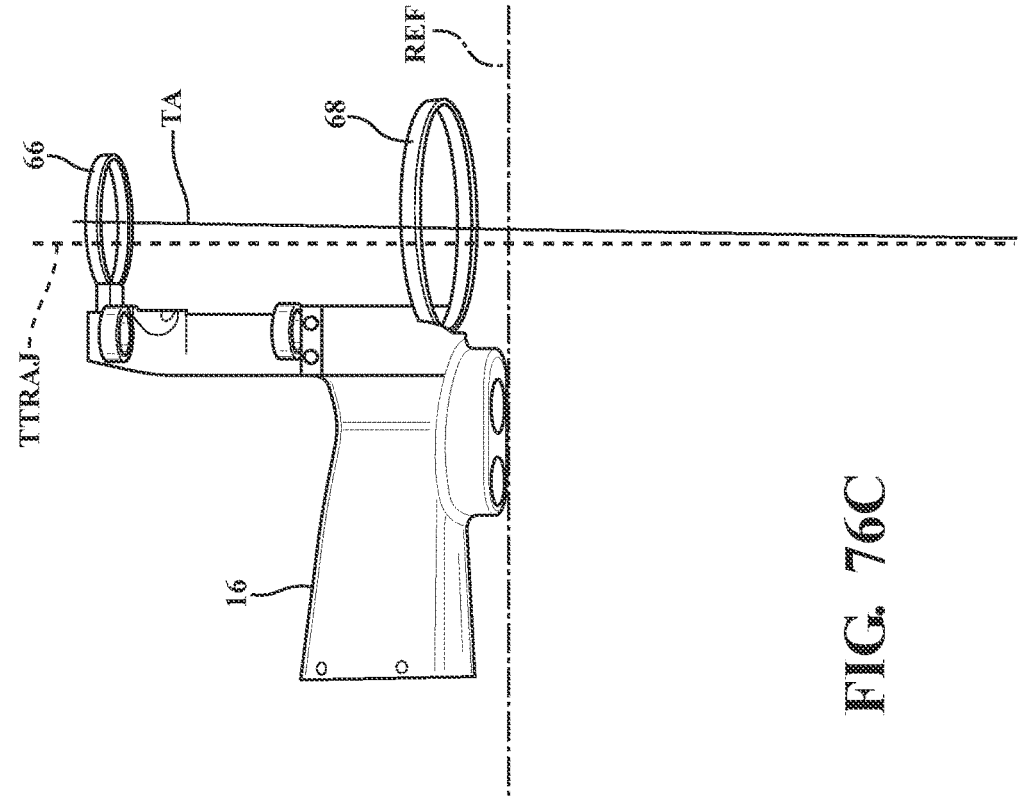
Figure 76E:
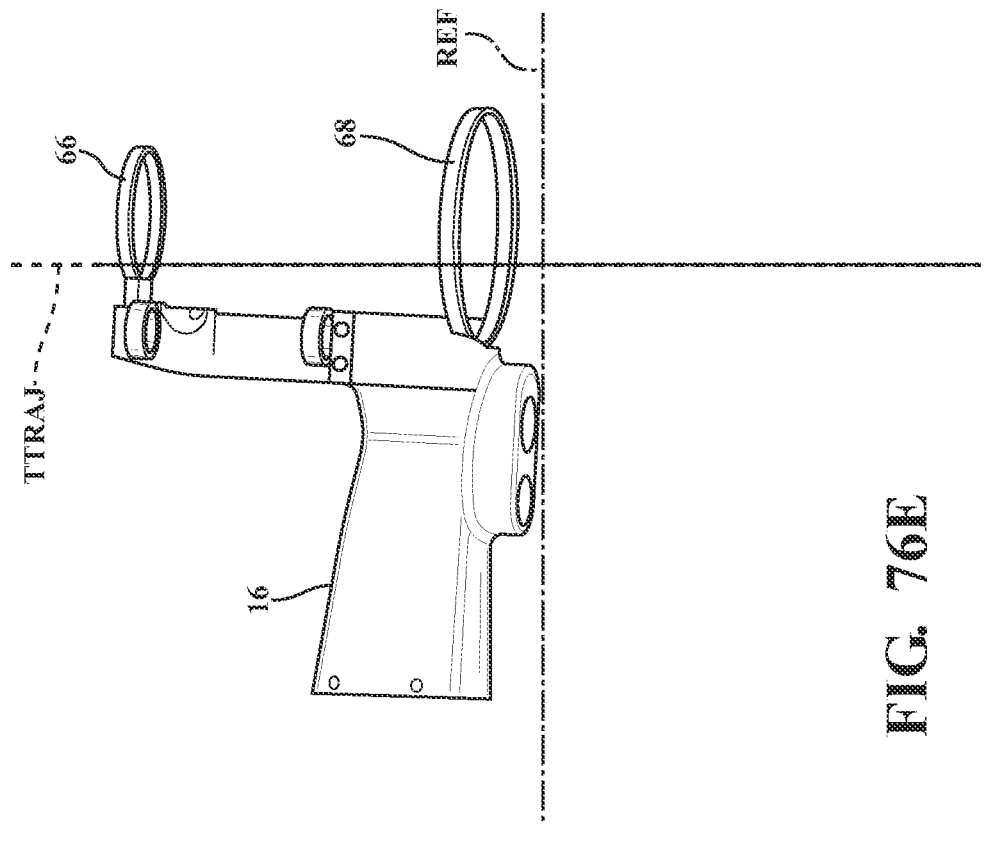

One example of the transition between on-target mode and off-target mode can be seen with respect to FIGS. 76A-76E. In FIGS. 76B-76D, the hand-held portion 16 of the instrument is positioned such that the tool axis TA can be aligned by the plurality of actuators to reach the target trajectory TTRAJ. This can be understood as operating in on-target mode. As the position of the hand-held portion 16 moves relative to the target trajectory TTRAJ in these figures, the actuators control the position of the tool axis in only two translation degrees of freedom. This can be visualized as the tool axis intersecting the proximal guide ring 66 and the distal guide ring at the same X, Y position. However, with FIGS. 76A and 76E, it can be understood that the tool axis violated the workspace limit in the proximal plane; in other words, the radius of the tool axis in the proximal plane $rt_p$ exceeded the transition radius in the proximal plane PP. The control system then transitions to operate in the off-target mode, and limits adjustments of the plurality of actuators to control the tool in only two orientation degrees of freedom, in particular, the instrument begins to operates in the pivot about the distal trajectory point control mode. This pivoting about the distal trajectory point can be visualized by closely examining FIG. 76A, where the position of the tool axis in the proximal guide ring 66 and distal guide ring 68 is no longer the same with respect to the X and Y degrees of freedom. Similarly, it can be seen that the angle of the-hand-held portion relative to the reference line REF is at a slightly adjusted angle when compared to the angle of the hand-held portion 16 in FIG. 76B. A similar relationship can be seen in FIG. 76E, where the hand-held portion 16 is at a slightly greater angle relative to REF when compared to the hand-held portion in FIG. 76D. The comparisons between FIGS. 76A and 76F to FIGS. 76B-76D shows the transition between on-target mode (FIGS. 76B-76D) and off-target mode (FIGS. 76A and 76B), and how that results in differences in the hand-held portion relative to the tool axis and target trajectory.

In an alternative implementation, the control system may select the on-target sub mode and the off-target sub-mode based on the state of at least one of the plurality of actuators and a joint limit. The state of the actuators is selected from commanded joint position of at least one actuator, a measured position of at least one actuator, a previous commanded position of at least one actuator, a previous measured position of at least one actuator, commanded joint angle of at least one actuator, a measured joint angle of at least one actuator, a previous commanded joint angle of at least one actuator, a previous measured joint angle of at least one actuator or combinations thereof. Similar to the implementation with respect to workspace limit implementation, the control system may compare the joint state to a joint transition threshold which may be a percentage of the joint limit for each actuator. The joint transition threshold may be 70% or 80% of the joint limit. If the joint state for one or more actuators exceeds the joint transition threshold, the control system may switch between the on-target control mode and the off-target control mode.

It should be appreciated that the control system may disable or stop the tool drive motor when the instrument transitions from the on-target mode to the off-target mode. Similarly, the control system may reenable the motor when the instrument reenters the on-target mode from the off-target mode.

The control system may be configured to select an appropriate control mode based on the degree of fixation of the tool in the tissue. In this manner, the control system is configured to monitor fixation between the surgical tool and the workpiece, such as the bone. When the control system determines that fixation has occurred, the control system may be configured to transition between control modes.

When the tool is fixed is fixed to tissue, the two degree of freedom control modes present a viable option as the tool may no longer be capable of moving in four degrees of freedom. In certain of the described two degree of freedom control modes, the tip of the tool creates a fixed pivot point.

Referring to FIGS. 73A-74B, in one implementation, the control system is configured to enter fixation test mode based on the state of the surgical tool 20. More particularly, the control system may be configured to monitor fixation by entering a fixation test mode based on the state of the surgical tool and the planned bone entry point PEnP. The planned bone entry point PEnP may be based on a planned pose of an implant or based on a target anatomical object or other planned trajectory. In one implementation, as shown in FIGS. 73A-73B, the control system may be configured to monitor fixation by being configured to enter a fixation test mode based on the state of the surgical tool 20 and an expected engagement boundary EEB. The expected engagement boundary EEB may be defined by any suitable virtual object, such as a three-dimensional object, like a sphere, or based on a plane or line, the plane or line which is perpendicular to the target trajectory TTRAJ, which may be aligned with the planned axis of the implant, IM. The three-dimensional object associated with EEB may be positioned based on the planned bone entry point PEnP.

Alternatively, the control system may compute a distance parameter between the tool and the planned bone entry point, and based on the computed distance parameter, the control system may enter the fixation test mode. Various distance parameter thresholds DP1, DP2, DP3 are illustrated in FIGS. 74A-74B. When the system determines that the instrument is within distance parameter threshold DP1, the control system may enter fixation test mode. Alternatively still, it is contemplated the user can select fixation test mode via the user input device.

In one exemplary fixation test mode, the control system may be configured to determine a second commanded position or angle for at least one of the plurality of actuators, and control the at least one of the plurality of actuators based on the second commanded position or angle, and detect fixation based on the pose of the tool after the plurality of actuators are controlled based on the second commanded position or angle. In the fixation test mode, the control system may detect fixation based on a measured pose of the surgical tool and a commanded pose of the surgical tool. In the fixation test mode, the control system is configured to determined that the commanded joint position or angled based on the commanded pose, and wherein the pose of the surgical tool is the measured pose of the surgical tool. In one implementation, the fixation parameter may be a distance parameter from a previously measure pose of the tool to a current position of the tool 20 and the fixation parameter threshold may be a distance threshold. The control system may detect that fixation has occurred when the distance parameter exceeds the distance threshold. In such an implementation, the distance threshold may be set at approximately 5 mm. The distance parameter may be the magnitude of the distance between the measured pose, such as the current measured pose or the previously measured pose of the surgical tool, i.e., the location of the tool based on the localizer, and the commanded pose is the pose that the control system that the control system instructs the plurality of actuators to move towards. If the tool is fixated, the tool will not be able to move from its current pose to the commanded pose because the tissue surround the tool prevents the tool from moving. As such, if there is fixation there will be a distance between the commanded pose and the measured pose of the tool. The commanded pose selected for fixation test mode may selected such that there is a sufficient distance between the commanded pose and the previously measured pose, such as at least 8 mm between the previously measured pose and the commanded pose at the distal end of the tool, the TCP. This virtual distance between the previously measured pose and the commanded pose at the distal end of the tool should result in one or more actuators attempting to move the tool in one or more degrees of freedom. If there is fixation of the tool in bone, and because the actuators are not configured to move the tool proximally within the bore hole, the actuators will not be able move the distal end of the tool to the commanded pose.

Alternatively, the control system may be configured to monitor fixation based on an output of a sensor FS associated with other aspects of the instrument, such as the drive motor, the plurality of actuators, the tool support, the hand-held portion, or the surgical tool. Exemplary fixation sensors are illustrated in FIG. 2. The control system may monitor fixation based on the output signal of such a sensor and a sensor threshold, referred to about as a fixation parameter threshold. For example, the control system may monitor fixation based on a sensor associated with the drive motor. The control system may monitor fixation based on the output sensor of such a sensor and a sensor threshold. Other sensors that may be associated with the drive motors include force sensors, or torque sensors. A tool drive parameter may also be used to determine fixation. Various tool drive parameters are described in US2021/0267608, which is hereby incorporated by reference. For example, if the sensor is a current sensor, the control system may compare the sensed current to a current threshold. If the sensed current exceeds the current threshold, the control system may determine that fixation has occurred. In instances where the sensor is associated with the plurality of actuators, the tool support, or the hand-held portion, the sensor may be configured to sense a force or a torque. For example, the sensor may be a strain gauge. Alternatively, the sensor may be a current sensor associated with the motors of one or more of the plurality of actuators.

With continued reference to FIG. 49, the control system can also assume fixation based on the state of the tool relative to a virtual boundary, referred to as a fixation boundary FB. For example, it is described above that the control system may determine that fixation occurs when the tool engages, such as crosses, the fixation boundary FB. The fixation boundary FB may be placed relative to the cortical surface of bone in the image data to be recessed approximately 3 mm, which is estimated potential error of the position of the distal end of the tool. Other recession distances are also contemplated.

It should be also appreciated that the system could determine fixation in ways other than using the position of the tool relative to the fixation boundary, and hence, use these other methodologies as a basis to transition between various control modes.

It should be appreciated that the methods of determining that fixation has occurred that do not depend on distance parameters or fixation boundaries may be advantageous in that these methodologies are not as dependent on the accuracy of the localizer. Thus, if there is an issue with the accuracy of the localizer, such as an error attributed to one of the trackers attached to the patient and/or the instrument, the control system will still be able to accurately determine the time at which fixation has occurred, and switch the control modes at the appropriate time/spatial relationship to bone.

As described above, the control system is configured to operate the instrument in a plurality of different control modes, such as the 4-degree of freedom trajectory mode, the 4-DOF pointing mode, the various 2-DOF modes, and the like. The control system may be configured to select any of these modes, or switch between any of these modes when the control system determines that fixation has occurred in one manner or another.

It also is contemplated that the instrument may be configured to control the tool drive motor based on the state of one or more of the plurality of actuators. For example, as described above, it is contemplated that the control system may adjust a motor parameter of the drive motor when one or more of plurality of actuators have a state that exceeds the one or more joint limits, or the control system may adjust a motor parameter of the drive motor when the tool support reaches one or more workspace limits. Such control is described in PCT Publication No. WO2022055980, filed Sep. 8, 2021, which is hereby incorporated by reference. It is specifically contemplated that in certain modes, such as the 2-DOF modes described above, that the tool drive motor parameter is not altered by the control system despite the joint position/angle being coincident with the joint limit and/or the tool being coincident with one or more workspace limits.

Referring still to FIG. 49, the control system may also be configured to control the tool drive motor based on boundaries other than the fixation boundary, such as the tool drive motor boundary, illustrated as a distal boundary DB1, DB2, DB3. This may result that, in certain 2-DOF modes, the control system controls the tool drive motor based on the state of the tool and a first boundary DB1, DB2, DB3, and control one or more of the plurality of actuators based on the state of the surgical tool and a second boundary FB, the first boundary being different from the second boundary. The second boundary may be positioned at the same location as the boundary that is used to determine fixation FB. Thus, when the tool crosses the second boundary FB, the control system may control the plurality of actuators in one of the described 2-DOF modes or the control system may control the plurality of actuators such that the positions of the actuator are essentially frozen, or moved in zero degrees of freedom. This would result in the system transitioning from four degrees of freedom to zero degrees of freedom.

In one particular implementation, with reference to FIG. 49, the control system 60 places the instrument 14 into a second control mode controlling the tool drive motor M based on state of one or more of the plurality of actuators 21, 22, 23, 24. In another example, the control system 60 is controls the tool drive motor M based on the state of the robotic instrument 14 and based on a boundary DB1, DB2, DB3. In another examples, when the instrument 14 is in the second control mode, the control system 60 is configured to control the tool drive motor M based on the state of the robotic instrument 14 and based on a boundary DB1, DB2, DB3. The control system 60 may control one or more of the actuators 21, 22, 23, 24 based on the state of the surgical tool and a second boundary FB, with the second boundary FB different from the first boundary DB1, DB2, DB3. The first boundary DB1, DB2, DB3 and the second boundary FB may be associated with the anatomical feature, such as corresponding to a distance from a reference point, a virtual object representing a portion of the anatomical feature, or both. In some examples, such as shown in FIG. 61, the first boundary DB1, DB2, DB3 and the second boundary FB are each determined based on a planned pose of an implant IM.

Figure 67:
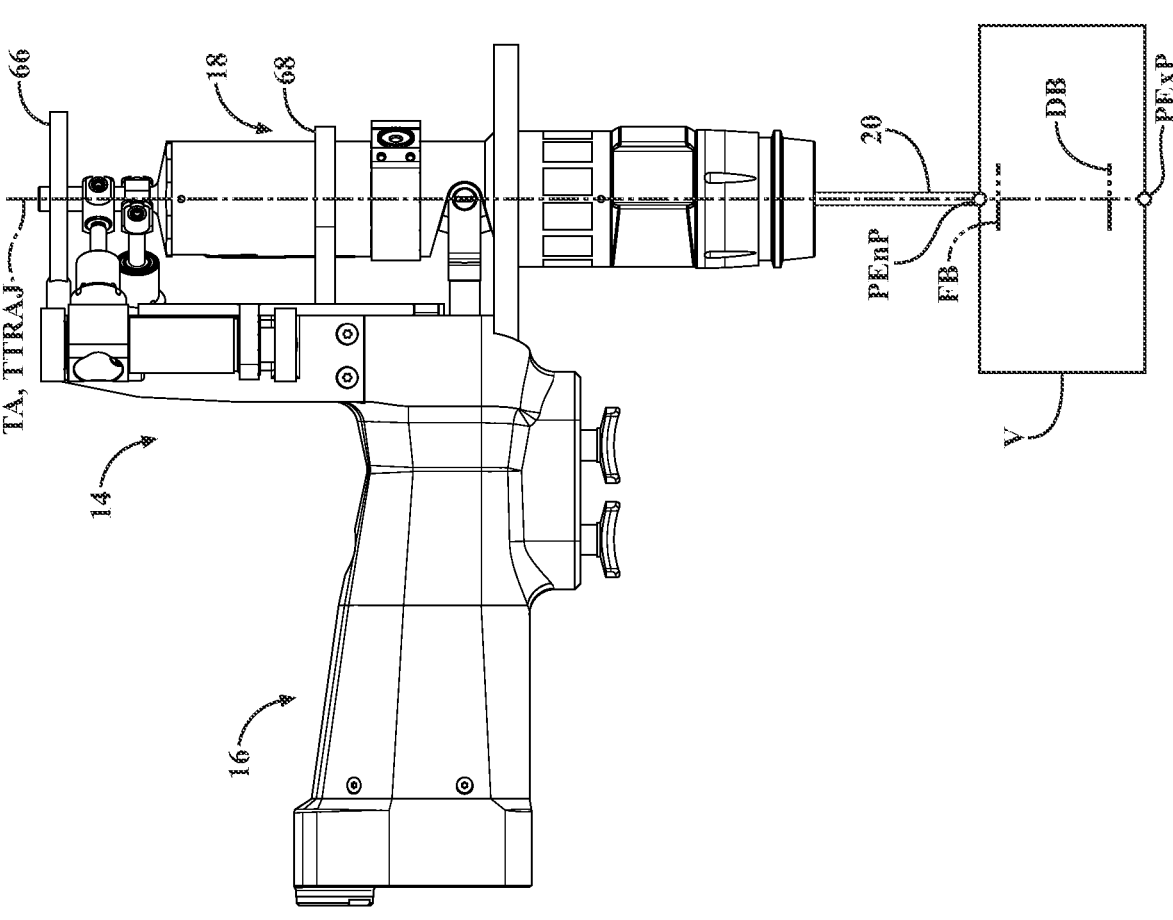
FIGS. 67-69 show the robotic instrument drilling into a target bone, moving the handpiece relative to the target trajectory and tool axis as the instrument reaches the target boundary.
Figure 68:
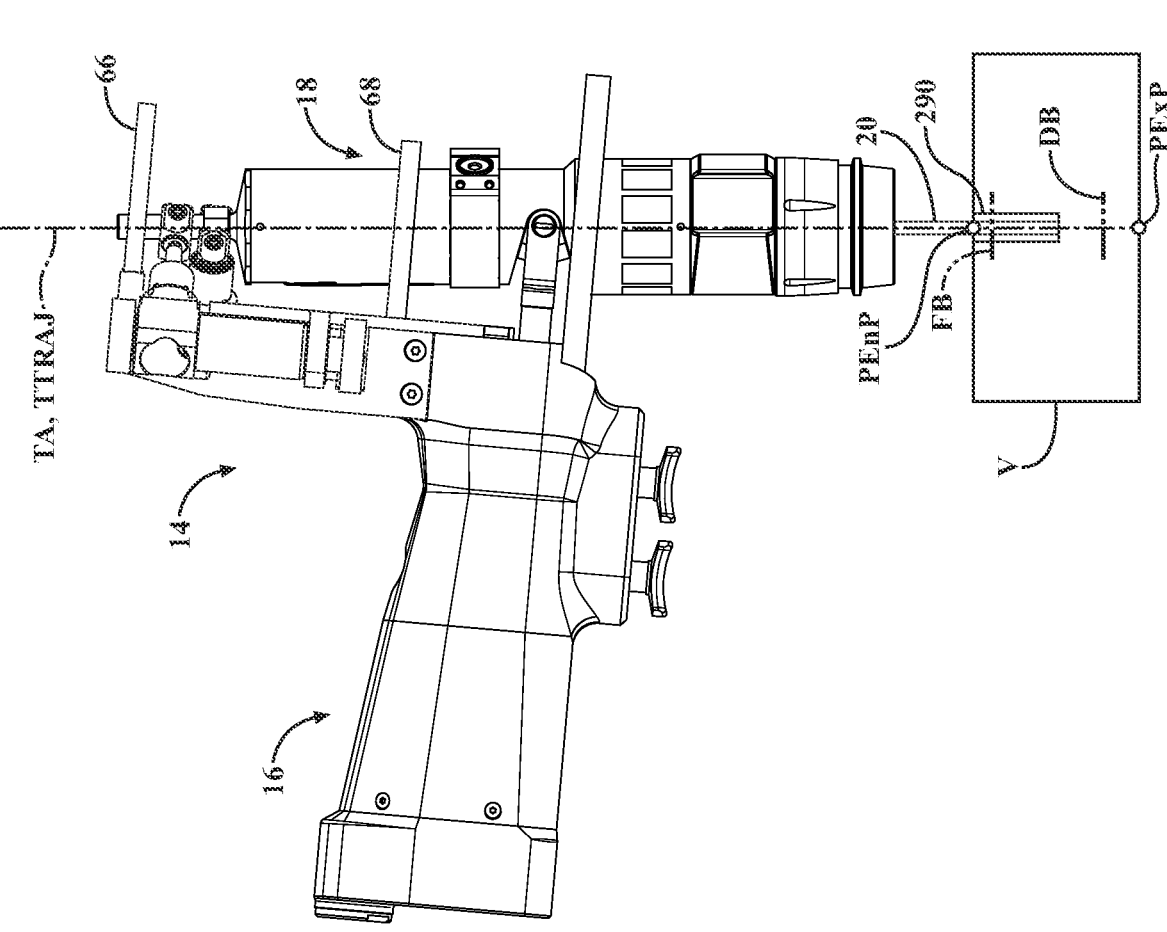
Figure 69:
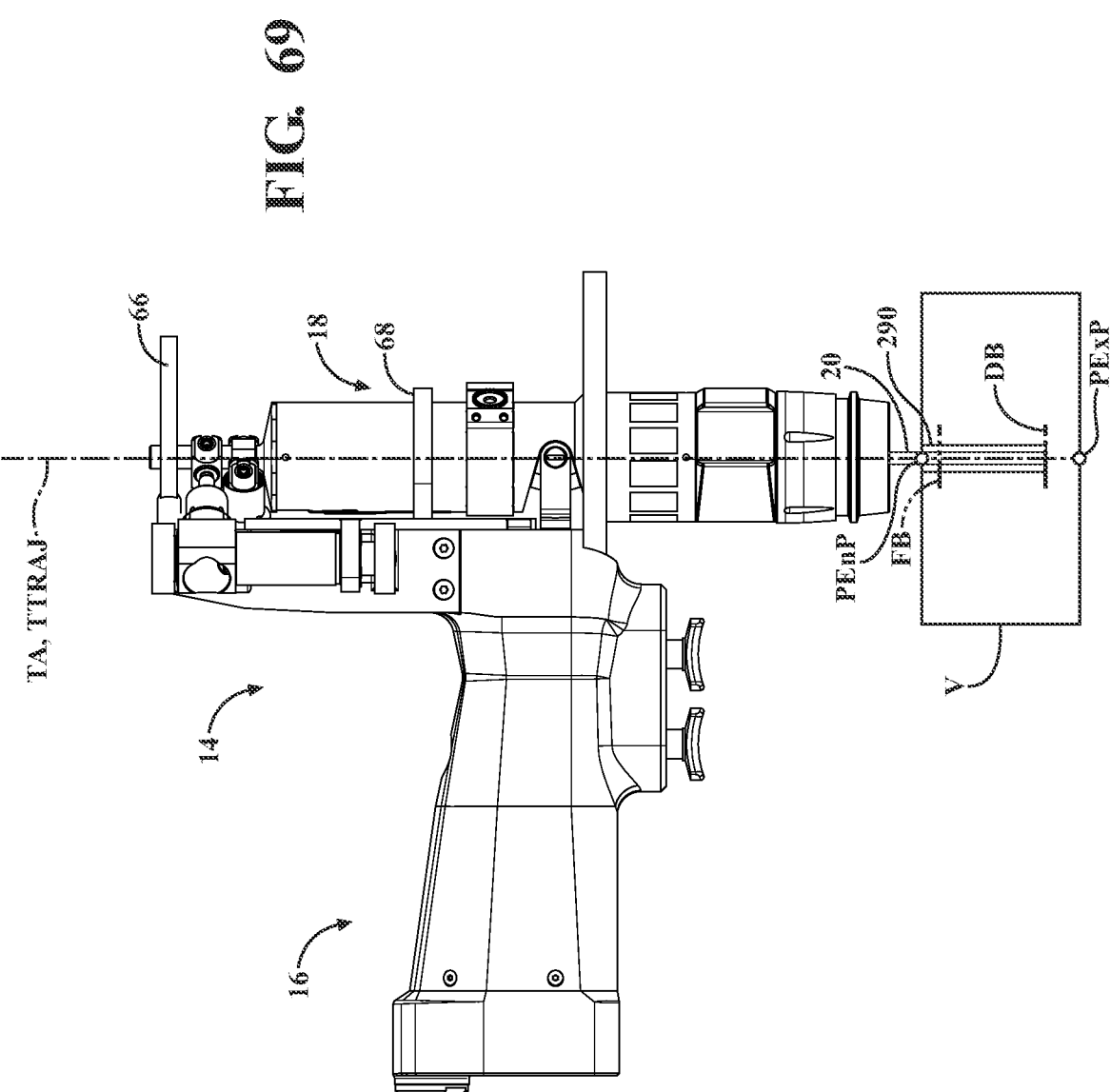

To further understand the relationship between the fixation boundary and one or more distal boundaries, FIGS. 67-69 are further described. Both of the boundaries FB, DB1-3 described immediately above may be based on a planned pose of an implant or the location of anatomical feature, i.e., a target, or other suitable aspect of the planned procedure. The fixation boundary FB may be located parallel to the tool drive motor boundary DB1-3, and may be offset from one another by a user-adjustable distance or based on the particular tool utilized with the instrument DB1, DB2, DB3, as described in WO2021062373, which is hereby incorporated by reference. When the tool crosses the fixation boundary FB, it can be understood that the tool is now fixed relative to bone except along the tool axis. Thus, at FIG. 67, the position of the tool axis can be adjusted as it is not yet in bone, or the tool has not yet crossed the fixation boundary FB. The tool drive motor can continue to operate as well because the tool has not yet crossed the distal boundary DB.

With reference to FIG. 68, the tool has crossed the fixation boundary or the control system has determined that fixation has occurred, and the instrument is no longer capable of adjusting the tool axis relative to bone as bone constrains movement of the tool. At the time that the tool violates fixation boundary or the control system determines that fixation has occurred, the instrument can transition from one control mode to another control mode, such as transitioning from the 4 degree of freedom trajectory mode to one of the two-degree freedom modes described above. Or, as mentioned above, the control system could transition from a first two-degree of freedom mode to a second degree of freedom mode. Despite the fact that the tool has violated the fixation boundary, the tool drive motor can still continue to operate as the tool has not yet violated the distal boundary DB.

In one potential implementation, the instrument would operate in the trajectory mode until the tool violated the fixation boundary. At that time, the control system would transition the instrument to operate in the two degree of freedom translation mode. So long as the tool axis did not violate the transition workspace limits, the instrument would be maintained in the two degree of freedom translation mode until the tool violated the distal boundary DB. However, if the tool axis did violate the transition workspace limits in one or more of the planes, the control system may begin controlling the instrument in the two orientation degree of freedom mode. Thus, during the drilling of one hole, it is contemplated that the control system could select the trajectory mode, then the 2-DOF translation mode once fixation has occurred. Then, depending on the position of the tool axis, switch to the 2-DOF orientation mode.

With reference to FIG. 69, the tool has already crossed the fixation boundary, and hence the instrument is potentially operating in one of the two-degree of freedom modes. Furthermore, because the tool 20 has now violated the distal boundary DB, the drive motor has been deactivated and the instrument is prevent from drilling or driving deeper within the tissue, vertebra V.

Figures 54, 55:
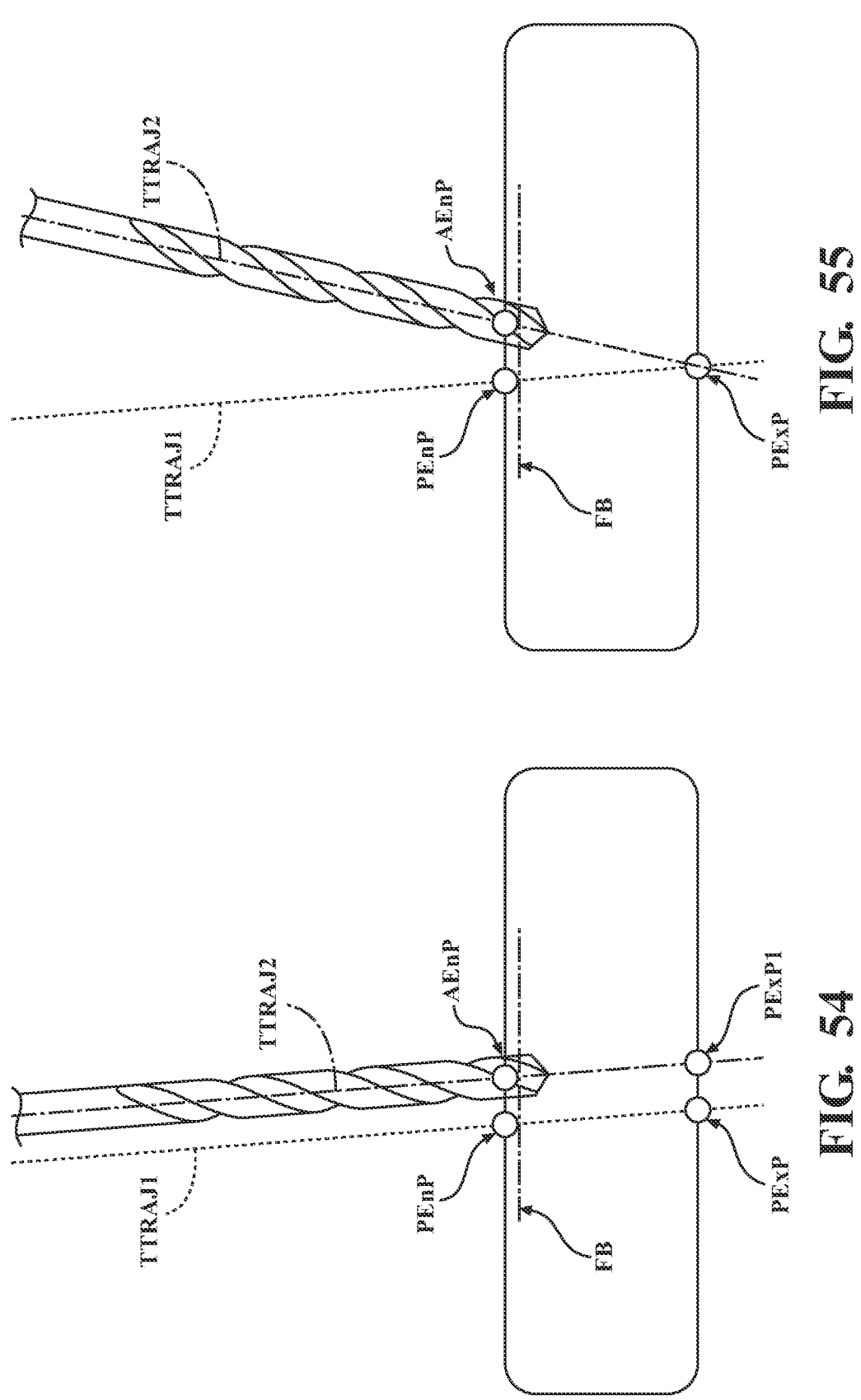
FIG. 54 illustrates a schematic view of the surgical instrument transitioning from a first trajectory to a second trajectory, with the second trajectory being parallel to the first trajectory.
FIG. 55 illustrates a schematic view of the surgical instrument transitioning from a first trajectory to a second trajectory, with the second trajectory sharing a point with the first trajectory.

With reference to FIGS. 54 and 55, in certain procedures, despite the control system's attempt to position the tool on the target trajectory, the user may inadvertently begin drilling in a location that is different from the planned trajectory TTRAJ1. In this implementation, as described above, one or more of the plurality of actuators would ordinarily 'push' on the user's hand via the hand-held portion as control system controls the plurality of actuators in an attempt to reposition the tool as the tool may be fixated into the inadvertently drilled bore. It is contemplated that the control system may be capable of dynamically adjusting the target trajectory to alleviate this fighting. In this implementation, the control system may receive the first target trajectory TTRAJ1 of the surgical tool in the known coordinate system. This first target trajectory TTRAJ1 may be planned pre-operatively, such as being based on the planned pose of an implant, such as a pedicle screw or plate. This first target trajectory TTRAJ1 can be understood as including a first target axis extending between a planned first bone entry PEnP point and a second point PExP. The control system may further determine a state of one of the surgical tool, hand-held portion, and the tool support in the known coordinate system, and determine a first commanded joint position or angle for each of the plurality of actuators based on the first target trajectory and based on the state of one of the surgical tool, hand-held portion, and the tool support, and control the plurality of actuators based on the commanded joint positions or angle for each of the plurality of actuators. This would result in the actuators moving the surgical tool towards the target trajectory TTRAJ1.

The control system may then select a second target trajectory TTRAJ2, which includes a second target axis extending through a second bone entry point AEnP, the second bone entry point AEnP being different from the planned first bone entry point PEnP, and the control system may determine the second commanded joint position or angle for each of the plurality of actuators based on the second target trajectory TTRAJ2 and based on the state of one of the surgical tool, hand-held portion, and the tool support.

With reference to FIG. 55, in one potential implementation, the second target trajectory TTRAJ2 extends through the second bone entry point AEnP and the second point PExP from the first target trajectory TTRAJ1. This can be advantageous in that the tool will ultimately reach a location near the originally planned second point PExP of the originally planned trajectory TTRAJ1. With reference to FIG. 54, in an alternative implementation, the second target axis TTRAJ2 may be selected such that it is parallel to the first target axis TTRAJ1. This can be advantageous in that the second target axis TTRAJ2 penetrates the bone or other structure at the same angle relative to the originally planned trajectory TTRAJ1.

The control system may switch, or otherwise select the second trajectory based on the state of one of the surgical tool, hand-held portion, and the tool support and a boundary, illustrated as FB in FIGS. 54 and 55. This boundary FB may be located perpendicular to the first planned trajectory, and within bone by approximately 5 mm. This boundary could be located in a similar location as the contemplated fixation boundary.

Alternatively, the control system may be configured to select the second trajectory when fixation of the tool has been determined. This may result in the trajectory being switched when the plurality of actuators are no longer able to adjust to reach the planned trajectory because of intervening tissue between the planned trajectory and the current axis of the tool.

Other factors that may be considered when selecting a target trajectory and manners of controlling the display of the patient image data are also contemplated, such as those described in U.S. Patent Pub. No 20210212767, filed Jan. 6, 2021, which is hereby incorporated by reference in its entirety.

Figure 77:
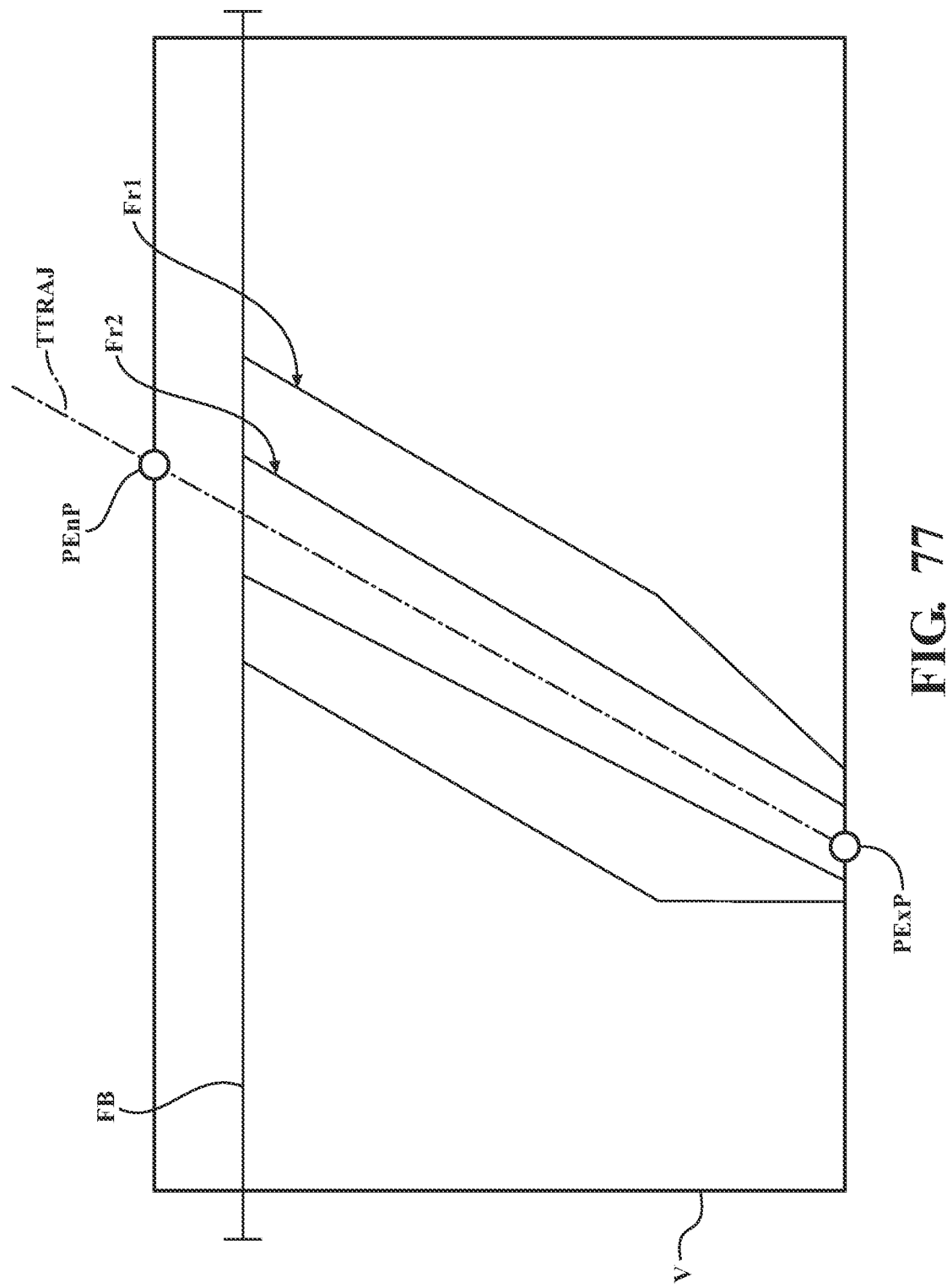
FIG. 77 shows a schematic view of various control frames with respect to a target trajectory.

With reference to FIG. 77, the control system may control the plurality of actuators and/or the drive motor with respect to various control frames and boundaries. While referred to as frames for this description, the frames could be alternatively referred to as zones, boundaries, or other virtual objects. Each of the frames FR1, FR2 may be positioned relative to the target trajectory based on predefined parameters, such as a fixed radius offset from the target trajectory, or by user-adjustable parameters, the users can select the radius/size and/or position of the various frames. It should be understood that the first frame is different spatially than the second frame. In certain implementations, the first frame may be entirely within the second frame.

The control system may control the tool drive motor based on the state of the tool and the position of the first frame FR1. More particularly, the control system may change a motor parameter of the drive motor if the tool violates the boundary defined by the first frame. This first frame may be active when the instrument is in four DOF trajectory mode, or in various 2-DOF modes, such as 2-DOF orientation mode or 2-DOF translation mode. This first frame FR1 provides assurance the tool cannot veer too far off the target trajectory. It should be appreciated that the first frame may only be activated after the control system has determined that the tool is fixated, whether that is because the tool crosses the fixation boundary or whether the control system determines that fixation has occurred through other methodologies described above. In other words, the control system may configured to assess the state of the tool relative to the first frame FR after fixation has occurred.

The control system may control one or more of the plurality of actuators based on the state of the tool and the position of the second frame FR2. For example, the control system may control the plurality of actuators to align with a second target trajectory if the tool violates the second frame FR2. The second target trajectory includes a second target axis extending through a second bone entry point, the second bone entry point being different from the planned first bone entry point PEnP, and the control system may determine the commanded joint positions or angles for each of the plurality of actuators based on the second target trajectory, such that the plurality actuators are positioning the tool to align with the second trajectory. Examples of how the control system may switch the target trajectories are described above with reference to FIGS. 54 and 55. It should be appreciated that the second frame may only be activated after the control system has determined that the tool is fixated, whether that is because the tool crosses the fixation boundary or whether the control system determines that fixation has occurred through other methodologies described above. In other words, the control system may configured to assess the state of the tool relative to the second control frame after fixation has occurred.

If the tool is positioned off the target trajectory despite control of the plurality of actuators in the trajectory mode (i.e., 4 DOF mode that tries to align the tool axis with the target trajectory), the control system may tolerate the deviation and maintain the same control mode (i.e., trajectory mode, 2DOF translation mode, 2DOF orientation mode and/or maintain operation of the drive motor as desired by the user, allowing the drive motor to operate).

As described above with respect to FIG. 1, the control system may set the second trajectory in different ways. It is contemplate that the control system may control an indicator, such as an icon on GUI, to prompt a user to select the criteria for the second target trajectory. The criteria may be a predefined relationship between the first target trajectory and the second target trajectory, such as having a common second point in their trajectories, or having a common angle between the trajectories.

It is also contemplated that the control system may control an indicator to indicate to a user that the tool is not aligned with the originally planned trajectory. In this manner, the control system may control an indicator based on the state of one of the surgical tool, hand-held portion, and the tool support and the first target trajectory. The control system may be configured to determine a current entry point based on the state of one of the surgical tool, hand-held portion, and the tool support, and the system is configured to control the indicator based on the current entry point and the first planned bone entry point. More particularly, the system of may be configured to control the indicator based on the current entry point, the first planned bone entry point, and a threshold. The threshold may be a distance threshold, and wherein the system is configured to control the indicator based on a distance between the current entry point, the first planned bone entry point, and the distance threshold. Various indicators are contemplated, such as a visual indicator, an audible indicator, or a tactile indicator.

In some examples, the instrument controller 28 may utilize one or more inputs to determine one or more outputs. The one or more inputs may include a pose of the bone determined by a patient tracker 54, 56, such as the reference location, the tool center point TCP of the tool 20 or pose of the TCP coordinate system by a tool tracker 52 on the tool support 18, the pose of the hand-held portion 16, a commanded pose of the tool 20, a distance parameter, positions of the first or second frames, actuator information (such as a commanded or measured position and/or pose, a current position and/or pose, a past position and/or pose, etc.), an input signal from a footswitch, trigger, or touch-screen, or a combination thereof. The one or more outputs of the instrument controller 28 may include changing a motor parameter of the drive motor M, adjusting a motion parameter (e.g.

changing the state or tuning parameter of a constraint) of the tool support 18, including changing force, acceleration or velocity, may turn off the boundary control, hold or freeze the tool 20 and tool support 18 relative to the hand-held portion 16, activate a homing mode, select the trajectory mode or the pointing mode, select one or more of the described 2DOF modes, or a combination thereof. Any suitable combination of inputs may be utilized with any suitable output.

The current state of the tool 20 and/or current state of one or more actuators relative to the target state and/or relative to the surgical site or relative to the commanded position may be output by the navigation system 32 and represented on the displays 38 via graphical representations of the tool 20, tool support 18, hand-held portion 16, actuators 21, 22, 23, 24, target state, virtual boundaries 184, and/or the surgical site, e.g., the vertebral body, or other anatomy. These graphical representations may update in real-time so that the user is able to visualize their movement relative to the target state, virtual boundaries 184, anatomy, etc. For example, the graphical representations of the tool 20 and anatomy may move on the displays 38 in real-time with actual movement of the tool 20 by the tool support 18 and actual movement of the anatomy.

It should be understood that the combination of position and orientation of an object is referred to as the pose of the object. Throughout this disclosure, it is contemplated that the term pose may be replaced by position and/or orientation in one or more degrees of freedom and vice-versa to achieve suitable alternatives of the concepts described herein. In other words, any use of the term pose can be replaced with position and any use of the term position may be replaced with pose.

In this application, including the definitions below, the term "controller" may be replaced with the term "circuit." The term "controller" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The controller(s) may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are the BLUETOOTH wireless networking standard from the Bluetooth Special Interest Group and IEEE Standard 802.15.4.

The controller may communicate with other controllers using the interface circuit(s). Although the controller may be depicted in the present disclosure as logically communicating directly with other controllers, in various configurations the controller may actually communicate via a communications system. The communications system includes physical and/or virtual networking equipment such as hubs, switches, routers, and gateways. In some configurations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various configurations, the functionality of the controller may be distributed among multiple controllers that are connected via the communications system. For example, multiple controllers may implement the same functionality distributed by a load balancing system. In a further example, the functionality of the controller may be split between a server (also known as remote, or cloud) controller and a client (or, user) controller.

Some or all hardware features of a controller may be defined using a language for hardware description, such as IEEE Standard 1364-2005 (commonly called "Verilog") and IEEE Standard 10182-2008 (commonly called "VHDL"). The hardware description language may be used to manufacture and/or program a hardware circuit. In some configurations, some or all features of a controller may be defined by a language, such as IEEE 1666-2005 (commonly called "SystemC"), that encompasses both code, as described below, and hardware description.

The various controller programs may be stored on a memory circuit. The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general-purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective C, Swift, Haskell, Go, SQL, R, Lisp, Java®, Fortran, Perl, Pascal, Curl, OCaml, JavaScript®, HTML5 (Hypertext Markup Language 5th revision), Ada, ASP (Active Server Pages), PUP (PHP: Hypertext Preprocessor), Scala, Eiffel, Smalltalk, Erlang, Ruby, Flash®, Visual Basic®, Lua, MATLAB, SENSORLINK, and Python®.

Additional clauses of the present invention are included below: I. A hand-held robotic instrument for use to perform surgery, the instrument comprising: a housing configured to be held by a user, the housing defining a remote axis of motion a tool support being movably coupled to the housing; an anchor post pivotably coupled to the tool support; a first set of actuators connected to the anchor post and the housing, a first actuator of the first set of actuators extends the anchor post relative to the remote axis of motion, and a second actuator of the first set is configured to pivot the anchor post about the remote axis of motion; and a second set of actuators coupling the tool support and the housing, wherein the first set of actuators and the second set of actuators work in concert to change the pose of the tool support in a plurality of degrees of freedom. II. A hand-held robotic instrument to perform surgery, the instrument comprising: a housing configured to be held by a user; a tool support being movably coupled to the housing; an anchor post pivotably coupled to the tool support; a first set of actuators operably coupled to the anchor post and the housing, the first set of actuators being configured to translate the anchor post relative to the housing and configured to pivot the anchor post about a remote axis of motion; a second set of actuators coupled to the tool support; and a controller in communication with the first set of actuators and the second set of actuators to change a pose of the tool support relative to the housing. III. A hand-held robotic instrument to perform surgery, the robotic instrument comprising: a housing configured to be held by a user, and defining a mount location; a tool support; a first linkage extending from the mount location on the housing to the tool support; a first actuator coupled to the first linkage and configured to cause the first linkage to extend from a first length to a second length; and a second actuator coupled to the first linkage and configured to cause the first linkage to pivot about the mount location on the housing. IV. A hand-held robotic instrument to perform surgery, the robotic instrument comprising: a housing configured to be held by a user; a tool support being movably coupled to the housing, including a positioning post; a first actuator and a second actuator movably coupled to the positioning post of the tool support and the housing for moving the tool support relative to the housing in a plurality of degrees of freedom, each of the first and second actuators including: a base; a rod connected to the base and moveable from a first length to a second length relative to the base, with the rod including a yoke; and a post slide pivotably coupled to the yoke, wherein the post slides of the first and second actuators are disposed about the positioning post and move along the positioning post; a linkage including a third actuator connected between the tool support and the housing. V. A hand-held robotic instrument to perform surgery, the robotic instrument comprising: a housing configured to be held by a user; a tool support being movably coupled to the housing; a first actuator a second actuator the first actuator coupling the second actuator and the housing, the second actuator coupling the first actuator and the tool support, wherein the first actuator includes a first motor, a first base coupled to the first motor, a first gear set coupled to the first motor, and a first rod coupled to the first gear set and the tool support, the first motor of the first actuator operable to extend and retract the first rod relative to the housing; wherein the second actuator operably coupled to the first rod and configured to articulate the first rod of the first actuator about an axis, a linkage; and a third actuator connected between the tool support and the housing, with the third actuator configured to move the tool support relative to the housing with the linkage. VI. A hand-held robotic instrument to perform surgery, the robotic instrument comprising: a housing configured to be held by a user; a tool support and being movably coupled to the housing, including a positioning post; a first actuator and a second actuator movably coupled to the positioning post of the tool support and the housing for moving the tool support relative to the housing in a plurality of degrees of freedom, the first actuator including a first motor and a first positioning link defining a first slot, the first motor configured to articulate the first positioning link about a first axis, with the first slot disposed about the positioning post; the second actuator including a second motor and a second positioning link defining a second slot, the second motor configured to articulate the second positioning link about a second axis, with the second slot disposed about the positioning post; a linkage; and a third actuator connected between the tool support and the housing with the third actuator configured to move the tool support relative to the housing with the linkage. VII. A hand-held robotic instrument to perform surgery, the robotic instrument comprising: a housing configured to be held by a user; a tool support and being movably coupled to the housing, the tool support defining an axis; an anchor post pivotably coupled to the tool support; a first set of actuators coupled between the anchor post and the housing, a first actuator of the first set of actuators is configured to change the position of the anchor post, and a second actuator of the first set configured to pivot the anchor post about a remote axis of motion; and a second set of actuators connected between the tool support and the housing, the second set of actuators including a first rotary actuator of the second set of actuators and a second linear actuator of the second set of actuators, the first rotary actuator being coupled to the second linear actuator to cause the second linear actuator to rotate about an axis and the second linear actuator of the second set of actuators configured to change length with the second linear actuator extending from the first rotary actuator of the second set of actuators to the tool support, wherein the first set of actuators and the second set of actuators work in concert to change a pose of the tool support.

VIII. A hand-held robotic instrument to perform surgery, the instrument comprising: an instrument comprising: a housing configured to be held by a user; a tool support being movably coupled to the housing, the tool support defining an axis; a first alignment guide extending from a first portion of the housing and surrounding at least a first portion of the tool support; a second alignment guide extending from a second portion of the housing and surrounding at least a second portion of the tool support, the second alignment guide spaced axially from the first alignment guide; a plurality of actuators between the housing and the tool support configured to move the tool support in a plurality of degrees of freedom relative to the housing; and a controller operatively connected to the plurality of actuators to change a pose of the axis relative to the housing in a plurality of degrees of freedom, the controller configured to automatically control each of the actuators to actively move the axis towards a target trajectory axis relative to the housing, wherein aligning the axis axially with the first alignment guide and second alignment guide, the tool support has an optimal range of motion relative to the housing.

IX. A hand-held robotic instrument to perform surgery, the robotic instrument comprising:

a hand-held portion to be held by a user; a tool support movably coupled to the hand-held portion;

a plurality of actuators operatively interconnecting the tool support and the hand-held portion to move the tool support in at least four degrees of freedom relative to the hand-held portion; and a linkage operatively interconnecting the tool support and the hand-held portion, the linkage being coupled to the tool support and the hand-held portion in a manner configured to constrain movement of the tool support relative to the hand-held portion in at least two degrees of freedom, wherein the linkage operatively interconnects the tool support and the hand-held portion independently of the plurality of actuators.

X. A hand-held robotic system for use with a surgical tool, the system comprising: an instrument comprising; a hand-held portion to be held by a user; a tool support coupled to the hand-held portion to support the surgical tool, the tool support comprising a tool drive motor; an actuator assembly operatively interconnecting the tool support and the hand-held portion to move the tool support in a plurality of degrees of freedom relative to the hand-held portion, the actuator assembly including a plurality of actuators; a localizer; a control system coupled to the plurality of actuators, the localizer, and the tool drive motor, the control system configured to: receive a first target trajectory of the surgical tool in a known coordinate system, wherein the first target trajectory includes a first target axis extending between a first planned bone entry point and a second point; determine a state of one of the surgical tool, hand-held portion, and the tool support in the known coordinate system; and control an indicator based on the state of one of the surgical tool, hand-held portion, and the tool support and the first target trajectory. XI. The system of clause X, wherein the system is configured to determine a current entry point based on the state of one of the surgical tool, hand-held portion, and the tool support, and the system is configured to control the indicator based on the current entry point and the first planned bone entry point. XII. The system of clause XI, wherein the system is configured to control the indicator based on the current entry point, the first planned bone entry point, and a threshold. XIII. The system of clause XII, wherein the threshold is a distance threshold, and wherein the system is configured to control the indicator based on a distance between the current entry point, the first planned bone entry point, and the distance threshold. XIV. The system of clause XIII, wherein the indicator is selected from a visual indicator, an audible indicator, or a tactile indicator. XV. A hand-held robotic system for use with a surgical tool, the system comprising: an instrument comprising; a hand-held portion to be held by a user; a tool support coupled to the hand-held portion to support the surgical tool, the tool support comprising a tool drive motor; an actuator assembly operatively interconnecting the tool support and the hand-held portion to move the tool support in a plurality of degrees of freedom relative to the hand-held portion, the actuator assembly including a plurality of actuators; a localizer; a control system coupled to the plurality of actuators, the localizer, and the tool drive motor, the control system configured to: determine a target pose of the surgical tool in a known coordinate system; determine a state of one of the surgical tool, hand-held portion, and the tool support in the known coordinate system; select a control mode from a first control mode and a second control mode based on the state of the surgical tool, the tool support, or the hand-held portion wherein in the first control mode, the plurality of actuators are controlled to move the surgical tool in at a first set of degrees of freedom and in the second control mode the plurality of actuators are controlled to move the surgical tool in a second set of degrees of freedom, the first set of degrees of freedom differing from the second set of degrees of freedom; determine a commanded joint position or angle for each of the plurality of actuators based on the target pose and based on the state of one of the surgical tool, hand-held portion, and the tool support; and control the plurality of actuators based on the respective commanded joint positions or angles. XVI. The system of clause XV, wherein the system is configured to select from the first control mode and the second control mode based on the state of the surgical tool and based on a boundary. XVII. The system of clause XVI, wherein the boundary is determined based on a planned pose of an implant. XVIII. The system of clause XVI, wherein the boundary is based on an anatomical feature. XIX. The system of clause XVII, wherein the first set of degrees of freedom includes at least two translation degrees of freedom and at least two orientation degrees of freedom. XX. The system of clause XIX, wherein the second set of degrees of freedom includes two or fewer degrees of freedom. XXI. The system of clause XIX, wherein the second set of degrees of freedom includes zero degrees of freedom. XXII. The system of clause XVII, wherein the implant is a pedicle screw. XXIII. A computer implemented method or software product for controlling a hand-held surgical robot, the hand-held surgical robot including a hand-held portion to be held by a user, a tool support coupled to the hand-held portion to support the surgical tool, the tool support comprising a tool drive motor, an actuator assembly operatively interconnecting the tool support and the hand-held portion to move the tool support in a plurality of degrees of freedom relative to the hand-held portion, and a control system, the method/product including instructions to: determine a target pose of the surgical tool in a known coordinate system; determine a state of one of the surgical tool, hand-held portion, and the tool support in the known coordinate system; determine a commanded joint position or angle for each of the plurality of actuators based on the target pose of the surgical tool and the state of one of the surgical tool, hand-held portion, and the tool support; control the plurality of actuators based on the respective commanded joint positions or angles; monitor fixation between the surgical tool and a workpiece; and select a control mode of the plurality of actuators based on the fixation. XXIV. A method for controlling a hand-held surgical robot, the hand-held surgical robot including a hand-held portion to be held by a user, a tool support coupled to the hand-held portion to support the surgical tool, the tool support comprising a tool drive motor, an actuator assembly operatively interconnecting the tool support and the hand-held portion to move the tool support in a plurality of degrees of freedom relative to the hand-held portion, and a control system the method comprising: determining a target pose of the surgical tool in a known coordinate system; determining a state of one of the surgical tool, hand-held portion, and the tool support in the known coordinate system;

determining a commanded joint position or angle for each of the plurality of actuators based on the target pose of the surgical tool and the state of one of the surgical tool, hand-held portion, and the tool support; controlling the plurality of actuators based on the respective commanded joint positions or angles; monitoring fixation between the surgical tool and a workpiece; and selecting a control mode of the plurality of actuators based on the fixation. XXV. A computer implemented method or software product for controlling a hand-held surgical robot, the hand-held surgical robot including a hand-held portion to be held by a user, a tool support coupled to the hand-held portion to support the surgical tool, the tool support comprising a tool drive motor, an actuator assembly operatively interconnecting the tool support and the hand-held portion to move the tool support in a plurality of degrees of freedom relative to the hand-held portion, and a control system, the method/product including instructions to: determine a commanded joint position or angle for each of the plurality of actuators based on the target pose and based on the state of one of the surgical tool, hand-held portion, and the tool support; control the plurality of actuators based on the respective commanded joint positions or angles; and select a control mode from a first control mode and a second control mode based on the pose of the tool, the tool support, or the hand-held portion wherein in the first control mode, the plurality of actuators are controlled to move the tool in at least four degrees of freedom and in the second control mode the plurality of actuators are controlled to move the tool in two or fewer degrees of freedom. XXVI. A method for controlling a hand-held surgical robot, the hand-held surgical robot including a hand-held portion to be held by a user, a tool support coupled to the hand-held portion to support the surgical tool, the tool support comprising a tool drive motor, an actuator assembly operatively interconnecting the tool support and the hand-held portion to move the tool support in a plurality of degrees of freedom relative to the hand-held portion, and a control system the method comprising: determining a commanded joint position or angle for each of the plurality of actuators based on the target pose and based on the state of one of the surgical tool, hand-held portion, and the tool support; controlling the plurality of actuators based on the respective commanded joint positions or angles; and selecting a control mode from a first control mode and a second control mode based on the pose of the tool, the tool support, or the hand-held portion wherein in the first control mode, the plurality of actuators are controlled to move the tool in at least four degrees of freedom and in the second control mode the plurality of actuators are controlled to move the tool in two or fewer degrees of freedom. XXVII. A computer implemented method or software product for controlling a hand-held surgical robot, the hand-held surgical robot including a hand-held portion to be held by a user, a tool support coupled to the hand-held portion to support the surgical tool, the tool support comprising a tool drive motor, an actuator assembly operatively interconnecting the tool support and the hand-held portion to move the tool support in a plurality of degrees of freedom relative to the hand-held portion, and a control system, the method/product including instructions to: determine a target pose of the surgical tool in a known coordinate system; determine a state of one of the surgical tool, hand-held portion, and the tool support in the known coordinate system; determine a commanded joint position or angle for each of the plurality of actuators based on the target pose and based on the state of one of the surgical tool, hand-held portion, and the tool support; control the plurality of actuators based on the respective commanded joint positions or angles; and select a control mode from a first control mode and a second control mode based on the pose of the tool, the tool support, or the hand-held portion wherein in the first control mode, the plurality of actuators are controlled to move the tool in at a first set of two degrees of freedom and in the second control mode the plurality of actuators are controlled to move the tool in a second set of two degrees of freedom, the first set of two degrees of freedom differing from the second set of two degrees of freedom. XXVIII. A method for controlling a hand-held surgical robot, the hand-held surgical robot including a hand-held portion to be held by a user, a tool support coupled to the hand-held portion to support the surgical tool, the tool support comprising a tool drive motor, an actuator assembly operatively interconnecting the tool support and the hand-held portion to move the tool support in a plurality of degrees of freedom relative to the hand-held portion, and a control system the method comprising: determining a target pose of the surgical tool in a known coordinate system; determining a state of one of the surgical tool, hand-held portion, and the tool support in the known coordinate system; determining a commanded joint position or angle for each of the plurality of actuators based on the target pose and based on the state of one of the surgical tool, hand-held portion, and the tool support; controlling the plurality of actuators based on the respective commanded joint positions or angles; and selecting a control mode from a first control mode and a second control mode based on the pose of the tool, the tool support, or the hand-held portion wherein in the first control mode, the plurality of actuators are controlled to move the tool in at a first set of two degrees of freedom and in the second control mode the plurality of actuators are controlled to move the tool in a second set of two degrees of freedom, the first set of two degrees of freedom differing from the second set of two degrees of freedom. XXIX. A computer implemented method or software product for controlling a hand-held surgical robot, the hand-held surgical robot including a hand-held portion to be held by a user, a tool support coupled to the hand-held portion to support the surgical tool, the tool support comprising a tool drive motor, an actuator assembly operatively interconnecting the tool support and the hand-held portion to move the tool support in a plurality of degrees of freedom relative to the hand-held portion, and a control system, the method/product including instructions to: determine a target pose of the surgical tool in a known coordinate system; determine a state of one of the surgical tool, hand-held portion, and the tool support in the known coordinate system; determine a commanded joint position or angle for each of the plurality of actuators based on the target pose and based on the state of one of the surgical tool, hand-held portion, and the tool support; control the plurality of actuators based on the respective commanded joint positions or angles; and wherein the control system is configured to select one of a pointing sub-mode and a trajectory sub-mode based on a target trajectory, a workspace limit, and the pose of one of the surgical tool, the tool support, and the hand-held portion; wherein the target trajectory includes a target axis extending between a bone entry point and a second point, wherein the control system is configured to control the plurality of actuators such that an axis of the tool is aligned with both the bone entry point and the second point when in the trajectory sub-mode and the control system is configured to control the plurality of actuators such that the axis of the tool is aligned with the bone entry point and a portion of the axis engages the workspace limit when in the pointing sub-mode. XXX. A method for controlling a hand-held surgical robot, the hand-held surgical robot including a hand-held portion to be held by a user, a tool support coupled to the hand-held portion to support the surgical tool, the tool support comprising a tool drive motor, an actuator assembly operatively interconnecting the tool support and the hand-held portion to move the tool support in a plurality of degrees of freedom relative to the hand-held portion, and a control system, the method comprising: determining a target pose of the surgical tool in a known coordinate system; determining a state of one of the surgical tool, hand-held portion, and the tool support in the known coordinate system; determining a commanded joint position or angle for each of the plurality of actuators based on the target pose and based on the state of one of the surgical tool, hand-held portion, and the tool support; controlling the plurality of actuators based on the respective commanded joint positions or angles; and wherein the control system is configured to select one of a pointing sub-mode and a trajectory sub-mode based on a target trajectory, a workspace limit, and the pose of one of the surgical tool, the tool support, and the hand-held portion; wherein the target trajectory includes a target axis extending between a bone entry point and a second point, wherein the control system is configured to control the plurality of actuators such that an axis of the tool is aligned with both the bone entry point and the second point when in the trajectory sub-mode and the control system is configured to control the plurality of actuators such that the axis of the tool is aligned with the bone entry point and a portion of the axis engages the workspace limit when in the pointing sub-mode. XXXI. A computer implemented method or software product for controlling a hand-held surgical robot, the hand-held surgical robot including a hand-held portion to be held by a user, a tool support coupled to the hand-held portion to support the surgical tool, the tool support comprising a tool drive motor, an actuator assembly operatively interconnecting the tool support and the hand-held portion to move the tool support in a plurality of degrees of freedom relative to the hand-held portion, and a control system, the method/product including instructions to: determine a target pose of the surgical tool in a known coordinate system; determine a state of one of the surgical tool, hand-held portion, and the tool support in the known coordinate system; determine a commanded joint position or angle for each of the plurality of actuators based on the target pose and based on the state of one of the surgical tool, hand-held portion, and the tool support; control the plurality of actuators based on the respective commanded joint positions or angles; and wherein the control system is configured to select one of a pointing sub-mode and a trajectory sub-mode based on a target trajectory, a joint limit, and a state of at least one actuator of the plurality of actuators; wherein the target trajectory includes a target axis extending between a bone entry point and a second point, wherein the control system is configured to control the plurality of actuators such that an axis of the tool is aligned with both the bone entry point and the second point when in the trajectory sub-mode and the control system is configured to control the plurality of actuators such that the axis of the tool is aligned with the bone entry point and the state of at least one actuators of the plurality of actuators is at the joint limit for that actuator. XXXII. A method for controlling a hand-held surgical robot, the hand-held surgical robot including a hand-held portion to be held by a user, a tool support coupled to the hand-held portion to support the surgical tool, the tool support comprising a tool drive motor, an actuator assembly operatively interconnecting the tool support and the hand-held portion to move the tool support in a plurality of degrees of freedom relative to the hand-held portion, and a control system, the method comprising: determining a target pose of the surgical tool in a known coordinate system; determining a state of one of the surgical tool, hand-held portion, and the tool support in the known coordinate system; determining a commanded joint position or angle for each of the plurality of actuators based on the target pose and based on the state of one of the surgical tool, hand-held portion, and the tool support; controlling the plurality of actuators based on the respective commanded joint positions or angles; and wherein the control system is configured to select one of a pointing sub-mode and a trajectory sub-mode based on a target trajectory, a joint limit, and a state of at least one actuator of the plurality of actuators; wherein the target trajectory includes a target axis extending between a bone entry point and a second point, wherein the control system is configured to control the plurality of actuators such that an axis of the tool is aligned with both the bone entry point and the second point when in the trajectory sub-mode and the control system is configured to control the plurality of actuators such that the axis of the tool is aligned with the bone entry point and the state of at least one actuators of the plurality of actuators is at the joint limit for that actuator. XXXIII. A computer implemented method or software product for controlling a hand-held surgical robot, the hand-held surgical robot including a hand-held portion to be held by a user, a tool support coupled to the hand-held portion to support the surgical tool, the tool support comprising a tool drive motor, an actuator assembly operatively interconnecting the tool support and the hand-held portion to move the tool support in a plurality of degrees of freedom relative to the hand-held portion, and a control system, the method/product including instructions to: receive a first target trajectory of the surgical tool in a known coordinate system, wherein the first target trajectory includes a first target axis extending between a planned first bone entry point and a second point; determine a state of one of the surgical tool, hand-held portion, and the tool support in the known coordinate system; determine a first commanded joint position or angle for each of the plurality of actuators based on the first target trajectory and based on the state of one of the surgical tool, hand-held portion, and the tool support; control the plurality of actuators based on the respective first commanded joint positions or angles; select a second target trajectory, wherein the second target trajectory includes a second target axis extending through a second bone entry point, the second bone entry point being different from the planned first bone entry point; and determine a second commanded joint position or angle for each of the plurality of actuators based on the second target trajectory and based on the state of one of the surgical tool, hand-held portion, and the tool support. XXXIV. A method for controlling a hand-held surgical robot, the hand-held surgical robot including a hand-held portion to be held by a user, a tool support coupled to the hand-held portion to support the surgical tool, the tool support comprising a tool drive motor, an actuator assembly operatively interconnecting the tool support and the hand-held portion to move the tool support in a plurality of degrees of freedom relative to the hand-held portion, and a control system, the method comprising: receiving a first target trajectory of the surgical tool in a known coordinate system, wherein the first target trajectory includes a first target axis extending between a planned first bone entry point and a second point; determining a state of one of the surgical tool, hand-held portion, and the tool support in the known coordinate system; determining a first commanded joint position or angle for each of the plurality of actuators based on the first target trajectory and based on the state of one of the surgical tool, hand-held portion, and the tool support; controlling the plurality of actuators based on the respective first commanded joint positions or angles; selecting a second target trajectory, wherein the second target trajectory includes a second target axis extending through a second bone entry point, the second bone entry point being different from the planned first bone entry point; and determining a second commanded joint position or angle for each of the plurality of actuators based on the second target trajectory and based on the state of one of the surgical tool, hand-held portion, and the tool support. XXXV. A computer implemented method or software product for controlling a hand-held surgical robot, the hand-held surgical robot including a hand-held portion to be held by a user, a tool support coupled to the hand-held portion to support the surgical tool, the tool support comprising a tool drive motor, an actuator assembly operatively interconnecting the tool support and the hand-held portion to move the tool support in a plurality of degrees of freedom relative to the hand-held portion, and a control system, the method/product including instructions to: determine a target pose of the surgical tool in a known coordinate system, the target pose of the surgical tool based on a first target trajectory; determine a state of one of the surgical tool, hand-held portion, and the tool support in the known coordinate system; determine a commanded joint position or angle for each of the plurality of actuators based on the target pose of the surgical tool and the state of one of the surgical tool, hand-held portion, and the tool support; control the plurality of actuators based on the respective commanded joint positions or angles; control the tool drive motor based on a first frame and the state of the surgical tool; select a second target trajectory based on a second frame and the state of the surgical tool, wherein the second target trajectory is different from first target trajectory; monitor fixation between the surgical tool and a workpiece; and select a control mode of the plurality of actuators based on the fixation. XXXVI. A hand-held robotic instrument to perform surgery, the instrument comprising: a housing configured to be held by a user; a tool support being movably coupled to the housing, the tool support including a tool; an anchor post pivotably coupled to the tool support; a first set of actuators operably coupled to the anchor post and the housing, the first set of actuators being configured to translate the anchor post relative to the housing and configured to pivot the anchor post about a remote axis of motion; and a controller in communication with the first set of actuators to change a pose of the tool support relative to the housing. XXXVII. A hand-held robotic instrument to perform surgery, the robotic instrument comprising: a housing configured to be held by a user, and defining a mount location; a tool support supporting a tool; a first linkage extending from the mount location on the housing to the tool support; a first actuator coupled to the first linkage and configured to cause the first linkage to extend from a first length to a second length; and a second actuator coupled to the first linkage and configured to cause the first linkage to pivot about the mount location on the housing. XXXVIII. A hand-held robotic instrument to perform surgery, the robotic instrument comprising: a housing configured to be held by a user; a tool support being movably coupled to the housing, the tool support supporting a tool, including a positioning post; a first actuator and a second actuator movably coupled to the positioning post of the tool support and the housing for moving the tool support relative to the housing in a plurality of degrees of freedom, each of the first and second actuators including: a base; a rod connected to the base and moveable from a first length to a second length relative to the base, with the rod including a yoke; and a post slide pivotably coupled to the yoke, wherein the post slides of the first and second actuators are disposed about the positioning post and move along the positioning post. XXXIX. A hand-held robotic instrument for use with a tool to perform surgery, the instrument comprising: an instrument comprising: a housing configured to be held by a user; a tool support to support the tool and being movably coupled to the housing, the tool support including a tool defining a tool axis; a first alignment guide extending from a first portion of the housing and surrounding at least a first portion of the tool support; a second alignment guide extending from a second portion of the housing and surrounding at least a second portion of the tool support, the second alignment guide spaced axially from the first alignment guide; an actuator assembly connecting the housing and the tool support configured to move the tool support in a plurality of degrees of freedom relative to the housing; and a controller operatively connected to the actuator assembly to change a pose of a tool axis relative to the housing in a plurality of degrees of freedom, the controller configured to automatically control the actuator assembly to actively move the tool axis towards a target trajectory axis relative to the housing. XL. A hand-held robotic instrument to perform surgery, the robotic instrument comprising: a hand-held portion to be held by a user; a tool support movably coupled to the hand-held portion, the tool support supporting a tool; an actuator assembly operatively interconnecting the tool support and the hand-held portion to move the tool support in at least two degrees of freedom relative to the hand-held portion; and a linkage operatively interconnecting the tool support and the hand-held portion, the linkage being coupled to the tool support and the hand-held portion in a manner configured to constrain movement of the tool support relative to the hand-held portion in at least two degrees of freedom, wherein the linkage operatively interconnects the tool support and the hand-held portion independently of the plurality of actuators. XLI. A hand-held robotic instrument for use with a tool to perform surgery, the robotic instrument comprising: a housing configured to be held by a user; a tool support to support the tool and being movably coupled to the housing; a first actuator, a second actuator, the first actuator coupling the second actuator and the housing, the second actuator coupling the first actuator and the tool support, wherein the first actuator includes a first motor, a first base coupled to the first motor, a first gear set coupled to the first motor, and a first rod coupled to the first gear set and the tool support, the first motor of the first actuator operable to extend and retract the first rod relative to the housing; wherein the second actuator operably coupled to the first rod and configured to articulate the first rod of the first actuator about an axis, and a linkage extending between the tool support and the housing. XLII. A hand-held robotic system for use with a surgical tool, the system comprising: an instrument comprising; a hand-held portion to be held by a user; a tool support coupled to the hand-held portion to support the tool, the tool support comprising a tool drive motor; an actuator assembly operatively interconnecting the tool support and the hand-held portion to move the tool support in a plurality of degrees of freedom relative to the hand-held portion, the actuator assembly including a plurality of actuators; a localizer; a control system coupled to the plurality of actuators, the localizer, and the tool drive motor, the control system configured to control the plurality of actuators in two degrees of freedom, the two degrees of freedom being two translation degrees of freedom. XLIII. The system of clause XLII, wherein the tool is a tool. XLIV. The system of clause XLII, wherein the control system is configured to control the plurality of actuators while maintaining the surgical tool in a perpendicular relationship with the hand-held portion. XLV. The system of clause XLII, wherein the control system is configured to control the plurality of actuators such that an axis of the surgical tool intersects a first virtual plane and a second virtual plane at the same position in a first degree of freedom and a second degree of freedom. XLVI. The system of clause XLII wherein the control system is configured to control the plurality of actuators such that an axis of the tool passes through the first virtual plane and the second virtual plane with the same coordinates in at least two degrees of freedom. XLVII. A hand-held robotic system for use with a surgical tool, the system comprising: an instrument comprising; a hand-held portion to be held by a user; a tool support coupled to the hand-held portion to support the tool, the tool support comprising a tool drive motor; an actuator assembly operatively interconnecting the tool support and the hand-held portion to move the tool support in a plurality of degrees of freedom relative to the hand-held portion, the actuator assembly including a plurality of actuators; a localizer; a control system coupled to the plurality of actuators, the localizer, and the tool drive motor, the control system configured to control the plurality of actuators in two degrees of freedom, the two degrees of freedom being two orientation degrees of freedom. XLVIII. The system of clause XLVII, wherein the tool is a drill bit. XLIX. The system of clause XLVII, wherein the tool is a screwdriver. L. The system of clause XLVII, wherein the control system is configured to control the plurality of actuators such that a location of an intersection of an axis of the tool in a first virtual plane is maintained and control the plurality of actuators to vary the location of the intersection of the axis of the tool in a second virtual plane. LI. The system of clause L, wherein the first virtual plane is a proximal virtual plane and the second virtual plane is a distal virtual plane or wherein the first virtual plane is a distal virtual plane and the second virtual plane is a proximal virtual plane.

Several examples have been discussed in the foregoing description. However, the examples discussed herein are not intended to be exhaustive or limit the teachings to any particular form. The terminology that has been used is intended to be in the nature of words of description rather than of limitation. Many modifications and variations are possible in light of the above teachings and the teachings may be practiced otherwise than as specifically described.

What is claimed is:

1. A hand-held robotic instrument for use with a tool to perform surgery, the instrument comprising:
   a housing configured to be held by a user, the housing defining a remote axis of motion;
   a tool support to support the tool and being movably coupled to the housing;
   an anchor post pivotably coupled to the tool support;
   a first set of actuators connected to the anchor post and the housing, a first actuator of the first set of actuators extends the anchor post relative to the remote axis of motion, and a second actuator of the first set is configured to pivot the anchor post about the remote axis of motion; and
   a second set of actuators coupling the tool support and the housing,
   wherein the first set of actuators and the second set of actuators work in concert to change a pose of the tool support in a plurality of degrees of freedom.

2. The instrument of claim 1, wherein the first set of actuators adjust a distal portion of the tool support and the second set of actuators adjust a proximal portion of the tool support to adjust a tool axis defined by the tool support.

3. The instrument of claim 1, wherein the remote axis of motion is defined by the housing.

4. The instrument of claim 3, wherein the anchor post is connected to the housing at a pivot joint, the pivot joint defining a pivot axis, the pivot axis defining the remote axis of motion.

5. The instrument of claim 4, wherein the second actuator of the first set of actuators includes a pinion gear and the anchor post includes a sector gear complimentary to the pinion gear of the second actuator of the first set; and
   wherein the anchor post is pivoted about the remote axis of motion when the second actuator of the first set of actuators is actuated.

6. The instrument of claim 4, wherein each of the second set of actuators include a motor, each motor defining a longitudinal axis, the longitudinal axis of the motors of the second set of actuators being parallel to the remote axis of motion.

7. The instrument of claim 6, wherein the second set of actuators includes a third actuator and a fourth actuator, the third actuator including a third motor, a first base coupled to the third motor, a first rod extendable from the first base upon actuation of the third motor, and the fourth actuator including a fourth motor, a second base coupled to the fourth motor, a second rod extendable from the second base upon actuation of the fourth motor, wherein the third motor defines a third axis, and wherein the fourth motor defines a fourth axis and the third axis is parallel to the fourth axis.

8. The instrument of claim 7, wherein at least one of the rods define a rod axis, and the rod axis is perpendicular to at least one of the third axis and the fourth axis.

9. The instrument of claim 1, wherein the housing defines a void, and wherein the first actuator is disposed within the void.

10. The instrument of claim 1, wherein the housing defines a void, and wherein the second actuator of the first set of actuators is disposed within the void.

11. The instrument of claim 1, wherein the first actuator of the first set of actuators is further defined as a lift assembly, wherein the lift assembly comprises a lift motor and a movement mechanism, the movement mechanism being operably coupled to the lift motor such that the movement mechanism causes translation of the anchor post in response to actuation of the lift motor.

12. The instrument of claim 11, wherein the movement mechanism comprises a plurality of lead screws, and a carriage threadably coupled to the plurality of lead screws, with the carriage coupled to the anchor post; and wherein the anchor post is rotatably coupled to the carriage.

13. The instrument of claim 1, wherein each of the second set of actuators include a base and a rod, the rods each including a yoke, each of the bases is rotatably connected with the housing, and each yoke is connected with the tool support, each of the rods extendable from each of the bases.

14. The instrument of claim 13, wherein each of the rods of the second set of actuators lay in offset planes, the offset planes being perpendicular to the remote axis of motion.

15. The instrument of claim 13, wherein the tool support defines a positioning post, and at least one portion of each actuator of the second set of actuators is movable along the positioning post of the tool support as the tool support is adjusted in the plurality of degrees of freedom.

16. A hand-held robotic instrument for use with a tool to perform surgery, the instrument comprising:

a housing configured to be held by a user;

a tool support to support the tool and being movably coupled to the housing, the tool support defining a tool axis;

an anchor post pivotably coupled to the tool support;

a first set of actuators operably coupled to the anchor post and the housing, the first set of actuators being configured to translate the anchor post relative to the housing and configured to pivot the anchor post about a remote axis of motion;

a second set of actuators coupled to the tool support; and a controller in communication with the first set of actuators and the second set of actuators to change a pose of the tool support relative to the housing to place the tool axis on a target trajectory while the user manipulates the housing.

17. The instrument of claim 16, wherein the first set of actuators including a first actuator and a second actuator, wherein the second actuator of the first set of actuators includes a pinion gear and the anchor post includes a sector gear complimentary to the pinion gear of the second actuator of the first set of actuators; and wherein the housing defines a void, and wherein the first actuator and the second actuator are each disposed within the void.

18. The instrument of claim 17, wherein the anchor post is pivoted about the remote axis of motion when the second actuator of the first set of actuators is actuated.

19. The instrument of claim 16, wherein a first actuator of the first set of actuators is further defined as a lift assembly, wherein the lift assembly comprises a lift motor and a movement mechanism, the movement mechanism being operably coupled to the lift motor such that the movement mechanism causes translation of the anchor post in response to actuation of the lift motor;

wherein the movement mechanism comprises a plurality of lead screws, and a carriage threadably coupled to the plurality of lead screws, with the carriage coupled to the anchor post; and wherein the anchor post is rotatably coupled to the carriage.

20. A hand-held robotic instrument for use with a tool to perform surgery, the robotic instrument comprising:

a housing configured to be held by a user;

a tool support to support the tool and being movably coupled to the housing, the tool support defining a tool axis;

an anchor post pivotably coupled to the tool support;

a first set of actuators coupled between the anchor post and the housing, a first actuator of the first set of actuators is configured to change a position of the anchor post, and a second actuator of the first set configured to pivot the anchor post about a remote axis of motion; and a second set of actuators connected between the tool support and the housing, the second set of actuators including a first rotary actuator of the second set of actuators and a second linear actuator of the second set of actuators, the first rotary actuator being coupled to the second linear actuator to cause the second linear actuator to rotate about an axis and the second linear actuator of the second set of actuators configured to change length with the second linear actuator extending from the first rotary actuator of the second set of actuators to the tool support, wherein the first set of actuators and the second set of actuators work in concert to change a pose of the tool support.

* * * * *